US012807703B2

(12) United States Patent
Hayashi et al.

(10) Patent No.: US 12,807,703 B2
(45) Date of Patent: Nov. 24, 2026

(54) OPTIC NERVE PROTECTING AGENT CONTAINING ANTI-LRP1 ANTIBODY

(71) Applicants: TOKYO UNIVERSITY OF PHARMACY & LIFE SCIENCES, Tokyo (JP); NATIONAL INSTITUTES OF BIOMEDICAL INNOVATION, HEALTH AND NUTRITION, Osaka (JP)

(72) Inventors: Hideki Hayashi, Tokyo (JP); Norio Takagi, Tokyo (JP); Yamato Kikkawa, Tokyo (JP); Haruhiko Kamada, Ibaraki (JP); Satoshi Nagata, Ibaraki (JP)

(73) Assignees: Tokyo University of Pharmacy & Life Sciences, Tokyo (JP); National Institutes of Biomedical Innovation, Health and Nutrition, Osaka (JP)

( * ) Notice: Subject to any disclaimer, the term of this patent is extended or adjusted under 35 U.S.C. 154(b) by 644 days.

(21) Appl. No.: 18/265,617

(22) PCT Filed: Nov. 26, 2021

(86) PCT No.: PCT/JP2021/043471
§ 371 (c)(1),
(2) Date: Jun. 6, 2023

(87) PCT Pub. No.: WO2022/124105
PCT Pub. Date: Jun. 16, 2022

(65) Prior Publication Data

US 2024/0034787 A1 Feb. 1, 2024

(30) Foreign Application Priority Data

Dec. 8, 2020 (JP) ................................ 2020-203477

(51) Int. Cl.
*C07K 16/28* (2006.01)
*A61P 27/02* (2006.01)

(52) U.S. Cl.
CPC .............. *C07K 16/28* (2013.01); *A61P 27/02* (2018.01); *C07K 2317/21* (2013.01); *C07K 2317/24* (2013.01)

(58) Field of Classification Search
None
See application file for complete search history.

(56) References Cited

U.S. PATENT DOCUMENTS

2014/0228299 A1 8/2014 Hayashi

OTHER PUBLICATIONS

Sanchez et al., Low-density lipoprotein receptor-related protein-1 (LRP-1) expression in a rat model of oxygen-induced retinal neovascularization. Experimental Eye Research 83 (2006) 1378e1385 (Year: 2006).*

Kussie et al., A single engineered amino acid substitution changes antibody fine specificity.J Immunol. Jan. 1, 1994;152(1):146-52. (Year: 1994).*

(Continued)

*Primary Examiner* — Aurora M Fontainhas
(74) *Attorney, Agent, or Firm* — Morgan, Lewis & Bockius LLP

(57) ABSTRACT

The present invention relates to an optic nerve protecting agent containing an anti-low density lipoprotein receptor-related protein 1 (LRP1) antibody or an anti-LRP1 antibody fragment.

13 Claims, 16 Drawing Sheets

Specification includes a Sequence Listing.

(56) References Cited

OTHER PUBLICATIONS

Edwards et al., The remarkable flexibility of the human antibody repertoire; isolation of over one thousand different antibodies to a single protein, BLyS. J Mol Biol. Nov. 14, 2003;334(1):103-18. (Year: 2003).*

Chen et al., Enhancement and destruction of antibody function by somatic mutation: unequal occurrence is controlled by V gene combinatorial associations. Embo J. Jun. 15, 1995;14(12):2784-94. (Year: 1995).*

Hayashi et al. "Roles of low density lipoprotein receptor-related protein 1 ligands in glaucomatous optic neuropathy," Abstracts of the Annual Meeting of the Japanese Pharmacological Society, vol. 92nd, #3-O-06 (2019).

Yoon et al., "Low-density Lipoprotein Receptor-related Protein 1 (LRP1)-dependent Cell Signaling Promotes Axonal Regeneration," Journal of Biological Chemistry, 288 (37): 26557-26568 (2013).

Hayashi et al., "Apolipoprotein E-Containing Lipoproteins Protect Neurons from Apoptosis via a Signaling Pathway Involving Low-Density Lipoprotein Receptor-Related Protein-1," Journal of Neuroscience, 27 (8): 1933-1941 (2007).

Hayashi et al., "Protection of neurons from apoptosis by apolipoprotein E-containing lipoproteins," Neurochemistry, vol. 49 No. 2_3, p. 483 (2010).

Hayashi et al., "Protection of Neurons from Apoptosis by Apolipoprotein E-containing Lipoproteins Does Not Require Lipoprotein Uptake and Involves Activation of Phospholipase Cγ1 and Inhibition of Calcineurin," The Journal of Biological Chemistry, 284 (43): 29605-29613 (2009).

Vance et al., "Review: Formation and function of apolipoprotein E-containing lipoproteins in the nervous system," Biochimica et Biophysica Acta, 1801: 806-818 (2010).

Hayashi, "Review: Lipid Metabolism and Glial Lipoproteins in the Central Nervous System," Biological and Pharmaceutical Bulletin, 34 (4): 453-461 (2011).

Hayashi et al., "A Potential Neuroprotective Role of Apolipoprotein E-containing Lipoproteins through Low Density Lipoprotein Receptor-related Protein 1 in Normal Tension Glaucoma," Journal of Biological Chemistry, 287 (30): 25395-25406 (2012).

International Search Report issued in corresponding International Patent Application No. PCT/JP2021/043471 dated Jan. 18, 2022.

Extended European Search Report issued in European Patent Application No. 21903209.1 dated Oct. 22, 2024.

* cited by examiner

[Figure 1]
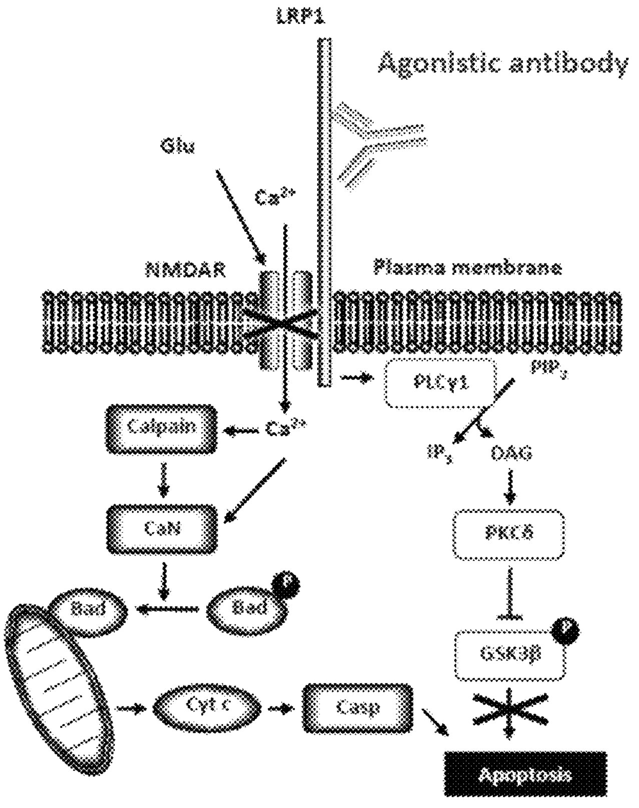

[Figure 2A]
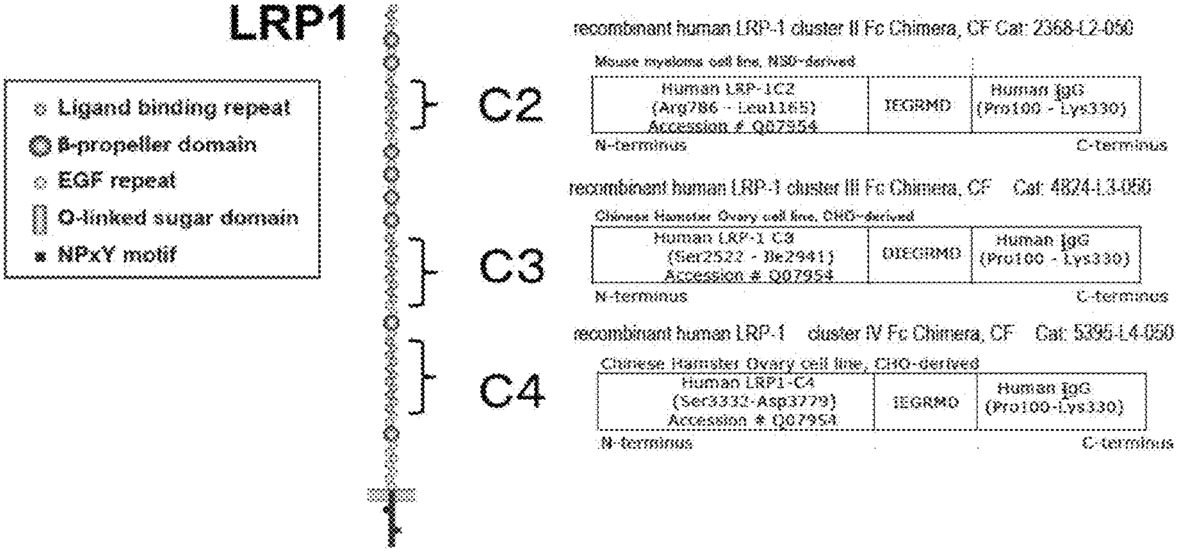
[Figure 2B]
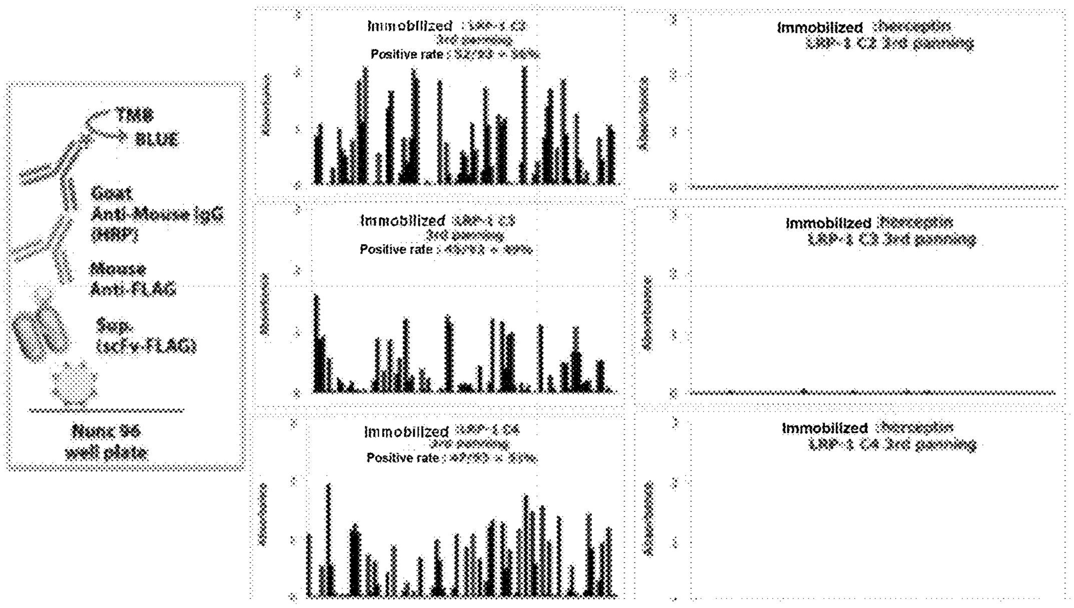

[Figure 2C]
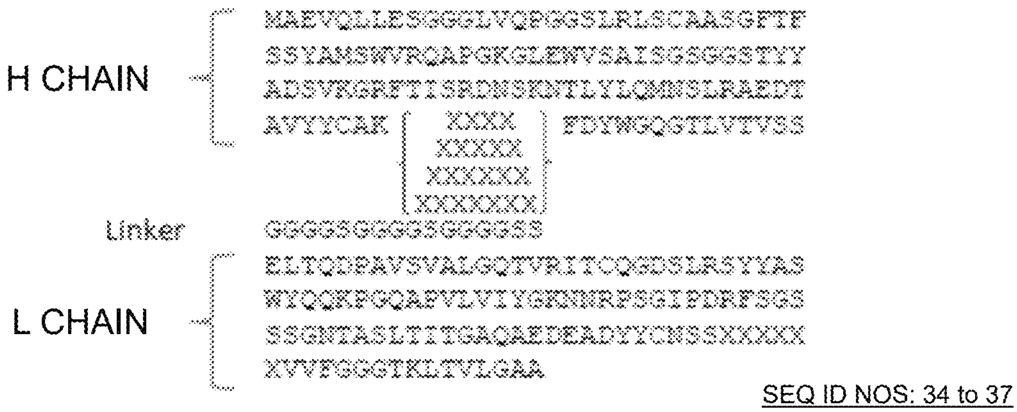
SEQ ID NOS: 34 to 37
The sequence having {XXXX} in H CHAIN: SEQ ID NO: 34
The sequence having {XXXXX} in H CHAIN: SEQ ID NO: 35
The sequence having {XXXXXX} in H CHAIN: SEQ ID NO: 36
The sequence having {XXXXXXX} in H CHAIN: SEQ ID NO: 37

[Figure 2D]
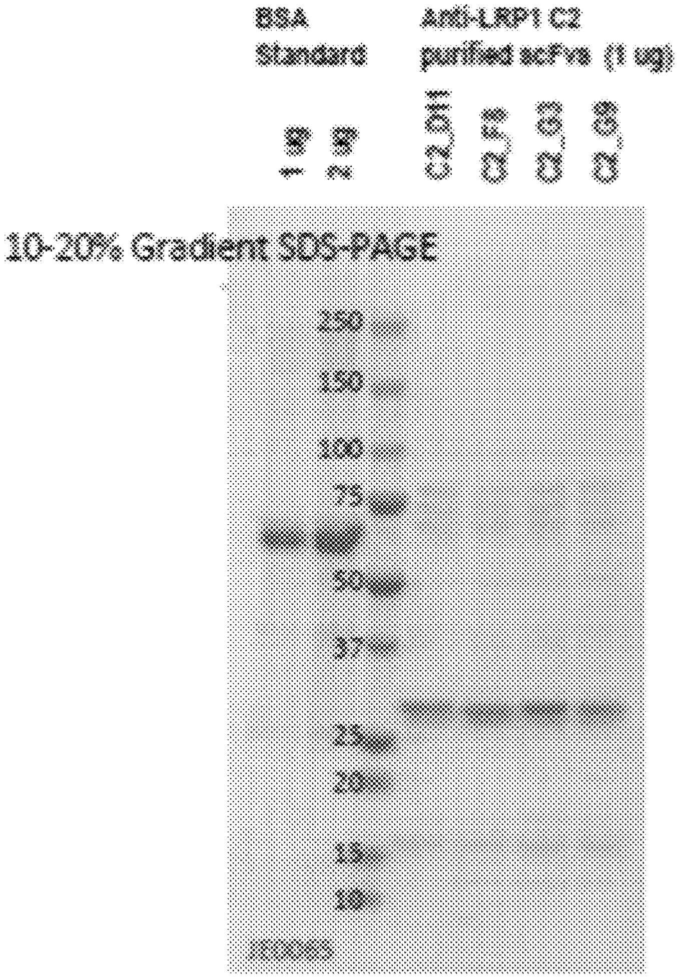

[Figure 2E]
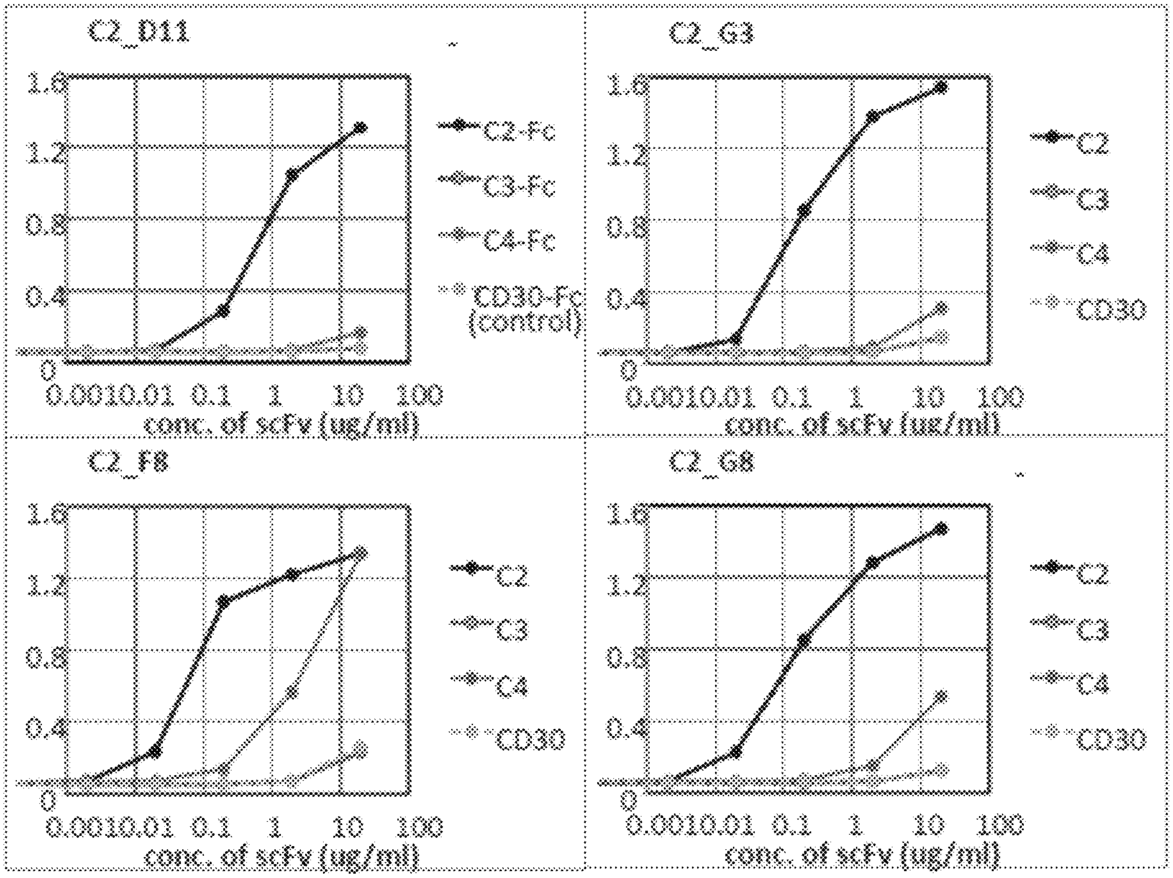

[Figure 3A]
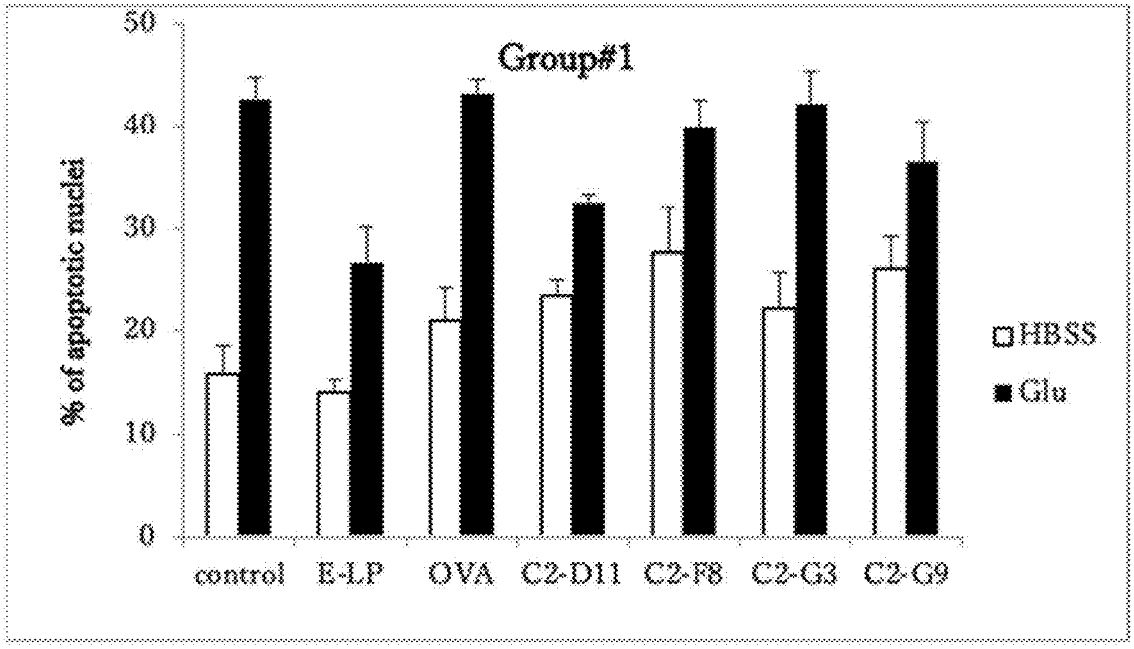
[Figure 3B]
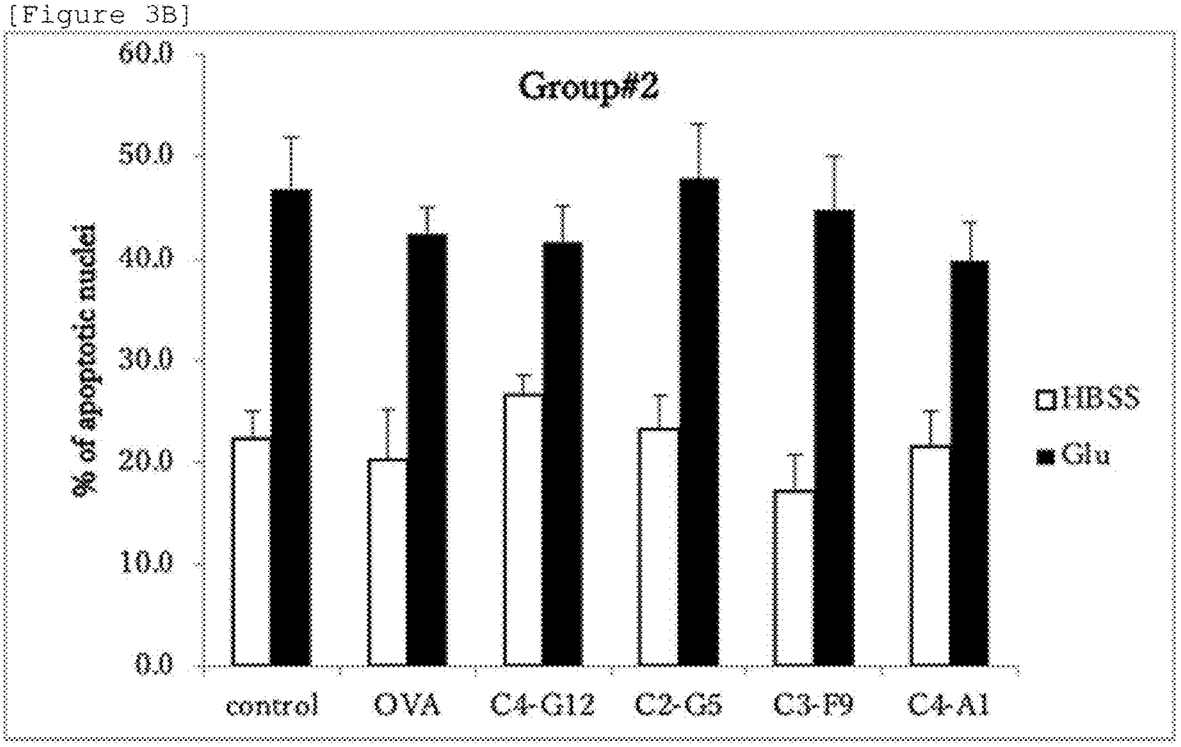

[Figure 3C]
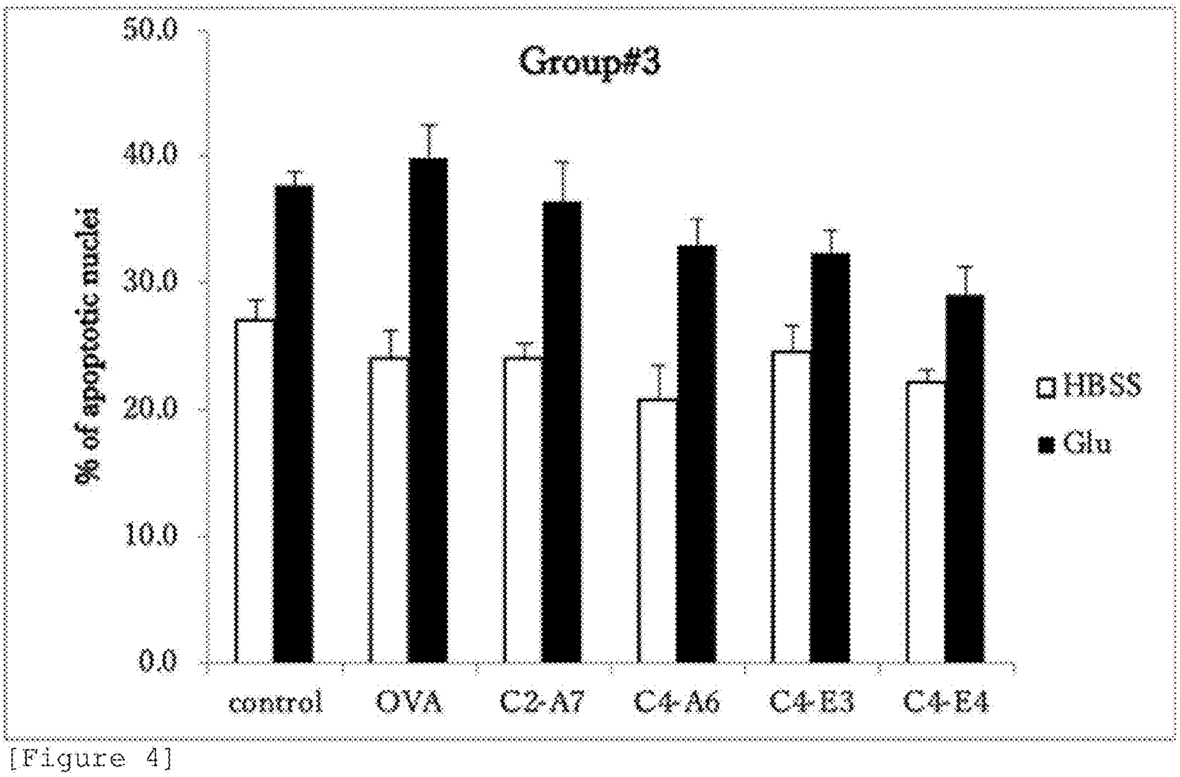
[Figure 4]
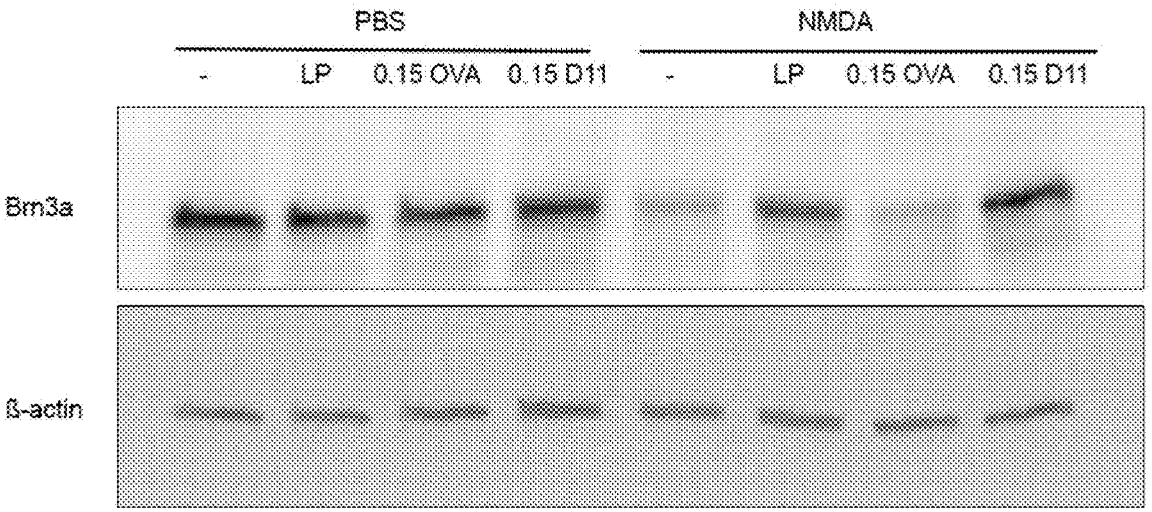

[Figure 5]
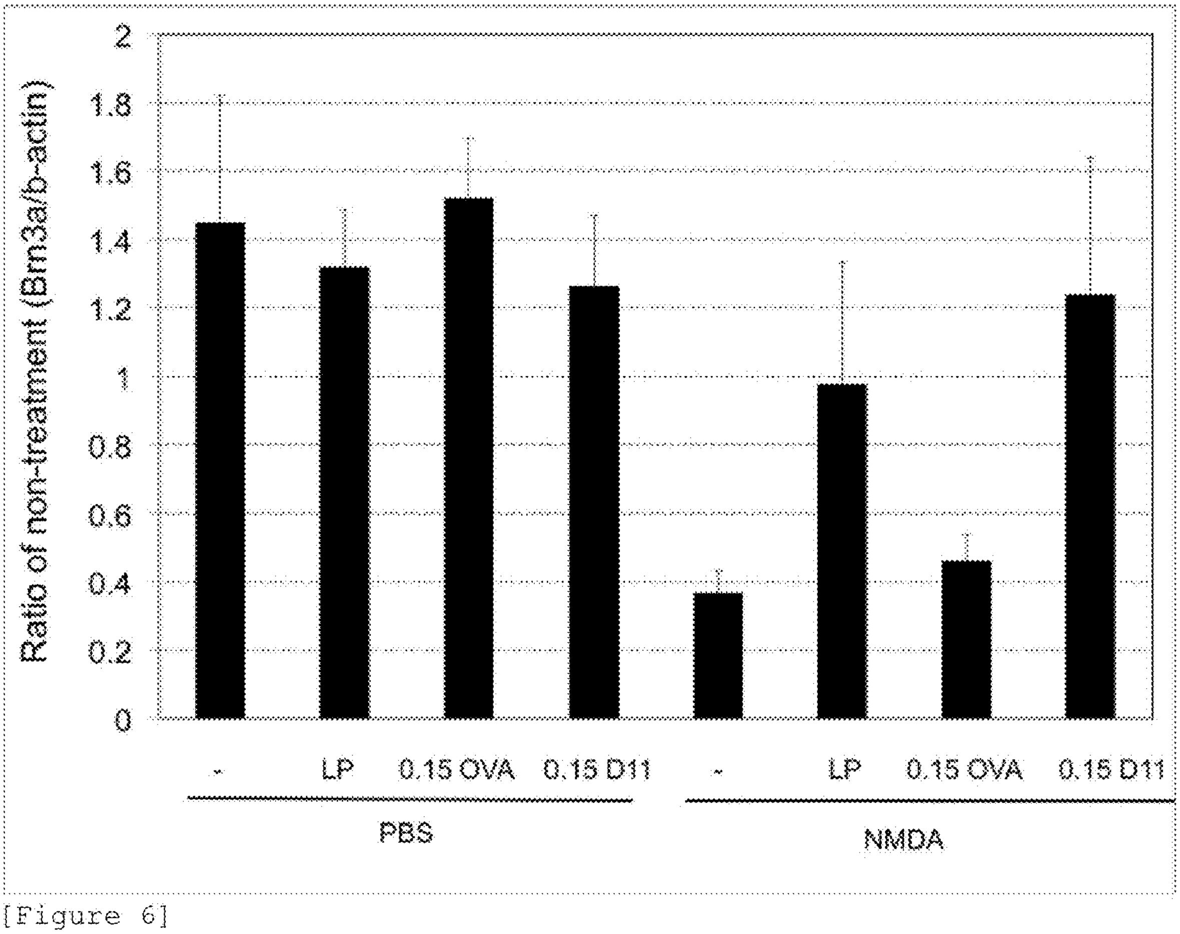
[Figure 6]
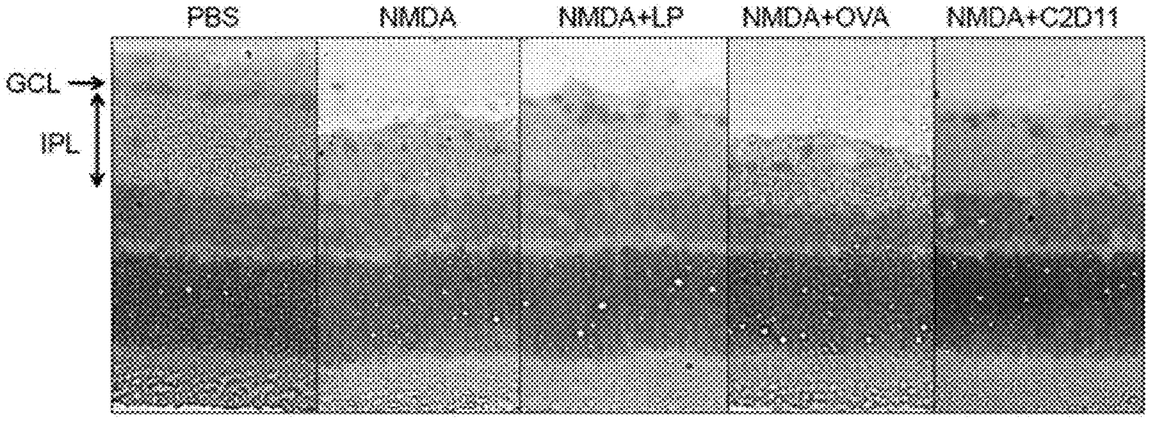
GCL: ganglion cell layer
IPL: inner plexiform layer

[Figure 7]
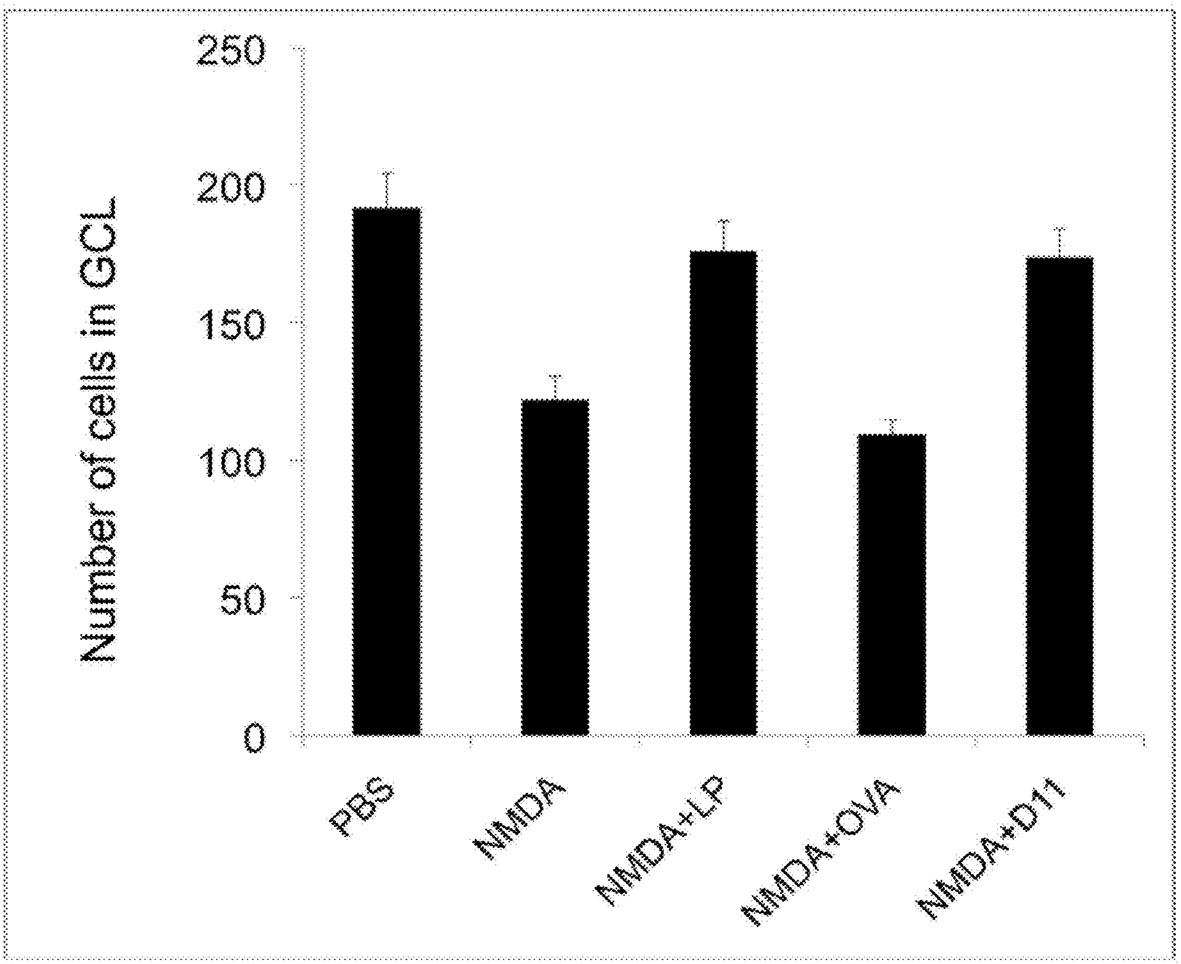

[Figure 8A]
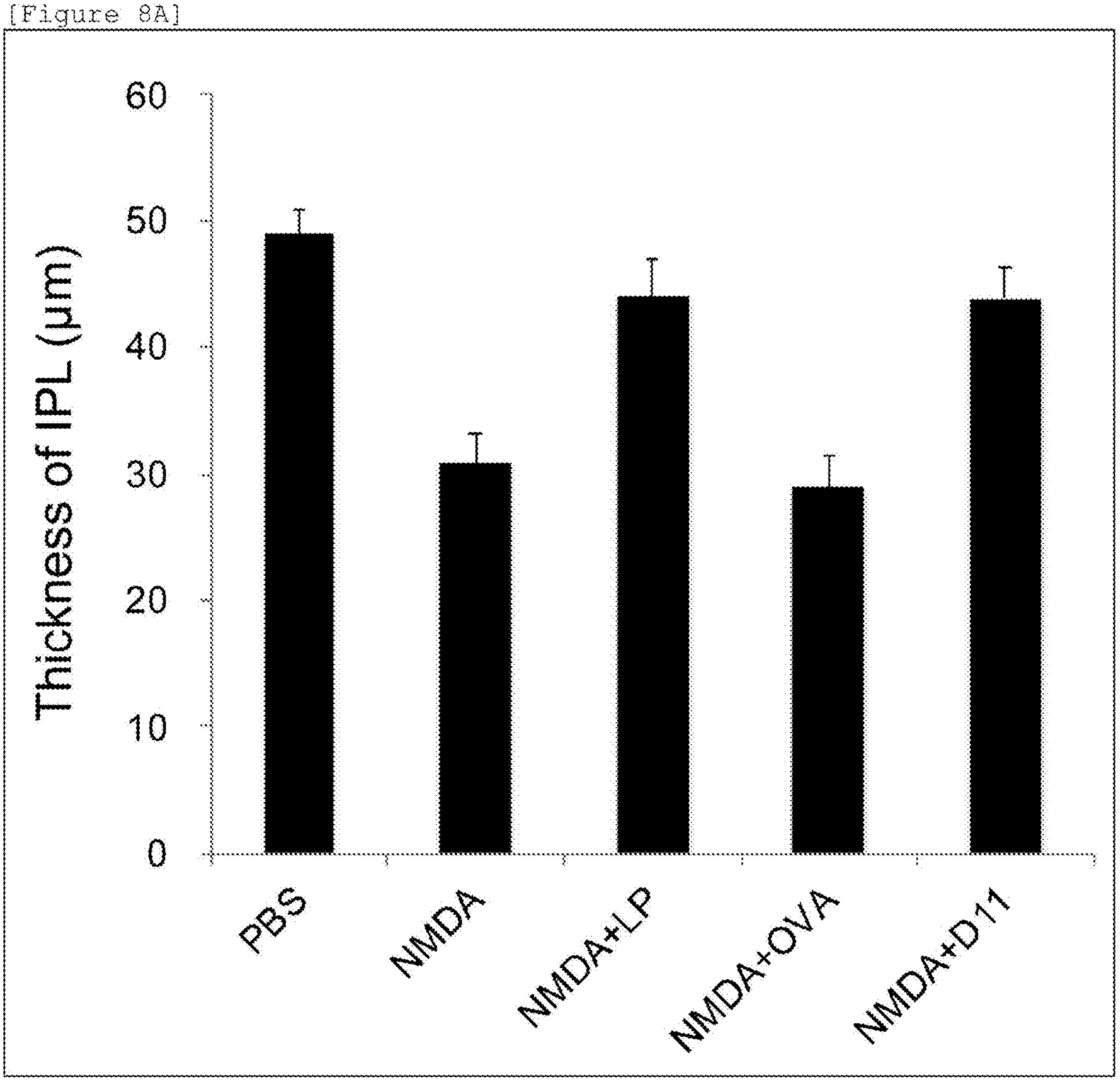
[Figure 8B]
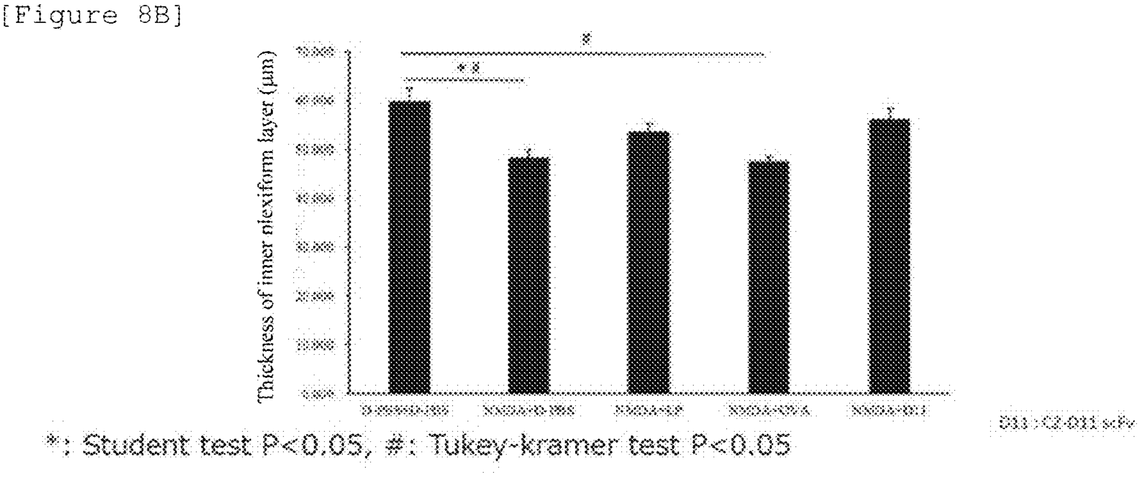
*: Student test P<0.05, #: Tukey-kramer test P<0.05

[Figure 9]
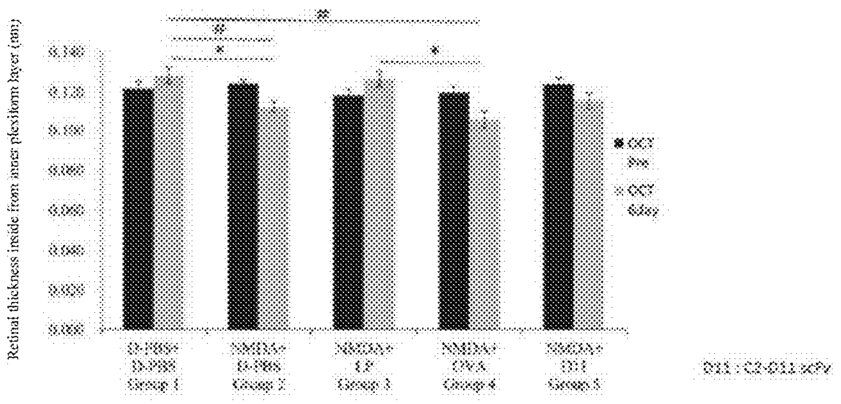
[Figure 10]
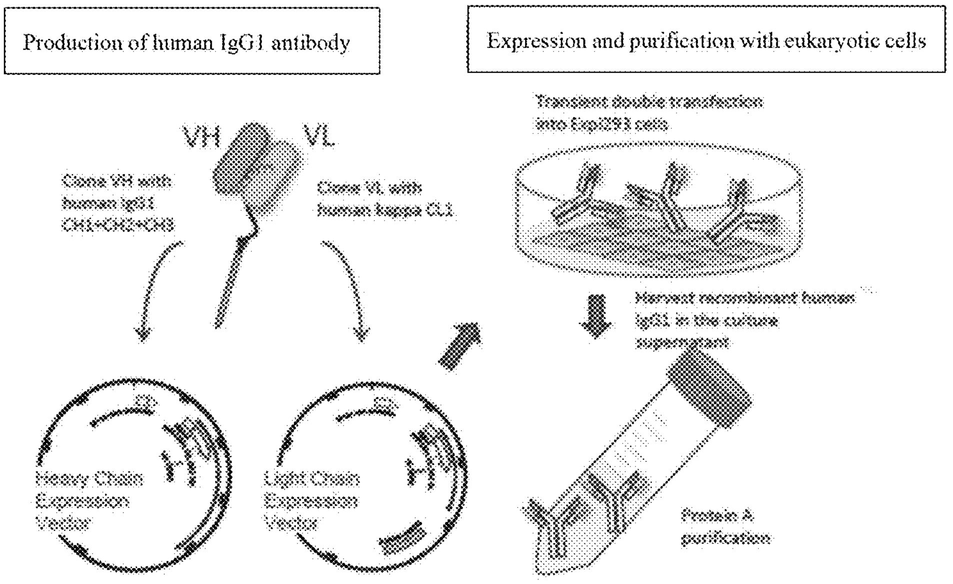

[Figure 11A]
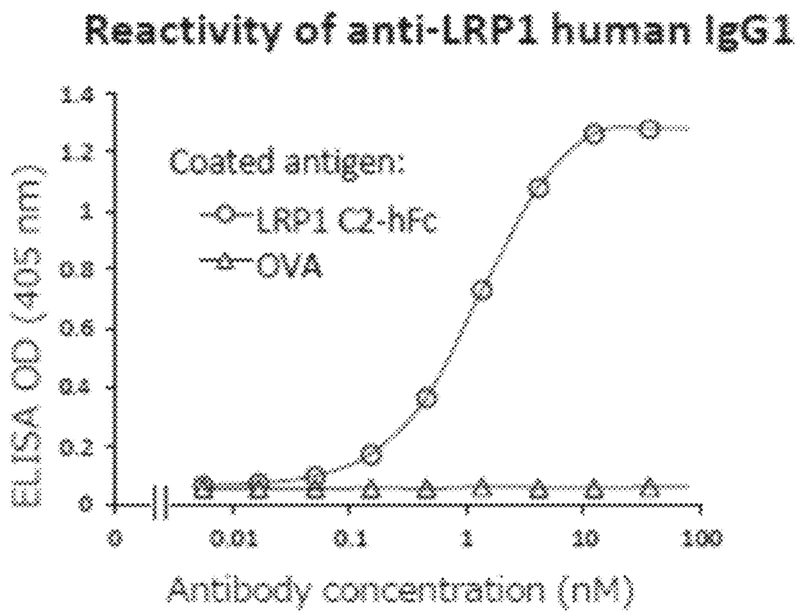
[Figure 11B]
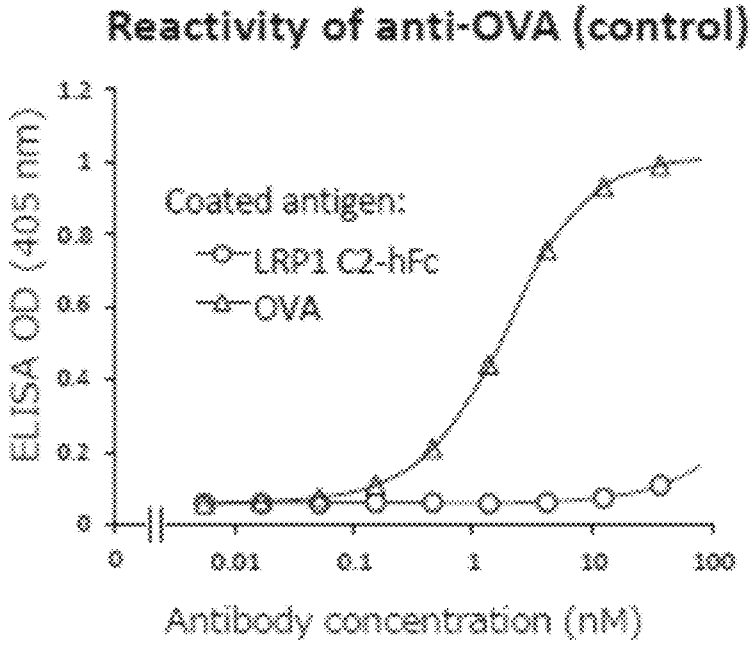

[Figure 12]
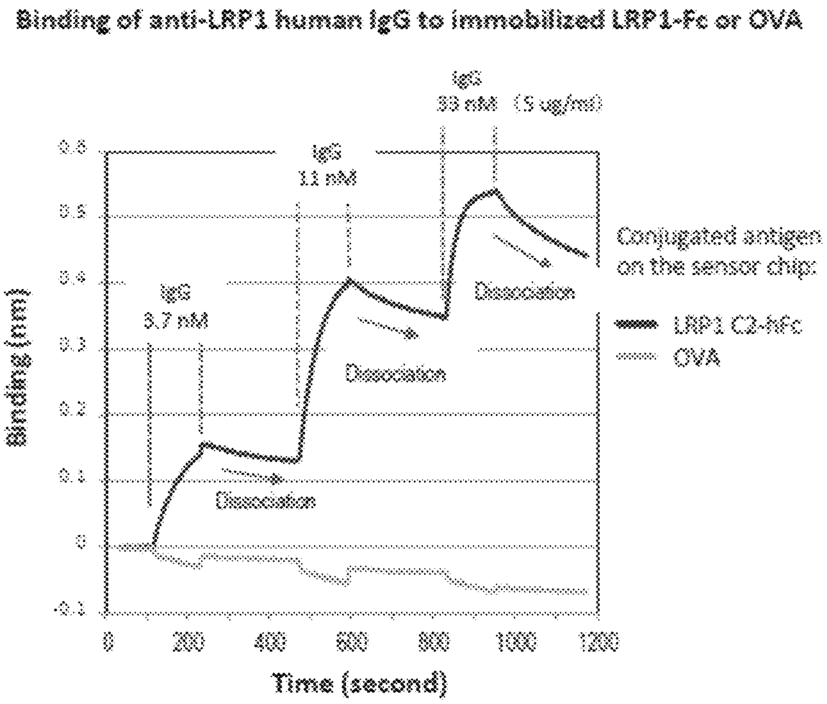

[Figure 13]
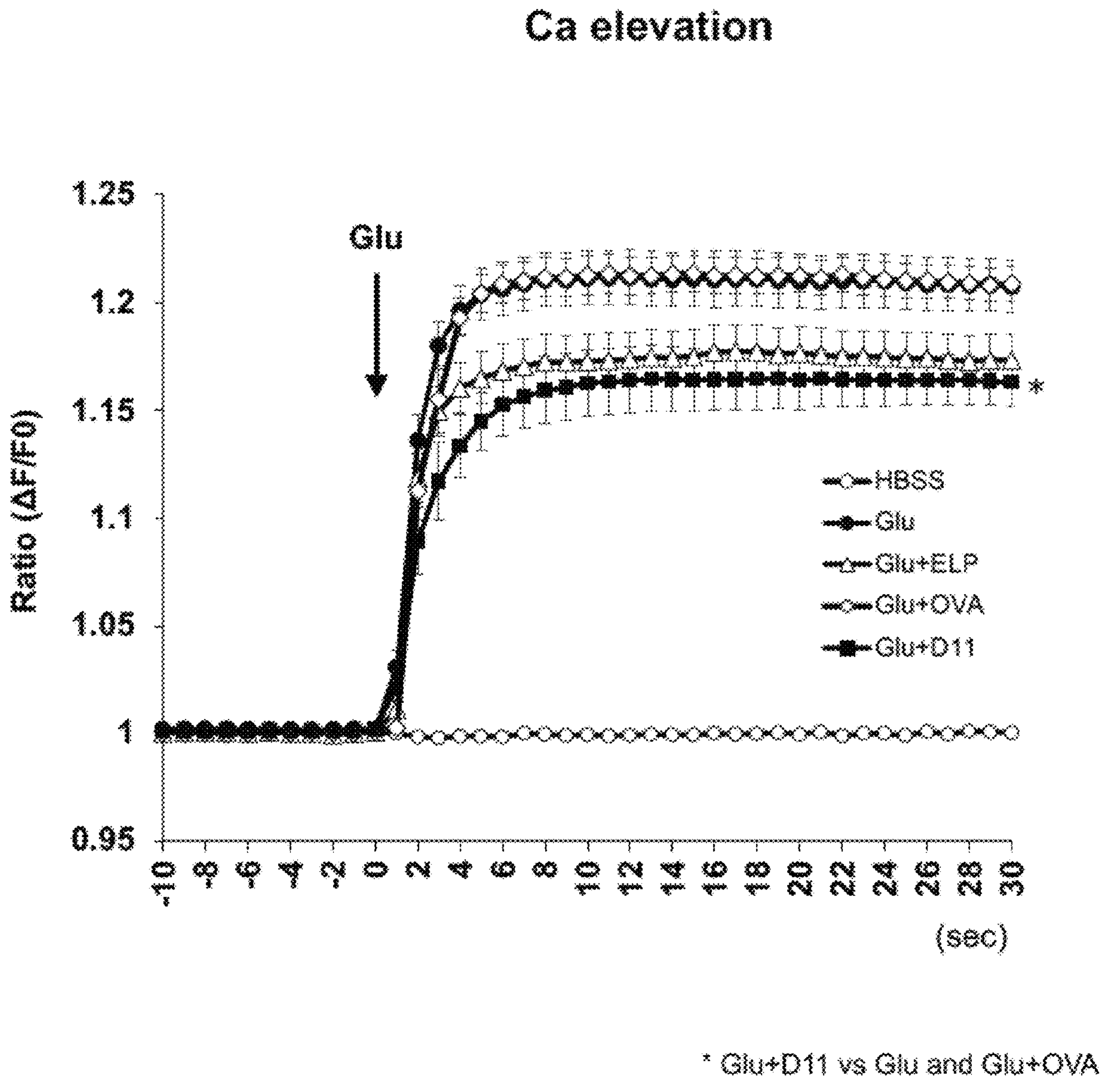

[Figure 14]
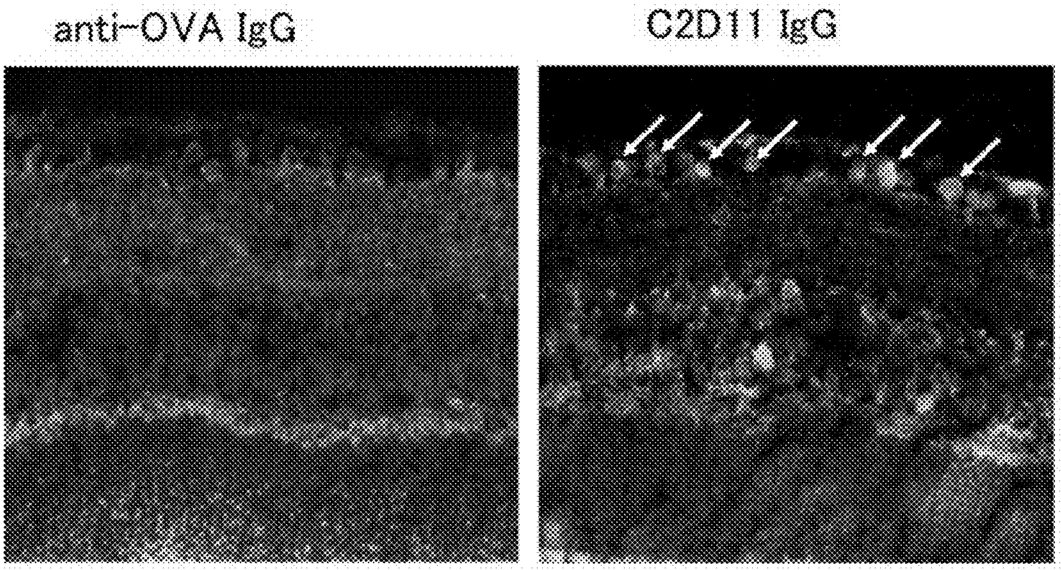
Nucleus: Hoechst 33342, LRP1: anti-LRP1(Bioss bs-2677R), Goat anti-human IgG Alexa 594
[Figure 15]
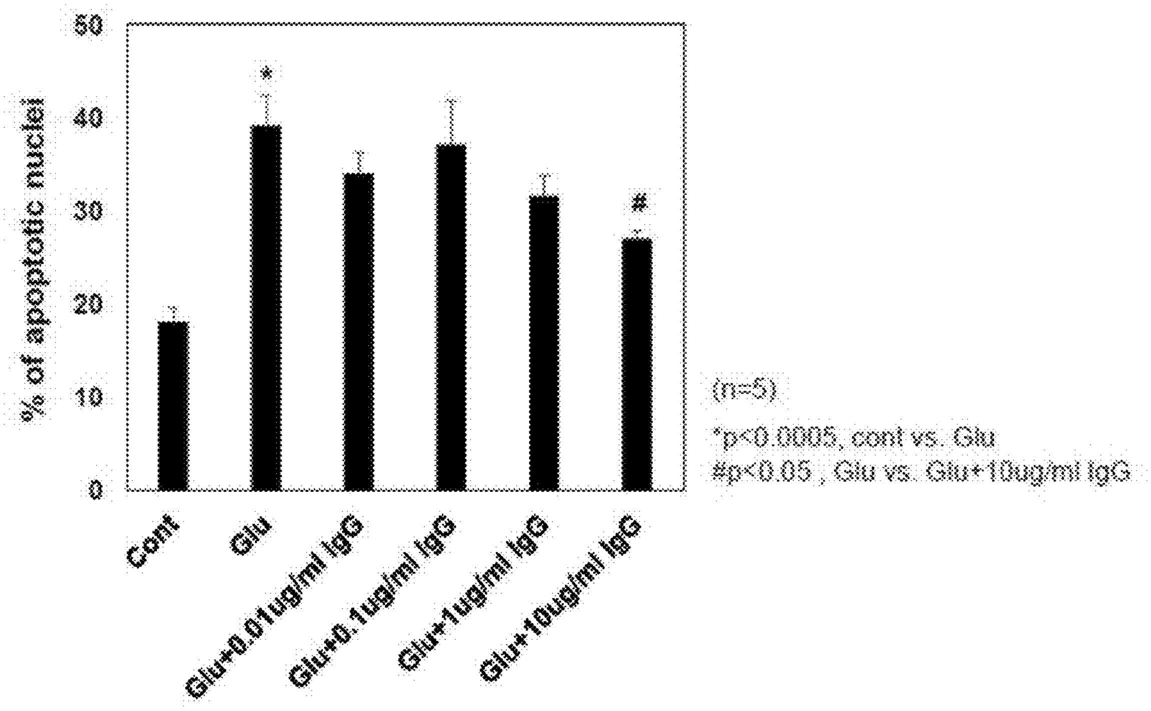

[Figure 16A]
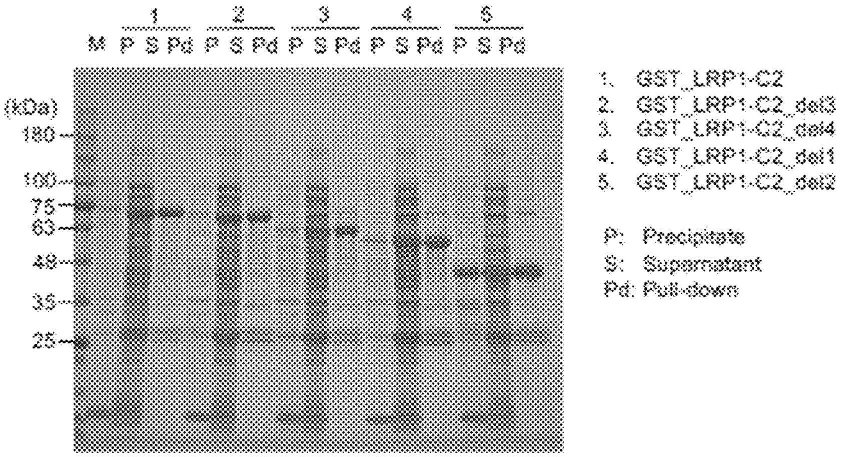
1. GST_LRP1-C2 : GST_EGF-like4_LDL receptor class A3_A4_A5_A6_A7_A8_A9_A10
2. GST_LRP1-C2_del3(11-23): GST_EGF-like4_LDL receptor class A3_A4_A5_A6_A7_A8_A9
3. GST_LRP1-C2_del4(11-22): GST_EGF-like4_LDL receptor class A3_A4_A5_A6_A7_A8
4. GST_LRP1-C2_del1(11-13): GST_EGF-like4_LDL receptor class A3_A4_A5_A6_A7
5. GST_LRP1-C2_del2(11-12): GST_EGF-like4_LDL receptor class A3_A4_A5
[Figure 16B]
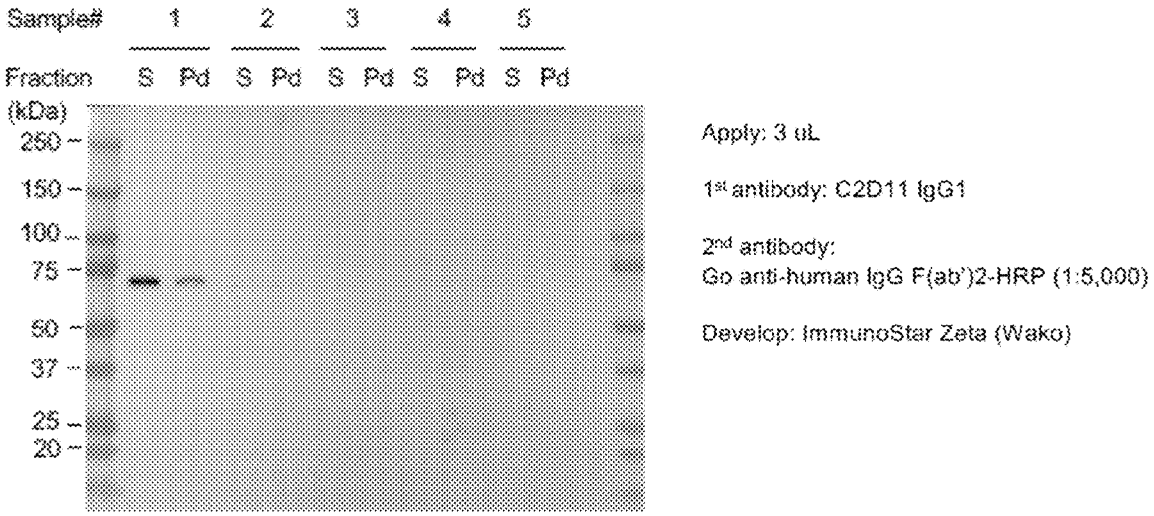
S: Supernatant
Pd: Glutathione-sepharose pull down

SEQUENCE LISTING

<160> NUMBER OF SEQ ID NOS: 37

<210> SEQ ID NO 1
<211> LENGTH: 4544
<212> TYPE: PRT
<213> ORGANISM: Homo sapiens

<400> SEQUENCE: 1

```
Met Leu Thr Pro Pro Leu Leu Leu Leu Leu Pro Leu Leu Ser Ala Leu
1               5                   10                  15

Val Ala Ala Ala Ile Asp Ala Pro Lys Thr Cys Ser Pro Lys Gln Phe
            20                  25                  30

Ala Cys Arg Asp Gln Ile Thr Cys Ile Ser Lys Gly Trp Arg Cys Asp
        35                  40                  45

Gly Glu Arg Asp Cys Pro Asp Gly Ser Asp Glu Ala Pro Glu Ile Cys
    50                  55                  60

Pro Gln Ser Lys Ala Gln Arg Cys Gln Pro Asn Glu His Asn Cys Leu
65                  70                  75                  80

Gly Thr Glu Leu Cys Val Pro Met Ser Arg Leu Cys Asn Gly Val Gln
                85                  90                  95

Asp Cys Met Asp Gly Ser Asp Glu Gly Pro His Cys Arg Glu Leu Gln
            100                 105                 110

Gly Asn Cys Ser Arg Leu Gly Cys Gln His His Cys Val Pro Thr Leu
        115                 120                 125

Asp Gly Pro Thr Cys Tyr Cys Asn Ser Ser Phe Gln Leu Gln Ala Asp
    130                 135                 140

Gly Lys Thr Cys Lys Asp Phe Asp Glu Cys Ser Val Tyr Gly Thr Cys
145                 150                 155                 160

Ser Gln Leu Cys Thr Asn Thr Asp Gly Ser Phe Ile Cys Gly Cys Val
                165                 170                 175

Glu Gly Tyr Leu Leu Gln Pro Asp Asn Arg Ser Cys Lys Ala Lys Asn
            180                 185                 190

Glu Pro Val Asp Arg Pro Pro Val Leu Leu Ile Ala Asn Ser Gln Asn
        195                 200                 205

Ile Leu Ala Thr Tyr Leu Ser Gly Ala Gln Val Ser Thr Ile Thr Pro
    210                 215                 220

Thr Ser Thr Arg Gln Thr Thr Ala Met Asp Phe Ser Tyr Ala Asn Glu
225                 230                 235                 240

Thr Val Cys Trp Val His Val Gly Asp Ser Ala Ala Gln Thr Gln Leu
                245                 250                 255

Lys Cys Ala Arg Met Pro Gly Leu Lys Gly Phe Val Asp Glu His Thr
            260                 265                 270

Ile Asn Ile Ser Leu Ser Leu His His Val Glu Gln Met Ala Ile Asp
        275                 280                 285

Trp Leu Thr Gly Asn Phe Tyr Phe Val Asp Asp Ile Asp Asp Arg Ile
    290                 295                 300

Phe Val Cys Asn Arg Asn Gly Asp Thr Cys Val Thr Leu Leu Asp Leu
305                 310                 315                 320

Glu Leu Tyr Asn Pro Lys Gly Ile Ala Leu Asp Pro Ala Met Gly Lys
                325                 330                 335

Val Phe Phe Thr Asp Tyr Gly Gln Ile Pro Lys Val Glu Arg Cys Asp
            340                 345                 350

Met Asp Gly Gln Asn Arg Thr Lys Leu Val Asp Ser Lys Ile Val Phe
        355                 360                 365
```

-continued

```
Pro His Gly Ile Thr Leu Asp Leu Val Ser Arg Leu Val Tyr Trp Ala
    370                 375                 380

Asp Ala Tyr Leu Asp Tyr Ile Glu Val Val Asp Tyr Glu Gly Lys Gly
385                 390                 395                 400

Arg Gln Thr Ile Ile Gln Gly Ile Leu Ile Glu His Leu Tyr Gly Leu
                405                 410                 415

Thr Val Phe Glu Asn Tyr Leu Tyr Ala Thr Asn Ser Asp Asn Ala Asn
            420                 425                 430

Ala Gln Gln Lys Thr Ser Val Ile Arg Val Asn Arg Phe Asn Ser Thr
        435                 440                 445

Glu Tyr Gln Val Val Thr Arg Val Asp Lys Gly Gly Ala Leu His Ile
    450                 455                 460

Tyr His Gln Arg Arg Gln Pro Arg Val Arg Ser His Ala Cys Glu Asn
465                 470                 475                 480

Asp Gln Tyr Gly Lys Pro Gly Gly Cys Ser Asp Ile Cys Leu Leu Ala
                485                 490                 495

Asn Ser His Lys Ala Arg Thr Cys Arg Cys Arg Ser Gly Phe Ser Leu
            500                 505                 510

Gly Ser Asp Gly Lys Ser Cys Lys Lys Pro Glu His Glu Leu Phe Leu
        515                 520                 525

Val Tyr Gly Lys Gly Arg Pro Gly Ile Ile Arg Gly Met Asp Met Gly
    530                 535                 540

Ala Lys Val Pro Asp Glu His Met Ile Pro Ile Glu Asn Leu Met Asn
545                 550                 555                 560

Pro Arg Ala Leu Asp Phe His Ala Glu Thr Gly Phe Ile Tyr Phe Ala
                565                 570                 575

Asp Thr Thr Ser Tyr Leu Ile Gly Arg Gln Lys Ile Asp Gly Thr Glu
            580                 585                 590

Arg Glu Thr Ile Leu Lys Asp Gly Ile His Asn Val Glu Gly Val Ala
        595                 600                 605

Val Asp Trp Met Gly Asp Asn Leu Tyr Trp Thr Asp Asp Gly Pro Lys
    610                 615                 620

Lys Thr Ile Ser Val Ala Arg Leu Glu Lys Ala Ala Gln Thr Arg Lys
625                 630                 635                 640

Thr Leu Ile Glu Gly Lys Met Thr His Pro Arg Ala Ile Val Val Asp
                645                 650                 655

Pro Leu Asn Gly Trp Met Tyr Trp Thr Asp Trp Glu Glu Asp Pro Lys
            660                 665                 670

Asp Ser Arg Arg Gly Arg Leu Glu Arg Ala Trp Met Asp Gly Ser His
        675                 680                 685

Arg Asp Ile Phe Val Thr Ser Lys Thr Val Leu Trp Pro Asn Gly Leu
    690                 695                 700

Ser Leu Asp Ile Pro Ala Gly Arg Leu Tyr Trp Val Asp Ala Phe Tyr
705                 710                 715                 720

Asp Arg Ile Glu Thr Ile Leu Leu Asn Gly Thr Asp Arg Lys Ile Val
                725                 730                 735

Tyr Glu Gly Pro Glu Leu Asn His Ala Phe Gly Leu Cys His His Gly
            740                 745                 750

Asn Tyr Leu Phe Trp Thr Glu Tyr Arg Ser Gly Ser Val Tyr Arg Leu
        755                 760                 765

Glu Arg Gly Val Gly Gly Ala Pro Pro Thr Val Thr Leu Leu Arg Ser
    770                 775                 780

Glu Arg Pro Pro Ile Phe Glu Ile Arg Met Tyr Asp Ala Gln Gln Gln
```

-continued

```
785                 790                 795                 800

Gln Val Gly Thr Asn Lys Cys Arg Val Asn Asn Gly Gly Cys Ser Ser
                805                 810                 815

Leu Cys Leu Ala Thr Pro Gly Ser Arg Gln Cys Ala Cys Ala Glu Asp
            820                 825                 830

Gln Val Leu Asp Ala Asp Gly Val Thr Cys Leu Ala Asn Pro Ser Tyr
        835                 840                 845

Val Pro Pro Pro Gln Cys Gln Pro Gly Glu Phe Ala Cys Ala Asn Ser
    850                 855                 860

Arg Cys Ile Gln Glu Arg Trp Lys Cys Asp Gly Asp Asn Asp Cys Leu
865                 870                 875                 880

Asp Asn Ser Asp Glu Ala Pro Ala Leu Cys His Gln His Thr Cys Pro
                885                 890                 895

Ser Asp Arg Phe Lys Cys Glu Asn Asn Arg Cys Ile Pro Asn Arg Trp
            900                 905                 910

Leu Cys Asp Gly Asp Asn Asp Cys Gly Asn Ser Glu Asp Glu Ser Asn
        915                 920                 925

Ala Thr Cys Ser Ala Arg Thr Cys Pro Pro Asn Gln Phe Ser Cys Ala
    930                 935                 940

Ser Gly Arg Cys Ile Pro Ile Ser Trp Thr Cys Asp Leu Asp Asp Asp
945                 950                 955                 960

Cys Gly Asp Arg Ser Asp Glu Ser Ala Ser Cys Ala Tyr Pro Thr Cys
                965                 970                 975

Phe Pro Leu Thr Gln Phe Thr Cys Asn Asn Gly Arg Cys Ile Asn Ile
            980                 985                 990

Asn Trp Arg Cys Asp Asn Asp Asn  Asp Cys Gly Asp Asn  Ser Asp Glu
        995                 1000                 1005

Ala Gly  Cys Ser His Ser Cys  Ser Ser Thr Gln Phe  Lys Cys Asn
    1010                 1015                 1020

Ser Gly  Arg Cys Ile Pro Glu  His Trp Thr Cys Asp  Gly Asp Asn
    1025                 1030                 1035

Asp Cys  Gly Asp Tyr Ser Asp  Glu Thr His Ala Asn  Cys Thr Asn
    1040                 1045                 1050

Gln Ala  Thr Arg Pro Pro Gly  Gly Cys His Thr Asp  Glu Phe Gln
    1055                 1060                 1065

Cys Arg  Leu Asp Gly Leu Cys  Ile Pro Leu Arg Trp  Arg Cys Asp
    1070                 1075                 1080

Gly Asp  Thr Asp Cys Met Asp  Ser Ser Asp Glu Lys  Ser Cys Glu
    1085                 1090                 1095

Gly Val  Thr His Val Cys Asp  Pro Ser Val Lys Phe  Gly Cys Lys
    1100                 1105                 1110

Asp Ser  Ala Arg Cys Ile Ser  Lys Ala Trp Val Cys  Asp Gly Asp
    1115                 1120                 1125

Asn Asp  Cys Glu Asp Asn Ser  Asp Glu Glu Asn Cys  Glu Ser Leu
    1130                 1135                 1140

Ala Cys  Arg Pro Pro Ser His  Pro Cys Ala Asn Asn  Thr Ser Val
    1145                 1150                 1155

Cys Leu  Pro Pro Asp Lys Leu  Cys Asp Gly Asn Asp  Asp Cys Gly
    1160                 1165                 1170

Asp Gly  Ser Asp Glu Gly Glu  Leu Cys Asp Gln Cys  Ser Leu Asn
    1175                 1180                 1185

Asn Gly  Gly Cys Ser His Asn  Cys Ser Val Ala Pro  Gly Glu Gly
    1190                 1195                 1200
```

```
Ile Val  Cys Ser Cys Pro Leu  Gly Met Glu Leu Gly  Pro Asp Asn
    1205                 1210                 1215

His Thr  Cys Gln Ile Gln Ser  Tyr Cys Ala Lys His  Leu Lys Cys
    1220                 1225                 1230

Ser Gln  Lys Cys Asp Gln Asn  Lys Phe Ser Val Lys  Cys Ser Cys
    1235                 1240                 1245

Tyr Glu  Gly Trp Val Leu Glu  Pro Asp Gly Glu Ser  Cys Arg Ser
    1250                 1255                 1260

Leu Asp  Pro Phe Lys Pro Phe  Ile Ile Phe Ser Asn  Arg His Glu
    1265                 1270                 1275

Ile Arg  Arg Ile Asp Leu His  Lys Gly Asp Tyr Ser  Val Leu Val
    1280                 1285                 1290

Pro Gly  Leu Arg Asn Thr Ile  Ala Leu Asp Phe His  Leu Ser Gln
    1295                 1300                 1305

Ser Ala  Leu Tyr Trp Thr Asp  Val Val Glu Asp Lys  Ile Tyr Arg
    1310                 1315                 1320

Gly Lys  Leu Leu Asp Asn Gly  Ala Leu Thr Ser Phe  Glu Val Val
    1325                 1330                 1335

Ile Gln  Tyr Gly Leu Ala Thr  Pro Glu Gly Leu Ala  Val Asp Trp
    1340                 1345                 1350

Ile Ala  Gly Asn Ile Tyr Trp  Val Glu Ser Asn Leu  Asp Gln Ile
    1355                 1360                 1365

Glu Val  Ala Lys Leu Asp Gly  Thr Leu Arg Thr Thr  Leu Leu Ala
    1370                 1375                 1380

Gly Asp  Ile Glu His Pro Arg  Ala Ile Ala Leu Asp  Pro Arg Asp
    1385                 1390                 1395

Gly Ile  Leu Phe Trp Thr Asp  Trp Asp Ala Ser Leu  Pro Arg Ile
    1400                 1405                 1410

Glu Ala  Ala Ser Met Ser Gly  Ala Gly Arg Arg Thr  Val His Arg
    1415                 1420                 1425

Glu Thr  Gly Ser Gly Gly Trp  Pro Asn Gly Leu Thr  Val Asp Tyr
    1430                 1435                 1440

Leu Glu  Lys Arg Ile Leu Trp  Ile Asp Ala Arg Ser  Asp Ala Ile
    1445                 1450                 1455

Tyr Ser  Ala Arg Tyr Asp Gly  Ser Gly His Met Glu  Val Leu Arg
    1460                 1465                 1470

Gly His  Glu Phe Leu Ser His  Pro Phe Ala Val Thr  Leu Tyr Gly
    1475                 1480                 1485

Gly Glu  Val Tyr Trp Thr Asp  Trp Arg Thr Asn Thr  Leu Ala Lys
    1490                 1495                 1500

Ala Asn  Lys Trp Thr Gly His  Asn Val Thr Val Val  Gln Arg Thr
    1505                 1510                 1515

Asn Thr  Gln Pro Phe Asp Leu  Gln Val Tyr His Pro  Ser Arg Gln
    1520                 1525                 1530

Pro Met  Ala Pro Asn Pro Cys  Glu Ala Asn Gly Gly  Gln Gly Pro
    1535                 1540                 1545

Cys Ser  His Leu Cys Leu Ile  Asn Tyr Asn Arg Thr  Val Ser Cys
    1550                 1555                 1560

Ala Cys  Pro His Leu Met Lys  Leu His Lys Asp Asn  Thr Thr Cys
    1565                 1570                 1575

Tyr Glu  Phe Lys Lys Phe Leu  Leu Tyr Ala Arg Gln  Met Glu Ile
    1580                 1585                 1590
```

-continued

```
Arg Gly Val Asp Leu Asp Ala Pro Tyr Tyr Asn Tyr Ile Ile Ser
    1595                1600                1605

Phe Thr Val Pro Asp Ile Asp Asn Val Thr Val Leu Asp Tyr Asp
    1610                1615                1620

Ala Arg Glu Gln Arg Val Tyr Trp Ser Asp Val Arg Thr Gln Ala
    1625                1630                1635

Ile Lys Arg Ala Phe Ile Asn Gly Thr Gly Val Glu Thr Val Val
    1640                1645                1650

Ser Ala Asp Leu Pro Asn Ala His Gly Leu Ala Val Asp Trp Val
    1655                1660                1665

Ser Arg Asn Leu Phe Trp Thr Ser Tyr Asp Thr Asn Lys Lys Gln
    1670                1675                1680

Ile Asn Val Ala Arg Leu Asp Gly Ser Phe Lys Asn Ala Val Val
    1685                1690                1695

Gln Gly Leu Glu Gln Pro His Gly Leu Val Val His Pro Leu Arg
    1700                1705                1710

Gly Lys Leu Tyr Trp Thr Asp Gly Asp Asn Ile Ser Met Ala Asn
    1715                1720                1725

Met Asp Gly Ser Asn Arg Thr Leu Leu Phe Ser Gly Gln Lys Gly
    1730                1735                1740

Pro Val Gly Leu Ala Ile Asp Phe Pro Glu Ser Lys Leu Tyr Trp
    1745                1750                1755

Ile Ser Ser Gly Asn His Thr Ile Asn Arg Cys Asn Leu Asp Gly
    1760                1765                1770

Ser Gly Leu Glu Val Ile Asp Ala Met Arg Ser Gln Leu Gly Lys
    1775                1780                1785

Ala Thr Ala Leu Ala Ile Met Gly Asp Lys Leu Trp Trp Ala Asp
    1790                1795                1800

Gln Val Ser Glu Lys Met Gly Thr Cys Ser Lys Ala Asp Gly Ser
    1805                1810                1815

Gly Ser Val Val Leu Arg Asn Ser Thr Thr Leu Val Met His Met
    1820                1825                1830

Lys Val Tyr Asp Glu Ser Ile Gln Leu Asp His Lys Gly Thr Asn
    1835                1840                1845

Pro Cys Ser Val Asn Asn Gly Asp Cys Ser Gln Leu Cys Leu Pro
    1850                1855                1860

Thr Ser Glu Thr Thr Arg Ser Cys Met Cys Thr Ala Gly Tyr Ser
    1865                1870                1875

Leu Arg Ser Gly Gln Gln Ala Cys Glu Gly Val Gly Ser Phe Leu
    1880                1885                1890

Leu Tyr Ser Val His Glu Gly Ile Arg Gly Ile Pro Leu Asp Pro
    1895                1900                1905

Asn Asp Lys Ser Asp Ala Leu Val Pro Val Ser Gly Thr Ser Leu
    1910                1915                1920

Ala Val Gly Ile Asp Phe His Ala Glu Asn Asp Thr Ile Tyr Trp
    1925                1930                1935

Val Asp Met Gly Leu Ser Thr Ile Ser Arg Ala Lys Arg Asp Gln
    1940                1945                1950

Thr Trp Arg Glu Asp Val Val Thr Asn Gly Ile Gly Arg Val Glu
    1955                1960                1965

Gly Ile Ala Val Asp Trp Ile Ala Gly Asn Ile Tyr Trp Thr Asp
    1970                1975                1980

Gln Gly Phe Asp Val Ile Glu Val Ala Arg Leu Asn Gly Ser Phe
```

-continued

```
    1985                1990                1995

Arg Tyr  Val Val Ile Ser Gln  Gly Leu Asp Lys Pro  Arg Ala Ile
    2000                2005                2010

Thr Val  His Pro Glu Lys Gly  Tyr Leu Phe Trp Thr  Glu Trp Gly
    2015                2020                2025

Gln Tyr  Pro Arg Ile Glu Arg  Ser Arg Leu Asp Gly  Thr Glu Arg
    2030                2035                2040

Val Val  Leu Val Asn Val Ser  Ile Ser Trp Pro Asn  Gly Ile Ser
    2045                2050                2055

Val Asp  Tyr Gln Asp Gly Lys  Leu Tyr Trp Cys Asp  Ala Arg Thr
    2060                2065                2070

Asp Lys  Ile Glu Arg Ile Asp  Leu Glu Thr Gly Glu  Asn Arg Glu
    2075                2080                2085

Val Val  Leu Ser Ser Asn Asn  Met Asp Met Phe Ser  Val Ser Val
    2090                2095                2100

Phe Glu  Asp Phe Ile Tyr Trp  Ser Asp Arg Thr His  Ala Asn Gly
    2105                2110                2115

Ser Ile  Lys Arg Gly Ser Lys  Asp Asn Ala Thr Asp  Ser Val Pro
    2120                2125                2130

Leu Arg  Thr Gly Ile Gly Val  Gln Leu Lys Asp Ile  Lys Val Phe
    2135                2140                2145

Asn Arg  Asp Arg Gln Lys Gly  Thr Asn Val Cys Ala  Val Ala Asn
    2150                2155                2160

Gly Gly  Cys Gln Gln Leu Cys  Leu Tyr Arg Gly Arg  Gly Gln Arg
    2165                2170                2175

Ala Cys  Ala Cys Ala His Gly  Met Leu Ala Glu Asp  Gly Ala Ser
    2180                2185                2190

Cys Arg  Glu Tyr Ala Gly Tyr  Leu Leu Tyr Ser Glu  Arg Thr Ile
    2195                2200                2205

Leu Lys  Ser Ile His Leu Ser  Asp Glu Arg Asn Leu  Asn Ala Pro
    2210                2215                2220

Val Gln  Pro Phe Glu Asp Pro  Glu His Met Lys Asn  Val Ile Ala
    2225                2230                2235

Leu Ala  Phe Asp Tyr Arg Ala  Gly Thr Ser Pro Gly  Thr Pro Asn
    2240                2245                2250

Arg Ile  Phe Phe Ser Asp Ile  His Phe Gly Asn Ile  Gln Gln Ile
    2255                2260                2265

Asn Asp  Asp Gly Ser Arg Arg  Ile Thr Ile Val Glu  Asn Val Gly
    2270                2275                2280

Ser Val  Glu Gly Leu Ala Tyr  His Arg Gly Trp Asp  Thr Leu Tyr
    2285                2290                2295

Trp Thr  Ser Tyr Thr Thr Ser  Thr Ile Thr Arg His  Thr Val Asp
    2300                2305                2310

Gln Thr  Arg Pro Gly Ala Phe  Glu Arg Glu Thr Val  Ile Thr Met
    2315                2320                2325

Ser Gly  Asp Asp His Pro Arg  Ala Phe Val Leu Asp  Glu Cys Gln
    2330                2335                2340

Asn Leu  Met Phe Trp Thr Asn  Trp Asn Glu Gln His  Pro Ser Ile
    2345                2350                2355

Met Arg  Ala Ala Leu Ser Gly  Ala Asn Val Leu Thr  Leu Ile Glu
    2360                2365                2370

Lys Asp  Ile Arg Thr Pro Asn  Gly Leu Ala Ile Asp  His Arg Ala
    2375                2380                2385
```

-continued

```
Glu Lys  Leu Tyr Phe Ser Asp  Ala Thr Leu Asp Lys  Ile Glu Arg
    2390                 2395                 2400

Cys Glu  Tyr Asp Gly Ser His  Arg Tyr Val Ile Leu  Lys Ser Glu
    2405                 2410                 2415

Pro Val  His Pro Phe Gly Leu  Ala Val Tyr Gly Glu  His Ile Phe
    2420                 2425                 2430

Trp Thr  Asp Trp Val Arg Arg  Ala Val Gln Arg Ala  Asn Lys His
    2435                 2440                 2445

Val Gly  Ser Asn Met Lys Leu  Leu Arg Val Asp Ile  Pro Gln Gln
    2450                 2455                 2460

Pro Met  Gly Ile Ile Ala Val  Ala Asn Asp Thr Asn  Ser Cys Glu
    2465                 2470                 2475

Leu Ser  Pro Cys Arg Ile Asn  Asn Gly Gly Cys Gln  Asp Leu Cys
    2480                 2485                 2490

Leu Leu  Thr His Gln Gly His  Val Asn Cys Ser Cys  Arg Gly Gly
    2495                 2500                 2505

Arg Ile  Leu Gln Asp Asp Leu  Thr Cys Arg Ala Val  Asn Ser Ser
    2510                 2515                 2520

Cys Arg  Ala Gln Asp Glu Phe  Glu Cys Ala Asn Gly  Glu Cys Ile
    2525                 2530                 2535

Asn Phe  Ser Leu Thr Cys Asp  Gly Val Pro His Cys  Lys Asp Lys
    2540                 2545                 2550

Ser Asp  Glu Lys Pro Ser Tyr  Cys Asn Ser Arg Arg  Cys Lys Lys
    2555                 2560                 2565

Thr Phe  Arg Gln Cys Ser Asn  Gly Arg Cys Val Ser  Asn Met Leu
    2570                 2575                 2580

Trp Cys  Asn Gly Ala Asp Asp  Cys Gly Asp Gly Ser  Asp Glu Ile
    2585                 2590                 2595

Pro Cys  Asn Lys Thr Ala Cys  Gly Val Gly Glu Phe  Arg Cys Arg
    2600                 2605                 2610

Asp Gly  Thr Cys Ile Gly Asn  Ser Ser Arg Cys Asn  Gln Phe Val
    2615                 2620                 2625

Asp Cys  Glu Asp Ala Ser Asp  Glu Met Asn Cys Ser  Ala Thr Asp
    2630                 2635                 2640

Cys Ser  Ser Tyr Phe Arg Leu  Gly Val Lys Gly Val  Leu Phe Gln
    2645                 2650                 2655

Pro Cys  Glu Arg Thr Ser Leu  Cys Tyr Ala Pro Ser  Trp Val Cys
    2660                 2665                 2670

Asp Gly  Ala Asn Asp Cys Gly  Asp Tyr Ser Asp Glu  Arg Asp Cys
    2675                 2680                 2685

Pro Gly  Val Lys Arg Pro Arg  Cys Pro Leu Asn Tyr  Phe Ala Cys
    2690                 2695                 2700

Pro Ser  Gly Arg Cys Ile Pro  Met Ser Trp Thr Cys  Asp Lys Glu
    2705                 2710                 2715

Asp Asp  Cys Glu His Gly Glu  Asp Glu Thr His Cys  Asn Lys Phe
    2720                 2725                 2730

Cys Ser  Glu Ala Gln Phe Glu  Cys Gln Asn His Arg  Cys Ile Ser
    2735                 2740                 2745

Lys Gln  Trp Leu Cys Asp Gly  Ser Asp Asp Cys Gly  Asp Gly Ser
    2750                 2755                 2760

Asp Glu  Ala Ala His Cys Glu  Gly Lys Thr Cys Gly  Pro Ser Ser
    2765                 2770                 2775
```

-continued

```
Phe Ser  Cys Pro Gly Thr His  Val Cys Val Pro Glu  Arg Trp Leu
    2780                 2785                 2790

Cys Asp  Gly Asp Lys Asp Cys  Ala Asp Gly Ala Asp  Glu Ser Ile
    2795                 2800                 2805

Ala Ala  Gly Cys Leu Tyr Asn  Ser Thr Cys Asp Asp  Arg Glu Phe
    2810                 2815                 2820

Met Cys  Gln Asn Arg Gln Cys  Ile Pro Lys His Phe  Val Cys Asp
    2825                 2830                 2835

His Asp  Arg Asp Cys Ala Asp  Gly Ser Asp Glu Ser  Pro Glu Cys
    2840                 2845                 2850

Glu Tyr  Pro Thr Cys Gly Pro  Ser Glu Phe Arg Cys  Ala Asn Gly
    2855                 2860                 2865

Arg Cys  Leu Ser Ser Arg Gln  Trp Glu Cys Asp Gly  Glu Asn Asp
    2870                 2875                 2880

Cys His  Asp Gln Ser Asp Glu  Ala Pro Lys Asn Pro  His Cys Thr
    2885                 2890                 2895

Ser Gln  Glu His Lys Cys Asn  Ala Ser Ser Gln Phe  Leu Cys Ser
    2900                 2905                 2910

Ser Gly  Arg Cys Val Ala Glu  Ala Leu Leu Cys Asn  Gly Gln Asp
    2915                 2920                 2925

Asp Cys  Gly Asp Ser Ser Asp  Glu Arg Gly Cys His  Ile Asn Glu
    2930                 2935                 2940

Cys Leu  Ser Arg Lys Leu Ser  Gly Cys Ser Gln Asp  Cys Glu Asp
    2945                 2950                 2955

Leu Lys  Ile Gly Phe Lys Cys  Arg Cys Arg Pro Gly  Phe Arg Leu
    2960                 2965                 2970

Lys Asp  Asp Gly Arg Thr Cys  Ala Asp Val Asp Glu  Cys Ser Thr
    2975                 2980                 2985

Thr Phe  Pro Cys Ser Gln Arg  Cys Ile Asn Thr His  Gly Ser Tyr
    2990                 2995                 3000

Lys Cys  Leu Cys Val Glu Gly  Tyr Ala Pro Arg Gly  Gly Asp Pro
    3005                 3010                 3015

His Ser  Cys Lys Ala Val Thr  Asp Glu Glu Pro Phe  Leu Ile Phe
    3020                 3025                 3030

Ala Asn  Arg Tyr Tyr Leu Arg  Lys Leu Asn Leu Asp  Gly Ser Asn
    3035                 3040                 3045

Tyr Thr  Leu Leu Lys Gln Gly  Leu Asn Asn Ala Val  Ala Leu Asp
    3050                 3055                 3060

Phe Asp  Tyr Arg Glu Gln Met  Ile Tyr Trp Thr Asp  Val Thr Thr
    3065                 3070                 3075

Gln Gly  Ser Met Ile Arg Arg  Met His Leu Asn Gly  Ser Asn Val
    3080                 3085                 3090

Gln Val  Leu His Arg Thr Gly  Leu Ser Asn Pro Asp  Gly Leu Ala
    3095                 3100                 3105

Val Asp  Trp Val Gly Gly Asn  Leu Tyr Trp Cys Asp  Lys Gly Arg
    3110                 3115                 3120

Asp Thr  Ile Glu Val Ser Lys  Leu Asn Gly Ala Tyr  Arg Thr Val
    3125                 3130                 3135

Leu Val  Ser Ser Gly Leu Arg  Glu Pro Arg Ala Leu  Val Val Asp
    3140                 3145                 3150

Val Gln  Asn Gly Tyr Leu Tyr  Trp Thr Asp Trp Gly  Asp His Ser
    3155                 3160                 3165

Leu Ile  Gly Arg Ile Gly Met  Asp Gly Ser Ser Arg  Ser Val Ile
```

-continued

```
    3170                3175                3180

Val Asp  Thr Lys Ile Thr Trp  Pro Asn Gly Leu Thr  Leu Asp Tyr
    3185                3190                3195

Val Thr  Glu Arg Ile Tyr Trp  Ala Asp Ala Arg Glu  Asp Tyr Ile
    3200                3205                3210

Glu Phe  Ala Ser Leu Asp Gly  Ser Asn Arg His Val  Val Leu Ser
    3215                3220                3225

Gln Asp  Ile Pro His Ile Phe  Ala Leu Thr Leu Phe  Glu Asp Tyr
    3230                3235                3240

Val Tyr  Trp Thr Asp Trp Glu  Thr Lys Ser Ile Asn  Arg Ala His
    3245                3250                3255

Lys Thr  Thr Gly Thr Asn Lys  Thr Leu Leu Ile Ser  Thr Leu His
    3260                3265                3270

Arg Pro  Met Asp Leu His Val  Phe His Ala Leu Arg  Gln Pro Asp
    3275                3280                3285

Val Pro  Asn His Pro Cys Lys  Val Asn Asn Gly Gly  Cys Ser Asn
    3290                3295                3300

Leu Cys  Leu Leu Ser Pro Gly  Gly Gly His Lys Cys  Ala Cys Pro
    3305                3310                3315

Thr Asn  Phe Tyr Leu Gly Ser  Asp Gly Arg Thr Cys  Val Ser Asn
    3320                3325                3330

Cys Thr  Ala Ser Gln Phe Val  Cys Lys Asn Asp Lys  Cys Ile Pro
    3335                3340                3345

Phe Trp  Trp Lys Cys Asp Thr  Glu Asp Asp Cys Gly  Asp His Ser
    3350                3355                3360

Asp Glu  Pro Pro Asp Cys Pro  Glu Phe Lys Cys Arg  Pro Gly Gln
    3365                3370                3375

Phe Gln  Cys Ser Thr Gly Ile  Cys Thr Asn Pro Ala  Phe Ile Cys
    3380                3385                3390

Asp Gly  Asp Asn Asp Cys Gln  Asp Asn Ser Asp Glu  Ala Asn Cys
    3395                3400                3405

Asp Ile  His Val Cys Leu Pro  Ser Gln Phe Lys Cys  Thr Asn Thr
    3410                3415                3420

Asn Arg  Cys Ile Pro Gly Ile  Phe Arg Cys Asn Gly  Gln Asp Asn
    3425                3430                3435

Cys Gly  Asp Gly Glu Asp Glu  Arg Asp Cys Pro Glu  Val Thr Cys
    3440                3445                3450

Ala Pro  Asn Gln Phe Gln Cys  Ser Ile Thr Lys Arg  Cys Ile Pro
    3455                3460                3465

Arg Val  Trp Val Cys Asp Arg  Asp Asn Asp Cys Val  Asp Gly Ser
    3470                3475                3480

Asp Glu  Pro Ala Asn Cys Thr  Gln Met Thr Cys Gly  Val Asp Glu
    3485                3490                3495

Phe Arg  Cys Lys Asp Ser Gly  Arg Cys Ile Pro Ala  Arg Trp Lys
    3500                3505                3510

Cys Asp  Gly Glu Asp Asp Cys  Gly Asp Gly Ser Asp  Glu Pro Lys
    3515                3520                3525

Glu Glu  Cys Asp Glu Arg Thr  Cys Glu Pro Tyr Gln  Phe Arg Cys
    3530                3535                3540

Lys Asn  Asn Arg Cys Val Pro  Gly Arg Trp Gln Cys  Asp Tyr Asp
    3545                3550                3555

Asn Asp  Cys Gly Asp Asn Ser  Asp Glu Glu Ser Cys  Thr Pro Arg
    3560                3565                3570
```

-continued

```
Pro Cys Ser Glu Ser Glu Phe Ser Cys Ala Asn Gly Arg Cys Ile
    3575                3580                3585

Ala Gly Arg Trp Lys Cys Asp Gly Asp His Asp Cys Ala Asp Gly
    3590                3595                3600

Ser Asp Glu Lys Asp Cys Thr Pro Arg Cys Asp Met Asp Gln Phe
    3605                3610                3615

Gln Cys Lys Ser Gly His Cys Ile Pro Leu Arg Trp Arg Cys Asp
    3620                3625                3630

Ala Asp Ala Asp Cys Met Asp Gly Ser Asp Glu Glu Ala Cys Gly
    3635                3640                3645

Thr Gly Val Arg Thr Cys Pro Leu Asp Glu Phe Gln Cys Asn Asn
    3650                3655                3660

Thr Leu Cys Lys Pro Leu Ala Trp Lys Cys Asp Gly Glu Asp Asp
    3665                3670                3675

Cys Gly Asp Asn Ser Asp Glu Asn Pro Glu Glu Cys Ala Arg Phe
    3680                3685                3690

Val Cys Pro Pro Asn Arg Pro Phe Arg Cys Lys Asn Asp Arg Val
    3695                3700                3705

Cys Leu Trp Ile Gly Arg Gln Cys Asp Gly Thr Asp Asn Cys Gly
    3710                3715                3720

Asp Gly Thr Asp Glu Glu Asp Cys Glu Pro Pro Thr Ala His Thr
    3725                3730                3735

Thr His Cys Lys Asp Lys Lys Glu Phe Leu Cys Arg Asn Gln Arg
    3740                3745                3750

Cys Leu Ser Ser Ser Leu Arg Cys Asn Met Phe Asp Asp Cys Gly
    3755                3760                3765

Asp Gly Ser Asp Glu Glu Asp Cys Ser Ile Asp Pro Lys Leu Thr
    3770                3775                3780

Ser Cys Ala Thr Asn Ala Ser Ile Cys Gly Asp Glu Ala Arg Cys
    3785                3790                3795

Val Arg Thr Glu Lys Ala Ala Tyr Cys Ala Cys Arg Ser Gly Phe
    3800                3805                3810

His Thr Val Pro Gly Gln Pro Gly Cys Gln Asp Ile Asn Glu Cys
    3815                3820                3825

Leu Arg Phe Gly Thr Cys Ser Gln Leu Cys Asn Asn Thr Lys Gly
    3830                3835                3840

Gly His Leu Cys Ser Cys Ala Arg Asn Phe Met Lys Thr His Asn
    3845                3850                3855

Thr Cys Lys Ala Glu Gly Ser Glu Tyr Gln Val Leu Tyr Ile Ala
    3860                3865                3870

Asp Asp Asn Glu Ile Arg Ser Leu Phe Pro Gly His Pro His Ser
    3875                3880                3885

Ala Tyr Glu Gln Ala Phe Gln Gly Asp Glu Ser Val Arg Ile Asp
    3890                3895                3900

Ala Met Asp Val His Val Lys Ala Gly Arg Val Tyr Trp Thr Asn
    3905                3910                3915

Trp His Thr Gly Thr Ile Ser Tyr Arg Ser Leu Pro Pro Ala Ala
    3920                3925                3930

Pro Pro Thr Thr Ser Asn Arg His Arg Arg Gln Ile Asp Arg Gly
    3935                3940                3945

Val Thr His Leu Asn Ile Ser Gly Leu Lys Met Pro Arg Gly Ile
    3950                3955                3960
```

```
Ala Ile  Asp Trp Val Ala Gly  Asn Val Tyr Trp Thr  Asp Ser Gly
    3965                 3970                 3975

Arg Asp  Val Ile Glu Val Ala  Gln Met Lys Gly Glu  Asn Arg Lys
    3980                 3985                 3990

Thr Leu  Ile Ser Gly Met Ile  Asp Glu Pro His Ala  Ile Val Val
    3995                 4000                 4005

Asp Pro  Leu Arg Gly Thr Met  Tyr Trp Ser Asp Trp  Gly Asn His
    4010                 4015                 4020

Pro Lys  Ile Glu Thr Ala Ala  Met Asp Gly Thr Leu  Arg Glu Thr
    4025                 4030                 4035

Leu Val  Gln Asp Asn Ile Gln  Trp Pro Thr Gly Leu  Ala Val Asp
    4040                 4045                 4050

Tyr His  Asn Glu Arg Leu Tyr  Trp Ala Asp Ala Lys  Leu Ser Val
    4055                 4060                 4065

Ile Gly  Ser Ile Arg Leu Asn  Gly Thr Asp Pro Ile  Val Ala Ala
    4070                 4075                 4080

Asp Ser  Lys Arg Gly Leu Ser  His Pro Phe Ser Ile  Asp Val Phe
    4085                 4090                 4095

Glu Asp  Tyr Ile Tyr Gly Val  Thr Tyr Ile Asn Asn  Arg Val Phe
    4100                 4105                 4110

Lys Ile  His Lys Phe Gly His  Ser Pro Leu Val Asn  Leu Thr Gly
    4115                 4120                 4125

Gly Leu  Ser His Ala Ser Asp  Val Val Leu Tyr His  Gln His Lys
    4130                 4135                 4140

Gln Pro  Glu Val Thr Asn Pro  Cys Asp Arg Lys Lys  Cys Glu Trp
    4145                 4150                 4155

Leu Cys  Leu Leu Ser Pro Ser  Gly Pro Val Cys Thr  Cys Pro Asn
    4160                 4165                 4170

Gly Lys  Arg Leu Asp Asn Gly  Thr Cys Val Pro Val  Pro Ser Pro
    4175                 4180                 4185

Thr Pro  Pro Pro Asp Ala Pro  Arg Pro Gly Thr Cys  Asn Leu Gln
    4190                 4195                 4200

Cys Phe  Asn Gly Gly Ser Cys  Phe Leu Asn Ala Arg  Arg Gln Pro
    4205                 4210                 4215

Lys Cys  Arg Cys Gln Pro Arg  Tyr Thr Gly Asp Lys  Cys Glu Leu
    4220                 4225                 4230

Asp Gln  Cys Trp Glu His Cys  Arg Asn Gly Gly Thr  Cys Ala Ala
    4235                 4240                 4245

Ser Pro  Ser Gly Met Pro Thr  Cys Arg Cys Pro Thr  Gly Phe Thr
    4250                 4255                 4260

Gly Pro  Lys Cys Thr Gln Gln  Val Cys Ala Gly Tyr  Cys Ala Asn
    4265                 4270                 4275

Asn Ser  Thr Cys Thr Val Asn  Gln Gly Asn Gln Pro  Gln Cys Arg
    4280                 4285                 4290

Cys Leu  Pro Gly Phe Leu Gly  Asp Arg Cys Gln Tyr  Arg Gln Cys
    4295                 4300                 4305

Ser Gly  Tyr Cys Glu Asn Phe  Gly Thr Cys Gln Met  Ala Ala Asp
    4310                 4315                 4320

Gly Ser  Arg Gln Cys Arg Cys  Thr Ala Tyr Phe Glu  Gly Ser Arg
    4325                 4330                 4335

Cys Glu  Val Asn Lys Cys Ser  Arg Cys Leu Glu Gly  Ala Cys Val
    4340                 4345                 4350

Val Asn  Lys Gln Ser Gly Asp  Val Thr Cys Asn Cys  Thr Asp Gly
```

```
    4355                4360                4365

Arg Val  Ala Pro Ser Cys Leu  Thr Cys Val Gly His  Cys Ser Asn
    4370                4375                4380

Gly Gly  Ser Cys Thr Met Asn  Ser Lys Met Met Pro  Glu Cys Gln
    4385                4390                4395

Cys Pro  Pro His Met Thr Gly  Pro Arg Cys Glu Glu  His Val Phe
    4400                4405                4410

Ser Gln  Gln Gln Pro Gly His  Ile Ala Ser Ile Leu  Ile Pro Leu
    4415                4420                4425

Leu Leu  Leu Leu Leu Leu Val  Leu Val Ala Gly Val  Val Phe Trp
    4430                4435                4440

Tyr Lys  Arg Arg Val Gln Gly  Ala Lys Gly Phe Gln  His Gln Arg
    4445                4450                4455

Met Thr  Asn Gly Ala Met Asn  Val Glu Ile Gly Asn  Pro Thr Tyr
    4460                4465                4470

Lys Met  Tyr Glu Gly Gly Glu  Pro Asp Asp Val Gly  Gly Leu Leu
    4475                4480                4485

Asp Ala  Asp Phe Ala Leu Asp  Pro Asp Lys Pro Thr  Asn Phe Thr
    4490                4495                4500

Asn Pro  Val Tyr Ala Thr Leu  Tyr Met Gly Gly His  Gly Ser Arg
    4505                4510                4515

His Ser  Leu Ala Ser Thr Asp  Glu Lys Arg Glu Leu  Leu Gly Arg
    4520                4525                4530

Gly Pro  Glu Asp Glu Ile Gly  Asp Pro Leu Ala
    4535                4540


<210> SEQ ID NO 2
<211> LENGTH: 4545
<212> TYPE: PRT
<213> ORGANISM: Mus musculus

<400> SEQUENCE: 2

Met Leu Thr Pro Pro Leu Leu Leu Leu Leu Pro Leu Leu Ser Ala Leu
1               5                   10                  15

Val Ser Gly Ala Thr Met Asp Ala Pro Lys Thr Cys Ser Pro Lys Gln
            20                  25                  30

Phe Ala Cys Arg Asp Gln Ile Thr Cys Ile Ser Lys Gly Trp Arg Cys
        35                  40                  45

Asp Gly Glu Arg Asp Cys Pro Asp Gly Ser Asp Glu Ala Pro Glu Ile
    50                  55                  60

Cys Pro Gln Ser Lys Ala Gln Arg Cys Pro Pro Asn Glu His Ser Cys
65                  70                  75                  80

Leu Gly Thr Glu Leu Cys Val Pro Met Ser Arg Leu Cys Asn Gly Ile
                85                  90                  95

Gln Asp Cys Met Asp Gly Ser Asp Glu Gly Ala His Cys Arg Glu Leu
            100                 105                 110

Arg Ala Asn Cys Ser Arg Met Gly Cys Gln His His Cys Val Pro Thr
        115                 120                 125

Pro Ser Gly Pro Thr Cys Tyr Cys Asn Ser Ser Phe Gln Leu Gln Ala
    130                 135                 140

Asp Gly Lys Thr Cys Lys Asp Phe Asp Glu Cys Ser Val Tyr Gly Thr
145                 150                 155                 160

Cys Ser Gln Leu Cys Thr Asn Thr Asp Gly Ser Phe Thr Cys Gly Cys
                165                 170                 175
```

```
Val Glu Gly Tyr Leu Leu Gln Pro Asp Asn Arg Ser Cys Lys Ala Lys
            180                 185                 190

Asn Glu Pro Val Asp Arg Pro Pro Val Leu Leu Ile Ala Asn Ser Gln
        195                 200                 205

Asn Ile Leu Ala Thr Tyr Leu Ser Gly Ala Gln Val Ser Thr Ile Thr
    210                 215                 220

Pro Thr Ser Thr Arg Gln Thr Thr Ala Met Asp Phe Ser Tyr Ala Asn
225                 230                 235                 240

Glu Thr Val Cys Trp Val His Val Gly Asp Ser Ala Ala Gln Thr Gln
                245                 250                 255

Leu Lys Cys Ala Arg Met Pro Gly Leu Lys Gly Phe Val Asp Glu His
            260                 265                 270

Thr Ile Asn Ile Ser Leu Ser Leu His His Val Glu Gln Met Ala Ile
        275                 280                 285

Asp Trp Leu Thr Gly Asn Phe Tyr Phe Val Asp Asp Ile Asp Asp Arg
    290                 295                 300

Ile Phe Val Cys Asn Arg Asn Gly Asp Thr Cys Val Thr Leu Leu Asp
305                 310                 315                 320

Leu Glu Leu Tyr Asn Pro Lys Gly Ile Ala Leu Asp Pro Ala Met Gly
                325                 330                 335

Lys Val Phe Phe Thr Asp Tyr Gly Gln Ile Pro Lys Val Glu Arg Cys
            340                 345                 350

Asp Met Asp Gly Gln Asn Arg Thr Lys Leu Val Asp Ser Lys Ile Val
        355                 360                 365

Phe Pro His Gly Ile Thr Leu Asp Leu Val Ser Arg Leu Val Tyr Trp
    370                 375                 380

Ala Asp Ala Tyr Leu Asp Tyr Ile Glu Val Val Asp Tyr Glu Gly Lys
385                 390                 395                 400

Gly Arg Gln Thr Ile Ile Gln Gly Ile Leu Ile Glu His Leu Tyr Gly
                405                 410                 415

Leu Thr Val Phe Glu Asn Tyr Leu Tyr Ala Thr Asn Ser Asp Asn Ala
            420                 425                 430

Asn Thr Gln Gln Lys Thr Ser Val Ile Arg Val Asn Arg Phe Asn Ser
        435                 440                 445

Thr Glu Tyr Gln Val Val Thr Arg Val Asp Lys Gly Gly Ala Leu His
    450                 455                 460

Ile Tyr His Gln Arg Arg Gln Pro Arg Val Arg Ser His Ala Cys Glu
465                 470                 475                 480

Asn Asp Gln Tyr Gly Lys Pro Gly Gly Cys Ser Asp Ile Cys Leu Leu
                485                 490                 495

Ala Asn Ser His Lys Ala Arg Thr Cys Arg Cys Arg Ser Gly Phe Ser
            500                 505                 510

Leu Gly Ser Asp Gly Lys Ser Cys Lys Lys Pro Glu His Glu Leu Phe
        515                 520                 525

Leu Val Tyr Gly Lys Gly Arg Pro Gly Ile Ile Arg Gly Met Asp Met
    530                 535                 540

Gly Ala Lys Val Pro Asp Glu His Met Ile Pro Ile Glu Asn Leu Met
545                 550                 555                 560

Asn Pro Arg Ala Leu Asp Phe His Ala Glu Thr Gly Phe Ile Tyr Phe
                565                 570                 575

Ala Asp Thr Thr Ser Tyr Leu Ile Gly Arg Gln Lys Ile Asp Gly Thr
            580                 585                 590

Glu Arg Glu Thr Ile Leu Lys Asp Gly Ile His Asn Val Glu Gly Val
```

```
        595                 600                 605

Ala Val Asp Trp Met Gly Asp Asn Leu Tyr Trp Thr Asp Asp Gly Pro
    610                 615                 620

Lys Lys Thr Ile Ser Val Ala Arg Leu Glu Lys Ala Ala Gln Thr Arg
625                 630                 635                 640

Lys Thr Leu Ile Glu Gly Lys Met Thr His Pro Arg Ala Ile Val Val
                645                 650                 655

Asp Pro Leu Asn Gly Trp Met Tyr Trp Thr Asp Trp Glu Glu Asp Pro
            660                 665                 670

Lys Asp Ser Arg Arg Gly Arg Leu Glu Arg Ala Trp Met Asp Gly Ser
        675                 680                 685

His Arg Asp Ile Phe Val Thr Ser Lys Thr Val Leu Trp Pro Asn Gly
    690                 695                 700

Leu Ser Leu Asp Ile Pro Ala Gly Arg Leu Tyr Trp Val Asp Ala Phe
705                 710                 715                 720

Tyr Asp Arg Ile Glu Thr Ile Leu Leu Asn Gly Thr Asp Arg Lys Ile
                725                 730                 735

Val Tyr Glu Gly Pro Glu Leu Asn His Ala Phe Gly Leu Cys His His
            740                 745                 750

Gly Asn Tyr Leu Phe Trp Thr Glu Tyr Arg Ser Gly Ser Val Tyr Arg
        755                 760                 765

Leu Glu Arg Gly Val Ala Gly Ala Pro Pro Thr Val Thr Leu Leu Arg
    770                 775                 780

Ser Glu Arg Pro Pro Ile Phe Glu Ile Arg Met Tyr Asp Ala Gln Gln
785                 790                 795                 800

Gln Gln Val Gly Thr Asn Lys Cys Arg Val Asn Asn Gly Gly Cys Ser
                805                 810                 815

Ser Leu Cys Leu Ala Thr Pro Gly Ser Arg Gln Cys Ala Cys Ala Glu
            820                 825                 830

Asp Gln Val Leu Asp Thr Asp Gly Val Thr Cys Leu Ala Asn Pro Ser
        835                 840                 845

Tyr Val Pro Pro Pro Gln Cys Gln Pro Gly Glu Phe Ala Cys Ala Asn
    850                 855                 860

Asn Arg Cys Ile Gln Glu Arg Trp Lys Cys Asp Gly Asp Asn Asp Cys
865                 870                 875                 880

Leu Asp Asn Ser Asp Glu Ala Pro Ala Leu Cys His Gln His Thr Cys
                885                 890                 895

Pro Ser Asp Arg Phe Lys Cys Glu Asn Asn Arg Cys Ile Pro Asn Arg
            900                 905                 910

Trp Leu Cys Asp Gly Asp Asn Asp Cys Gly Asn Ser Glu Asp Glu Ser
        915                 920                 925

Asn Ala Thr Cys Ser Ala Arg Thr Cys Pro Pro Asn Gln Phe Ser Cys
    930                 935                 940

Ala Ser Gly Arg Cys Ile Pro Ile Ser Trp Thr Cys Asp Leu Asp Asp
945                 950                 955                 960

Asp Cys Gly Asp Arg Ser Asp Glu Ser Ala Ser Cys Ala Tyr Pro Thr
                965                 970                 975

Cys Phe Pro Leu Thr Gln Phe Thr Cys Asn Asn Gly Arg Cys Ile Asn
            980                 985                 990

Ile Asn Trp Arg Cys Asp Asn Asp  Asn Asp Cys Gly Asp  Asn Ser Asp
        995                 1000                1005

Glu Ala  Gly Cys Ser His Ser  Cys Ser Ser Thr Gln  Phe Lys Cys
    1010                1015                1020
```

```
Asn Ser  Gly Arg Cys Ile Pro  Glu His Trp Thr Cys  Asp Gly Asp
    1025                 1030                 1035

Asn Asp  Cys Gly Asp Tyr Ser  Asp Glu Thr His Ala  Asn Cys Thr
    1040                 1045                 1050

Asn Gln  Ala Thr Arg Pro Pro  Gly Gly Cys His Ser  Asp Glu Phe
    1055                 1060                 1065

Gln Cys  Arg Leu Asp Gly Leu  Cys Ile Pro Leu Arg  Trp Arg Cys
    1070                 1075                 1080

Asp Gly  Asp Thr Asp Cys Met  Asp Ser Ser Asp Glu  Lys Ser Cys
    1085                 1090                 1095

Glu Gly  Val Thr His Val Cys  Asp Pro Asn Val Lys  Phe Gly Cys
    1100                 1105                 1110

Lys Asp  Ser Ala Arg Cys Ile  Ser Lys Ala Trp Val  Cys Asp Gly
    1115                 1120                 1125

Asp Ser  Asp Cys Glu Asp Asn  Ser Asp Glu Glu Asn  Cys Glu Ala
    1130                 1135                 1140

Leu Ala  Cys Arg Pro Pro Ser  His Pro Cys Ala Asn  Asn Thr Ser
    1145                 1150                 1155

Val Cys  Leu Pro Pro Asp Lys  Leu Cys Asp Gly Lys  Asp Asp Cys
    1160                 1165                 1170

Gly Asp  Gly Ser Asp Glu Gly  Glu Leu Cys Asp Gln  Cys Ser Leu
    1175                 1180                 1185

Asn Asn  Gly Gly Cys Ser His  Asn Cys Ser Val Ala  Pro Gly Glu
    1190                 1195                 1200

Gly Ile  Val Cys Ser Cys Pro  Leu Gly Met Glu Leu  Gly Ser Asp
    1205                 1210                 1215

Asn His  Thr Cys Gln Ile Gln  Ser Tyr Cys Ala Lys  His Leu Lys
    1220                 1225                 1230

Cys Ser  Gln Lys Cys Asp Gln  Asn Lys Phe Ser Val  Lys Cys Ser
    1235                 1240                 1245

Cys Tyr  Glu Gly Trp Val Leu  Glu Pro Asp Gly Glu  Ser Cys Arg
    1250                 1255                 1260

Ser Leu  Asp Pro Phe Lys Pro  Phe Ile Ile Phe Ser  Asn Arg His
    1265                 1270                 1275

Glu Ile  Arg Arg Ile Asp Leu  His Lys Gly Asp Tyr  Ser Val Leu
    1280                 1285                 1290

Val Pro  Gly Leu Arg Asn Thr  Ile Ala Leu Asp Phe  His Leu Ser
    1295                 1300                 1305

Gln Ser  Ala Leu Tyr Trp Thr  Asp Val Val Glu Asp  Lys Ile Tyr
    1310                 1315                 1320

Arg Gly  Lys Leu Leu Asp Asn  Gly Ala Leu Thr Ser  Phe Glu Val
    1325                 1330                 1335

Val Ile  Gln Tyr Gly Leu Ala  Thr Pro Glu Gly Leu  Ala Val Asp
    1340                 1345                 1350

Trp Ile  Ala Gly Asn Ile Tyr  Trp Val Glu Ser Asn  Leu Asp Gln
    1355                 1360                 1365

Ile Glu  Val Ala Lys Leu Asp  Gly Thr Leu Arg Thr  Thr Leu Leu
    1370                 1375                 1380

Ala Gly  Asp Ile Glu His Pro  Arg Ala Ile Ala Leu  Asp Pro Arg
    1385                 1390                 1395

Asp Gly  Ile Leu Phe Trp Thr  Asp Trp Asp Ala Ser  Leu Pro Arg
    1400                 1405                 1410
```

-continued

```
Ile Glu  Ala Ala Ser Met Ser  Gly Ala Gly Arg Arg  Thr Ile His
    1415                 1420                 1425

Arg Glu  Thr Gly Ser Gly Gly  Trp Pro Asn Gly Leu  Thr Val Asp
    1430                 1435                 1440

Tyr Leu  Glu Lys Arg Ile Leu  Trp Ile Asp Ala Arg  Ser Asp Ala
    1445                 1450                 1455

Ile Tyr  Ser Ala Arg Tyr Asp  Gly Ser Gly His Met  Glu Val Leu
    1460                 1465                 1470

Arg Gly  His Glu Phe Leu Ser  His Pro Phe Ala Val  Thr Leu Tyr
    1475                 1480                 1485

Gly Gly  Glu Val Tyr Trp Thr  Asp Trp Arg Thr Asn  Thr Leu Ala
    1490                 1495                 1500

Lys Ala  Asn Lys Trp Thr Gly  His Asn Val Thr Val  Val Gln Arg
    1505                 1510                 1515

Thr Asn  Thr Gln Pro Phe Asp  Leu Gln Val Tyr His  Pro Ser Arg
    1520                 1525                 1530

Gln Pro  Met Ala Pro Asn Pro  Cys Glu Ala Asn Gly  Gly Arg Gly
    1535                 1540                 1545

Pro Cys  Ser His Leu Cys Leu  Ile Asn Tyr Asn Arg  Thr Val Ser
    1550                 1555                 1560

Cys Ala  Cys Pro His Leu Met  Lys Leu His Lys Asp  Asn Thr Thr
    1565                 1570                 1575

Cys Tyr  Glu Phe Lys Lys Phe  Leu Leu Tyr Ala Arg  Gln Met Glu
    1580                 1585                 1590

Ile Arg  Gly Val Asp Leu Asp  Ala Pro Tyr Tyr Asn  Tyr Ile Ile
    1595                 1600                 1605

Ser Phe  Thr Val Pro Asp Ile  Asp Asn Val Thr Val  Leu Asp Tyr
    1610                 1615                 1620

Asp Ala  Arg Glu Gln Arg Val  Tyr Trp Ser Asp Val  Arg Thr Gln
    1625                 1630                 1635

Ala Ile  Lys Arg Ala Phe Ile  Asn Gly Thr Gly Val  Glu Thr Val
    1640                 1645                 1650

Val Ser  Ala Asp Leu Pro Asn  Ala His Gly Leu Ala  Val Asp Trp
    1655                 1660                 1665

Val Ser  Arg Asn Leu Phe Trp  Thr Ser Tyr Asp Thr  Asn Lys Lys
    1670                 1675                 1680

Gln Ile  Asn Val Ala Arg Leu  Asp Gly Ser Phe Lys  Asn Ala Val
    1685                 1690                 1695

Val Gln  Gly Leu Glu Gln Pro  His Gly Leu Val Val  His Pro Leu
    1700                 1705                 1710

Arg Gly  Lys Leu Tyr Trp Thr  Asp Gly Asp Asn Ile  Ser Met Ala
    1715                 1720                 1725

Asn Met  Asp Gly Ser Asn His  Thr Leu Leu Phe Ser  Gly Gln Lys
    1730                 1735                 1740

Gly Pro  Val Gly Leu Ala Ile  Asp Phe Pro Glu Ser  Lys Leu Tyr
    1745                 1750                 1755

Trp Ile  Ser Ser Gly Asn His  Thr Ile Asn Arg Cys  Asn Leu Asp
    1760                 1765                 1770

Gly Ser  Glu Leu Glu Val Ile  Asp Thr Met Arg Ser  Gln Leu Gly
    1775                 1780                 1785

Lys Ala  Thr Ala Leu Ala Ile  Met Gly Asp Lys Leu  Trp Trp Ala
    1790                 1795                 1800

Asp Gln  Val Ser Glu Lys Met  Gly Thr Cys Asn Lys  Ala Asp Gly
```

```
    1805                1810                1815

Ser Gly  Ser Val Val Leu Arg  Asn Ser Thr Thr Leu  Val Met His
    1820                1825                1830

Met Lys  Val Tyr Asp Glu Ser  Ile Gln Leu Glu His  Glu Gly Thr
    1835                1840                1845

Asn Pro  Cys Ser Val Asn Asn  Gly Asp Cys Ser Gln  Leu Cys Leu
    1850                1855                1860

Pro Thr  Ser Glu Thr Thr Arg  Ser Cys Met Cys Thr  Ala Gly Tyr
    1865                1870                1875

Ser Leu  Arg Ser Gly Gln Gln  Ala Cys Glu Gly Val  Gly Ser Phe
    1880                1885                1890

Leu Leu  Tyr Ser Val His Glu  Gly Ile Arg Gly Ile  Pro Leu Asp
    1895                1900                1905

Pro Asn  Asp Lys Ser Asp Ala  Leu Val Pro Val Ser  Gly Thr Ser
    1910                1915                1920

Leu Ala  Val Gly Ile Asp Phe  His Ala Glu Asn Asp  Thr Ile Tyr
    1925                1930                1935

Trp Val  Asp Met Gly Leu Ser  Thr Ile Ser Arg Ala  Lys Arg Asp
    1940                1945                1950

Gln Thr  Trp Arg Glu Asp Val  Val Thr Asn Gly Ile  Gly Arg Val
    1955                1960                1965

Glu Gly  Ile Ala Val Asp Trp  Ile Ala Gly Asn Ile  Tyr Trp Thr
    1970                1975                1980

Asp Gln  Gly Phe Asp Val Ile  Glu Val Ala Arg Leu  Asn Gly Ser
    1985                1990                1995

Phe Arg  Tyr Val Val Ile Ser  Gln Gly Leu Asp Lys  Pro Arg Ala
    2000                2005                2010

Ile Thr  Val His Pro Glu Lys  Gly Tyr Leu Phe Trp  Thr Glu Trp
    2015                2020                2025

Gly His  Tyr Pro Arg Ile Glu  Arg Ser Arg Leu Asp  Gly Thr Glu
    2030                2035                2040

Arg Val  Val Leu Val Asn Val  Ser Ile Ser Trp Pro  Asn Gly Ile
    2045                2050                2055

Ser Val  Asp Tyr Gln Gly Gly  Lys Leu Tyr Trp Cys  Asp Ala Arg
    2060                2065                2070

Met Asp  Lys Ile Glu Arg Ile  Asp Leu Glu Thr Gly  Glu Asn Arg
    2075                2080                2085

Glu Val  Val Leu Ser Ser Asn  Asn Met Asp Met Phe  Ser Val Ser
    2090                2095                2100

Val Phe  Glu Asp Phe Ile Tyr  Trp Ser Asp Arg Thr  His Ala Asn
    2105                2110                2115

Gly Ser  Ile Lys Arg Gly Cys  Lys Asp Asn Ala Thr  Asp Ser Val
    2120                2125                2130

Pro Leu  Arg Thr Gly Ile Gly  Val Gln Leu Lys Asp  Ile Lys Val
    2135                2140                2145

Phe Asn  Arg Asp Arg Gln Lys  Gly Thr Asn Val Cys  Ala Val Ala
    2150                2155                2160

Asn Gly  Gly Cys Gln Gln Leu  Cys Leu Tyr Arg Gly  Gly Gly Gln
    2165                2170                2175

Arg Ala  Cys Ala Cys Ala His  Gly Met Leu Ala Glu  Asp Gly Ala
    2180                2185                2190

Ser Cys  Arg Glu Tyr Ala Gly  Tyr Leu Leu Tyr Ser  Glu Arg Thr
    2195                2200                2205
```

```
Ile Leu Lys Ser Ile His Leu Ser Asp Glu Arg Asn Leu Asn Ala
    2210                2215                2220

Pro Val Gln Pro Phe Glu Asp Pro Glu His Met Lys Asn Val Ile
    2225                2230                2235

Ala Leu Ala Phe Asp Tyr Arg Ala Gly Thr Ser Pro Gly Thr Pro
    2240                2245                2250

Asn Arg Ile Phe Phe Ser Asp Ile His Phe Gly Asn Ile Gln Gln
    2255                2260                2265

Ile Asn Asp Asp Gly Ser Gly Arg Thr Thr Ile Val Glu Asn Val
    2270                2275                2280

Gly Ser Val Glu Gly Leu Ala Tyr His Arg Gly Trp Asp Thr Leu
    2285                2290                2295

Tyr Trp Thr Ser Tyr Thr Thr Ser Thr Ile Thr Arg His Thr Val
    2300                2305                2310

Asp Gln Thr Arg Pro Gly Ala Phe Glu Arg Glu Thr Val Ile Thr
    2315                2320                2325

Met Ser Gly Asp Asp His Pro Arg Ala Phe Val Leu Asp Glu Cys
    2330                2335                2340

Gln Asn Leu Met Phe Trp Thr Asn Trp Asn Glu Leu His Pro Ser
    2345                2350                2355

Ile Met Arg Ala Ala Leu Ser Gly Ala Asn Val Leu Thr Leu Ile
    2360                2365                2370

Glu Lys Asp Ile Arg Thr Pro Asn Gly Leu Ala Ile Asp His Arg
    2375                2380                2385

Ala Glu Lys Leu Tyr Phe Ser Asp Ala Thr Leu Asp Lys Ile Glu
    2390                2395                2400

Arg Cys Glu Tyr Asp Gly Ser His Arg Tyr Val Ile Leu Lys Ser
    2405                2410                2415

Glu Pro Val His Pro Phe Gly Leu Ala Val Tyr Gly Glu His Ile
    2420                2425                2430

Phe Trp Thr Asp Trp Val Arg Arg Ala Val Gln Arg Ala Asn Lys
    2435                2440                2445

Tyr Val Gly Ser Asp Met Lys Leu Leu Arg Val Asp Ile Pro Gln
    2450                2455                2460

Gln Pro Met Gly Ile Ile Ala Val Ala Asn Asp Thr Asn Ser Cys
    2465                2470                2475

Glu Leu Ser Pro Cys Arg Ile Asn Asn Gly Gly Cys Gln Asp Leu
    2480                2485                2490

Cys Leu Leu Thr His Gln Gly His Val Asn Cys Ser Cys Arg Gly
    2495                2500                2505

Gly Arg Ile Leu Gln Glu Asp Phe Thr Cys Arg Ala Val Asn Ser
    2510                2515                2520

Ser Cys Arg Ala Gln Asp Glu Phe Glu Cys Ala Asn Gly Glu Cys
    2525                2530                2535

Ile Ser Phe Ser Leu Thr Cys Asp Gly Val Ser His Cys Lys Asp
    2540                2545                2550

Lys Ser Asp Glu Lys Pro Ser Tyr Cys Asn Ser Arg Arg Cys Lys
    2555                2560                2565

Lys Thr Phe Arg Gln Cys Asn Asn Gly Arg Cys Val Ser Asn Met
    2570                2575                2580

Leu Trp Cys Asn Gly Val Asp Asp Cys Gly Asp Gly Ser Asp Glu
    2585                2590                2595
```

```
Ile Pro Cys Asn Lys Thr Ala Cys Gly Val Gly Glu Phe Arg Cys
    2600                2605                2610

Arg Asp Gly Ser Cys Ile Gly Asn Ser Ser Arg Cys Asn Gln Phe
    2615                2620                2625

Val Asp Cys Glu Asp Ala Ser Asp Glu Met Asn Cys Ser Thr Thr
    2630                2635                2640

Asp Cys Ser Ser Tyr Phe Arg Leu Gly Val Lys Gly Val Leu Phe
    2645                2650                2655

Gln Pro Cys Glu Arg Thr Ser Leu Cys Tyr Ala Pro Ser Trp Val
    2660                2665                2670

Cys Asp Gly Ala Asn Asp Cys Gly Asp Tyr Ser Asp Glu Arg Asp
    2675                2680                2685

Cys Pro Gly Val Lys Arg Pro Arg Cys Pro Leu Asn Tyr Phe Ala
    2690                2695                2700

Cys Pro Ser Gly Arg Cys Ile Pro Met Ser Trp Thr Cys Asp Lys
    2705                2710                2715

Glu Asp Asp Cys Glu Asn Gly Glu Asp Glu Thr His Cys Asn Lys
    2720                2725                2730

Phe Cys Ser Glu Ala Gln Phe Glu Cys Gln Asn His Arg Cys Ile
    2735                2740                2745

Ser Lys Gln Trp Leu Cys Asp Gly Ser Asp Asp Cys Gly Asp Gly
    2750                2755                2760

Ser Asp Glu Ala Ala His Cys Glu Gly Lys Thr Cys Gly Pro Ser
    2765                2770                2775

Ser Phe Ser Cys Pro Gly Thr His Val Cys Val Pro Glu Arg Trp
    2780                2785                2790

Leu Cys Asp Gly Asp Lys Asp Cys Thr Asp Gly Ala Asp Glu Ser
    2795                2800                2805

Val Thr Ala Gly Cys Leu Tyr Asn Ser Thr Cys Asp Asp Arg Glu
    2810                2815                2820

Phe Met Cys Gln Asn Arg Leu Cys Ile Pro Lys His Phe Val Cys
    2825                2830                2835

Asp His Asp Arg Asp Cys Ala Asp Gly Ser Asp Glu Ser Pro Glu
    2840                2845                2850

Cys Glu Tyr Pro Thr Cys Gly Pro Asn Glu Phe Arg Cys Ala Asn
    2855                2860                2865

Gly Arg Cys Leu Ser Ser Arg Gln Trp Glu Cys Asp Gly Glu Asn
    2870                2875                2880

Asp Cys His Asp His Ser Asp Glu Ala Pro Lys Asn Pro His Cys
    2885                2890                2895

Thr Ser Pro Glu His Lys Cys Asn Ala Ser Ser Gln Phe Leu Cys
    2900                2905                2910

Ser Ser Gly Arg Cys Val Ala Glu Ala Leu Leu Cys Asn Gly Gln
    2915                2920                2925

Asp Asp Cys Gly Asp Gly Ser Asp Glu Arg Gly Cys His Val Asn
    2930                2935                2940

Glu Cys Leu Ser Arg Lys Leu Ser Gly Cys Ser Gln Asp Cys Glu
    2945                2950                2955

Asp Leu Lys Ile Gly Phe Lys Cys Arg Cys Arg Pro Gly Phe Arg
    2960                2965                2970

Leu Lys Asp Asp Gly Arg Thr Cys Ala Asp Leu Asp Glu Cys Ser
    2975                2980                2985

Thr Thr Phe Pro Cys Ser Gln Leu Cys Ile Asn Thr His Gly Ser
```

```
    2990                2995                3000

Tyr Lys  Cys Leu Cys Val Glu  Gly Tyr Ala Pro Arg  Gly Gly Asp
    3005                3010                3015

Pro His  Ser Cys Lys Ala Val  Thr Asp Glu Glu Pro  Phe Leu Ile
    3020                3025                3030

Phe Ala  Asn Arg Tyr Tyr Leu  Arg Lys Leu Asn Leu  Asp Gly Ser
    3035                3040                3045

Asn Tyr  Thr Leu Leu Lys Gln  Gly Leu Asn Asn Ala  Val Ala Leu
    3050                3055                3060

Asp Phe  Asp Tyr Arg Glu Gln  Met Ile Tyr Trp Thr  Asp Val Thr
    3065                3070                3075

Thr Gln  Gly Ser Met Ile Arg  Arg Met His Leu Asn  Gly Ser Asn
    3080                3085                3090

Val Gln  Val Leu His Arg Thr  Gly Leu Ser Asn Pro  Asp Gly Leu
    3095                3100                3105

Ala Val  Asp Trp Val Gly Gly  Asn Leu Tyr Trp Cys  Asp Lys Gly
    3110                3115                3120

Arg Asp  Thr Ile Glu Val Ser  Lys Leu Asn Gly Ala  Tyr Arg Thr
    3125                3130                3135

Val Leu  Val Ser Ser Gly Leu  Arg Glu Pro Arg Ala  Leu Val Val
    3140                3145                3150

Asp Val  Gln Asn Gly Tyr Leu  Tyr Trp Thr Asp Trp  Gly Asp His
    3155                3160                3165

Ser Leu  Ile Gly Arg Ile Gly  Met Asp Gly Ser Gly  Arg Ser Ile
    3170                3175                3180

Ile Val  Asp Thr Lys Ile Thr  Trp Pro Asn Gly Leu  Thr Val Asp
    3185                3190                3195

Tyr Val  Thr Glu Arg Ile Tyr  Trp Ala Asp Ala Arg  Glu Asp Tyr
    3200                3205                3210

Ile Glu  Phe Ala Ser Leu Asp  Gly Ser Asn Arg His  Val Val Leu
    3215                3220                3225

Ser Gln  Asp Ile Pro His Ile  Phe Ala Leu Thr Leu  Phe Glu Asp
    3230                3235                3240

Tyr Val  Tyr Trp Thr Asp Trp  Glu Thr Lys Ser Ile  Asn Arg Ala
    3245                3250                3255

His Lys  Thr Thr Gly Ala Asn  Lys Thr Leu Leu Ile  Ser Thr Leu
    3260                3265                3270

His Arg  Pro Met Asp Leu His  Val Phe His Ala Leu  Arg Gln Pro
    3275                3280                3285

Asp Val  Pro Asn His Pro Cys  Lys Val Asn Asn Gly  Gly Cys Ser
    3290                3295                3300

Asn Leu  Cys Leu Leu Ser Pro  Gly Gly Gly His Lys  Cys Ala Cys
    3305                3310                3315

Pro Thr  Asn Phe Tyr Leu Gly  Gly Asp Gly Arg Thr  Cys Val Ser
    3320                3325                3330

Asn Cys  Thr Ala Ser Gln Phe  Val Cys Lys Asn Asp  Lys Cys Ile
    3335                3340                3345

Pro Phe  Trp Trp Lys Cys Asp  Thr Glu Asp Asp Cys  Gly Asp His
    3350                3355                3360

Ser Asp  Glu Pro Pro Asp Cys  Pro Glu Phe Lys Cys  Arg Pro Gly
    3365                3370                3375

Gln Phe  Gln Cys Ser Thr Gly  Ile Cys Thr Asn Pro  Ala Phe Ile
    3380                3385                3390
```

-continued

```
Cys Asp Gly Asp Asn Asp Cys Gln Asp Asn Ser Asp Glu Ala Asn
    3395                3400                3405

Cys Asp Ile His Val Cys Leu Pro Ser Gln Phe Lys Cys Thr Asn
    3410                3415                3420

Thr Asn Arg Cys Ile Pro Gly Ile Phe Arg Cys Asn Gly Gln Asp
    3425                3430                3435

Asn Cys Gly Asp Gly Glu Asp Glu Arg Asp Cys Pro Glu Val Thr
    3440                3445                3450

Cys Ala Pro Asn Gln Phe Gln Cys Ser Ile Thr Lys Arg Cys Ile
    3455                3460                3465

Pro Arg Val Trp Val Cys Asp Arg Asp Asn Asp Cys Val Asp Gly
    3470                3475                3480

Ser Asp Glu Pro Ala Asn Cys Thr Gln Met Thr Cys Gly Val Asp
    3485                3490                3495

Glu Phe Arg Cys Lys Asp Ser Gly Arg Cys Ile Pro Ala Arg Trp
    3500                3505                3510

Lys Cys Asp Gly Glu Asp Asp Cys Gly Asp Gly Ser Asp Glu Pro
    3515                3520                3525

Lys Glu Glu Cys Asp Glu Arg Thr Cys Glu Pro Tyr Gln Phe Arg
    3530                3535                3540

Cys Lys Asn Asn Arg Cys Val Pro Gly Arg Trp Gln Cys Asp Tyr
    3545                3550                3555

Asp Asn Asp Cys Gly Asp Asn Ser Asp Glu Glu Ser Cys Thr Pro
    3560                3565                3570

Arg Pro Cys Ser Glu Ser Glu Phe Ser Cys Ala Asn Gly Arg Cys
    3575                3580                3585

Ile Ala Gly Arg Trp Lys Cys Asp Gly Asp His Asp Cys Ala Asp
    3590                3595                3600

Gly Ser Asp Glu Lys Asp Cys Thr Pro Arg Cys Asp Met Asp Gln
    3605                3610                3615

Phe Gln Cys Lys Ser Gly His Cys Ile Pro Leu Arg Trp Arg Cys
    3620                3625                3630

Asp Ala Asp Ala Asp Cys Met Asp Gly Ser Asp Glu Glu Ala Cys
    3635                3640                3645

Gly Thr Gly Val Arg Thr Cys Pro Leu Asp Glu Phe Gln Cys Asn
    3650                3655                3660

Asn Thr Leu Cys Lys Pro Leu Ala Trp Lys Cys Asp Gly Glu Asp
    3665                3670                3675

Asp Cys Gly Asp Asn Ser Asp Glu Asn Pro Glu Glu Cys Ala Arg
    3680                3685                3690

Phe Ile Cys Pro Pro Asn Arg Pro Phe Arg Cys Lys Asn Asp Arg
    3695                3700                3705

Val Cys Leu Trp Ile Gly Arg Gln Cys Asp Gly Val Asp Asn Cys
    3710                3715                3720

Gly Asp Gly Thr Asp Glu Glu Asp Cys Glu Pro Pro Thr Ala Gln
    3725                3730                3735

Asn Pro His Cys Lys Asp Lys Lys Glu Phe Leu Cys Arg Asn Gln
    3740                3745                3750

Arg Cys Leu Ser Ser Ser Leu Arg Cys Asn Met Phe Asp Asp Cys
    3755                3760                3765

Gly Asp Gly Ser Asp Glu Glu Asp Cys Ser Ile Asp Pro Lys Leu
    3770                3775                3780
```

-continued

```
Thr Ser  Cys Ala Thr Asn Ala  Ser Met Cys Gly Asp  Glu Ala Arg
    3785                 3790                 3795

Cys Val  Arg Thr Glu Lys Ala  Ala Tyr Cys Ala Cys  Arg Ser Gly
    3800                 3805                 3810

Phe His  Thr Val Pro Gly Gln  Pro Gly Cys Gln Asp  Ile Asn Glu
    3815                 3820                 3825

Cys Leu  Arg Phe Gly Thr Cys  Ser Gln Leu Cys Asn  Asn Thr Lys
    3830                 3835                 3840

Gly Gly  His Leu Cys Ser Cys  Ala Arg Asn Phe Met  Lys Thr His
    3845                 3850                 3855

Asn Thr  Cys Lys Ala Glu Gly  Ser Glu Tyr Gln Val  Leu Tyr Ile
    3860                 3865                 3870

Ala Asp  Asp Asn Glu Ile Arg  Ser Leu Phe Pro Gly  His Pro His
    3875                 3880                 3885

Ser Ala  Tyr Glu Gln Thr Phe  Gln Gly Asp Glu Ser  Val Arg Ile
    3890                 3895                 3900

Asp Ala  Met Asp Val His Val  Lys Ala Gly Arg Val  Tyr Trp Thr
    3905                 3910                 3915

Asn Trp  His Thr Gly Thr Ile  Ser Tyr Arg Ser Leu  Pro Pro Ala
    3920                 3925                 3930

Ala Pro  Pro Thr Thr Ser Asn  Arg His Arg Arg Gln  Ile Asp Arg
    3935                 3940                 3945

Gly Val  Thr His Leu Asn Ile  Ser Gly Leu Lys Met  Pro Arg Gly
    3950                 3955                 3960

Ile Ala  Ile Asp Trp Val Ala  Gly Asn Val Tyr Trp  Thr Asp Ser
    3965                 3970                 3975

Gly Arg  Asp Val Ile Glu Val  Ala Gln Met Lys Gly  Glu Asn Arg
    3980                 3985                 3990

Lys Thr  Leu Ile Ser Gly Met  Ile Asp Glu Pro His  Ala Ile Val
    3995                 4000                 4005

Val Asp  Pro Leu Arg Gly Thr  Met Tyr Trp Ser Asp  Trp Gly Asn
    4010                 4015                 4020

His Pro  Lys Ile Glu Thr Ala  Ala Met Asp Gly Thr  Leu Arg Glu
    4025                 4030                 4035

Thr Leu  Val Gln Asp Asn Ile  Gln Trp Pro Thr Gly  Leu Ala Val
    4040                 4045                 4050

Asp Tyr  His Asn Glu Arg Leu  Tyr Trp Ala Asp Ala  Lys Leu Ser
    4055                 4060                 4065

Val Ile  Gly Ser Ile Arg Leu  Asn Gly Thr Asp Pro  Ile Val Ala
    4070                 4075                 4080

Ala Asp  Ser Lys Arg Gly Leu  Ser His Pro Phe Ser  Ile Asp Val
    4085                 4090                 4095

Phe Glu  Asp Tyr Ile Tyr Gly  Val Thr Tyr Ile Asn  Asn Arg Val
    4100                 4105                 4110

Phe Lys  Ile His Lys Phe Gly  His Ser Pro Leu Ile  Asn Leu Thr
    4115                 4120                 4125

Gly Gly  Leu Ser His Ala Ser  Asp Val Val Leu Tyr  His Gln His
    4130                 4135                 4140

Lys Gln  Pro Glu Val Thr Asn  Pro Cys Asp Arg Lys  Lys Cys Glu
    4145                 4150                 4155

Trp Leu  Cys Leu Leu Ser Pro  Ser Gly Pro Val Cys  Thr Cys Pro
    4160                 4165                 4170

Asn Gly  Lys Arg Leu Asp Asn  Gly Thr Cys Val Pro  Val Pro Ser
```

```
    4175                4180                4185

Pro Thr  Pro Pro Pro Asp Ala  Pro Arg Pro Gly Thr  Cys Thr Leu
    4190                4195                4200

Gln Cys  Phe Asn Gly Gly Ser  Cys Phe Leu Asn Ala  Arg Arg Gln
    4205                4210                4215

Pro Lys  Cys Arg Cys Gln Pro  Arg Tyr Thr Gly Asp  Lys Cys Glu
    4220                4225                4230

Leu Asp  Gln Cys Trp Glu Tyr  Cys His Asn Gly Gly  Thr Cys Ala
    4235                4240                4245

Ala Ser  Pro Ser Gly Met Pro  Thr Cys Arg Cys Pro  Thr Gly Phe
    4250                4255                4260

Thr Gly  Pro Lys Cys Thr Ala  Gln Val Cys Ala Gly  Tyr Cys Ser
    4265                4270                4275

Asn Asn  Ser Thr Cys Thr Val  Asn Gln Gly Asn Gln  Pro Gln Cys
    4280                4285                4290

Arg Cys  Leu Pro Gly Phe Leu  Gly Asp Arg Cys Gln  Tyr Arg Gln
    4295                4300                4305

Cys Ser  Gly Phe Cys Glu Asn  Phe Gly Thr Cys Gln  Met Ala Ala
    4310                4315                4320

Asp Gly  Ser Arg Gln Cys Arg  Cys Thr Val Tyr Phe  Glu Gly Pro
    4325                4330                4335

Arg Cys  Glu Val Asn Lys Cys  Ser Arg Cys Leu Gln  Gly Ala Cys
    4340                4345                4350

Val Val  Asn Lys Gln Thr Gly  Asp Val Thr Cys Asn  Cys Thr Asp
    4355                4360                4365

Gly Arg  Val Ala Pro Ser Cys  Leu Thr Cys Ile Asp  His Cys Ser
    4370                4375                4380

Asn Gly  Gly Ser Cys Thr Met  Asn Ser Lys Met Met  Pro Glu Cys
    4385                4390                4395

Gln Cys  Pro Pro His Met Thr  Gly Pro Arg Cys Glu  Glu Gln Val
    4400                4405                4410

Val Ser  Gln Gln Gln Pro Gly  His Met Ala Ser Ile  Leu Ile Pro
    4415                4420                4425

Leu Leu  Leu Leu Leu Leu Leu  Leu Leu Val Ala Gly  Val Val Phe
    4430                4435                4440

Trp Tyr  Lys Arg Arg Val Arg  Gly Ala Lys Gly Phe  Gln His Gln
    4445                4450                4455

Arg Met  Thr Asn Gly Ala Met  Asn Val Glu Ile Gly  Asn Pro Thr
    4460                4465                4470

Tyr Lys  Met Tyr Glu Gly Gly  Glu Pro Asp Asp Val  Gly Gly Leu
    4475                4480                4485

Leu Asp  Ala Asp Phe Ala Leu  Asp Pro Asp Lys Pro  Thr Asn Phe
    4490                4495                4500

Thr Asn  Pro Val Tyr Ala Thr  Leu Tyr Met Gly Gly  His Gly Ser
    4505                4510                4515

Arg His  Ser Leu Ala Ser Thr  Asp Glu Lys Arg Glu  Leu Leu Gly
    4520                4525                4530

Arg Gly  Pro Glu Asp Glu Ile  Gly Asp Pro Leu Ala
    4535                4540                4545
```

<210> SEQ ID NO 3
<211> LENGTH: 4544
<212> TYPE: PRT
<213> ORGANISM: Macaca mulatta

<400> SEQUENCE: 3

Met Leu Thr Pro Pro Leu Leu Leu Leu Leu Pro Leu Leu Ser Ala Leu
1               5                   10                  15

Val Ala Ala Ala Ile Asp Ala Pro Lys Thr Cys Ser Pro Lys Gln Phe
            20                  25                  30

Ala Cys Arg Asp Gln Ile Thr Cys Ile Ser Lys Gly Trp Arg Cys Asp
        35                  40                  45

Gly Glu Arg Asp Cys Pro Asp Gly Ser Asp Glu Ala Pro Glu Ile Cys
    50                  55                  60

Pro Gln Ser Lys Ala Gln Arg Cys Gln Pro Asn Glu His Asn Cys Leu
65                  70                  75                  80

Gly Thr Glu Leu Cys Val Pro Met Ser Arg Leu Cys Asn Gly Val Gln
                85                  90                  95

Asp Cys Met Asp Gly Ser Asp Glu Gly Pro His Cys Arg Glu Leu Arg
            100                 105                 110

Gly Asn Cys Ser Arg Leu Gly Cys Gln His His Cys Val Pro Thr Leu
        115                 120                 125

Asp Gly Pro Thr Cys Tyr Cys Asn Ser Ser Phe Gln Leu Gln Ala Asp
    130                 135                 140

Ser Lys Thr Cys Lys Asp Phe Asp Glu Cys Ser Val Tyr Gly Thr Cys
145                 150                 155                 160

Ser Gln Leu Cys Thr Asn Thr Asp Gly Ser Phe Ile Cys Gly Cys Val
                165                 170                 175

Glu Gly Tyr Leu Leu Gln Pro Asp Asn Arg Ser Cys Lys Ala Lys Asn
            180                 185                 190

Glu Pro Val Asp Arg Pro Pro Val Leu Leu Ile Ala Asn Ser Gln Asn
        195                 200                 205

Ile Leu Ala Thr Tyr Leu Ser Gly Ala Gln Val Ser Thr Ile Thr Pro
    210                 215                 220

Thr Ser Thr Arg Gln Thr Thr Ala Met Asp Phe Ser Tyr Ala Asn Glu
225                 230                 235                 240

Thr Val Cys Trp Val His Val Gly Asp Asn Ala Ala Gln Thr Gln Leu
                245                 250                 255

Lys Cys Ala Arg Met Pro Gly Leu Lys Gly Phe Val Asp Glu His Thr
            260                 265                 270

Ile Asn Ile Ser Leu Ser Leu His His Val Glu Gln Met Ala Ile Asp
        275                 280                 285

Trp Leu Thr Gly Asn Phe Tyr Phe Val Asp Asp Ile Asp Asp Arg Ile
    290                 295                 300

Phe Val Cys Asn Arg Asn Gly Asp Thr Cys Val Thr Leu Leu Asp Leu
305                 310                 315                 320

Glu Leu Tyr Asn Pro Lys Gly Ile Ala Leu Asp Pro Ala Met Gly Lys
                325                 330                 335

Val Phe Phe Thr Asp Tyr Gly Gln Ile Pro Lys Val Glu Arg Cys Asp
            340                 345                 350

Met Asp Gly Gln Asn Arg Thr Lys Leu Val Asp Ser Lys Ile Val Phe
        355                 360                 365

Pro His Gly Ile Thr Leu Asp Leu Val Ser Arg Leu Val Tyr Trp Ala
    370                 375                 380

Asp Ala Tyr Leu Asp Tyr Ile Glu Val Val Asp Tyr Glu Gly Lys Gly
385                 390                 395                 400

Arg Gln Thr Ile Ile Gln Gly Ile Leu Ile Glu His Leu Tyr Gly Leu

```
                405                 410                 415

Thr Val Phe Glu Asn Tyr Leu Tyr Ala Thr Asn Ser Asp Asn Ala Asn
            420                 425                 430

Ala Gln Gln Lys Thr Ser Val Ile Arg Val Asn Arg Phe Asn Ser Thr
        435                 440                 445

Glu Tyr Gln Val Val Thr Arg Val Asp Lys Gly Gly Ala Leu His Ile
    450                 455                 460

Tyr His Gln Arg Arg Gln Pro Arg Val Arg Ser His Ala Cys Glu Asn
465                 470                 475                 480

Asp Gln Tyr Gly Lys Pro Gly Gly Cys Ser Asp Ile Cys Leu Leu Ala
                485                 490                 495

Asn Ser His Lys Ala Arg Thr Cys Arg Cys Arg Ser Gly Phe Ser Leu
            500                 505                 510

Gly Ser Asp Gly Lys Ser Cys Lys Lys Pro Glu His Glu Leu Phe Leu
        515                 520                 525

Val Tyr Gly Lys Gly Arg Pro Gly Ile Ile Arg Gly Met Asp Met Gly
    530                 535                 540

Ala Lys Val Pro Asp Glu His Met Ile Pro Ile Glu Asn Leu Met Asn
545                 550                 555                 560

Pro Arg Ala Leu Asp Phe His Ala Glu Thr Gly Phe Ile Tyr Phe Ala
                565                 570                 575

Asp Thr Thr Ser Tyr Leu Ile Gly Arg Gln Lys Ile Asp Gly Thr Glu
            580                 585                 590

Arg Glu Thr Ile Leu Lys Asp Gly Ile His Asn Val Glu Gly Val Ala
        595                 600                 605

Val Asp Trp Met Gly Asp Asn Leu Tyr Trp Thr Asp Asp Gly Pro Lys
    610                 615                 620

Lys Thr Ile Ser Val Ala Arg Leu Glu Lys Ala Ala Gln Thr Arg Lys
625                 630                 635                 640

Thr Leu Ile Glu Gly Lys Met Thr His Pro Arg Ala Ile Val Val Asp
                645                 650                 655

Pro Leu Asn Gly Trp Met Tyr Trp Thr Asp Trp Glu Glu Asp Pro Lys
            660                 665                 670

Asp Ser Arg Arg Gly Arg Leu Glu Arg Ala Trp Met Asp Gly Ser His
        675                 680                 685

Arg Asp Ile Phe Val Thr Ser Lys Thr Val Leu Trp Pro Asn Gly Leu
    690                 695                 700

Ser Leu Asp Ile Pro Ala Gly Arg Leu Tyr Trp Val Asp Ala Phe Tyr
705                 710                 715                 720

Asp Arg Ile Glu Thr Ile Leu Leu Asn Gly Thr Asp Arg Lys Ile Val
                725                 730                 735

Tyr Glu Gly Pro Glu Leu Asn His Ala Phe Gly Leu Cys His His Gly
            740                 745                 750

Asn Tyr Leu Phe Trp Thr Glu Tyr Arg Ser Gly Ser Val Tyr Arg Leu
        755                 760                 765

Glu Arg Gly Val Gly Gly Ala Pro Pro Thr Val Thr Leu Leu Arg Ser
    770                 775                 780

Glu Arg Pro Pro Ile Phe Glu Ile Arg Met Tyr Asp Ala Gln Gln Gln
785                 790                 795                 800

Gln Val Gly Thr Asn Lys Cys Arg Val Asn Asn Gly Gly Cys Ser Ser
                805                 810                 815

Leu Cys Leu Ala Thr Pro Gly Ser Arg Gln Cys Ala Cys Ala Glu Asp
            820                 825                 830
```

```
Gln Val Leu Asp Ala Asp Gly Val Thr Cys Leu Ala Asn Pro Ser Tyr
        835                 840                 845

Val Pro Pro Pro Gln Cys Gln Pro Gly Glu Phe Ala Cys Ala Asn Ser
    850                 855                 860

Arg Cys Ile Gln Glu Arg Trp Lys Cys Asp Gly Asp Asn Asp Cys Leu
865                 870                 875                 880

Asp Asn Ser Asp Glu Ala Pro Ala Leu Cys His Gln His Thr Cys Pro
                885                 890                 895

Ser Asp Arg Phe Lys Cys Glu Asn Asn Arg Cys Ile Pro Asn Arg Trp
            900                 905                 910

Leu Cys Asp Gly Asp Asn Asp Cys Gly Asn Ser Glu Asp Glu Ser Asn
        915                 920                 925

Ala Thr Cys Ser Ala Arg Thr Cys Pro Pro Asn Gln Phe Ser Cys Ala
    930                 935                 940

Ser Gly Arg Cys Ile Pro Ile Ser Trp Thr Cys Asp Leu Asp Asp Asp
945                 950                 955                 960

Cys Gly Asp Arg Ser Asp Glu Ser Ala Ser Cys Ala Tyr Pro Thr Cys
                965                 970                 975

Phe Pro Leu Thr Gln Phe Thr Cys Asn Asn Gly Arg Cys Ile Asn Ile
            980                 985                 990

Asn Trp Arg Cys Asp Asn Asp Asn  Asp Cys Gly Asp Asn  Ser Asp Glu
        995                 1000                1005

Ala Gly  Cys Ser His Ser Cys  Ser Ser Thr Gln Phe  Lys Cys Asn
    1010                 1015                 1020

Ser Gly  Arg Cys Ile Pro Glu  His Trp Thr Cys Asp  Gly Asp Asn
    1025                 1030                 1035

Asp Cys  Gly Asp Tyr Ser Asp  Glu Thr His Ala Asn  Cys Thr Asn
    1040                 1045                 1050

Gln Ala  Thr Arg Pro Pro Gly  Gly Cys His Thr Asp  Glu Phe Gln
    1055                 1060                 1065

Cys Arg  Leu Asp Gly Leu Cys  Ile Pro Leu Arg Trp  Arg Cys Asp
    1070                 1075                 1080

Gly Asp  Thr Asp Cys Met Asp  Ser Ser Asp Glu Lys  Ser Cys Glu
    1085                 1090                 1095

Gly Val  Thr His Val Cys Asp  Pro Ser Val Lys Phe  Gly Cys Lys
    1100                 1105                 1110

Asp Ser  Ala Arg Cys Ile Ser  Lys Ala Trp Val Cys  Asp Gly Asp
    1115                 1120                 1125

Asn Asp  Cys Glu Asp Asn Ser  Asp Glu Glu Asn Cys  Glu Ser Leu
    1130                 1135                 1140

Ala Cys  Arg Pro Pro Ser His  Pro Cys Ala Asn Asn  Thr Ser Val
    1145                 1150                 1155

Cys Leu  Pro Pro Asp Lys Leu  Cys Asp Gly Asn Asp  Asp Cys Gly
    1160                 1165                 1170

Asp Gly  Ser Asp Glu Gly Glu  Leu Cys Asp Gln Cys  Ser Leu Asn
    1175                 1180                 1185

Asn Gly  Gly Cys Ser His Asn  Cys Ser Val Ala Pro  Gly Glu Gly
    1190                 1195                 1200

Ile Val  Cys Ser Cys Pro Leu  Gly Met Glu Leu Gly  Pro Asp Asn
    1205                 1210                 1215

His Thr  Cys Gln Ile Gln Ser  Tyr Cys Ala Lys His  Leu Lys Cys
    1220                 1225                 1230
```

```
Ser Gln  Lys Cys Asp Gln Asn  Lys Phe Ser Val Lys  Cys Ser Cys
    1235                 1240                 1245

Tyr Glu  Gly Trp Val Leu Glu  Pro Asp Gly Glu Ser  Cys Arg Ser
    1250                 1255                 1260

Leu Asp  Pro Phe Lys Pro Phe  Ile Ile Phe Ser Asn  Arg His Glu
    1265                 1270                 1275

Ile Arg  Arg Ile Asp Leu His  Lys Gly Asp Tyr Ser  Val Leu Val
    1280                 1285                 1290

Pro Gly  Leu Arg Asn Thr Ile  Ala Leu Asp Phe His  Leu Ser Gln
    1295                 1300                 1305

Ser Ala  Leu Tyr Trp Thr Asp  Val Val Glu Asp Lys  Ile Tyr Arg
    1310                 1315                 1320

Gly Lys  Leu Leu Asp Asn Gly  Ala Leu Thr Ser Phe  Glu Val Val
    1325                 1330                 1335

Ile Gln  Tyr Gly Leu Ala Thr  Pro Glu Gly Leu Ala  Val Asp Trp
    1340                 1345                 1350

Ile Ala  Gly Asn Ile Tyr Trp  Val Glu Ser Asn Leu  Asp Gln Ile
    1355                 1360                 1365

Glu Val  Ala Lys Leu Asp Gly  Thr Leu Arg Thr Thr  Leu Leu Ala
    1370                 1375                 1380

Gly Asp  Ile Glu His Pro Arg  Ala Ile Ala Leu Asp  Pro Arg Asp
    1385                 1390                 1395

Gly Ile  Leu Phe Trp Thr Asp  Trp Asp Ala Ser Leu  Pro Arg Ile
    1400                 1405                 1410

Glu Ala  Ala Ser Met Ser Gly  Ala Gly Arg Arg Thr  Val His Arg
    1415                 1420                 1425

Glu Thr  Gly Ser Gly Gly Trp  Pro Asn Gly Leu Thr  Val Asp Tyr
    1430                 1435                 1440

Leu Glu  Lys Arg Ile Leu Trp  Ile Asp Ala Arg Ser  Asp Ala Ile
    1445                 1450                 1455

Tyr Ser  Ala Arg Tyr Asp Gly  Ser Gly His Met Glu  Val Leu Arg
    1460                 1465                 1470

Gly His  Glu Phe Leu Ser His  Pro Phe Ala Val Thr  Leu Tyr Gly
    1475                 1480                 1485

Gly Glu  Val Tyr Trp Thr Asp  Trp Arg Thr Asn Thr  Leu Ala Lys
    1490                 1495                 1500

Ala Asn  Lys Trp Thr Gly His  Asn Val Thr Val Val  Gln Arg Thr
    1505                 1510                 1515

Asn Thr  Gln Pro Phe Asp Leu  Gln Val Tyr His Pro  Ser Arg Gln
    1520                 1525                 1530

Pro Met  Ala Pro Asn Pro Cys  Glu Ala Asn Gly Gly  Arg Gly Pro
    1535                 1540                 1545

Cys Ser  His Leu Cys Leu Ile  Asn Tyr Asn Arg Thr  Val Ser Cys
    1550                 1555                 1560

Ala Cys  Pro His Leu Met Lys  Leu His Lys Asp Lys  Thr Thr Cys
    1565                 1570                 1575

Tyr Glu  Phe Lys Lys Phe Leu  Leu Tyr Ala Arg Gln  Met Glu Ile
    1580                 1585                 1590

Arg Gly  Val Asp Leu Asp Ala  Pro Tyr Tyr Asn Tyr  Ile Ile Ser
    1595                 1600                 1605

Phe Thr  Val Pro Asp Ile Asp  Asn Val Thr Val Leu  Asp Tyr Asp
    1610                 1615                 1620

Ala Arg  Glu Gln Arg Val Tyr  Trp Ser Asp Val Arg  Thr Gln Ala
```

```
    1625                1630                1635

Ile Lys  Arg Ala Phe Ile Asn  Gly Thr Gly Val Glu  Thr Val Val
    1640                1645                1650

Ser Ala  Asp Leu Pro Asn Ala  His Gly Leu Ala Val  Asp Trp Val
    1655                1660                1665

Ser Arg  Asn Leu Phe Trp Thr  Ser Tyr Asp Thr Asn  Lys Lys Gln
    1670                1675                1680

Ile Asn  Val Ala Arg Leu Asp  Gly Ser Phe Lys Asn  Ala Val Val
    1685                1690                1695

Gln Gly  Leu Glu Gln Pro His  Gly Leu Val Val His  Pro Leu Arg
    1700                1705                1710

Gly Lys  Leu Tyr Trp Thr Asp  Gly Asp Asn Ile Ser  Met Ala Asn
    1715                1720                1725

Met Asp  Gly Ser Asn Arg Thr  Leu Leu Phe Ser Gly  Gln Lys Gly
    1730                1735                1740

Pro Val  Gly Leu Ala Ile Asp  Phe Pro Glu Ser Lys  Leu Tyr Trp
    1745                1750                1755

Ile Ser  Ser Gly Asn His Thr  Ile Asn Arg Cys Asn  Leu Asp Gly
    1760                1765                1770

Ser Gly  Leu Glu Val Ile Asp  Ala Met Arg Ser Gln  Leu Gly Lys
    1775                1780                1785

Ala Thr  Ala Leu Ala Ile Met  Gly Asp Lys Leu Trp  Trp Ala Asp
    1790                1795                1800

Gln Val  Ser Glu Lys Met Gly  Thr Cys Ser Lys Ala  Asp Gly Ser
    1805                1810                1815

Gly Ser  Ile Val Leu Arg Asn  Ser Thr Thr Leu Val  Met His Met
    1820                1825                1830

Lys Val  Tyr Asp Glu Ser Ile  Gln Leu Asp His Lys  Gly Thr Asn
    1835                1840                1845

Pro Cys  Ser Val Asn Asn Gly  Asp Cys Ser Gln Leu  Cys Leu Pro
    1850                1855                1860

Thr Ser  Glu Thr Thr Arg Ser  Cys Met Cys Thr Ala  Gly Tyr Ser
    1865                1870                1875

Leu Arg  Ser Gly Gln Gln Ala  Cys Glu Gly Val Gly  Ser Phe Leu
    1880                1885                1890

Leu Tyr  Ser Val His Glu Gly  Ile Arg Gly Ile Pro  Leu Asp Pro
    1895                1900                1905

Asn Asp  Lys Ser Asp Ala Leu  Val Pro Val Ser Gly  Thr Ser Leu
    1910                1915                1920

Ala Val  Gly Ile Asp Phe His  Ala Glu Asn Asp Thr  Ile Tyr Trp
    1925                1930                1935

Val Asp  Met Gly Leu Ser Thr  Ile Ser Arg Ala Lys  Arg Asp Gln
    1940                1945                1950

Thr Trp  Arg Glu Asp Val Val  Thr Asn Gly Ile Gly  Arg Val Glu
    1955                1960                1965

Gly Ile  Ala Val Asp Trp Ile  Ala Gly Asn Ile Tyr  Trp Thr Asp
    1970                1975                1980

Gln Gly  Phe Asp Val Ile Glu  Val Ala Arg Leu Asn  Gly Ser Phe
    1985                1990                1995

Arg Tyr  Val Val Ile Ser Gln  Gly Leu Asp Lys Pro  Arg Ala Ile
    2000                2005                2010

Thr Val  His Pro Glu Lys Gly  Tyr Leu Phe Trp Thr  Glu Trp Gly
    2015                2020                2025
```

-continued

```
Gln Tyr  Pro Arg Ile Glu Arg  Ser Arg Leu Asp Gly  Thr Glu Arg
    2030                 2035                 2040

Val Val  Leu Val Asn Val Ser  Ile Ser Trp Pro Asn  Gly Ile Ser
    2045                 2050                 2055

Val Asp  Tyr Gln Asp Gly Lys  Leu Tyr Trp Cys Asp  Ala Arg Thr
    2060                 2065                 2070

Asp Lys  Ile Glu Arg Ile Asp  Leu Glu Thr Gly Glu  Asn Arg Glu
    2075                 2080                 2085

Val Val  Leu Ser Ser Asn Asn  Met Asp Met Phe Ser  Val Ser Val
    2090                 2095                 2100

Phe Glu  Asp Phe Ile Tyr Trp  Ser Asp Arg Thr His  Ala Asn Gly
    2105                 2110                 2115

Ser Ile  Lys Arg Gly Ser Lys  Asp Asn Ala Thr Asp  Ser Val Pro
    2120                 2125                 2130

Leu Arg  Thr Gly Ile Gly Val  Gln Leu Lys Asp Ile  Lys Val Phe
    2135                 2140                 2145

Asn Arg  Asp Arg Gln Lys Gly  Thr Asn Val Cys Ala  Val Ala Asn
    2150                 2155                 2160

Gly Gly  Cys Gln Gln Leu Cys  Leu Tyr Arg Gly Arg  Gly Gln Arg
    2165                 2170                 2175

Ala Cys  Ala Cys Ala His Gly  Met Leu Ala Glu Asp  Gly Ala Ser
    2180                 2185                 2190

Cys Arg  Glu Tyr Ala Gly Tyr  Leu Leu Tyr Ser Glu  Arg Thr Ile
    2195                 2200                 2205

Leu Lys  Ser Ile His Leu Ser  Asp Glu Arg Asn Leu  Asn Ala Pro
    2210                 2215                 2220

Val Gln  Pro Phe Glu Asp Pro  Glu His Met Lys Asn  Val Ile Ala
    2225                 2230                 2235

Leu Ala  Phe Asp Tyr Arg Ala  Gly Thr Ser Pro Gly  Thr Pro Asn
    2240                 2245                 2250

Arg Ile  Phe Phe Ser Asp Ile  His Phe Gly Asn Ile  Gln Gln Ile
    2255                 2260                 2265

Asn Asp  Asp Gly Ser Arg Arg  Ile Thr Ile Val Glu  Asn Val Gly
    2270                 2275                 2280

Ser Val  Glu Gly Leu Ala Tyr  His Arg Gly Trp Asp  Thr Leu Tyr
    2285                 2290                 2295

Trp Thr  Ser Tyr Thr Thr Ser  Thr Ile Thr Arg His  Thr Val Asp
    2300                 2305                 2310

Gln Thr  Arg Pro Gly Ala Phe  Glu Arg Glu Thr Val  Ile Thr Met
    2315                 2320                 2325

Ser Gly  Asp Asp His Pro Arg  Ala Phe Val Leu Asp  Glu Cys Gln
    2330                 2335                 2340

Asn Leu  Met Phe Trp Thr Asn  Trp Asn Glu Gln His  Pro Ser Ile
    2345                 2350                 2355

Met Arg  Ala Ala Leu Ser Gly  Ala Asn Val Leu Thr  Leu Ile Glu
    2360                 2365                 2370

Lys Asp  Ile Arg Thr Pro Asn  Gly Leu Ala Ile Asp  His Arg Ala
    2375                 2380                 2385

Glu Lys  Leu Tyr Phe Ser Asp  Ala Thr Leu Asp Lys  Ile Glu Arg
    2390                 2395                 2400

Cys Glu  Tyr Asp Gly Ser His  Arg Tyr Val Ile Leu  Lys Ser Glu
    2405                 2410                 2415
```

-continued

```
Pro Val  His Pro Phe Gly Leu  Ala Val Tyr Gly Glu  His Ile Phe
    2420                 2425                 2430

Trp Thr  Asp Trp Val Arg Arg  Ala Val Gln Arg Ala  Asn Lys His
    2435                 2440                 2445

Val Gly  Ser Asn Met Lys Leu  Leu Arg Val Asp Ile  Pro Gln Gln
    2450                 2455                 2460

Pro Met  Gly Ile Ile Ala Val  Ala Asn Asp Thr Asn  Ser Cys Glu
    2465                 2470                 2475

Leu Ser  Pro Cys Arg Ile Asn  Asn Gly Gly Cys Gln  Asp Leu Cys
    2480                 2485                 2490

Leu Leu  Thr His Gln Gly His  Val Asn Cys Ser Cys  Arg Gly Gly
    2495                 2500                 2505

Arg Ile  Leu Gln Asp Asp Leu  Thr Cys Arg Ala Val  Asn Ser Ser
    2510                 2515                 2520

Cys Arg  Ala Gln Asp Glu Phe  Glu Cys Ala Asn Gly  Glu Cys Ile
    2525                 2530                 2535

Asn Phe  Ser Leu Thr Cys Asp  Gly Val Pro His Cys  Lys Asp Lys
    2540                 2545                 2550

Ser Asp  Glu Lys Pro Ser Tyr  Cys Asn Ser Arg Arg  Cys Lys Lys
    2555                 2560                 2565

Thr Phe  Arg Gln Cys Ser Asn  Gly Arg Cys Val Ser  Asn Met Leu
    2570                 2575                 2580

Trp Cys  Asn Gly Ala Asp Asp  Cys Gly Asp Gly Ser  Asp Glu Ile
    2585                 2590                 2595

Pro Cys  Asn Lys Thr Ala Cys  Gly Val Gly Glu Phe  Arg Cys Arg
    2600                 2605                 2610

Asp Gly  Thr Cys Ile Gly Asn  Ser Ser Arg Cys Asn  Gln Phe Val
    2615                 2620                 2625

Asp Cys  Glu Asp Ala Ser Asp  Glu Met Asn Cys Ser  Ala Thr Asp
    2630                 2635                 2640

Cys Ser  Ser Tyr Phe Arg Leu  Gly Val Lys Gly Val  Leu Phe Gln
    2645                 2650                 2655

Pro Cys  Glu Arg Thr Ser Leu  Cys Tyr Ala Pro Ser  Trp Val Cys
    2660                 2665                 2670

Asp Gly  Ala Asn Asp Cys Gly  Asp Tyr Ser Asp Glu  Arg Asp Cys
    2675                 2680                 2685

Pro Gly  Val Lys Arg Pro Arg  Cys Pro Leu Asn Tyr  Phe Ala Cys
    2690                 2695                 2700

Pro Ser  Gly Arg Cys Ile Pro  Met Ser Trp Thr Cys  Asp Lys Glu
    2705                 2710                 2715

Asp Asp  Cys Glu His Gly Glu  Asp Glu Thr His Cys  Asn Lys Phe
    2720                 2725                 2730

Cys Ser  Glu Ala Gln Phe Glu  Cys Gln Asn His Arg  Cys Ile Ser
    2735                 2740                 2745

Lys Gln  Trp Leu Cys Asp Gly  Ser Asp Asp Cys Gly  Asp Gly Ser
    2750                 2755                 2760

Asp Glu  Ala Ala His Cys Glu  Gly Lys Thr Cys Gly  Pro Ser Ser
    2765                 2770                 2775

Phe Ser  Cys Pro Gly Thr His  Val Cys Val Pro Glu  Arg Trp Leu
    2780                 2785                 2790

Cys Asp  Gly Asp Lys Asp Cys  Ala Asp Gly Ala Asp  Glu Ser Ile
    2795                 2800                 2805

Ala Ala  Gly Cys Leu Tyr Asn  Ser Thr Cys Asp Asp  Arg Glu Phe
```

```
    2810                2815                2820

Met Cys  Gln Asn Arg Gln Cys  Ile Pro Lys His Phe  Val Cys Asp
    2825                2830                2835

His Asp  Arg Asp Cys Ala Asp  Gly Ser Asp Glu Ser  Pro Glu Cys
    2840                2845                2850

Glu Tyr  Pro Thr Cys Gly Pro  Ser Glu Phe Arg Cys  Ala Asn Gly
    2855                2860                2865

Arg Cys  Leu Ser Ser Arg Gln  Trp Glu Cys Asp Gly  Glu Asn Asp
    2870                2875                2880

Cys His  Asp Gln Ser Asp Glu  Ala Pro Lys Asn Pro  His Cys Thr
    2885                2890                2895

Ser Pro  Glu His Lys Cys Asn  Ala Ser Ser Gln Phe  Leu Cys Ser
    2900                2905                2910

Ser Gly  Arg Cys Val Ala Glu  Val Leu Leu Cys Asn  Gly Gln Asp
    2915                2920                2925

Asp Cys  Gly Asp Gly Ser Asp  Glu Arg Gly Cys His  Ile Asn Glu
    2930                2935                2940

Cys Leu  Ser His Lys Leu Ser  Gly Cys Ser Gln Asp  Cys Glu Asp
    2945                2950                2955

Leu Lys  Ile Gly Phe Lys Cys  Arg Cys Arg Pro Gly  Phe Arg Leu
    2960                2965                2970

Lys Asp  Asp Gly Arg Thr Cys  Ala Asp Val Asp Glu  Cys Ser Thr
    2975                2980                2985

Thr Phe  Pro Cys Ser Gln Arg  Cys Ile Asn Thr His  Gly Ser Tyr
    2990                2995                3000

Lys Cys  Leu Cys Val Glu Gly  Tyr Ala Pro Arg Gly  Gly Asp Pro
    3005                3010                3015

His Ser  Cys Lys Ala Val Thr  Asp Glu Glu Pro Phe  Leu Ile Phe
    3020                3025                3030

Ala Asn  Arg Tyr Tyr Leu Arg  Lys Leu Asn Leu Asp  Gly Ser Asn
    3035                3040                3045

Tyr Thr  Leu Leu Lys Gln Gly  Leu Asn Asn Ala Val  Ala Leu Asp
    3050                3055                3060

Phe Asp  Tyr Arg Glu Gln Met  Ile Tyr Trp Thr Asp  Val Thr Thr
    3065                3070                3075

Gln Gly  Ser Met Ile Arg Arg  Met His Leu Asn Gly  Ser Asn Val
    3080                3085                3090

Gln Val  Leu His Arg Thr Gly  Leu Ser Asn Pro Asp  Gly Leu Ala
    3095                3100                3105

Val Asp  Trp Val Gly Gly Asn  Leu Tyr Trp Cys Asp  Lys Gly Arg
    3110                3115                3120

Asp Thr  Ile Glu Val Ser Lys  Leu Asn Gly Ala Tyr  Arg Thr Val
    3125                3130                3135

Leu Val  Ser Ser Gly Leu Arg  Glu Pro Arg Ala Leu  Val Val Asp
    3140                3145                3150

Val Gln  Asn Gly Tyr Leu Tyr  Trp Thr Asp Trp Gly  Asp His Ser
    3155                3160                3165

Leu Ile  Gly Arg Ile Gly Met  Asp Gly Ser Ser Arg  Ser Val Ile
    3170                3175                3180

Val Asp  Thr Lys Ile Thr Trp  Pro Asn Gly Leu Thr  Leu Asp Tyr
    3185                3190                3195

Val Thr  Glu Arg Ile Tyr Trp  Ala Asp Ala Arg Glu  Asp Tyr Ile
    3200                3205                3210
```

```
Glu Phe  Ala Ser Leu Asp Gly  Ser Asn Arg His Val  Val Leu Ser
    3215                 3220                 3225

Gln Asp  Ile Pro His Ile Phe  Ala Leu Thr Leu Phe  Glu Asp Tyr
    3230                 3235                 3240

Val Tyr  Trp Thr Asp Trp Glu  Thr Lys Ser Ile Asn  Arg Ala His
    3245                 3250                 3255

Lys Thr  Thr Gly Thr Asn Lys  Thr Leu Leu Ile Ser  Thr Leu His
    3260                 3265                 3270

Arg Pro  Met Asp Leu His Val  Phe His Ala Leu Arg  Gln Pro Asp
    3275                 3280                 3285

Val Pro  Asn His Pro Cys Lys  Val Asn Asn Gly Gly  Cys Ser Asn
    3290                 3295                 3300

Leu Cys  Leu Leu Ser Pro Gly  Gly Gly His Lys Cys  Ala Cys Pro
    3305                 3310                 3315

Thr Asn  Phe Tyr Leu Gly Ser  Asp Gly Arg Thr Cys  Val Ser Asn
    3320                 3325                 3330

Cys Thr  Ala Ser Gln Phe Val  Cys Lys Asn Asp Lys  Cys Ile Pro
    3335                 3340                 3345

Phe Trp  Trp Lys Cys Asp Thr  Glu Asp Asp Cys Gly  Asp His Ser
    3350                 3355                 3360

Asp Glu  Pro Pro Asp Cys Pro  Glu Phe Lys Cys Arg  Pro Gly Gln
    3365                 3370                 3375

Phe Gln  Cys Ser Thr Gly Ile  Cys Thr Asn Pro Ala  Phe Ile Cys
    3380                 3385                 3390

Asp Gly  Asp Asn Asp Cys Gln  Asp Asn Ser Asp Glu  Ala Asn Cys
    3395                 3400                 3405

Asp Ile  His Val Cys Leu Pro  Ser Gln Phe Lys Cys  Thr Asn Thr
    3410                 3415                 3420

Asn Arg  Cys Ile Pro Gly Ile  Phe Arg Cys Asn Gly  Gln Asp Asn
    3425                 3430                 3435

Cys Gly  Asp Gly Glu Asp Glu  Arg Asp Cys Pro Glu  Val Thr Cys
    3440                 3445                 3450

Ala Pro  Asn Gln Phe Gln Cys  Ser Ile Thr Lys Arg  Cys Ile Pro
    3455                 3460                 3465

Arg Val  Trp Val Cys Asp Arg  Asp Asn Asp Cys Val  Asp Gly Ser
    3470                 3475                 3480

Asp Glu  Pro Ala Asn Cys Thr  Gln Met Thr Cys Gly  Val Asp Glu
    3485                 3490                 3495

Phe Arg  Cys Lys Asp Ser Gly  Arg Cys Ile Pro Ala  Arg Trp Lys
    3500                 3505                 3510

Cys Asp  Gly Glu Asp Asp Cys  Gly Asp Gly Ser Asp  Glu Pro Lys
    3515                 3520                 3525

Glu Glu  Cys Asp Glu Arg Thr  Cys Glu Pro Tyr Gln  Phe Arg Cys
    3530                 3535                 3540

Lys Asn  Asn Arg Cys Val Pro  Gly Arg Trp Gln Cys  Asp Tyr Asp
    3545                 3550                 3555

Asn Asp  Cys Gly Asp Asn Ser  Asp Glu Glu Ser Cys  Thr Pro Arg
    3560                 3565                 3570

Pro Cys  Ser Glu Ser Glu Phe  Ser Cys Ala Asn Gly  Arg Cys Ile
    3575                 3580                 3585

Ala Gly  Arg Trp Lys Cys Asp  Gly Asp His Asp Cys  Ala Asp Gly
    3590                 3595                 3600
```

-continued

```
Ser Asp  Glu Lys Asp Cys Thr  Pro Arg Cys Asp Met  Asp Gln Phe
    3605                 3610                 3615

Gln Cys  Lys Ser Gly His Cys  Ile Pro Leu Arg Trp  Arg Cys Asp
    3620                 3625                 3630

Ala Asp  Ala Asp Cys Met Asp  Gly Ser Asp Glu Glu  Ala Cys Gly
    3635                 3640                 3645

Thr Gly  Val Arg Thr Cys Pro  Leu Asp Glu Phe Gln  Cys Asn Asn
    3650                 3655                 3660

Thr Leu  Cys Lys Pro Leu Ala  Trp Lys Cys Asp Gly  Glu Asp Asp
    3665                 3670                 3675

Cys Gly  Asp Asn Ser Asp Glu  Asn Pro Glu Glu Cys  Ala Arg Phe
    3680                 3685                 3690

Val Cys  Pro Pro Asn Arg Pro  Phe Arg Cys Lys Asn  Asp Arg Val
    3695                 3700                 3705

Cys Leu  Trp Ile Gly Arg Gln  Cys Asp Gly Met Asp  Asn Cys Gly
    3710                 3715                 3720

Asp Gly  Thr Asp Glu Glu Asp  Cys Glu Pro Pro Thr  Ala Gln Thr
    3725                 3730                 3735

Thr His  Cys Lys Asp Lys Lys  Glu Phe Leu Cys Arg  Asn Gln Arg
    3740                 3745                 3750

Cys Leu  Ser Ser Ser Leu Arg  Cys Asn Met Phe Asp  Asp Cys Gly
    3755                 3760                 3765

Asp Gly  Ser Asp Glu Glu Asp  Cys Ser Ile Asp Pro  Lys Leu Thr
    3770                 3775                 3780

Ser Cys  Ala Thr Asn Ala Ser  Ile Cys Gly Asp Glu  Ala Arg Cys
    3785                 3790                 3795

Val Arg  Thr Glu Lys Ala Ala  Tyr Cys Ala Cys Arg  Ser Gly Phe
    3800                 3805                 3810

His Thr  Val Pro Gly Gln Pro  Gly Cys Gln Asp Ile  Asn Glu Cys
    3815                 3820                 3825

Leu Arg  Phe Gly Thr Cys Ser  Gln Leu Cys Asn Asn  Thr Lys Gly
    3830                 3835                 3840

Gly His  Leu Cys Ser Cys Ala  Arg Asn Phe Met Lys  Thr His Asn
    3845                 3850                 3855

Thr Cys  Lys Ala Glu Gly Ser  Glu Tyr Gln Val Leu  Tyr Ile Ala
    3860                 3865                 3870

Asp Asp  Asn Glu Ile Arg Ser  Leu Phe Pro Gly His  Pro His Ser
    3875                 3880                 3885

Ala Tyr  Glu Gln Ala Phe Gln  Gly Asp Glu Ser Val  Arg Ile Asp
    3890                 3895                 3900

Ala Met  Asp Val His Val Lys  Ala Gly Arg Val Tyr  Trp Thr Asn
    3905                 3910                 3915

Trp His  Thr Gly Thr Ile Ser  Tyr Arg Ser Leu Pro  Pro Ala Ala
    3920                 3925                 3930

Pro Pro  Thr Thr Ser Asn Arg  His Arg Arg Gln Ile  Asp Arg Gly
    3935                 3940                 3945

Val Thr  His Leu Asn Ile Ser  Gly Leu Lys Met Pro  Arg Gly Ile
    3950                 3955                 3960

Ala Ile  Asp Trp Val Ala Gly  Asn Val Tyr Trp Thr  Asp Ser Gly
    3965                 3970                 3975

Arg Asp  Val Ile Glu Val Ala  Gln Met Lys Gly Glu  Asn Arg Lys
    3980                 3985                 3990

Thr Leu  Ile Ser Gly Met Ile  Asp Glu Pro His Ala  Ile Val Val
```

```
    3995                4000                4005

Asp Pro  Leu Arg Gly Thr Met  Tyr Trp Ser Asp Trp  Gly Asn His
    4010                4015                4020

Pro Lys  Ile Glu Thr Ala Ala  Met Asp Gly Thr Leu  Arg Glu Thr
    4025                4030                4035

Leu Val  Gln Asp Asn Ile Gln  Trp Pro Thr Gly Leu  Ala Val Asp
    4040                4045                4050

Tyr His  Asn Glu Arg Leu Tyr  Trp Ala Asp Ala Lys  Leu Ser Val
    4055                4060                4065

Ile Gly  Ser Ile Arg Leu Asn  Gly Thr Asp Pro Ile  Val Ala Ala
    4070                4075                4080

Asp Ser  Lys Arg Gly Leu Ser  His Pro Phe Ser Ile  Asp Val Phe
    4085                4090                4095

Glu Asp  Tyr Ile Tyr Gly Val  Thr Tyr Ile Asn Asn  Arg Val Phe
    4100                4105                4110

Lys Ile  His Lys Phe Gly His  Ser Pro Leu Val Asn  Leu Thr Gly
    4115                4120                4125

Gly Leu  Ser His Ala Ser Asp  Val Val Leu Tyr His  Gln His Lys
    4130                4135                4140

Gln Pro  Glu Val Thr Asn Pro  Cys Asp Arg Lys Lys  Cys Glu Trp
    4145                4150                4155

Leu Cys  Leu Leu Ser Pro Ser  Gly Pro Val Cys Thr  Cys Pro Asn
    4160                4165                4170

Gly Lys  Arg Leu Asp Asn Gly  Thr Cys Val Pro Val  Pro Ser Pro
    4175                4180                4185

Thr Pro  Pro Pro Asp Ala Pro  Arg Pro Gly Thr Cys  Asn Leu Gln
    4190                4195                4200

Cys Phe  Asn Gly Gly Ser Cys  Phe Leu Asn Ala Arg  Arg Gln Pro
    4205                4210                4215

Lys Cys  Arg Cys Gln Pro Arg  Tyr Thr Gly Asp Lys  Cys Glu Leu
    4220                4225                4230

Asp Gln  Cys Trp Glu His Cys  Arg Asn Gly Gly Thr  Cys Ala Ala
    4235                4240                4245

Ser Pro  Ser Gly Met Pro Thr  Cys Arg Cys Pro Thr  Gly Phe Thr
    4250                4255                4260

Gly Pro  Lys Cys Thr Gln Gln  Val Cys Ala Gly Tyr  Cys Ala Asn
    4265                4270                4275

Asn Ser  Thr Cys Thr Val Asn  Gln Gly Asn Gln Pro  Gln Cys Arg
    4280                4285                4290

Cys Leu  Pro Gly Phe Leu Gly  Asp Arg Cys Gln Tyr  Arg Gln Cys
    4295                4300                4305

Ser Gly  Tyr Cys Glu Asn Phe  Gly Thr Cys Gln Met  Ala Ala Asp
    4310                4315                4320

Gly Ser  Arg Gln Cys Arg Cys  Thr Ala Tyr Phe Glu  Gly Leu Arg
    4325                4330                4335

Cys Glu  Val Asn Lys Cys Ser  Arg Cys Leu Glu Gly  Ala Cys Val
    4340                4345                4350

Val Asn  Lys Gln Ser Gly Asp  Val Thr Cys Asn Cys  Thr Asp Gly
    4355                4360                4365

Arg Val  Ala Pro Ser Cys Leu  Thr Cys Ile Gly His  Cys Ser Asn
    4370                4375                4380

Gly Gly  Ser Cys Thr Met Asn  Ser Lys Met Met Pro  Glu Cys Gln
    4385                4390                4395
```

```
Cys Pro  Pro His Met Thr Gly  Pro Arg Cys Glu Glu  His Val Phe
    4400                 4405                 4410

Ser Gln  Gln Gln Pro Gly His  Ile Ala Ser Ile Leu  Ile Pro Leu
    4415                 4420                 4425

Leu Leu  Leu Leu Leu Val Leu  Leu Val Ala Gly Val  Val Phe Trp
    4430                 4435                 4440

Tyr Lys  Arg Arg Val Gln Gly  Ala Lys Gly Phe Gln  His Gln Arg
    4445                 4450                 4455

Met Thr  Asn Gly Ala Met Asn  Val Glu Ile Gly Asn  Pro Thr Tyr
    4460                 4465                 4470

Lys Met  Tyr Glu Gly Gly Glu  Pro Asp Asp Val Gly  Gly Leu Leu
    4475                 4480                 4485

Asp Ala  Asp Phe Ala Leu Asp  Pro Asp Lys Pro Thr  Asn Phe Thr
    4490                 4495                 4500

Asn Pro  Val Tyr Ala Thr Leu  Tyr Met Gly Gly His  Gly Ser Arg
    4505                 4510                 4515

His Ser  Leu Ala Ser Thr Asp  Glu Lys Arg Glu Leu  Leu Gly Arg
    4520                 4525                 4530

Gly Pro  Glu Asp Glu Ile Gly  Asp Pro Leu Ala
    4535                 4540


<210> SEQ ID NO 4
<211> LENGTH: 4545
<212> TYPE: PRT
<213> ORGANISM: Rattus norvegicus

<400> SEQUENCE: 4

Met Leu Thr Pro Pro Leu Leu Leu Leu Leu Pro Leu Leu Ser Ala Leu
1               5                   10                  15

Val Ala Gly Ala Thr Met Asp Ala Pro Lys Thr Cys Ser Pro Lys Gln
            20                  25                  30

Phe Ala Cys Arg Asp Gln Ile Thr Cys Ile Ser Lys Gly Trp Arg Cys
        35                  40                  45

Asp Gly Glu Arg Asp Cys Pro Asp Gly Ser Asp Glu Ala Pro Glu Ile
    50                  55                  60

Cys Pro Gln Ser Lys Ala Gln Arg Cys Pro Pro Asn Glu His Ser Cys
65                  70                  75                  80

Leu Gly Thr Glu Leu Cys Val Pro Met Ser Arg Leu Cys Asn Gly Ile
                85                  90                  95

Gln Asp Cys Met Asp Gly Ser Asp Glu Gly Ala His Cys Arg Glu Leu
            100                 105                 110

Arg Val Asn Cys Ser Arg Met Gly Cys Gln His His Cys Val Pro Thr
        115                 120                 125

Pro Ser Gly Pro Thr Cys Tyr Cys Asn Asn Ser Phe Gln Leu Gln Ala
    130                 135                 140

Asp Gly Lys Thr Cys Lys Asp Phe Asp Glu Cys Ser Val Tyr Gly Thr
145                 150                 155                 160

Cys Ser Gln Leu Cys Thr Asn Thr Asp Gly Ser Phe Thr Cys Gly Cys
                165                 170                 175

Val Glu Gly Tyr Leu Leu Gln Pro Asp Asn Arg Ser Cys Lys Ala Lys
            180                 185                 190

Asn Glu Pro Val Asp Arg Pro Pro Val Leu Leu Ile Ala Asn Ser Gln
        195                 200                 205

Asn Ile Leu Ala Thr Tyr Leu Ser Gly Ala Gln Val Ser Thr Ile Thr
```

```
    210                 215                 220

Pro Thr Ser Thr Arg Gln Thr Thr Ala Met Asp Phe Ser Tyr Ala Asn
225                 230                 235                 240

Glu Thr Val Cys Trp Val His Val Gly Asp Ser Ala Ala Gln Thr Gln
                245                 250                 255

Leu Lys Cys Ala Arg Met Pro Ser Leu Lys Gly Phe Val Asp Glu His
            260                 265                 270

Thr Ile Asn Ile Ser Leu Ser Leu His His Val Glu Gln Met Ala Ile
        275                 280                 285

Asp Trp Leu Thr Gly Asn Phe Tyr Phe Val Asp Asp Ile Asp Asp Arg
    290                 295                 300

Ile Phe Val Cys Asn Arg Asn Gly Asp Thr Cys Val Thr Leu Leu Asp
305                 310                 315                 320

Leu Glu Leu Tyr Asn Pro Lys Gly Ile Ala Leu Asp Pro Ala Met Gly
                325                 330                 335

Lys Val Phe Phe Thr Asp Tyr Gly Gln Ile Pro Lys Val Glu Arg Cys
            340                 345                 350

Asp Met Asp Gly Gln Asn Arg Thr Lys Leu Val Asp Ser Lys Ile Val
        355                 360                 365

Phe Pro His Gly Ile Thr Leu Asp Leu Val Ser Arg Leu Val Tyr Trp
    370                 375                 380

Ala Asp Ala Tyr Leu Asp Tyr Ile Glu Val Val Asp Tyr Glu Gly Lys
385                 390                 395                 400

Gly Arg Gln Thr Ile Ile Gln Gly Ile Leu Ile Glu His Leu Tyr Gly
                405                 410                 415

Leu Thr Val Phe Glu Asn Tyr Leu Tyr Ala Thr Asn Ser Asp Asn Ala
            420                 425                 430

Asn Thr Gln Gln Lys Thr Ser Val Ile Arg Val Asn Arg Phe Asn Ser
        435                 440                 445

Thr Glu Tyr Gln Val Val Thr Arg Val Asp Lys Gly Gly Ala Leu His
    450                 455                 460

Ile Tyr His Gln Arg Arg Gln Pro Arg Val Arg Ser His Ala Cys Glu
465                 470                 475                 480

Asn Asp Gln Tyr Gly Lys Pro Gly Gly Cys Ser Asp Ile Cys Leu Leu
                485                 490                 495

Ala Asn Ser His Lys Ala Arg Thr Cys Arg Cys Arg Ser Gly Phe Ser
            500                 505                 510

Leu Gly Ser Asp Gly Lys Ser Cys Lys Lys Pro Glu His Glu Leu Phe
        515                 520                 525

Leu Val Tyr Gly Lys Gly Arg Pro Gly Ile Ile Arg Gly Met Asp Met
    530                 535                 540

Gly Ala Lys Val Pro Asp Glu His Met Ile Pro Ile Glu Asn Leu Met
545                 550                 555                 560

Asn Pro Arg Ala Leu Asp Phe His Ala Glu Thr Gly Phe Ile Tyr Phe
                565                 570                 575

Ala Asp Thr Thr Ser Tyr Leu Ile Gly Arg Gln Lys Ile Asp Gly Thr
            580                 585                 590

Glu Arg Glu Thr Ile Leu Lys Asp Gly Ile His Asn Val Glu Gly Val
        595                 600                 605

Ala Val Asp Trp Met Gly Asp Asn Leu Tyr Trp Thr Asp Asp Gly Pro
    610                 615                 620

Lys Lys Thr Ile Ser Val Ala Arg Leu Glu Lys Ala Ala Gln Thr Arg
625                 630                 635                 640
```

```
Lys Thr Leu Ile Glu Gly Lys Met Thr His Pro Arg Ala Ile Val Val
                645                 650                 655

Asp Pro Leu Asn Gly Trp Met Tyr Trp Thr Asp Trp Glu Glu Asp Pro
            660                 665                 670

Lys Asp Ser Arg Arg Gly Arg Leu Glu Arg Ala Trp Met Asp Gly Ser
        675                 680                 685

His Arg Asp Ile Phe Val Thr Ser Lys Thr Val Leu Trp Pro Asn Gly
    690                 695                 700

Leu Ser Leu Asp Ile Pro Ala Gly Arg Leu Tyr Trp Val Asp Ala Phe
705                 710                 715                 720

Tyr Asp Arg Ile Glu Thr Ile Leu Leu Asn Gly Thr Asp Arg Lys Ile
                725                 730                 735

Val Tyr Glu Gly Pro Glu Leu Asn His Ala Phe Gly Leu Cys His His
            740                 745                 750

Gly Asn Tyr Leu Phe Trp Thr Glu Tyr Arg Ser Gly Ser Val Tyr Arg
        755                 760                 765

Leu Glu Arg Gly Val Ala Gly Ala Gln Pro Thr Val Thr Leu Leu Arg
    770                 775                 780

Ser Glu Arg Pro Pro Ile Phe Glu Ile Arg Met Tyr Asp Ala Gln Gln
785                 790                 795                 800

Gln Gln Val Gly Thr Asn Lys Cys Arg Val Asn Asn Gly Gly Cys Ser
                805                 810                 815

Ser Leu Cys Leu Ala Thr Pro Gly Ser Arg Gln Cys Ala Cys Ala Glu
            820                 825                 830

Asp Gln Val Leu Asp Ala Asp Gly Val Thr Cys Leu Ala Asn Pro Ser
        835                 840                 845

Tyr Val Pro Pro Pro Gln Cys Gln Pro Gly Glu Phe Ala Cys Ala Asn
    850                 855                 860

Asn Arg Cys Ile Gln Glu Arg Trp Lys Cys Asp Gly Asp Asn Asp Cys
865                 870                 875                 880

Leu Asp Asn Ser Asp Glu Ala Pro Ala Leu Cys His Gln His Thr Cys
                885                 890                 895

Pro Ser Asp Arg Phe Lys Cys Glu Asn Asn Arg Cys Ile Pro Asn Arg
            900                 905                 910

Trp Leu Cys Asp Gly Asp Asn Asp Cys Gly Asn Ser Glu Asp Glu Ser
        915                 920                 925

Asn Ala Thr Cys Ser Ala Arg Thr Cys Pro Pro Asn Gln Phe Ser Cys
    930                 935                 940

Ala Ser Gly Arg Cys Ile Pro Ile Ser Trp Thr Cys Asp Leu Asp Asp
945                 950                 955                 960

Asp Cys Gly Asp Arg Ser Asp Glu Ser Ala Ser Cys Ala Tyr Pro Thr
                965                 970                 975

Cys Phe Pro Leu Thr Gln Phe Thr Cys Asn Asn Gly Arg Cys Ile Asn
            980                 985                 990

Ile Asn Trp Arg Cys Asp Asn Asp  Asn Asp Cys Gly Asp  Asn Ser Asp
        995                 1000                 1005

Glu Ala  Gly Cys Ser His Ser  Cys Ser Ser Thr Gln  Phe Lys Cys
    1010                 1015                 1020

Asn Ser  Gly Arg Cys Ile Pro  Glu His Trp Thr Cys  Asp Gly Asp
    1025                 1030                 1035

Asn Asp  Cys Gly Asp Tyr Ser  Asp Glu Thr His Ala  Asn Cys Thr
    1040                 1045                 1050
```

-continued

```
Asn Gln  Ala Thr Arg Pro Pro  Gly Gly Cys His Ser  Asp Glu Phe
    1055                 1060                 1065

Gln Cys  Arg Leu Asp Gly Leu  Cys Ile Pro Leu Arg  Trp Arg Cys
    1070                 1075                 1080

Asp Gly  Asp Thr Asp Cys Met  Asp Ser Ser Asp Glu  Lys Gly Cys
    1085                 1090                 1095

Glu Gly  Val Thr His Val Cys  Asp Pro Asn Val Lys  Phe Gly Cys
    1100                 1105                 1110

Lys Asp  Ser Ala Arg Cys Ile  Ser Lys Ala Trp Val  Cys Asp Gly
    1115                 1120                 1125

Asp Ser  Asp Cys Glu Asp Asn  Ser Asp Glu Glu Asn  Cys Glu Ala
    1130                 1135                 1140

Leu Ala  Cys Arg Pro Pro Ser  His Pro Cys Ala Asn  Asn Thr Ser
    1145                 1150                 1155

Val Cys  Leu Ser Pro Asp Lys  Leu Cys Asp Gly Lys  Asp Asp Cys
    1160                 1165                 1170

Gly Asp  Gly Ser Asp Glu Gly  Glu Leu Cys Asp Gln  Cys Ser Leu
    1175                 1180                 1185

Asn Asn  Gly Gly Cys Ser His  Asn Cys Ser Val Ala  Pro Gly Glu
    1190                 1195                 1200

Gly Ile  Val Cys Ser Cys Pro  Leu Gly Met Glu Leu  Gly Pro Asp
    1205                 1210                 1215

Asn His  Thr Cys Gln Ile Gln  Ser Tyr Cys Ala Lys  His Leu Lys
    1220                 1225                 1230

Cys Ser  Gln Lys Cys Asp Gln  Asn Lys Phe Ser Val  Lys Cys Ser
    1235                 1240                 1245

Cys Tyr  Glu Gly Trp Val Leu  Glu Pro Asp Gly Glu  Ser Cys Arg
    1250                 1255                 1260

Ser Leu  Asp Pro Phe Lys Pro  Phe Ile Ile Phe Ser  Asn Arg His
    1265                 1270                 1275

Glu Ile  Arg Arg Ile Asp Leu  His Lys Gly Asp Tyr  Ser Val Leu
    1280                 1285                 1290

Val Pro  Gly Leu Arg Asn Thr  Ile Ala Leu Asp Phe  His Leu Ser
    1295                 1300                 1305

Gln Ser  Ala Leu Tyr Trp Thr  Asp Val Val Glu Asp  Lys Ile Tyr
    1310                 1315                 1320

Arg Gly  Lys Leu Leu Asp Asn  Gly Ala Leu Thr Ser  Phe Glu Val
    1325                 1330                 1335

Val Ile  Gln Tyr Gly Leu Ala  Thr Pro Glu Gly Leu  Ala Val Asp
    1340                 1345                 1350

Trp Ile  Ala Gly Asn Ile Tyr  Trp Val Glu Ser Asn  Leu Asp Gln
    1355                 1360                 1365

Ile Glu  Val Ala Lys Leu Asp  Gly Thr Leu Arg Thr  Thr Leu Leu
    1370                 1375                 1380

Ala Gly  Asp Ile Glu His Pro  Arg Ala Ile Ala Leu  Asp Pro Arg
    1385                 1390                 1395

Asp Gly  Ile Leu Phe Trp Thr  Asp Trp Asp Ala Ser  Leu Pro Arg
    1400                 1405                 1410

Ile Glu  Ala Ala Ser Met Ser  Gly Ala Gly Arg Arg  Thr Ile His
    1415                 1420                 1425

Arg Glu  Thr Gly Ser Gly Gly  Trp Pro Asn Gly Leu  Thr Val Asp
    1430                 1435                 1440

Tyr Leu  Glu Lys Arg Ile Leu  Trp Ile Asp Ala Arg  Ser Asp Ala
```

```
    1445                1450                1455

Ile Tyr  Ser Ala Arg Tyr Asp  Gly Ser Gly His Met  Glu Val Leu
    1460                1465                1470

Arg Gly  His Glu Phe Leu Ser  His Pro Phe Ala Val  Thr Leu Tyr
    1475                1480                1485

Gly Gly  Glu Val Tyr Trp Thr  Asp Trp Arg Thr Asn  Thr Leu Ala
    1490                1495                1500

Lys Ala  Asn Lys Trp Thr Gly  His Asn Val Thr Val  Val Gln Arg
    1505                1510                1515

Thr Asn  Thr Gln Pro Phe Asp  Leu Gln Val Tyr His  Pro Ser Arg
    1520                1525                1530

Gln Pro  Met Ala Pro Asn Pro  Cys Glu Ala Asn Gly  Gly Arg Gly
    1535                1540                1545

Pro Cys  Ser His Leu Cys Leu  Ile Asn Tyr Asn Arg  Thr Val Ser
    1550                1555                1560

Cys Ala  Cys Pro His Leu Met  Lys Leu His Asn Asp  Asn Thr Thr
    1565                1570                1575

Cys Tyr  Glu Phe Lys Lys Phe  Leu Leu Tyr Ala Arg  Gln Met Glu
    1580                1585                1590

Ile Arg  Gly Val Asp Leu Asp  Ala Pro Tyr Tyr Asn  Tyr Ile Ile
    1595                1600                1605

Ser Phe  Thr Val Pro Asp Ile  Asp Asn Val Thr Val  Leu Asp Tyr
    1610                1615                1620

Asp Ala  Arg Glu Gln Arg Val  Tyr Trp Ser Asp Val  Arg Thr Gln
    1625                1630                1635

Ala Ile  Lys Arg Ala Phe Ile  Asn Gly Thr Gly Val  Glu Thr Val
    1640                1645                1650

Val Ser  Ala Asp Leu Pro Asn  Ala His Gly Leu Ala  Val Asp Trp
    1655                1660                1665

Val Ser  Arg Asn Leu Phe Trp  Thr Ser Tyr Asp Thr  Asn Lys Lys
    1670                1675                1680

Gln Ile  Asn Val Ala Arg Leu  Asp Gly Ser Phe Lys  Asn Ala Val
    1685                1690                1695

Val Gln  Gly Leu Glu Gln Pro  His Gly Leu Val Val  His Pro Leu
    1700                1705                1710

Arg Gly  Lys Leu Tyr Trp Thr  Asp Gly Asp Asn Ile  Ser Met Val
    1715                1720                1725

Asn Met  Asp Gly Ser Asn Arg  Thr Leu Leu Phe Ser  Gly Gln Lys
    1730                1735                1740

Gly Pro  Val Gly Leu Ala Ile  Asp Phe Pro Glu Ser  Lys Leu Tyr
    1745                1750                1755

Trp Ile  Ser Ser Gly Asn His  Thr Ile Asn Arg Cys  Asn Leu Asp
    1760                1765                1770

Gly Ser  Glu Leu Glu Val Ile  Asp Thr Met Arg Ser  Gln Leu Gly
    1775                1780                1785

Lys Ala  Thr Ala Leu Ala Ile  Met Gly Asp Lys Leu  Trp Trp Ala
    1790                1795                1800

Asp Gln  Val Ser Glu Lys Met  Gly Thr Cys Asn Lys  Ala Asp Gly
    1805                1810                1815

Ser Gly  Ser Val Val Leu Arg  Asn Ser Thr Thr Leu  Val Met His
    1820                1825                1830

Met Lys  Val Tyr Asp Glu Ser  Ile Gln Leu Glu His  Glu Gly Thr
    1835                1840                1845
```

```
Asn Pro  Cys Ser Val Asn Asn  Gly Asp Cys Ser Gln  Leu Cys Leu
    1850                 1855                 1860

Pro Thr  Ser Glu Thr Thr Arg  Ser Cys Met Cys Thr  Ala Gly Tyr
    1865                 1870                 1875

Ser Leu  Arg Ser Gly Gln Gln  Ala Cys Glu Gly Val  Gly Ser Phe
    1880                 1885                 1890

Leu Leu  Tyr Ser Val His Glu  Gly Ile Arg Gly Ile  Pro Leu Asp
    1895                 1900                 1905

Pro Asn  Asp Lys Ser Asp Ala  Leu Val Pro Val Ser  Gly Thr Ser
    1910                 1915                 1920

Leu Ala  Val Gly Ile Asp Phe  His Ala Glu Asn Asp  Thr Ile Tyr
    1925                 1930                 1935

Trp Val  Asp Met Gly Leu Ser  Thr Ile Ser Arg Ala  Lys Arg Asp
    1940                 1945                 1950

Gln Thr  Trp Arg Glu Asp Val  Val Thr Asn Gly Ile  Gly Arg Val
    1955                 1960                 1965

Glu Gly  Ile Ala Val Asp Trp  Ile Ala Gly Asn Ile  Tyr Trp Thr
    1970                 1975                 1980

Asp Gln  Gly Phe Asp Val Ile  Glu Val Ala Arg Leu  Asn Gly Ser
    1985                 1990                 1995

Phe Arg  Tyr Val Val Ile Ser  Gln Gly Leu Asp Lys  Pro Arg Ala
    2000                 2005                 2010

Ile Thr  Val His Pro Glu Lys  Gly Tyr Leu Phe Trp  Thr Glu Trp
    2015                 2020                 2025

Gly His  Tyr Pro Arg Ile Glu  Arg Ser Arg Leu Asp  Gly Thr Glu
    2030                 2035                 2040

Arg Val  Val Leu Val Asn Val  Ser Ile Ser Trp Pro  Asn Gly Ile
    2045                 2050                 2055

Ser Val  Asp Tyr Gln Gly Gly  Lys Leu Tyr Trp Cys  Asp Ala Arg
    2060                 2065                 2070

Met Asp  Lys Ile Glu Arg Ile  Asp Leu Glu Thr Gly  Glu Asn Arg
    2075                 2080                 2085

Glu Val  Val Leu Ser Ser Asn  Asn Met Asp Met Phe  Ser Val Ser
    2090                 2095                 2100

Val Phe  Glu Asp Phe Ile Tyr  Trp Ser Asp Arg Thr  His Ala Asn
    2105                 2110                 2115

Gly Ser  Ile Lys Arg Gly Cys  Lys Asp Asn Ala Thr  Asp Ser Val
    2120                 2125                 2130

Pro Leu  Arg Thr Gly Ile Gly  Val Gln Leu Lys Asp  Ile Lys Val
    2135                 2140                 2145

Phe Asn  Arg Asp Arg Gln Lys  Gly Thr Asn Val Cys  Ala Val Ala
    2150                 2155                 2160

Asn Gly  Gly Cys Gln Gln Leu  Cys Leu Tyr Arg Gly  Gly Gly Gln
    2165                 2170                 2175

Arg Ala  Cys Ala Cys Ala His  Gly Met Leu Ala Glu  Asp Gly Ala
    2180                 2185                 2190

Ser Cys  Arg Glu Tyr Ala Gly  Tyr Leu Leu Tyr Ser  Glu Arg Thr
    2195                 2200                 2205

Ile Leu  Lys Ser Ile His Leu  Ser Asp Glu Arg Asn  Leu Asn Ala
    2210                 2215                 2220

Pro Val  Gln Pro Phe Glu Asp  Pro Glu His Met Lys  Asn Val Ile
    2225                 2230                 2235
```

```
Ala Leu Ala Phe Asp Tyr Arg Ala Gly Thr Ser Pro Gly Thr Pro
    2240                2245                2250

Asn Arg Ile Phe Phe Ser Asp Ile His Phe Gly Asn Ile Gln Gln
    2255                2260                2265

Ile Asn Asp Asp Gly Ser Gly Arg Thr Thr Ile Val Glu Asn Val
    2270                2275                2280

Gly Ser Val Glu Gly Leu Ala Tyr His Arg Gly Trp Asp Thr Leu
    2285                2290                2295

Tyr Trp Thr Ser Tyr Thr Thr Ser Thr Ile Thr Arg His Thr Val
    2300                2305                2310

Asp Gln Thr Arg Pro Gly Ala Phe Glu Arg Glu Thr Val Ile Thr
    2315                2320                2325

Met Ser Gly Asp Asp His Pro Arg Ala Phe Val Leu Asp Glu Cys
    2330                2335                2340

Gln Asn Leu Met Phe Trp Thr Asn Trp Asn Glu Leu His Pro Ser
    2345                2350                2355

Ile Met Arg Ala Ala Leu Ser Gly Ala Asn Val Leu Thr Leu Ile
    2360                2365                2370

Glu Lys Asp Ile Arg Thr Pro Asn Gly Leu Ala Ile Asp His Arg
    2375                2380                2385

Ala Glu Lys Leu Tyr Phe Ser Asp Ala Thr Leu Asp Lys Ile Glu
    2390                2395                2400

Arg Cys Glu Tyr Asp Gly Ser His Arg Tyr Val Ile Leu Lys Ser
    2405                2410                2415

Glu Pro Val His Pro Phe Gly Leu Ala Val Tyr Gly Glu His Ile
    2420                2425                2430

Phe Trp Thr Asp Trp Val Arg Arg Ala Val Gln Arg Ala Asn Lys
    2435                2440                2445

Tyr Val Gly Ser Asp Met Lys Leu Leu Arg Val Asp Ile Pro Gln
    2450                2455                2460

Gln Pro Met Gly Ile Ile Ala Val Ala Asn Asp Thr Asn Ser Cys
    2465                2470                2475

Glu Leu Ser Pro Cys Arg Ile Asn Asn Gly Gly Cys Gln Asp Leu
    2480                2485                2490

Cys Leu Leu Thr His Gln Gly His Val Asn Cys Ser Cys Arg Gly
    2495                2500                2505

Gly Arg Ile Leu Gln Glu Asp Phe Thr Cys Arg Ala Met Asn Ser
    2510                2515                2520

Ser Cys Arg Ala Gln Asp Glu Phe Glu Cys Ala Asn Gly Glu Cys
    2525                2530                2535

Ile Ser Phe Ser Leu Thr Cys Asp Gly Val Ser His Cys Lys Asp
    2540                2545                2550

Lys Ser Asp Glu Lys Pro Ser Tyr Cys Asn Ser Arg Arg Cys Lys
    2555                2560                2565

Lys Thr Phe Arg Gln Cys Asn Asn Gly Arg Cys Val Ser Asn Met
    2570                2575                2580

Leu Trp Cys Asn Gly Val Asp Asp Cys Gly Asp Gly Ser Asp Glu
    2585                2590                2595

Ile Pro Cys Asn Lys Thr Ala Cys Gly Val Gly Glu Phe Arg Cys
    2600                2605                2610

Arg Asp Gly Ser Cys Ile Gly Asn Ser Ser Arg Cys Asn Gln Phe
    2615                2620                2625

Val Asp Cys Glu Asp Ala Ser Asp Glu Met Asn Cys Ser Ala Thr
```

```
    2630                2635                2640

Asp Cys  Ser Ser Tyr Phe Arg  Leu Gly Val Lys Gly  Val Leu Phe
    2645                2650                2655

Gln Pro  Cys Glu Arg Thr Ser  Leu Cys Tyr Ala Pro  Ser Trp Val
    2660                2665                2670

Cys Asp  Gly Ala Asn Asp Cys  Gly Asp Tyr Ser Asp  Glu Arg Asp
    2675                2680                2685

Cys Pro  Gly Val Lys Arg Pro  Arg Cys Pro Leu Asn  Tyr Phe Ala
    2690                2695                2700

Cys Pro  Ser Gly Arg Cys Ile  Pro Met Ser Trp Thr  Cys Asp Lys
    2705                2710                2715

Glu Asp  Asp Cys Glu Asn Gly  Glu Asp Glu Thr His  Cys Asn Lys
    2720                2725                2730

Phe Cys  Ser Glu Ala Gln Phe  Glu Cys Gln Asn His  Arg Cys Ile
    2735                2740                2745

Ser Lys  Gln Trp Leu Cys Asp  Gly Ser Asp Asp Cys  Gly Asp Gly
    2750                2755                2760

Ser Asp  Glu Ala Ala His Cys  Glu Gly Lys Thr Cys  Gly Pro Ser
    2765                2770                2775

Ser Phe  Ser Cys Pro Gly Thr  His Val Cys Val Pro  Glu Arg Trp
    2780                2785                2790

Leu Cys  Asp Gly Asp Lys Asp  Cys Ala Asp Gly Ala  Asp Glu Ser
    2795                2800                2805

Ile Ser  Ala Gly Cys Leu Tyr  Asn Ser Thr Cys Asp  Asp Arg Glu
    2810                2815                2820

Phe Met  Cys Gln Asn Arg Leu  Cys Ile Pro Lys His  Phe Val Cys
    2825                2830                2835

Asp His  Asp Arg Asp Cys Ala  Asp Gly Ser Asp Glu  Ser Pro Glu
    2840                2845                2850

Cys Glu  Tyr Pro Thr Cys Gly  Pro Asn Glu Phe Arg  Cys Ala Asn
    2855                2860                2865

Gly Arg  Cys Leu Ser Ser Arg  Gln Trp Glu Cys Asp  Gly Glu Asn
    2870                2875                2880

Asp Cys  His Asp His Ser Asp  Glu Ala Pro Lys Asn  Pro His Cys
    2885                2890                2895

Thr Ser  Pro Glu His Lys Cys  Asn Ala Ser Ser Gln  Phe Leu Cys
    2900                2905                2910

Ser Ser  Gly Arg Cys Val Ala  Glu Ala Leu Leu Cys  Asn Gly Gln
    2915                2920                2925

Asp Asp  Cys Gly Asp Gly Ser  Asp Glu Arg Gly Cys  His Val Asn
    2930                2935                2940

Glu Cys  Leu Ser Arg Lys Leu  Ser Gly Cys Ser Gln  Asp Cys Glu
    2945                2950                2955

Asp Leu  Lys Ile Gly Phe Lys  Cys Arg Cys Arg Pro  Gly Phe Arg
    2960                2965                2970

Leu Lys  Asp Asp Gly Arg Thr  Cys Ala Asp Val Asp  Glu Cys Ser
    2975                2980                2985

Thr Thr  Phe Pro Cys Ser Gln  Leu Cys Ile Asn Thr  His Gly Ser
    2990                2995                3000

Tyr Lys  Cys Leu Cys Val Glu  Gly Tyr Ala Pro Arg  Gly Gly Asp
    3005                3010                3015

Pro His  Ser Cys Lys Ala Val  Thr Asp Glu Glu Pro  Phe Leu Ile
    3020                3025                3030
```

```
Phe Ala  Asn Arg Tyr Tyr Leu  Arg Lys Leu Asn Leu  Asp Gly Ser
    3035                 3040                 3045

Asn Tyr  Thr Leu Leu Lys Gln  Gly Leu Asn Asn Ala  Val Ala Leu
    3050                 3055                 3060

Asp Phe  Asp Tyr Arg Gly Gln  Met Ile Tyr Trp Thr  Asp Val Thr
    3065                 3070                 3075

Thr Gln  Gly Ser Met Ile Arg  Arg Met His Leu Asn  Gly Ser Asn
    3080                 3085                 3090

Val Gln  Val Leu His Arg Thr  Gly Leu Ser Asn Pro  Asp Gly Leu
    3095                 3100                 3105

Ala Val  Asp Trp Val Gly Gly  Asn Leu Tyr Trp Cys  Asp Lys Gly
    3110                 3115                 3120

Arg Asp  Thr Ile Glu Val Ser  Lys Leu Asn Gly Ala  Tyr Arg Thr
    3125                 3130                 3135

Val Leu  Val Ser Ser Gly Leu  Arg Glu Pro Arg Ala  Leu Val Val
    3140                 3145                 3150

Asp Val  Gln Asn Gly Tyr Leu  Tyr Trp Thr Asp Trp  Gly Asp His
    3155                 3160                 3165

Ser Leu  Ile Gly Arg Ile Gly  Met Asp Gly Ser Gly  Arg Ser Ile
    3170                 3175                 3180

Ile Val  Asp Thr Lys Ile Thr  Trp Pro Asn Gly Leu  Thr Val Asp
    3185                 3190                 3195

Tyr Val  Thr Glu Arg Ile Tyr  Trp Ala Asp Ala Arg  Glu Asp Tyr
    3200                 3205                 3210

Ile Glu  Phe Ala Ser Leu Asp  Gly Ser Asn Arg His  Val Val Leu
    3215                 3220                 3225

Ser Gln  Asp Ile Pro His Ile  Phe Ala Leu Thr Leu  Phe Glu Asp
    3230                 3235                 3240

Tyr Val  Tyr Trp Thr Asp Trp  Glu Thr Lys Ser Ile  Asn Arg Ala
    3245                 3250                 3255

His Lys  Thr Thr Gly Ala Asn  Lys Thr Leu Leu Ile  Ser Thr Leu
    3260                 3265                 3270

His Arg  Pro Met Asp Leu His  Val Phe His Ala Leu  Arg Gln Pro
    3275                 3280                 3285

Asp Val  Pro Asn His Pro Cys  Lys Val Asn Asn Gly  Gly Cys Ser
    3290                 3295                 3300

Asn Leu  Cys Leu Leu Ser Pro  Gly Gly Gly His Lys  Cys Ala Cys
    3305                 3310                 3315

Pro Thr  Asn Phe Tyr Leu Gly  Gly Asp Gly Arg Thr  Cys Val Ser
    3320                 3325                 3330

Asn Cys  Thr Ala Ser Gln Phe  Val Cys Lys Asn Asp  Lys Cys Ile
    3335                 3340                 3345

Pro Phe  Trp Trp Lys Cys Asp  Thr Glu Asp Asp Cys  Gly Asp His
    3350                 3355                 3360

Ser Asp  Glu Pro Pro Asp Cys  Pro Glu Phe Lys Cys  Arg Pro Gly
    3365                 3370                 3375

Gln Phe  Gln Cys Ser Thr Gly  Ile Cys Thr Asn Pro  Ala Phe Ile
    3380                 3385                 3390

Cys Asp  Gly Asp Asn Asp Cys  Gln Asp Asn Ser Asp  Glu Ala Asn
    3395                 3400                 3405

Cys Asp  Ile His Val Cys Leu  Pro Ser Gln Phe Lys  Cys Thr Asn
    3410                 3415                 3420
```

```
Thr Asn Arg Cys Ile Pro Gly Ile Phe Arg Cys Asn Gly Gln Asp
    3425                3430                3435

Asn Cys Gly Asp Gly Glu Asp Glu Arg Asp Cys Pro Glu Val Thr
    3440                3445                3450

Cys Ala Pro Asn Gln Phe Gln Cys Ser Ile Thr Lys Arg Cys Ile
    3455                3460                3465

Pro Arg Val Trp Val Cys Asp Arg Asp Asn Asp Cys Val Asp Gly
    3470                3475                3480

Ser Asp Glu Pro Ala Asn Cys Thr Gln Met Thr Cys Gly Val Asp
    3485                3490                3495

Glu Phe Arg Cys Lys Asp Ser Gly Arg Cys Ile Pro Ala Arg Trp
    3500                3505                3510

Lys Cys Asp Gly Glu Asp Asp Cys Gly Asp Gly Ser Asp Glu Pro
    3515                3520                3525

Lys Glu Glu Cys Asp Glu Arg Thr Cys Glu Pro Tyr Gln Phe Arg
    3530                3535                3540

Cys Lys Asn Asn Arg Cys Val Pro Gly Arg Trp Gln Cys Asp Tyr
    3545                3550                3555

Asp Asn Asp Cys Gly Asp Asn Ser Asp Glu Glu Ser Cys Thr Pro
    3560                3565                3570

Arg Pro Cys Ser Glu Ser Glu Phe Ser Cys Ala Asn Gly Arg Cys
    3575                3580                3585

Ile Ala Gly Arg Trp Lys Cys Asp Gly Asp His Asp Cys Ala Asp
    3590                3595                3600

Gly Ser Asp Glu Lys Asp Cys Thr Pro Arg Cys Asp Met Asp Gln
    3605                3610                3615

Phe Gln Cys Lys Ser Gly His Cys Ile Pro Leu Arg Trp Arg Cys
    3620                3625                3630

Asp Ala Asp Ala Asp Cys Met Asp Gly Ser Asp Glu Glu Ala Cys
    3635                3640                3645

Gly Thr Gly Val Arg Thr Cys Pro Leu Asp Glu Phe Gln Cys Asn
    3650                3655                3660

Asn Thr Leu Cys Lys Pro Leu Ala Trp Lys Cys Asp Gly Glu Asp
    3665                3670                3675

Asp Cys Gly Asp Asn Ser Asp Glu Asn Pro Glu Glu Cys Thr Arg
    3680                3685                3690

Phe Gln Cys Pro Pro Asn Arg Pro Phe Arg Cys Lys Asn Asp Arg
    3695                3700                3705

Val Cys Leu Trp Ile Gly Arg Gln Cys Asp Gly Thr Asp Asn Cys
    3710                3715                3720

Gly Asp Gly Thr Asp Glu Glu Asp Cys Glu Pro Pro Thr Ala Gln
    3725                3730                3735

Asn Pro His Cys Lys Asp Lys Lys Glu Phe Leu Cys Arg Asn Gln
    3740                3745                3750

Arg Cys Leu Ser Ser Ser Leu Arg Cys Asn Met Phe Asp Asp Cys
    3755                3760                3765

Gly Asp Gly Ser Asp Glu Glu Asp Cys Ser Ile Asp Pro Lys Leu
    3770                3775                3780

Thr Ser Cys Ala Thr Asn Ala Ser Met Cys Gly Asp Glu Ala Arg
    3785                3790                3795

Cys Val Arg Thr Glu Lys Ala Ala Tyr Cys Ala Cys Arg Pro Gly
    3800                3805                3810

Phe His Thr Val Pro Gly Gln Pro Gly Cys Gln Asp Ile Asn Glu
```

```
    3815                3820                3825

Cys Leu  Arg Phe Gly Thr Cys  Ser Gln Leu Cys Asn  Asn Thr Lys
    3830                3835                3840

Gly Gly  His Leu Cys Ser Cys  Ala Arg Asn Phe Met  Lys Thr His
    3845                3850                3855

Asn Thr  Cys Lys Ala Glu Gly  Ser Glu Tyr Gln Val  Leu Tyr Ile
    3860                3865                3870

Ala Asp  Asp Asn Glu Ile Arg  Ser Leu Phe Pro Gly  His Pro His
    3875                3880                3885

Ser Ala  Tyr Glu Gln Ala Phe  Gln Gly Asp Glu Ser  Val Arg Ile
    3890                3895                3900

Asp Ala  Met Asp Val His Val  Lys Ala Gly Arg Val  Tyr Trp Thr
    3905                3910                3915

Asn Trp  His Thr Gly Thr Ile  Ser Tyr Arg Ser Leu  Pro Pro Ala
    3920                3925                3930

Ala Pro  Pro Thr Thr Ser Asn  Arg His Arg Arg Gln  Ile Asp Arg
    3935                3940                3945

Gly Val  Thr His Leu Asn Ile  Ser Gly Leu Lys Met  Pro Arg Gly
    3950                3955                3960

Ile Ala  Ile Asp Trp Val Ala  Gly Asn Val Tyr Trp  Thr Asp Ser
    3965                3970                3975

Gly Arg  Asp Val Ile Glu Val  Ala Gln Met Lys Gly  Glu Asn Arg
    3980                3985                3990

Lys Thr  Leu Ile Ser Gly Met  Ile Asp Glu Pro His  Ala Ile Val
    3995                4000                4005

Val Asp  Pro Leu Arg Gly Thr  Met Tyr Trp Ser Asp  Trp Gly Asn
    4010                4015                4020

His Pro  Lys Ile Glu Thr Ala  Ala Met Asp Gly Thr  Leu Arg Glu
    4025                4030                4035

Thr Leu  Val Gln Asp Asn Ile  Gln Trp Pro Thr Gly  Leu Ala Val
    4040                4045                4050

Asp Tyr  His Asn Glu Arg Leu  Tyr Trp Ala Asp Ala  Lys Leu Ser
    4055                4060                4065

Val Ile  Gly Ser Ile Arg Leu  Asn Gly Thr Asp Pro  Ile Val Ala
    4070                4075                4080

Val Asp  Ser Lys Arg Gly Leu  Ser His Pro Phe Ser  Ile Asp Val
    4085                4090                4095

Phe Glu  Asp Tyr Ile Tyr Gly  Val Thr Tyr Ile Asn  Asn Arg Val
    4100                4105                4110

Phe Lys  Ile His Lys Phe Gly  His Ser Pro Leu Ile  Asn Leu Thr
    4115                4120                4125

Gly Gly  Leu Ser His Ala Ser  Asp Val Val Leu Tyr  His Gln His
    4130                4135                4140

Lys Gln  Pro Glu Val Thr Asn  Pro Cys Asp Arg Lys  Lys Cys Glu
    4145                4150                4155

Trp Leu  Cys Leu Leu Ser Pro  Ser Gly Pro Val Cys  Thr Cys Pro
    4160                4165                4170

Asn Gly  Lys Arg Leu Asp Asn  Gly Thr Cys Val Pro  Val Pro Ser
    4175                4180                4185

Pro Thr  Pro Pro Pro Asp Ala  Pro Arg Pro Gly Thr  Cys Thr Leu
    4190                4195                4200

Gln Cys  Phe Asn Gly Gly Ser  Cys Phe Leu Asn Ala  Arg Arg Gln
    4205                4210                4215
```

```
Pro Lys Cys Arg Cys Gln Pro Arg Tyr Thr Gly Asp Lys Cys Glu
    4220                4225                4230

Leu Asp Gln Cys Trp Glu Tyr Cys His Asn Gly Gly Thr Cys Ala
    4235                4240                4245

Ala Ser Pro Ser Gly Met Pro Thr Cys Arg Cys Pro Thr Gly Phe
    4250                4255                4260

Thr Gly Pro Arg Cys Thr Gln Gln Val Cys Ala Gly Tyr Cys Ala
    4265                4270                4275

Asn Asn Ser Thr Cys Thr Val Asn Gln Gly Asn Gln Pro Gln Cys
    4280                4285                4290

Arg Cys Leu Pro Gly Phe Leu Gly Asp Arg Cys Gln Tyr Arg Gln
    4295                4300                4305

Cys Ser Gly Phe Cys Glu Asn Phe Gly Thr Cys Gln Met Ala Ala
    4310                4315                4320

Asp Gly Ser Arg Gln Cys Arg Cys Thr Val Tyr Phe Glu Gly Thr
    4325                4330                4335

Arg Cys Glu Val Asn Lys Cys Ser Arg Cys Leu Gln Gly Ala Cys
    4340                4345                4350

Val Val Asn Lys Gln Thr Gly Asp Val Thr Cys Asn Cys Thr Asp
    4355                4360                4365

Gly Arg Val Ala Pro Ser Cys Leu Thr Cys Ile Asp His Cys Ser
    4370                4375                4380

Asn Gly Gly Ser Cys Thr Met Asn Ser Lys Met Met Pro Glu Cys
    4385                4390                4395

Gln Cys Pro Pro His Met Thr Gly Pro Arg Cys Glu Glu Gln Val
    4400                4405                4410

Val Ser Gln Gln Gln Pro Gly His Met Thr Ser Ile Leu Ile Pro
    4415                4420                4425

Leu Leu Leu Leu Leu Leu Leu Leu Leu Val Ala Gly Val Val Phe
    4430                4435                4440

Trp Tyr Lys Arg Arg Val Arg Gly Ala Lys Gly Phe Gln His Gln
    4445                4450                4455

Arg Met Thr Asn Gly Ala Met Asn Val Glu Ile Gly Asn Pro Thr
    4460                4465                4470

Tyr Lys Met Tyr Glu Gly Gly Glu Pro Asp Asp Val Gly Gly Leu
    4475                4480                4485

Leu Asp Ala Asp Phe Ala Leu Asp Pro Asp Lys Pro Thr Asn Phe
    4490                4495                4500

Thr Asn Pro Val Tyr Ala Thr Leu Tyr Met Gly Gly His Gly Ser
    4505                4510                4515

Arg His Ser Leu Ala Ser Thr Asp Glu Lys Arg Glu Leu Leu Gly
    4520                4525                4530

Arg Gly Pro Glu Asp Glu Ile Gly Asp Pro Leu Ala
    4535                4540                4545
```

```
<210> SEQ ID NO 5
<211> LENGTH: 14923
<212> TYPE: DNA
<213> ORGANISM: Homo sapiens

<400> SEQUENCE: 5

acttcagtcc ggggaacagc ggtgcgagct ccaggcccat gcactgagga ggcggaaaca      60

aggggagccc ccagagctcc atcaagcccc ctccaaaggc tcccctaccc ggtccacgcc     120
```

-continued

```
ccccaccccc cctccccgcc tcctcccaat tgtgcatttt tgcagccgga ggcggctccg    180

agatggggct gtgagcttcg cccggggagg gggaaagagc agcgaggagt gaagcggggg    240

ggtggggtga agggtttgga tttcggggca gggggcgcac ccccgtcagc aggccctccc    300

caaggggctc ggaactctac ctcttcaccc acgcccctgg tgcgctttgc cgaaggaaag    360

aataagaaca gagaaggagg aggggaaag gaggaaaagg gggaccccc aactgggggg    420

ggtgaaggag agaagtagca ggaccagagg ggaaggggct gctgcttgca tcagcccaca    480

ccatgctgac cccgccgttg ctcctgctgc tgcccctgct ctcagctctg gtcgcggcgg    540

ctatcgacgc ccctaagact tgcagcccca agcagtttgc ctgcagagat caaataacct    600

gtatctcaaa gggctggcgg tgcgacggtg agagggactg cccagacgga tctgacgagg    660

cccctgagat ttgtccacag agtaaggccc agcgatgcca gccaaacgag cataactgcc    720

tgggtactga gctgtgtgtt cccatgtccc gcctctgcaa tggggtccag gactgcatgg    780

acggctcaga tgaggggccc cactgccgag agctccaagg caactgctct cgcctgggct    840

gccagcacca ttgtgtcccc acactcgatg ggcccacctg ctactgcaac agcagctttc    900

agcttcaggc agatggcaag acctgcaaag attttgatga gtgctcagtg tacggcacct    960

gcagccagct atgcaccaac acagacggct ccttcatatg tggctgtgtt gaaggatacc   1020

tcctgcagcc ggataaccgc tcctgcaagg ccaagaacga gccagtagac cggccccctg   1080

tgctgttgat agccaactcc cagaacatct tggccacgta cctgagtggg gcccaggtgt   1140

ctaccatcac acctacgagc acgcggcaga ccacagccat ggacttcagc tatgccaacg   1200

agaccgtatg ctgggtgcat gttggggaca gtgctgctca gacgcagctc aagtgtgccc   1260

gcatgcctgg cctaaagggc ttcgtggatg agcacaccat caacatctcc ctcagtctgc   1320

accacgtgga acagatggcc atcgactggc tgacaggcaa cttctacttt gtggatgaca   1380

tcgatgatag gatctttgtc tgcaacagaa atggggacac atgtgtcaca ttgctagacc   1440

tggaactcta caaccccaag ggcattgccc tggaccctgc catggggaag gtgtttttca   1500

ctgactatgg gcagatccca aaggtggaac gctgtgacat ggatgggcag aaccgcacca   1560

agctcgtcga cagcaagatt gtgtttcctc atggcatcac gctggacctg gtcagccgcc   1620

ttgtctactg ggcagatgcc tatctggact atattgaagt ggtggactat gagggcaagg   1680

gccgccagac catcatccag ggcatcctga ttgagcacct gtacggcctg actgtgtttg   1740

agaattatct ctatgccacc aactcggaca atgccaatgc ccagcagaag acgagtgtga   1800

tccgtgtgaa ccgctttaac agcaccgagt accaggttgt cacccgggtg gacaagggtg   1860

gtgccctcca catctaccac cagaggcgtc agccccgagt gaggagccat gcctgtgaaa   1920

acgaccagta tgggaagccg ggtggctgct ctgacatctg cctgctggcc aacagccaca   1980

aggcgcggac ctgccgctgc cgttccggct tcagcctggg cagtgacggg aagtcatgca   2040

agaagccgga gcatgagctg ttcctcgtgt atggcaaggg ccggccaggc atcatccggg   2100

gcatggatat gggggccaag gtcccggatg agcacatgat ccccattgaa aacctcatga   2160

acccccgagc cctggacttc cacgctgaga ccggcttcat ctactttgcc gacaccacca   2220

gctacctcat tggccgccag aagattgatg gcactgagcg ggagaccatc ctgaaggacg   2280

gcatccacaa tgtggagggt gtggccgtgg actggatggg agacaatctg tactggacgg   2340

acgatgggcc caaaaagaca atcagcgtgg ccaggctgga gaaagctgct cagacccgca   2400

agactttaat cgagggcaaa atgacacacc ccagggctat tgtggtggat ccactcaatg   2460

ggtggatgta ctggacagac tgggaggagg accccaagga cagtcggcgt gggcggctgg   2520
```

```
agagggcgtg gatggatggc tcacaccgag acatctttgt cacctccaag acagtgcttt   2580
ggcccaatgg gctaagcctg gacatcccgg ctgggcgcct ctactgggtg gatgccttct   2640
acgaccgcat cgagacgata ctgctcaatg gcacagaccg gaagattgtg tatgaaggtc   2700
ctgagctgaa ccacgccttt ggcctgtgtc accatggcaa ctacctcttc tggactgagt   2760
atcggagtgg cagtgtctac cgcttggaac ggggtgtagg aggcgcaccc cccactgtga   2820
cccttctgcg cagtgagcgg ccccccatct ttgagatccg aatgtatgat gcccagcagc   2880
agcaagttgg caccaacaaa tgccgggtga acaatggcgg ctgcagcagc ctgtgcttgg   2940
ccacccctgg gagccgccag tgcgcctgtg ctgaggacca ggtgttggac gcagacggcg   3000
tcacttgctt ggcgaaccca tcctacgtgc ctccacccca gtgccagcca ggcgagtttg   3060
cctgtgccaa cagccgctgc atccaggagc gctggaagtg tgacggagac aacgattgcc   3120
tggacaacag tgatgaggcc ccagccctct gccatcagca cacctgcccc tcggaccgat   3180
tcaagtgcga gaacaaccgg tgcatcccca accgctggct ctgcgacggg gacaatgact   3240
gtgggaacag tgaagatgag tccaatgcca cttgttcagc ccgcacctgc ccccccaacc   3300
agttctcctg tgccagtggc cgctgcatcc ccatctcctg gacgtgtgat ctggatgacg   3360
actgtgggga ccgctctgat gagtctgctt cgtgtgccta tcccacctgc ttcccccctga   3420
ctcagtttac ctgcaacaat ggcagatgta tcaacatcaa ctggagatgc gacaatgaca   3480
atgactgtgg ggacaacagt gacgaagccg gctgcagcca ctcctgttct agcacccagt   3540
tcaagtgcaa cagcgggcgt tgcatccccg agcactggac ctgcgatggg gacaatgact   3600
gcggagacta cagtgatgag acacacgcca actgcaccaa ccaggccacg aggcccccctg   3660
gtggctgcca cactgatgag ttccagtgcc ggctggatgg actatgcatc cccctgcggt   3720
ggcgctgcga tggggacact gactgcatgg actccagcga tgagaagagc tgtgagggag   3780
tgacccacgt ctgcgatccc agtgtcaagt ttggctgcaa ggactcagct cggtgcatca   3840
gcaaagcgtg ggtgtgtgat ggcgacaatg actgtgagga taactcggac gaggagaact   3900
gcgagtccct ggcctgcagg ccaccctcgc acccttgtgc caacaacacc tcagtctgcc   3960
tgccccctga caagctgtgt gatggcaacg acgactgtgg cgacggctca gatgagggcg   4020
agctctgcga ccagtgctct ctgaataacg gtggctgcag ccacaactgc tcagtggcac   4080
ctggcgaagg cattgtgtgt tcctgccctc tgggcatgga gctggggccc gacaaccaca   4140
cctgccagat ccagagctac tgtgccaagc atctcaaatg cagccaaaag tgcgaccaga   4200
acaagttcag cgtgaagtgc tcctgctacg agggctgggt cctggaacct gacggcgaga   4260
gctgccgcag cctggacccc ttcaagccgt tcatcatttt ctccaaccgc catgaaatcc   4320
ggcgcatcga tcttcacaaa ggagactaca gcgtcctggt gcccggcctg cgcaacacca   4380
tcgccctgga cttccacctc agccagagcg ccctctactg gaccgacgtg gtggaggaca   4440
agatctaccg cgggaagctg ctggacaacg gagccctgac tagtttcgag gtggtgattc   4500
agtatggcct ggccacaccc gagggcctgg ctgtagactg gattgcaggc aacatctact   4560
gggtggagag taacctggat cagatcgagg tggccaagct ggatgggacc ctccggacca   4620
ccctgctggc cggtgacatt gagcacccaa gggcaatcgc actggatccc cgggatggga   4680
tcctgttttg gacagactgg gatgccagcc tgccccgcat tgaggcagcc tccatgagtg   4740
gggctgggcg ccgcaccgtg caccgggaga ccggctctgg gggctggccc aacgggctca   4800
ccgtggacta cctggagaag cgcatccttt ggattgacgc caggtcagat gccatttact   4860
```

```
cagcccgtta cgacggctct ggccacatgg aggtgcttcg gggacacgag ttcctgtcgc   4920
acccgtttgc agtgacgctg tacggggggg aggtctactg gactgactgg cgaacaaaca   4980
cactggctaa ggccaacaag tggaccggcc acaatgtcac cgtggtacag aggaccaaca   5040
cccagccctt tgacctgcag gtgtaccacc cctcccgcca gcccatggct cccaatccct   5100
gtgaggccaa tgggggccag ggcccctgct cccacctgtg tctcatcaac tacaaccgga   5160
ccgtgtcctg cgcctgcccc cacctcatga agctccacaa ggacaacacc acctgctatg   5220
agtttaagaa gttcctgctg tacgcacgtc agatggagat ccgaggtgtg gacctggatg   5280
ctccctacta caactacatc atctccttca cggtgcccga catcgacaac gtcacagtgc   5340
tagactacga tgcccgcgag cagcgtgtgt actggtctga cgtgcggaca caggccatca   5400
agcgggcctt catcaacggc acaggcgtgg agacagtcgt ctctgcagac ttgccaaatg   5460
cccacgggct ggctgtggac tgggtctccc gaaacctgtt ctggacaagc tatgacacca   5520
ataagaagca gatcaatgtg gcccggctgg atggctcctt caagaacgca gtggtgcagg   5580
gcctggagca gccccatggc cttgtcgtcc accctctgcg tgggaagctc tactggaccg   5640
atggtgacaa catcagcatg gccaacatgg atggcagcaa tcgcaccctg ctcttcagtg   5700
gccagaaggg ccccgtgggc ctggctattg acttccctga aagcaaactc tactggatca   5760
gctccgggaa ccataccatc aaccgctgca acctggatgg gagtgggctg gaggtcatcg   5820
atgccatgcg gagccagctg ggcaaggcca ccgccctggc catcatgggg gacaagctgt   5880
ggtgggctga tcaggtgtcg gaaaagatgg gcacatgcag caaggctgac ggctcgggct   5940
ccgtggtcct tcggaacagc accaccctgg tgatgcacat gaaggtctat gacgagagca   6000
tccagctgga ccataagggc accaacccct gcagtgtcaa caacggtgac tgctcccagc   6060
tctgcctgcc cacgtcagag acgacccgct cctgcatgtg cacagccggc tatagcctcc   6120
ggagtggcca gcaggcctgc gagggcgtag gttcctttct cctgtactct gtgcatgagg   6180
gaatcagggg aattcccctg gatcccaatg acaagtcaga tgccctggtc ccagtgtccg   6240
ggacctcgct ggctgtcggc atcgacttcc acgctgaaaa tgacaccatc tactgggtgg   6300
acatgggcct gagcacgatc agccgggcca agcgggacca gacgtggcgt gaagacgtgg   6360
tgaccaatgg cattggccgt gtggagggca ttgcagtgga ctggatcgca ggcaacatct   6420
actggacaga ccagggcttt gatgtcatcg aggtcgcccg gctcaatggc tccttccgct   6480
acgtggtgat ctcccagggt ctagacaagc cccgggccat caccgtccac ccggagaaag   6540
ggtacttgtt ctggactgag tggggtcagt atccgcgtat tgagcggtct cggctagatg   6600
gcacggagcg tgtggtgctg gtcaacgtca gcatcagctg gcccaacggc atctcagtgg   6660
actaccagga tgggaagctg tactggtgcg atgcacggac agacaagatt gaacggatcg   6720
acctggagac aggtgagaac cgcgaggtgg ttctgtccag caacaacatg gacatgtttt   6780
cagtgtctgt gtttgaggat ttcatctact ggagtgacag gactcatgcc aacggctcta   6840
tcaagcgcgg gagcaaagac aatgccacag actccgtgcc cctgcgaacc ggcatcggcg   6900
tccagcttaa agacatcaaa gtcttcaacc gggaccggca gaaaggcacc aacgtgtgcg   6960
cggtggccaa tggcgggtgc cagcagctgt gcctgtaccg ggccgtgggg cagcgggcct   7020
gcgcctgtgc ccacgggatg ctggctgaag acggagcatc gtgccgcgag tatgccggct   7080
acctgctcta ctcagagcgc accattctca agagtatcca cctgtcggat gagcgcaacc   7140
tcaatgcgcc cgtgcagccc ttcgaggacc ctgagcacat gaagaacgtc atcgccctgg   7200
cctttgacta ccgggcaggc acctctccgg gcacccccaa tcgcatcttc ttcagcgaca   7260
```

```
tccactttgg gaacatccaa cagatcaacg acgatggctc caggaggatc accattgtgg   7320
aaaacgtggg ctccgtggaa ggcctggcct atcaccgtgg ctgggacact ctctattgga   7380
caagctacac gacatccacc atcacgcgcc acacagtgga ccagacccgc ccaggggcct   7440
tcgagcgtga gaccgtcatc actatgtctg gagatgacca cccacgggcc ttcgttttgg   7500
acgagtgcca gaacctcatg ttctggacca actggaatga gcagcatccc agcatcatgc   7560
gggcggcgct ctcgggagcc aatgtcctga cccttatcga gaaggacatc cgtacccccca   7620
atggcctggc catcgaccac cgtgccgaga agctctactt ctctgacgcc accctggaca   7680
agatcgagcg gtgcgagtat gacggctccc accgctatgt gatcctaaag tcagagcctg   7740
tccacccctt cgggctggcc gtgtatgggg agcacatttt ctggactgac tgggtgcggc   7800
gggcagtgca gcgggccaac aagcacgtgg gcagcaacat gaagctgctg cgcgtggaca   7860
tcccccagca gcccatgggc atcatcgccg tggccaacga caccaacagc tgtgaactct   7920
ctccatgccg aatcaacaac ggtggctgcc aggacctgtg tctgctcact caccagggcc   7980
atgtcaactg ctcatgccga gggggccgaa tcctccagga tgacctcacc tgccgagcgg   8040
tgaattcctc ttgccgagca caagatgagt ttgagtgtgc caatggcgag tgcatcaact   8100
tcagcctgac ctgcgacggc gtcccccact gcaaggacaa gtccgatgag aagccatcct   8160
actgcaactc ccgccgctgc aagaagactt tccggcagtg cagcaatggg cgctgtgtgt   8220
ccaacatgct gtggtgcaac ggggccgacg actgtgggga tggctctgac gagatccctt   8280
gcaacaagac agcctgtggt gtgggcgagt tccgctgccg ggacgggacc tgcatcggga   8340
actccagccg ctgcaaccag tttgtggatt gtgaggacgc ctcagatgag atgaactgca   8400
gtgccaccga ctgcagcagc tacttccgcc tgggcgtgaa gggcgtgctc ttccagccct   8460
gcgagcggac ctcactctgc tacgcaccca gctgggtgtg tgatggcgcc aatgactgtg   8520
gggactacag tgatgagcgc gactgcccag gtgtgaaacg ccccagatgc cctctgaatt   8580
acttcgcctg ccctagtggg cgctgcatcc ccatgagctg gacgtgtgac aaagaggatg   8640
actgtgaaca tggcgaggac gagacccact gcaacaagtt ctgctcagag gcccagtttg   8700
agtgccagaa ccatcgctgc atctccaagc agtggctgtg tgacggcagc gatgactgtg   8760
gggatggctc agacgaggct gctcactgtg aaggcaagac gtgcggcccc tcctccttct   8820
cctgccctgg cacccacgtg tgcgtccccg agcgctggct ctgtgacggt gacaaagact   8880
gtgctgatgg tgcagacgag agcatcgcag ctggttgctt gtacaacagc acttgtgacg   8940
accgtgagtt catgtgccag aaccgccagt gcatccccaa gcacttcgtg tgtgaccacg   9000
accgtgactg tgcagatggc tctgatgagt cccccgagtg tgagtacccg acctgcggcc   9060
ccagtgagtt ccgctgtgcc aatgggcgct gtctgagctc ccgccagtgg gagtgtgatg   9120
gcgagaatga ctgccacgac cagagtgacg aggctcccaa gaacccacac tgcaccagcc   9180
aagagcacaa gtgcaatgcc tcgtcacagt tcctgtgcag cagtgggcgc tgtgtggctg   9240
aggcactgct ctgcaacggc caggatgact gtggcgacag ctcggacgag cgtggctgcc   9300
acatcaatga gtgtctcagc cgcaagctca gtggctgcag ccaggactgt gaggacctca   9360
agatcggctt caagtgccgc tgtcgccctg gcttccggct gaaggacgac ggccggacgt   9420
gtgctgatgt ggacgagtgc agcaccacct tcccctgcag ccagcgctgc atcaacactc   9480
atggcagcta taagtgtctg tgtgtggagg gctatgcacc ccgcggcggc gacccccaca   9540
gctgcaaggc tgtgactgac gaggaaccgt ttctgatctt cgccaaccgg tactacctgc   9600
```

-continued

```
gcaagctcaa cctggacggg tccaactaca cgttacttaa gcagggcctg aacaacgccg   9660
ttgccttgga ttttgactac cgagagcaga tgatctactg gacagatgtg accacccagg   9720
gcagcatgat ccgaaggatg caccttaacg ggagcaatgt gcaggtccta caccgtacag   9780
gcctcagcaa ccccgatggg ctggctgtgg actgggtggg tggcaacctg tactggtgcg   9840
acaaaggccg ggacaccatc gaggtgtcca agctcaatgg ggcctatcgg acggtgctgg   9900
tcagctctgg cctccgtgag cccagggctc tggtggtgga tgtgcagaat gggtacctgt   9960
actggacaga ctggggtgac cattcactga tcggccgcat cggcatggat gggtccagcc  10020
gcagcgtcat cgtggacacc aagatcacat ggcccaatgg cctgacgctg gactatgtca  10080
ctgagcgcat ctactgggcc gacgcccgcg aggactacat tgaatttgcc agcctggatg  10140
gctccaatcg ccacgttgtg ctgagccagg acatcccgca catctttgca ctgaccctgt  10200
ttgaggacta cgtctactgg accgactggg aaacaaagtc cattaaccga gcccacaaga  10260
ccacgggcac caacaaaacg ctcctcatca gcacgctgca ccggcccatg gacctgcatg  10320
tcttccatgc cctgcgccag ccagacgtgc ccaatcaccc ctgcaaggtc aacaatggtg  10380
gctgcagcaa cctgtgcctg ctgtcccccg ggggagggca caaatgtgcc tgccccacca  10440
acttctacct gggcagcgat gggcgcacct gtgtgtccaa ctgcacggct agccagtttg  10500
tatgcaagaa cgacaagtgc atcccctct ggtggaagtg tgacaccgag gacgactgcg  10560
ggaccactc agacgagccc ccggactgcc ctgagttcaa gtgccggccc ggacagttcc  10620
agtgctccac aggtatctgc acaaaccctg ccttcatctg cgatggcgac aatgactgcc  10680
aggacaacag tgacgaggcc aactgtgaca tccacgtctg cttgcccagt cagttcaaat  10740
gcaccaacac caaccgctgt attcccggca tcttccgctg caatgggcag gacaactgcg  10800
gagatgggga ggatgagagg gactgccccg aggtgacctg cgcccccaac cagttccagt  10860
gctccattac caaacggtgc atcccccggg tctgggtctg cgaccgggac aatgactgtg  10920
tggatggcag tgatgagccc gccaactgca cccagatgac ctgtggtgtg gacgagttcc  10980
gctgcaagga ttcgggccgc tgcatcccag cgcgttggaa gtgtgacgga gaggatgact  11040
gtggggatgg ctcggatgag cccaaggaag agtgtgatga acgcacctgt gagccatacc  11100
agttccgctg caagaacaac cgctgcgtgc ccggccgctg gcagtgcgac tacgacaacg  11160
attgcggtga caactccgat gaagagagct gcacccctcg gccctgctcc gagagtgagt  11220
tctcctgtgc caacggccgc tgcatcgcgg ggcgctggaa atgcgatgga gaccacgact  11280
gcgcggacgg ctcggacgag aaagactgca ccccccgctg tgacatggac cagttccagt  11340
gcaagagcgg ccactgcatc cccctgcgct ggcgctgtga cgcagacgcc gactgcatgg  11400
acggcagcga cgaggaggcc tgcggcactg gcgtgcggac ctgcccctg gacgagttcc  11460
agtgcaacaa caccttgtgc aagccgctgg cctggaagtg cgatggcgag gatgactgtg  11520
gggacaactc agatgagaac cccgaggagt gtgcccggtt cgtgtgccct cccaaccggc  11580
ccttccgttg caagaatgac cgcgtctgtc tgtggatcgg gcgccaatgc gatggcacgg  11640
acaactgtgg ggatgggact gatgaagagg actgtgagcc ccccacagcc cacaccaccc  11700
actgcaaaga caagaaggag tttctgtgcc ggaaccagcg ctgcctctcc tcctccctgc  11760
gctgcaacat gttcgatgac tgcggggacg gctctgacga ggaggactgc agcatcgacc  11820
ccaagctgac cagctgcgcc accaatgcca gcatctgtgg ggacgaggca cgctgcgtgc  11880
gcaccgagaa agcggcctac tgtgcctgcc gctcgggctt ccacaccgtg cccggccagc  11940
ccggatgcca agacatcaac gagtgcctgc gcttcggcac ctgctcccag ctctgcaaca  12000
```

acaccaaggg cggccacctc tgcagctgcg ctcggaactt catgaagacg cacaacacct 12060
gcaaggccga aggctctgag taccaggtcc tgtacatcgc tgatgacaat gagatccgca 12120
gcctgttccc cggccacccc cattcggctt acgagcaggc attccagggt gacgagagtg 12180
tccgcattga tgctatggat gtccatgtca aggctggccg tgtctattgg accaactggc 12240
acacgggcac catctcctac cgcagcctgc cacctgctgc gcctcctacc acttccaacc 12300
gccaccggcg acagattgac cggggtgtca cccacctcaa catttcaggg ctgaagatgc 12360
ccagaggcat cgccatcgac tgggtggccg gaaacgtgta ctggaccgac tcgggccgag 12420
atgtgattga ggtggcgcag atgaagggcg agaaccgcaa gacgctcatc tcgggcatga 12480
ttgacgagcc ccacgccatt gtggtggacc cactgagggg gaccatgtac tggtcagact 12540
ggggcaacca ccccaagatt gagacggcag cgatggatgg gacgcttcgg gagacactgg 12600
tgcaggacaa cattcagtgg cccacaggcc tggccgtgga ttatcacaat gagcggctgt 12660
actgggcaga cgccaagctt tcagtcatcg gcagcatccg gctcaatggc acggacccca 12720
ttgtggctgc tgacagcaaa cgaggcctaa gtcacccctt cagcatcgac gtctttgagg 12780
attacatcta tggtgtcacc tacatcaata atcgtgtctt caagatccat aagtttggcc 12840
acagcccctt ggtcaacctg acagggggcc tgagccacgc ctctgacgtg gtcctttacc 12900
atcagcacaa gcagcccgaa gtgaccaacc catgtgaccg caagaaatgc gagtggctct 12960
gcctgctgag ccccagtggg cctgtctgca cctgtcccaa tgggaagcgg ctggacaacg 13020
gcacatgcgt gcctgtgccc tctccaacgc cccccccaga tgctccccgg cctggaacct 13080
gtaacctgca gtgcttcaac ggtggcagct gtttcctcaa tgcacggagg cagcccaagt 13140
gccgctgcca accccgctac acgggtgaca agtgtgaact ggaccagtgc tgggagcact 13200
gtcgcaatgg gggcacctgt gctgcctccc cctctggcat gcccacgtgc cggtgcccca 13260
cgggcttcac gggccccaaa tgcacccagc aggtgtgtgc gggctactgt gccaacaaca 13320
gcacctgcac tgtcaaccag ggcaaccagc cccagtgccg atgcctaccc ggcttcctgg 13380
gcgaccgctg ccagtaccgg cagtgctctg gctactgtga gaactttggc acatgccaga 13440
tggctgctga tggctcccga caatgccgct gcactgccta ctttgaggga tcgaggtgtg 13500
aggtgaacaa gtgcagccgc tgtctcgaag ggcctgtgt ggtcaacaag cagagtgggg 13560
atgtcacctg caactgcacg gatggccggg tggcccccag ctgtctgacc tgcgtcggcc 13620
actgcagcaa tggcggctcc tgtaccatga acagcaaaat gatgcctgag tgccagtgcc 13680
caccccacat gacagggccc cggtgtgagg agcacgtctt cagccagcag cagccaggac 13740
atatagcctc catcctaatc cctctgctgt tgctgctgct gctggttctg gtggccggag 13800
tggtattctg gtataagcgg cgagtccaag ggctaaggg cttccagcac caacggatga 13860
ccaacggggc catgaacgtg gagattggaa accccaccta caagatgtac gaaggcggag 13920
agcctgatga tgtgggaggc ctactggacg ctgactttgc cctggaccct gacaagccca 13980
ccaacttcac caaccccgtg tatgccacac tctacatggg gggccatggc agtcgccact 14040
ccctggccag cacggacgag aagcgagaac tcctgggccg gggccctgag gacgagatag 14100
gggacccctt ggcatagggc cctgccccgt cggactgccc ccagaaagcc tcctgccccc 14160
tgccagtgaa gtccttcagt gagcccctcc ccagccagcc cttccctggc cccgccggat 14220
gtataaatgt aaaaatgaag gaattacatt ttatatgtga gcgagcaagc cggcaagcga 14280
gcacagtatt atttctccat cccctccctg cctgctcctt ggcaccccca tgctgccttc 14340
agggagacag gcagggaggg cttggggctg cacctcctac cctcccacca gaacgcaccc 14400
cactgggaga gctggtggtg cagccttccc ctccctgtat aagacacttt gccaaggctc 14460
tcccctctcg ccccatccct gcttgcccgc tcccacagct tcctgagggc taattctggg 14520
aagggagagt tctttgctgc ccctgtctgg aagacgtggc tctgggtgag gtaggcggga 14580
aaggatggag tgttttagtt cttgggggag gccaccccaa accccagccc caactccagg 14640
ggcacctatg agatggccat gctcaacccc cctcccagac aggccctccc tgtctccagg 14700
gcccccaccg aggttcccag ggctggagac ttcctctggt aaacattcct ccagcctccc 14760
ctcccctggg gacgccaagg aggtgggcca cacccaggaa gggaaagcgg gcagccccgt 14820
tttggggacg tgaacgtttt aataattttt gctgaattcc tttacaacta aataacacag 14880
atattgttat aaataaaatt gtaaaaaaaa aaaaaaaaaa aaa 14923

<210> SEQ ID NO 6
<211> LENGTH: 14907
<212> TYPE: DNA
<213> ORGANISM: Mus musculus

<400> SEQUENCE: 6
agtcagggga gcagcggtgc gagctccagg ccagtgcact gaggaggcgg aaacggggga 60
gcccctagtg ctccatcagg cccctaccaa ggcaccccca tcgggtccac gccccccacc 120
ccccaccccg cctcctccca attgtgcatt tttgcagcca gaggcggctc cgagatgggg 180
ctgtgagctt cgccctggga gggggagagg agcgaggagt aaagcagggg tgaagggttc 240
gaatttgggg gcagggggcg cacccgcgtc agcaggccct tcccaggggg ctcggaactg 300
taccatttca cctatgcccc tggttcgctt tgcttaagga aaggataaga atagaagagt 360
cggggagagg aagataaagg gggacccccc aattgggggg ggcgaggaca agaagtaaca 420
ggaccagagg gtgggggctg ctgtttgcat cggcccacac catgctgacc ccgccgttgc 480
tgctgctgct gccgctgctt tcagctctgg tctccggggc cactatggat gcccctaaaa 540
cttgcagccc taagcagttt gcctgcagag accaaatcac ctgtatctca aagggctggc 600
ggtgtgacgg tgaaagagat tgccccgacg gctctgatga agcccctgag atctgtccac 660
agagtaaagc ccagagatgc ccgccaaatg agcacagttg tctggggact gagctatgtg 720
tccccatgtc tcgtctctgc aacgggatcc aggactgcat ggatggctca gacgagggtg 780
ctcactgccg agagctccga gccaactgtt ctcgaatggg ttgtcaacac cattgtgtac 840
ctacacccag tgggcccacg tgctactgta acagcagctt ccagctgcag gcagatggca 900
agacgtgcaa agattttgac gagtgttccg tgtatggcac ctgcagccag ctttgcacca 960
acacagatgg ctccttcaca tgtggctgtg ttgaaggcta cctgctgcaa ccggacaacc 1020
gctcctgcaa ggccaagaat gagccagtag atcggccgcc agtgctactg attgccaact 1080
ctcagaacat cctagctacg tacctgagtg gggcccaagt gtctaccatc acacccacca 1140
gcacccgaca aaccacggcc atggacttca gttatgccaa tgagaccgta tgctgggtgc 1200
acgttgggga cagtgctgcc cagacacagc tcaagtgtgc ccggatgcct ggcctgaagg 1260
gctttgtgga tgagcatacc atcaacatct ccctcagcct gcaccacgtg gagcagatgg 1320
caatcgactg gctgacggga aacttctact ttgtcgacga cattgacgac aggatctttg 1380
tctgtaaccg aaacggggac acctgtgtca ctctgctgga cctggaactc tacaacccca 1440
aaggcatcgc cttggacccc gccatgggga aggtgttctt cactgactac gggcagatcc 1500
caaaggtgga gcgctgtgac atggatggac agaaccgcac caagctggtg gatagcaaga 1560

```
tcgtgtttcc acacggcatc accctggacc tggtcagccg cctcgtctac tgggcggacg   1620
cctacctaga ctacatcgag gtggtagact acgaagggaa gggtcggcag accatcatcc   1680
aaggcatcct gatcgagcac ctgtacggcc tgaccgtgtt tgagaactat ctctacgcca   1740
ccaactcgga caatgccaac acgcagcaga agacgagcgt gatccgagtg aaccggttca   1800
acagtactga gtaccaggtc gtcacccgtg tggacaaggg tggtgccctg catatctacc   1860
accagcgacg ccagccccga gtgcggagtc acgcctgtga gaatgaccag tacgggaagc   1920
caggtggctg ctccgacatc tgcctcctgg ccaacagtca caaggcaagg acctgcaggt   1980
gcaggtctgg cttcagcctg ggaagtgatg ggaagtcttg taagaaacct gaacatgagc   2040
tgttcctcgt gtatggcaag ggccgaccag gcatcattag aggcatggac atgggggcca   2100
aggtcccaga tgagcacatg atccccatcg agaaccttat gaatccacgc gctctggact   2160
tccacgccga gaccggcttc atctactttg ctgacaccac cagctacctc attggccgcc   2220
agaaaattga tggcacggag agagagacta tcctgaagga tggcatccac aatgtggagg   2280
gcgtagccgt ggactggatg ggagacaatc tttactggac tgatgatggc cccaagaaga   2340
ccattagtgt ggccaggctg gagaaagccg ctcagacccg gaagactcta attgagggca   2400
agatgacaca ccccagggcc attgtagtgg atccactcaa tgggtggatg tactggacag   2460
actgggagga ggaccccaag gacagtcggc gagggcggct cgagagggct tggatggacg   2520
gctcacaccg agatatcttt gtcacctcca agacagtgct ttggcccaat gggctaagcc   2580
tggatatccc agccggacgc ctctactggg tggatgcctt ctatgaccga attgagacca   2640
tactgctcaa tggcacagac cggaagattg tatatgaggg tcctgaactg aatcatgcct   2700
tcggcctgtg tcaccatggc aactacctct tttggaccga gtaccggagc ggcagcgtct   2760
accgcttgga acggggcgtg gcaggcgcac cgcccactgt gacccttctg cgcagcgaga   2820
gaccgcctat ctttgagatc cgaatgtacg acgcgcagca gcagcaagtg ggtaccaaca   2880
aatgccgggt aaataacgga ggctgcagca gcctgtgcct cgccaccccc gggagccgcc   2940
agtgtgcctg tgccgaggac caggtgttgg acacagatgg tgtcacctgc ttggcgaacc   3000
catcctacgt gcccccaccc cagtgccagc cgggcgagtt tgcctgtgcc aacaaccgct   3060
gcatccagga gcgctggaag tgtgacggag acaacgactg tctggacaac agcgatgagg   3120
ccccagcact gtgccatcaa cacacctgtc cctcggaccg attcaagtgt gagaacaacc   3180
ggtgtatccc caaccgctgg ctctgtgatg gggataatga ttgtggcaac agcgaggacg   3240
aatccaatgc cacgtgctca gcccgcacct gtccacccaa ccagttctcc tgtgccagtg   3300
gccgatgcat tcctatctca tggacctgtg atctggatga tgactgtggg gaccggtccg   3360
atgagtcagc ctcatgcgcc taccccacct gcttccccct gactcaattt acctgcaaca   3420
atggcagatg tattaacatc aactggcggt gtgacaacga caatgactgt ggggacaaca   3480
gcgacgaagc cggctgcagt cactcctgct ccagtaccca gttcaagtgc aacagtggca   3540
gatgcatccc cgagcactgg acgtgtgatg gggacaatga ttgtggggac tacagcgacg   3600
agacacacgc caactgtacc aaccaggcta caagacctcc tggtggctgc cactcggatg   3660
agttccagtg ccgcctagat ggcctgtgca tcccctgag gtggcgctgc gacggggaca   3720
ccgactgcat ggattccagc gatgagaaga gctgtgaggg cgtgacccat gtttgtgacc   3780
cgaatgtcaa gtttggctgc aaggactccg cccggtgcat cagcaaggcg tgggtgtgtg   3840
atggcgacag cgactgtgaa gataactccg acgaggagaa ctgtgaggcc ctggcctgca   3900
```

-continued

```
ggccaccctc ccatccctgc gccaacaaca cctctgtctg cctgcctcct gacaagctgt   3960
gcgacggcaa ggatgactgt ggagacggct cggatgaggg cgagctctgt gaccagtgtt   4020
ctctgaataa tggtggctgt agtcacaact gctcagtggc ccctggtgaa ggcatcgtgt   4080
gctcttgccc tctgggcatg gagctgggct ctgacaacca cacctgccag atccagagct   4140
actgtgccaa gcacctcaaa tgcagccaga agtgtgacca gaacaagttc agtgtgaagt   4200
gctcctgcta cgagggctgg gtcttggagc ctgacgggga aagctgccgc agtctggatc   4260
ccttcaaacc gttcatcatc ttctccaacc gccacgagat caggcgcatt gaccttcaca   4320
agggggacta cagcgtccta gtgcctggcc tgcgcaacac tattgccctg gacttccacc   4380
tcagccagag tgccctctac tggaccgacg tggtagagga caagatctac cgtgggaaac   4440
tcctggacaa cggagccctg accagctttg aggtggtgat tcagtatggc ttggccacac   4500
cagagggcct ggctgtagat tggattgcag gcaacatcta ctgggtggag agcaacctgg   4560
accagatcga agtggccaag ctggacggaa ccctccgaac cactctgctg gcgggtgaca   4620
ttgagcaccc gagggccatc gctctggacc ctcgggatgg gattctgttt tggacagact   4680
gggatgccag cctgccacga atcgaggctg cgtccatgag tggggctggc cgccgaacca   4740
tccaccggga gacaggctct gggggctggc ccaacgggct caccgtggat tacctggaga   4800
agcgcatcct ctggattgat gctaggtcag atgccatcta ttcagcccgg tatgacggct   4860
ccggccacat ggaggtgctt cggggacacg agttcctgtc acacccattt gccgtgacac   4920
tgtacggtgg ggaggtgtac tggaccgact ggcgaacaaa tacactggct aaggccaaca   4980
agtggactgg ccacaacgtc accgtggtac agaggaccaa cacccagccc ttcgacctgc   5040
aggtgtatca cccttcccgg cagcccatgg ctccaaaccc atgtgaggcc aatggcggcc   5100
ggggcccctg ttcccatctg tgcctcatca actacaaccg gaccgtctcc tgcgcctgtc   5160
cccacctcat gaagctgcac aaggacaaca ccacctgcta tgagtttaag aagttcctgc   5220
tgtacgcacg tcagatggag atccggggcg tggacctgga tgccccgtac tacaattata   5280
tcatctcctt cacggtgcct gatatcgaca atgtcacggt gctggactat gatgcccgag   5340
agcagcgagt ttactggtct gatgtgcgga ctcaagccat caaaagggca tttatcaacg   5400
gcactggcgt ggagaccgtt gtctctgcag acttgcccaa cgcccacggg ctggctgtgg   5460
actgggtctc ccgaaatctg ttttggacaa gttacgacac caacaagaag cagattaacg   5520
tggcccggct ggacggctcc ttcaagaatg cggtggtgca gggcctggag cagccccacg   5580
gcctggtcgt ccacccgctt cgtggcaagc tctactggac tgatggggac aacatcagca   5640
tggccaacat ggatgggagc aaccacactc tgctcttcag tggccagaag ggccctgtgg   5700
ggttggccat tgacttccct gagagcaaac tctactggat cagctctggg aaccacacaa   5760
tcaaccgttg caatctggat gggagcgagc tggaggtcat cgacaccatg cggagccagc   5820
tgggcaaggc cactgccctg gccatcatgg gggacaagct gtggtgggca gatcaggtgt   5880
cagagaagat gggcacgtgc aacaaagccg atggctctgg gtccgtggtg ctgcggaaca   5940
gtaccacgtt ggttatgcac atgaaggtgt atgacgagag catccagcta gagcatgagg   6000
gcaccaaccc ctgcagtgtc aacaacggag actgttccca gctctgcctg ccaacatcag   6060
agacgactcg ctcctgtatg tgtacagccg gttacagcct ccggagcgga cagcaggcct   6120
gtgagggtgt gggctctttt ctcctgtact ctgtacatga gggaattcgg gggattccac   6180
tagatcccaa tgacaagtcg gatgccctgg tcccagtgtc cggaacttca ctggctgtcg   6240
gaatcgactt ccatgccgaa aatgacacta tttattgggt ggatatgggc ctaagcacca   6300
```

```
tcagcagggc caagcgtgac cagacatggc gagaggatgt ggtgaccaac ggtattggcc   6360
gtgtggaggg catcgcggtg gactggatcg caggcaacat atactggacg gaccagggct   6420
tcgatgtcat cgaggttgcc cggctcaatg gctcttttcg ttatgtggtc atttcccagg   6480
gtctggacaa gcctcgggcc atcactgtcc acccagagaa ggggtacttg ttctggaccg   6540
agtggggtca ttacccacgt attgagcggt ctcgccttga tggcacagag agagtggtgt   6600
tggttaatgt cagcatcagc tggcccaatg gcatctcagt agactatcag ggcggcaagc   6660
tctactggtg tgatgctcgg atggacaaga tcgagcgcat cgacctggaa acgggcgaga   6720
accgggaggt ggtcctgtcc agcaataaca tggatatgtt ctccgtgtcc gtgtttgagg   6780
acttcatcta ctggagtgac agaactcacg ccaatggctc catcaagcgc ggctgcaaag   6840
acaatgctac agactccgtg cctctgagga caggcattgg tgttcagctt aaagacatca   6900
aggtcttcaa cagggacagg cagaagggta ccaatgtgtg cgcggtagcc aacggcgggt   6960
gccagcagct ctgcttgtat cggggtggcg gacagcgagc ctgtgcctgt gcccacggga   7020
tgctggcaga agacggggcc tcatgccgag agtacgctgg ctacctgctc tactcagagc   7080
ggaccatcct caagagcatc cacctgtcgg atgagcgtaa cctcaacgca ccggtgcagc   7140
cctttgaaga ccccgagcac atgaaaaatg tcatcgccct ggcctttgac taccgagcag   7200
gcacctcccc ggggacccct aaccgcatct tcttcagtga catccacttt gggaacatcc   7260
agcagatcaa tgacgatggc tcgggcagga ccaccatcgt ggaaaatgtg ggctctgtgg   7320
aaggcctggc ctatcaccgt ggctgggaca cactgtactg gacaagctac accacatcca   7380
ccatcacccg ccacaccgtg gaccagactc gcccaggggc cttcgagagg gagacagtca   7440
tcaccatgtc cggagacgac cacccgagag cctttgtgct ggatgagtgc cagaacctga   7500
tgttctggac caattggaac gagctccatc caagcatcat gcgggcagcc ctatccggag   7560
ccaacgtcct gaccctcatt gagaaggaca tccgcacgcc caatgggttg gccatcgacc   7620
accgggcgga gaagctgtac ttctcggatg ccaccttgga caagatcgag cgctgcgagt   7680
acgacggctc ccaccgctat gtgatcctaa agtcggagcc cgtccacccc tttgggttgg   7740
cggtgtacgg agagcacatt ttctggactg actgggtgcg gcgggctgtg cagcgagcca   7800
acaagtatgt gggcagcgac atgaagctgc ttcgggtgga cattccccag caacccatgg   7860
gcatcatcgc cgtggccaac gacaccaaca gctgtgaact ctcccccctgc cgtatcaaca   7920
atggaggctg ccaggatctg tgtctgctca cccaccaagg ccacgtcaac tgttcctgtc   7980
gaggggggccg gatcctccag gaggacttca cctgccgggc tgtgaactcc tcttgtcggg   8040
cacaagatga gtttgagtgt gccaatgggg aatgtatcag cttcagcctc acctgtgatg   8100
gcgtctccca ctgcaaggac aagtccgatg agaagccctc ctactgcaac tcacgccgct   8160
gcaagaagac tttccgccag tgtaacaatg gtcgctgtgt atccaacatg ctgtggtgca   8220
atggggtgga tgactgtggg gatggctctg atgagattcc ttgcaacaag actgcctgtg   8280
gtgtgggtga gttccgctgc cgggatgggt cctgcatcgg gaactccagt cgctgcaacc   8340
agtttgtgga ttgtgaggat gcctcggatg agatgaattg cagtaccaca gactgcagca   8400
gctatttccg cctgggcgtg aaaggtgtcc tcttccagcc gtgcgagcgg acatccctgt   8460
gctacgcacc tagctgggtg tgtgatggcg ccaacgactg tggagactac agcgatgaac   8520
gtgactgtcc aggtgtgaag cgccctaggt gcccgctcaa ttactttgcc tgccccagcg   8580
ggcgctgtat ccccatgagc tggacgtgtg acaaggagga tgactgtgag aacggcgagg   8640
```

-continued

```
acgagaccca ctgcaacaag ttctgctcag aggcacagtt cgagtgccag aaccaccggt   8700
gtatctccaa gcagtggctg tgtgacggta gcgatgattg cggggatggc tccgatgagg   8760
cagctcactg tgaaggcaag acatgtggcc cctcctcctt ctcctgtccc ggcacccacg   8820
tgtgtgtccc tgagcgctgg ctctgtgatg gcgacaagga ctgtaccgat ggcgcggatg   8880
agagtgtcac tgctggctgc ctgtacaaca gcacctgtga tgaccgtgag ttcatgtgcc   8940
agaaccgctt gtgtattccc aagcatttcg tgtgcgacca tgaccgtgac tgtgctgatg   9000
gctctgatga atcccctgag tgtgagtacc caacctgcgg ccccaatgaa ttccgctgtg   9060
ccaatgggcg ttgtctgagc tcccgtcagt gggaatgtga tggggagaat gactgtcacg   9120
accacagcga tgaggctccc aagaacccac actgcaccag cccagagcac aaatgcaatg   9180
cctcatcaca gttcctgtgc agcagcgggc gctgcgtggc tgaggcgttg ctctgcaacg   9240
gccaggacga ctgtggggac ggttcagacg aacgcgggtg ccatgtcaac gagtgtctca   9300
gccgcaagct cagtggctgc agtcaggact gcgaggacct caagataggc tttaagtgcc   9360
gctgtcgccc gggcttccgg ctaaaggacg atggcaggac ctgtgccgac ctggatgagt   9420
gcagcaccac cttcccctgc agccagctct gcatcaacac ccacggaagt tacaagtgtc   9480
tgtgtgtgga gggctatgca ccccgtggcg gtgacccccca cagctgcaaa gctgtgaccg   9540
atgaggagcc atttctcatc tttgccaacc ggtactacct gcggaagctc aacctggacg   9600
gctccaacta cacactgctt aagcagggcc tgaacaatgc ggtcgccttg gactttgact   9660
accgagagca gatgatctac tggacggacg tgaccaccca gggcagcatg attcgcagga   9720
tgcacctcaa cggcagcaac gtgcaggttc tgcaccggac gggccttagt aacccagatg   9780
ggctggctgt ggactgggtg ggtggcaacc tgtactggtg tgacaagggc agagatacca   9840
ttgaggtgtc caagcttaac ggggcctatc ggacagtgct ggtcagctct ggcctccggg   9900
agcccagagc tctggtagtg gatgtacaga atgggtacct gtactggaca gactggggtg   9960
accactcact gatcggccgg attggcatgg atggatctgg ccgcagcatc atcgtggaca  10020
ctaagatcac atggcccaat ggcctgaccg tggactacgt cacggaacgc atctactggg  10080
ctgacgcccg tgaggactac atcgagttcg ccagcctgga tggctccaac cgtcacgttg  10140
tgctgagcca agacatccca cacatctttg cgctgaccct atttgaagac tacgtctact  10200
ggacagactg ggaaacgaag tccatcaacc gggcccacaa gaccacgggt gccaacaaaa  10260
cactcctcat cagcaccctg caccggccca tggacttaca tgtattccac gccctgcgcc  10320
agccagatgt gcccaatcac ccctgcaaag tcaacaatgg tggctgcagc aacctgtgcc  10380
tgctgtcccc tgggggtggt cataaatgcg cctgccccac caacttctat ctgggtggcg  10440
atggccgtac ctgtgtgtcc aactgcacag caagccagtt tgtgtgcaaa aatgacaagt  10500
gcatcccctt ctggtggaag tgtgacacgg aggacgactg tggggatcac tcagacgagc  10560
ctccagactg tcccgagttc aagtgccgcc caggccagtt ccagtgctcc accggcatct  10620
gcaccaaccc tgccttcatc tgtgatgggg acaatgactg ccaagacaat agtgatgagg  10680
ccaattgcga cattcacgtc tgcttgccca gccaattcaa gtgcaccaac accaaccgct  10740
gcattcctgg catcttccgt tgcaatgggc aggacaactg cggggacggc gaggatgagc  10800
gggattgccc tgaggtgacc tgcgccccca accagttcca gtgctccatc accaagcgct  10860
gcatccctcg cgtctgggtc tgtgacaggg ataatgactg tgtggacggc agtgatgagc  10920
ctgccaactg tacccaaatg acctgtggag tggatgagtt ccgctgcaag gattctggcc  10980
gctgcatccc cgcgcgctgg aagtgtgacg gagaagatga ctgtggggat ggttcagatg  11040
```

```
agcccaagga agagtgtgat gagcgcacct gtgagccata ccagttccgc tgcaaaaaca  11100
accgctgtgt cccaggccgt tggcaatgtg actacgacaa cgactgcgga gataactcgg  11160
acgaggagag ctgcacacct cggccctgct ctgagagtga gttttcctgt gccaatggcc  11220
gctgcatcgc tgggcgctgg aagtgtgatg ggaccatga ctgtgccgac ggctcagacg  11280
agaaagactg caccccccgc tgtgatatgg accagttcca gtgcaagagt ggccactgca  11340
tccccctgcg ctggcgctgt gacgcggatg ctgactgtat ggacggcagt gacgaggaag  11400
cctgtggcac tggggtgagg acctgcccat tggatgagtt tcaatgtaac aacaccttgt  11460
gcaagccgct ggcctggaag tgtgatggag aggacgactg tggggacaac tcagatgaga  11520
accccgagga atgcgcccgg ttcatctgcc ctcccaaccg gcctttccgc tgcaagaatg  11580
accgagtctg cctgtggatt gggcgccagt gtgatggcgt ggacaactgt ggagatggga  11640
ctgacgagga ggactgtgag ccccccacgg cccagaaccc ccactgcaaa gacaagaagg  11700
agttcctgtg ccgaaaccag cgctgtctat catcctccct gcgctgtaac atgttcgatg  11760
actgcggcga tggctccgat gaagaagatt gcagcatcga ccccaagctg accagctgtg  11820
ccaccaatgc cagcatgtgt ggggacgaag ctcgttgtgt gcgcactgag aaagctgcct  11880
actgtgcctg ccgctcgggc ttccatactg tgccgggcca gcccggatgc caggacatca  11940
acgagtgcct gcgctttggt acctgctctc agctctgcaa caacaccaag ggaggccacc  12000
tctgcagctg tgcccgcaac ttcatgaaga cacacaacac ctgcaaagct gaaggctccg  12060
agtaccaggt gctatacatc gcggatgaca acgagatccg cagcttgttc ccgggccacc  12120
cccactcagc ctacgagcag acattccagg gcgatgagag tgtccgcata gatgccatgg  12180
atgtccatgt caaggccggc cgtgtctact ggactaactg gcacacgggc acaatctcct  12240
acaggagcct gccccctgcc gcccctccta ccacttccaa ccgccaccgg aggcagatcg  12300
accggggtgt cacccacctc aatatttcag ggctgaagat gccgaggggt atcgctatcg  12360
actgggtggc cgggaatgtg tactggaccg attccggccg agacgtgatt gaggtggcgc  12420
aaatgaaggg cgagaaccgc aagacgctca tctcgggcat gattgatgag ccccatgcca  12480
tcgtggtgga ccctctgagg ggcaccatgt actggtcaga ctgggggaac caccccaaga  12540
ttgaaacagc agcgatggat ggcacccttc gggagactct cgtgcaagac aacattcagt  12600
ggcctacagg gctggctgtg gactatcaca atgaacggct ctactgggca gatgccaagc  12660
tttcggtcat cggcagcatc cggctcaacg gcactgaccc cattgtggct gctgacagca  12720
aacgaggcct aagtcacccc ttcagcatcg atgtgtttga agactacatc tacggagtca  12780
cttacatcaa taatcgtgtc ttcaagatcc acaagtttgg acacagcccc ttgatcaacc  12840
taactggggg cctgagccat gcctctgatg tagtccttta ccatcaacac aagcagcctg  12900
aagtgaccaa cccctgtgac cgcaagaaat gtgaatggct gtgtctgctg agccccagcg  12960
ggcctgtctg cacctgtccc aatggaaaga ggctggataa tggcacctgt gtgcctgtgc  13020
cctctccaac acccccctcca gatgccccta ggcctggaac ctgcactctg cagtgcttca  13080
atggtggtag ttgtttcctc aatgctcgga ggcagcccaa gtgccgttgc cagccccgtt  13140
acacaggcga taagtgtgag ctggatcagt gctgggaata ctgtcacaac ggaggcacct  13200
gtgcggcttc cccatctggc atgcccacgt gccgctgtcc cactggcttc acgggcccca  13260
aatgcaccgc acaggtgtgt gcaggctact gctctaacaa cagcacctgc accgtcaacc  13320
agggcaacca gccccagtgc cgatgtctac ctggcttcct gggcgaccgt tgccagtacc  13380
```

ggcagtgctc tggcttctgt gagaactttg gcacctgtca gatggctgct gatggctccc 13440
gacaatgtcg ctgcaccgtc tactttgagg gaccaaggtg tgaggtgaac aagtgtagtc 13500
gctgtctcca aggcgcctgt gtggtcaata agcagaccgg agatgtcaca tgcaactgca 13560
ctgatggccg ggtagccccc agttgtctga cctgcatcga tcactgtagc aatggtggct 13620
cctgcaccat gaacagcaag atgatgcctg agtgccagtg cccgccccat atgacaggac 13680
cccggtgcga ggagcaggtt gttagtcagc aacagcctgg gcatatggcc tccatcctga 13740
tccctctgct gctgcttctc ctgctgcttc tggtggctgg cgtggtgttc tggtataagc 13800
ggcgagtccg aggggctaag ggcttccagc accagcggat gaccaatggg gccatgaatg 13860
tggaaattgg aaaccctacc tacaagatgt atgaaggtgg agagcccgat gatgtcgggg 13920
gcctactgga tgctgatttt gcccttgacc ctgacaagcc taccaacttc accaacccag 13980
tgtatgccac gctctacatg gggggccacg gcagccgcca ttccctggcc agcacggacg 14040
agaagcgaga actgctgggc cggggacctg aagacgagat aggagatccc ttggcatagg 14100
gccctgcccc gacggatgtc cccagaaagc cccctgccac atgagtcttt caatgaaccc 14160
cctccccagc cggcccttct ccggccctgc cgggtgtaca aatgtaaaaa tgaaggaatt 14220
actttttata tgtgagcgag caagcgagca agcacagtat tatctctttg catttccttc 14280
ctgcctgctc ctcagtatcc cccccatgct gccttgaggg ggcggggagg gctttgtggc 14340
tcaaaggtat gaaggagtcc acatgttccc taccgagcat acccctggaa gctggcggca 14400
cggcctcccc accacgcctg tgcaagacac tcaacggggc tccgtgtccc agctttcctt 14460
tccttggctc tctggggtta gttcagggga ggtggagtcc tctgctgacc ctgtctggaa 14520
gatttggctc tagctgagga aggagtcttt tagttgaggg aagtcacccc aaaccccagc 14580
tcccactttc aggggcacct ctcagatggc catgctcagt atcccttcca gacaggccct 14640
cccctctcta gcgcccccctc tgtggctcct agggctgaac acattctttg gtaactgtcc 14700
cccaagcctc ccatcccccct gagggccagg aagagtcggg gcacaccaag gaagggcaag 14760
cgggcagccc cattttgggg acgtgaacgt tttaataatt tttgctgaat tcctttacaa 14820
ctaaataaca cagatattgt tataaataaa attgtaaaaa aggaaaaaaa aaagaaaaga 14880
aaagaaaaga aaaaaaaaaa aaaaaaa 14907

<210> SEQ ID NO 7
<211> LENGTH: 14900
<212> TYPE: DNA
<213> ORGANISM: Macaca mulatta

<400> SEQUENCE: 7
cagcggtgcg agctccaggc ccatgcactg aggaggcgga aacgagggga acccccagag 60
ctccatcaag ccccccttgaa aggctcccct acccggtcca cgccccccac cccccctccc 120
cgcctcctcc caattgtgca tttttgcagc cggaggcggc tccgagatgg ggctgtgagc 180
ttcgcccggg gagggggaaa gagcagcgag gagtgaagcg ggggggtggg gtgaagggtt 240
tggatttggg ggcaggggcg caccccagtc agcaggccct ccccaagggg ctcggaactc 300
tacctcttca cccacgcccc tggtgcgctt tgccgaagga aagaataaga atagagaagg 360
aggaggggga aaggaggaaa agggggaccc cccaattggg ggggtgaagg agagaagtag 420
caggaccaga ggggaagggg ctgctgcttg catcagccca caccatgctg accccgccgt 480
tgctcctgct gctgcccctg ctctcagctc tggtcgcggc cgctatcgac gcccctaaga 540
cttgcagccc caagcagttt gcctgcagag atcaaatcac ctgtatctca aagggctggc 600

```
ggtgtgatgg tgagagggac tgcccagacg gatctgacga ggcccctgag atttgtccac    660
agagcaaggc ccagcgatgc cagccgaacg agcataactg cctgggtacc gagctgtgtg    720
ttcccatgtc tcgcctctgc aatggagtcc aggactgcat ggatggctcc gatgaggggc    780
cccactgccg agagcttcga ggcaactgct ctcgcctggg ctgccagcac cattgtgtcc    840
ccacactcga tgggcccacc tgctactgca acagcagctt tcagcttcag gcagacagca    900
agacctgcaa agattttgat gagtgttcag tgtacggcac ctgtagccag ctatgcacca    960
acacagatgg ctcctttata tgtggctgtg tcgaaggata cctgctgcag ccggataacc   1020
gctcctgcaa ggccaagaat gagccagtag accggccccc tgtgctgttg atagccaact   1080
cccagaacat cttggccacg tacctgagtg gggcccaggt gtctaccatc acacctacga   1140
gcactcggca gaccacagcc atggacttca gctacgccaa tgagaccgta tgctgggtgc   1200
atgttgggga caatgctgcc cagacgcagc tcaagtgtgc ccgcatgcct ggcctaaagg   1260
gcttcgtgga tgagcacacc atcaacatct ccctcagtct gcaccacgtg gaacagatgg   1320
ccatcgactg gctgacaggc aacttctact ttgtggatga catcgatgat aggatctttg   1380
tctgcaacag aaatggggac acatgtgtca cattgctaga cctggaactc tacaacccca   1440
agggcattgc cctggatcct gccatgggga aggtgttttt cactgactat gggcagatcc   1500
caaaggtgga acgttgtgac atggatgggc agaaccgcac caagcttgtc gacagcaaga   1560
ttgtgtttcc tcacggcatc acgctggacc tggtcagccg ccttgtctac tgggcagatg   1620
cctacctgga ctatattgaa gtggtggact atgagggcaa aggccgccag accatcatcc   1680
agggcatcct gatcgagcac ctgtatggcc tgaccgtgtt tgagaattac ctctatgcca   1740
ccaactcgga caatgccaat gcccagcaga agacgagtgt gatccgtgtg aaccgcttta   1800
atagcaccga gtaccaggtt gtcacccggg tggacaaggg tggtgccctc cacatctacc   1860
accagcggcg tcagccccga gtgaggagcc atgcctgtga aaacgaccag tacgggaagc   1920
cgggtggctg ctctgacatc tgcctactgg ccaatagcca caaggcgagg acctgccgct   1980
gccgctccgg cttcagcctg ggcagtgatg ggaagtcatg caagaagccg gagcacgagc   2040
tgttcctcgt gtatggcaag ggccggccag gcatcatccg gggcatggat atgggggcca   2100
aggtcccgga cgaacacatg atccccattg aaaacctcat gaacccccga gccctggact   2160
tccacgctga gaccggcttc atctactttg ctgacaccac cagctacctc attggccgcc   2220
agaagatcga tggcactgag cgggagacca tcctgaagga cggcatccac aatgtggagg   2280
gtgtggctgt ggactggatg ggggacaatc tgtactggac ggacgatggg cccaaaaaga   2340
caatcagcgt ggccaggctg gagaaagctg ctcagacccg caagacttta attgagggca   2400
aaatgacaca ccccagggct attgtggtag atccgctcaa tgggtggatg tactggacag   2460
actgggagga ggaccccaag gacagtcggc gtgggcggct ggagagggcc tggatggatg   2520
gctcacaccg agacatcttt gtcacctcca agacagtgct ttggcccaat gggctaagcc   2580
tggacatccc agctgggcgc ctctactggg tggatgcctt ctacgaccgc attgagacga   2640
tactgctcaa tggcacagac cggaagattg tgtatgaagg tcctgagctg aaccacgcct   2700
ttggcctgtg tcaccatggc aactacctct tctggactga gtatcggagt ggcagtgtct   2760
accgcttgga acggggtgta ggaggtgcac cccccactgt gacccttctg cgcagtgagc   2820
ggcccccccat ctttgagatc cgaatgtatg atgcccagca gcagcaagtt ggcaccaaca   2880
aatgccgggt gaacaatggc ggctgcagca gcctgtgctt ggccacccct gggagccgcc   2940
```

-continued

```
agtgcgcctg tgctgaggac caggtgttgg acgcagatgg cgtcacttgt ttggcgaacc   3000
catcctacgt gcctccaccc cagtgccagc cgggcgagtt tgcctgtgcc aacagccgct   3060
gcatccagga gcgctggaag tgtgatggag acaacgactg cctggacaac agtgatgagg   3120
ccccagccct ctgccatcag catacctgcc cctcggaccg attcaagtgt gagaacaacc   3180
ggtgcatccc caaccgctgg ctctgtgacg gggacaatga ctgtgggaac agtgaagatg   3240
agtccaatgc cacttgttca gcccgcacct gccccccaa ccagttctcc tgtgccagtg    3300
gccgctgcat ccccatctcc tggacgtgtg atctggatga tgactgtggg gaccgctctg   3360
acgagtccgc ctcgtgtgcc tatcccacct gcttcccct gactcagttt acctgcaaca    3420
atggcagatg tatcaacatc aactggcgat gtgacaatga caatgactgt ggggacaaca   3480
gtgacgaagc cggctgcagc cactcctgct ctagcaccca gttcaagtgc aacagcgggc   3540
gctgcatccc cgagcactgg acctgcgatg gggacaatga ctgcggagat tatagtgatg   3600
agacgcatgc caactgcacc aaccaggcca cgaggccccc tggtggctgc cacactgatg   3660
agttccagtg ccggctggat ggactgtgca tcccctgcg gtggcgctgt gatggggaca    3720
ctgactgcat ggactccagc gacgagaaga gctgtgaggg agtgacccac gtctgcgacc   3780
ccagtgtcaa gtttggctgc aaggactcag ctcggtgcat cagcaaagcg tgggtgtgtg   3840
atggcgacaa cgactgtgag gataactcag atgaggagaa ctgcgagtcc ctggcctgca   3900
ggccaccctc acacccctgt gccaacaaca cctcagtctg cctgccccct gacaagctgt   3960
gtgatggcaa cgacgactgt ggcgacggct cagatgaggg cgagctctgc gaccagtgct   4020
ctctgaataa cggtggctgc agccacaact gctcagtggc acctggcgaa ggcattgtgt   4080
gttcctgccc tctgggcatg gagctagggc ccgacaacca cacctgccag atccagagct   4140
actgtgccaa gcatctcaaa tgcagccaaa agtgcgacca gaacaagttc agcgtgaagt   4200
gctcctgcta cgagggctgg gtcctggagc ctgatgggga gagctgccgc agcctggacc   4260
ccttcaagcc gttcatcatc ttctccaacc ggcatgagat ccggcgcatc gatcttcaca   4320
aaggagacta cagcgtcctg gtacccggcc tgcgcaacac catcgccctg gactttcacc   4380
tcagccagag cgccctctac tggaccgacg tggtggagga caagatctat cgcgggaagc   4440
tgctggacaa cggagccctg actagttttg aggtggtgat tcagtacggc ctggccacac   4500
ccgagggcct ggctgtagac tggattgcag gcaacatcta ctgggtggag agtaacctgg   4560
accagatcga ggtggccaag ctggatggga ccctccggac cactctgctg gccggtgaca   4620
ttgagcaccc aagggcaatc gcactggatc cccgggatgg gatcctgttt tggacagact   4680
gggatgccag cctgccccgc atcgaggcag cctccatgag tggggccggg cgccgcaccg   4740
tgcaccggga gaccggctct gggggctggc ccaacgggct cactgtggac tacctggaga   4800
agcgcatcct ttggattgac gccaggtcag atgccattta ctcagcccgt tacgacggct   4860
ctggccacat ggaggtgctt cggggacacg agttcctgtc gcacccattt gcagtgacgc   4920
tgtacggggg ggaggtctac tggactgact ggcgaacaaa cacgctggct aaggccaaca   4980
agtggaccgg ccacaatgtc actgtggtac agaggaccaa cacccagccc tttgacctgc   5040
aggtgtacca cccttcccgc cagcccatgg ctcccaatcc ctgtgaggcc aatgggggcc   5100
ggggccccctg ctcccacctg tgtctcatca actacaaccg gaccgtgtcc tgcgcctgcc  5160
cccacctcat gaagctccac aaggacaaaa ctacttgcta tgagtttaag aagttcctgc   5220
tgtacgcacg tcagatggag atccgaggtg tggacctgga tgcccctac tacaactaca    5280
tcatctcctt cacggtgccc gacatcgaca acgtcacagt gctagactac gatgcccgtg   5340
```

```
agcagcgtgt gtactggtct gacgtgcgga cacaggccat caagcgggcc ttcatcaatg   5400
gcacaggcgt ggagacagtc gtctctgcag acttgccaaa tgcccatggg ctggctgtgg   5460
actgggtctc ccgaaacctg ttctggacaa gctatgacac caataagaag cagatcaatg   5520
tggcccggct ggatggctcc ttcaagaacg cagtggtgca gggcctggag cagccccatg   5580
gccttgtcgt ccaccctctg cgtgggaagc tctactggac cgatggtgac aacatcagca   5640
tggccaacat ggacggcagc aatcgcaccc tgctcttcag tggccagaag ggccccgtgg   5700
gtctggctat tgacttccct gaaagcaaac tctactggat cagctccggg aaccatacca   5760
tcaaccgctg caacctggat gggagtgggc tggaggtcat cgacgccatg cggagccagc   5820
tgggcaaggc cactgccctg gccatcatgg gggacaagct gtggtgggca gatcaggtgt   5880
cggagaagat gggcacatgc agcaaggccg acggctcggg ctccatcgtc ctgcggaaca   5940
gcaccaccct ggtgatgcac atgaaggtct atgacgagag catccagctg gaccataagg   6000
gcaccaaccc ctgcagtgtc aacaacggtg actgctccca gctctgcctg cccacgtcag   6060
agacgacccg ctcctgcatg tgcacagccg gctatagcct ccggagtggc cagcaggcct   6120
gtgagggcgt gggttccttt ctcctgtact ctgtgcacga aggaatcagg ggaattcctc   6180
tggatcccaa tgacaagtca gatgccctgg tcccagtgtc cgggacctcg ctggctgtcg   6240
gcatcgactt ccatgctgaa aatgacacca tctactgggt ggacatgggc ctgagcacga   6300
tcagccgggc caagcgggac cagacgtggc gtgaagacgt ggtgaccaat ggcattggcc   6360
gcgtggaggg catcgcagtg gactggatcg caggcaacat ctactggacg gaccagggct   6420
tcgatgtcat cgaggtcgcc cggctcaatg gctccttccg ctacgtggtg atctcccagg   6480
gtctagacaa gccccgggcc atcaccgtcc acccagagaa agggtacctg ttctggactg   6540
agtggggtca gtatccacgt attgagcggt ctcggctaga tggcacagaa cgtgtggtgc   6600
tggtcaacgt cagcatcagc tggcccaatg gcatctcagt ggactaccag gatgggaagc   6660
tgtactggtg tgatgcacgg acagacaaga ttgaacggat cgacctggag acgggtgaga   6720
accgcgaggt ggttctgtcc agcaacaaca tggacatgtt ttcagtgtct gtgtttgagg   6780
atttcatcta ctggagtgac aggactcacg ccaacggctc tatcaagcga gggagcaaag   6840
acaatgccac agactccgtg cccctgcgaa ccggcatcgg cgtccagctt aaagatatca   6900
aagtcttcaa ccgggaccgg cagaaaggca cgaacgtgtg cgcggtggcc aatggtgggt   6960
gccagcagct gtgcctgtac cggggccgtg ggcagcgggc ctgcgcctgt gcccacggga   7020
tgctggctga agacggagca tcgtgccgcg agtacgccgg ctacctgctc tactcggagc   7080
gcaccattct caagagcatc cacctgtcgg atgagcgcaa cctcaatgcg cccgtgcagc   7140
ccttcgagga ccctgagcac atgaagaacg tcattgccct ggcctttgac taccgggcag   7200
gcacctctcc gggcaccccc aatcgcatct tcttcagcga catccacttt gggaacattc   7260
agcagatcaa cgacgatggc tccaggagga tcaccattgt ggagaatgtg ggctccgtag   7320
aaggcctggc ctatcaccgt ggctgggaca ctctctattg gacaagctac acgacatcca   7380
ccatcacgcg ccacacagtg gaccagaccc gcccaggggc cttcgagcgt gaaaccgtca   7440
tcactatgtc cggagatgac cacccacggg ccttcgtgtt ggatgagtgc cagaacctca   7500
tgttctggac caactggaat gagcagcatc ccagcatcat gcgggcagcg ctctcgggag   7560
ccaatgtcct gaccctcatc gagaaggata tccgcacccc caacggcctg gccatcgacc   7620
accgtgccga gaagctctac ttctctgacg ccaccctgga caagattgag cggtgcgagt   7680
```

-continued

```
atgacggctc ccaccgctat gtgatcctaa agtcagagcc tgtccacccc ttcgggctgg   7740
ccgtgtatgg ggagcacatt ttctggaccg actgggtgcg gcgggcagtg cagcgggcca   7800
acaagcacgt gggcagcaac atgaagctgc tgcgcgtgga catcccccag cagcccatgg   7860
gcatcatcgc cgtggccaac gacaccaaca gctgtgaact ctctccatgc cgaatcaaca   7920
atggtggctg ccaggacctg tgtctgctca ctcaccaggg ccatgtcaac tgctcgtgcc   7980
gagggggccg aatcctccag gatgacctca cctgccgagc ggtgaattcc tcttgccgag   8040
cacaagatga gtttgagtgt gccaatggcg agtgcatcaa cttcagcctg acctgcgacg   8100
gcgtccccca ctgcaaggac aagtccgatg agaagccatc ctactgcaac tcccgccgct   8160
gcaagaagac tttccgccag tgcagcaatg ggcgctgtgt gtccaacatg ctgtggtgca   8220
acggggccga cgactgtggg gatggttctg atgagatccc ctgcaacaag acagcctgtg   8280
gtgtgggcga gttccgctgc cgggacggga cctgcatcgg gaactccagc cgctgcaacc   8340
agtttgtgga ttgtgaggat gcctcagatg agatgaactg cagtgccacc gactgcagca   8400
gctacttccg cctgggcgtg aagggcgtgc tcttccagcc ctgtgagcgg acctcgctct   8460
gctacgcacc cagctgggtg tgtgacggcg ccaacgactg cggggactac agtgatgagc   8520
gcgactgccc aggtgtgaaa cgccccagat gcccccctgaa ttacttcgcc tgccctagtg   8580
ggcgctgcat ccccatgagc tggacgtgtg acaaggagga tgactgtgaa cacggcgagg   8640
acgagaccca ctgcaacaag ttctgctcag aggcccagtt tgagtgccag aaccatcgct   8700
gcatctccaa gcagtggctg tgtgacggca gcgatgactg tggggacggc tcggacgagg   8760
ctgctcactg tgaaggcaag acgtgcggcc cctcctcctt ctcctgccct ggcacccacg   8820
tgtgcgtccc cgagcgctgg ctctgtgacg gtgacaaaga ctgtgctgat ggtgcagacg   8880
agagcatcgc agctggttgc ttgtacaaca gcacctgcga cgaccgtgag ttcatgtgcc   8940
agaaccgcca gtgcatcccc aagcacttcg tgtgcgacca tgaccgtgac tgtgcagatg   9000
gctccgatga gtcccccgag tgtgagtacc cgacctgcgg ccccagtgag ttccgctgtg   9060
ccaatgggcg ctgtctgagc tcccgccagt gggagtgtga tggcgagaat gactgccacg   9120
accagagtga cgaggctccc aagaacccac actgcaccag cccagagcac aagtgcaatg   9180
cctcgtctca gttcctgtgc agcagcgggc gctgtgtggc tgaggtactg ctctgcaatg   9240
gccaggatga ctgtggtgac ggctcggatg agcgtggctg ccacatcaac gagtgtctca   9300
gccacaagct cagtggctgc agccaggact gtgaggacct caagattggc ttcaagtgcc   9360
gctgtcgccc tggcttccgg ctgaaggacg acggccggac atgtgccgat gtggatgagt   9420
gcagcaccac cttcccctgc agccagcgct gcatcaacac ccatggcagc tataagtgtc   9480
tgtgtgtgga gggctacgca ccccgcggcg gcgaccccca cagctgcaag gctgtgactg   9540
acgaggaacc gtttctgatc tttgccaacc ggtactacct acgcaagctc aacctggatg   9600
ggtccaacta cacgttactt aagcagggcc tgaacaatgc cgttgccttg gactttgact   9660
accgagagca aatgatctac tggacagatg tgacaaccca gggcagcatg atccgaagga   9720
tgcaccttaa tgggagcaac gtgcaggtcc tacaccgtac aggcctcagc aaccccgacg   9780
ggctggctgt ggactgggtg ggtggcaacc tgtactggtg cgacaaaggc cgggacacca   9840
ttgaggtgtc caagctcaat ggggcctatc ggacggtgct ggtcagctct ggcctccgcg   9900
agcccagggc tctggtggtg gatgtgcaga atgggtacct gtactggaca gactggggtg   9960
accactcact gattggccgc atcggcatgg atgggtccag tcgcagcgtc attgtggaca  10020
ccaagatcac atggcccaac ggcctgacgc tggactatgt cactgagcgc atctactggg  10080
```

```
ctgacgcccg cgaggactac attgagtttg ccagcctgga tggctccaat cgccacgttg  10140
tgctgagcca ggacatcccg cacatctttg cactgaccct gtttgaggac tacgtctact  10200
ggaccgactg ggaaacaaag tccatcaacc gagcccacaa gaccacgggc accaacaaaa  10260
cgctcctcat cagcacgctg caccggccca tggacctgca cgtcttccac gccctgcgcc  10320
agccggacgt gcccaatcac ccctgcaagg tcaacaatgg tggctgcagc aacctgtgcc  10380
tgctgtcccc cgggggaggg cacaaatgtg cctgccccac caacttctac ctgggcagcg  10440
atgggcgcac ctgtgtgtcc aactgcacag cgagccagtt tgtgtgcaag aacgacaagt  10500
gcatcccctt ctggtggaag tgtgacaccg aggacgactg cggggaccac tcagatgagc  10560
ccccggactg ccccgagttc aagtgccggc ccggacagtt ccagtgctcc acaggcatct  10620
gcacaaaccc tgccttcatc tgcgatggag acaatgactg ccaggacaac agtgacgagg  10680
ccaactgtga catccacgtc tgcttgccca gtcagttcaa atgtaccaat accaaccgct  10740
gtattcccgg catcttccgc tgcaacgggc aggacaactg cggagacggg gaggacgaga  10800
gggactgccc cgaggtgacc tgcgctccca accagttcca gtgctccatt accaaacggt  10860
gcatcccccg ggtctgggtc tgcgaccggg acaatgactg tgtggatggc agtgatgagc  10920
ccgccaactg cacccagatg acctgtggcg tggacgagtt ccgctgcaag gattcgggcc  10980
gatgcatccc agcgcgctgg aagtgtgatg gagaggatga ctgcggggat ggctcagatg  11040
agcccaagga agagtgtgat gagcgcacct gtgagccata ccagttccgc tgcaagaaca  11100
accgctgcgt gcccggccgc tggcagtgtg actacgacaa cgattgtggc gacaactccg  11160
acgaggagag ctgcacccct cgaccctgct ccgagagtga gttctcctgt gccaacggcc  11220
gctgcatcgc ggggcgctgg aaatgcgatg gagaccacga ctgcgctgac ggctcagacg  11280
agaaagactg caccccccgc tgtgacatgg accagttcca gtgcaagagc ggccactgca  11340
tcccccctgcg ctggcgctgt gacgcagacg ctgactgcat ggacggcagc gacgaggagg  11400
cctgcggcac tggcgtgcgg acctgccccc tggatgagtt ccagtgcaac aacaccttgt  11460
gcaagccgct ggcctggaag tgcgatggcg aggatgactg tggggacaac tcagatgaga  11520
accccgagga gtgtgcccgg ttcgtgtgcc ctcccaaccg gcccttccgt tgcaagaatg  11580
accgtgtctg tctgtggatc ggacgccaat gcgacggcat ggacaactgt ggggatggga  11640
ctgatgaaga ggactgtgag ccccccacgg cccagaccac ccactgcaaa gataagaagg  11700
agtttctgtg ccggaaccag cgctgcctct cctcctccct acgctgcaac atgttcgacg  11760
actgcgggga tggctctgac gaggaggact gcagcatcga ccccaagctg accagctgcg  11820
ccaccaatgc cagcatctgt ggggacgagg cacgctgcgt acgcaccgag aaagcagcct  11880
actgtgcctg ccgctctggc ttccacaccg tgcccggcca gcccggatgt caagacatca  11940
acgagtgcct gcgcttcggc acctgctccc agctctgcaa caacaccaag ggcggccacc  12000
tctgcagctg cgctcggaac ttcatgaaga cgcacaacac ctgcaaggct gaaggctctg  12060
agtaccaggt cctgtacatt gctgatgaca atgagatccg cagcctgttc cctgggcacc  12120
cccattcggc ttacgagcag gcattccagg gcgacgagag cgtccgcatt gatgccatgg  12180
atgtccatgt caaggctggc cgtgtctatt ggaccaactg gcacacgggc accatctcct  12240
accgcagcct gccacctgct gcgcctccta ccacttccaa ccgccaccgg cgacagattg  12300
accggggtgt cacccacctc aacatttcag ggctgaagat gcccagaggc attgccatcg  12360
attgggtggc cggaaacgtg tactggactg actcgggccg agatgtgatt gaggtggcac  12420
```

-continued agatgaaggg cgagaaccgc aagacactca tctcgggcat gattgatgag ccccacgcca 12480
ttgtggtgga cccactgagg ggcaccatgt actggtcaga ctggggcaac caccccaaga 12540
ttgagacagc agcgatggat gggacccttc gggagacact ggtgcaggac aacattcagt 12600
ggcccacagg cctggccgtg gattatcaca atgagcggtt gtactgggca gatgccaagc 12660
tttcagtcat cggcagcatc cggctcaatg gcacggaccc cattgtggct gctgacagca 12720
aacgaggcct aagtcacccc ttcagcatcg acgtctttga ggattacatc tatggtgtca 12780
cctacatcaa taatcgtgtc ttcaagatcc ataagtttgg ccacagcccc ttggtcaacc 12840
tgacaggggg cctgagccat gcctctgatg tggtcctgta ccatcagcac aagcagcccg 12900
aagtgaccaa cccatgtgac cgcaagaaat gcgagtggct ctgcctgctg agccccagtg 12960
ggcctgtctg cacctgtccc aatgggaaac ggctggacaa cggcacatgc gtgcctgtgc 13020
cctctccaac acccccccca gatgctcccc ggcctggaac ctgtaacctg cagtgcttca 13080
acggtggcag ctgtttcctc aatgcacgga ggcagcccaa gtgccgctgc cagccccgct 13140
acacgggtga caaatgtgaa ctggaccaat gctgggagca ctgtcgcaat gggggcacct 13200
gtgctgcctc tccctctggc atgcccacgt gccggtgccc cacgggcttc acgggcccca 13260
aatgcaccca gcaggtgtgt gcaggctact gtgccaacaa cagcacctgc actgtcaacc 13320
agggcaacca gccccagtgc cgatgcctac ccggcttcct gggcgaccgc tgccagtacc 13380
ggcagtgctc tggctactgt gagaactttg gcacatgcca gatggccgct gatggctccc 13440
gacaatgtcg ctgcactgcc tactttgagg gactgaggtg tgaggtgaac aagtgcagcc 13500
gctgtctcga aggggcctgt gtggtcaaca agcagagtgg ggatgtcacc tgcaactgca 13560
cggacggccg ggtggccccc agctgtctga cctgcatcgg ccactgcagc aatggcggct 13620
cctgcaccat gaacagcaaa atgatgcctg agtgccagtg cccaccccac atgacagggc 13680
cccggtgtga ggagcacgtc ttcagccagc agcagccagg acatatagcc tccatcctaa 13740
tccctctgct cttgctgctg ctggtgcttc tggtggccgg agtggtattc tggtataagc 13800
ggcgagtcca aggggctaag ggcttccagc accagcggat gaccaacggg gccatgaatg 13860
tggagattgg gaaccccacc tacaagatgt acgaaggcgg agagcctgat gacgtgggag 13920
gcctactgga cgccgacttt gccctggacc ctgacaagcc caccaacttc accaaccccg 13980
tgtatgccac actctacatg gggggccatg gcagtcgcca ctccctggcc agcacggacg 14040
agaagcgaga actcctgggc cggggccctg aggacgagat aggggacccc ttggcatagg 14100
gccctgcccc gtcgcacttc cccagaaag cctcctgccc cctgccagtg aagtccttca 14160
gtgagcccct ccccagccag cccttccccg gcctcgccgg atgtataaat gtaaaaatga 14220
aggaattacg ttttatatgt gagcgagcaa gccagcaagc gagcacagta ttatttctcc 14280
atcccctccc tgcctgctcc tcggcacccc catgctgcct tcagggaggc aggcagggag 14340
ggcttggggc tgcacttcct accctcccac cagaacacac cccaccggga gagctggtgg 14400
tgcagcctcc ccctccctgt ataagacact ttgccaaggc tctcccttct cgaccctacc 14460
cctgcttgcc cactcccaca gctcccggag ggctaattct ggggaaggag agttctttgc 14520
tgcccctgtc tggaagacgt ggctctgggt gaggtaggca ggaaaggatg gagtgtttta 14580
gttcttgggg gaggccaccc caaagcccag ccctgactcc aggggcacct atgagatggc 14640
catgctgaat ccccctccca gacaggccct tcccatctcc agggccccca ctgaggttcc 14700
cagggctgga gacttcctct ggtaaacatt cccccagcct cccctcccct ggggacactg 14760
aggaggtggg ccacacccag gaagggcaag tgggcagccc cgttttgggg acgtgaacgt 14820
tttaataatt tttgctgaat tcctttacaa cgaaataaca cagatattgt tataaataaa 14880
attgtaaaaa aaaaaaaagt 14900

<210> SEQ ID NO 8
<211> LENGTH: 14714
<212> TYPE: DNA
<213> ORGANISM: Rattus norvegicus

<400> SEQUENCE: 8
caccccccac cccgcctcct cccaattgtg catttttgca gccggaggcg gctccgagat 60
ggggctgtga gcttcgccct gggaggggga gaggagcgag gagtaaagca ggggtgaagg 120
gttcgaattt gggggcaggg ggcgcacccg cgtcagcagg cccttcccag ggggctcgga 180
actgtatcat ttcacctatg cccctgattc gctttgctta aggaaaggat aagaatagaa 240
gagtcaggga gaggaagata aagggggacc ccccaattgg ggggggcgag gacaagaagt 300
aacaggacca gagggtgggg gctgctgttt ccatcggccc acaccatgct gaccccgccg 360
ttgctgctgc tgctgcccct gctttcagct ctggtcgccg gggccactat ggatgcccct 420
aaaacttgca gccctaagca gtttgcctgc agagaccaaa tcacctgtat ctcgaagggc 480
tggcggtgtg acggggaaag agattgtccg gacggctctg atgaagcccc cgagatctgt 540
ccacagagta aagcccagag atgcccacca aatgagcaca gttgcctggg gaccgagctg 600
tgtgtcccca tgtctcgtct ctgcaacggg atccaggatt gcatggatgg ctcagatgag 660
ggtgctcact gccgagagct ccgtgtcaac tgttctcgaa tgggctgtca gcaccattgc 720
gtccctacgc ccagtgggcc cacatgctac tgtaataaca gcttccagct tcaggcagac 780
ggcaagacat gcaaagattt tgacgaatgc tctgtgtatg gcacttgcag ccagctttgc 840
accaacacag atggctcctt cacatgtggc tgtgttgaag gttacctgct gcaaccggac 900
aaccgctcat gcaaggccaa gaatgagcca gtagatcggc cccggtgct actgattgcc 960 aactcccaga acatcctagc tacgtacctg agcggagccc aggtgtctac catcacaccc 1020
accagcaccc gacagaccac agccatggac ttcagttatg ccaacgagac tgtatgctgg 1080
gtacatgttg gggacagtgc tgcccagacg cagctcaagt gtgcccggat gcctagcctg 1140
aagggcttcg tggatgagca taccatcaac atctccctga gtctgcacca cgttgagcag 1200
atggctatcg actggctgac tgggaacttc tactttgtgg atgacatcga tgacaggatc 1260
tttgtctgta accgaaatgg ggacacctgt gtcactttgc tggacctgga gctctacaat 1320
cccaaaggca tcgccctgga ccctgccatg gggaaggtgt tcttcactga ctacgggcag 1380
atcccaaagg tggaacgctg tgacatggac ggacagaacc gcaccaagct ggtcgatagc 1440
aagattgtat ttccacatgg catcaccctg gacctggtca gccgcctcgt gtactgggcg 1500
gacgcctacc ttgactatat cgaggtggta gactatgaag gaaagggccg gcagaccatc 1560
atccaaggca tcctgattga gcacctctat ggcctgactg tgtttgagaa ctacctctac 1620
gccaccaact cagacaacgc caacacccag cagaagacga gcgtgatccg agtgaaccgg 1680
ttcaacagta ccgagtacca ggtggtcacc cgtgtggaca agggcggtgc cctgcatatc 1740
tatcaccagc gacgccagcc ccgagtgcgg agtcatgcct gtgagaatga ccagtatggg 1800
aagccaggag gctgctctga catctgcctg ctggccaaca gccacaaggc aaggacctgc 1860
aggtgccggt ctggcttcag tctgggaagt gacgggaaat cctgcaagaa acctgaacat 1920
gagctgttcc tcgtgtatgg caagggccgg ccaggcatca tccgaggcat ggacatggga 1980
gccaaggtcc cagatgagca catgatcccc atcgagaacc ttatgaatcc acgggctctg 2040
gacttccacg ctgagactgg cttcatctac tttgctgaca ccaccagcta cctcattggc 2100
cgccagaaaa ttgatggcac ggagagagag accatcctga aggacggcat ccacaacgtg 2160
gagggcgtag ctgtagactg gatgggggac aacctttact ggactgatga cggccccaag 2220
aagaccatta gtgtggccag gctggagaaa gctgcccaga cacgaaagac tctaatcgag 2280
ggcaagatga cacaccccag ggccattgta gtggatccac tcaatgggtg gatgtactgg 2340
acagactggg aggaagaccc caaggatagc cggcgagggc ggcttgagag ggcttggatg 2400
gacggctcac accgagatat ctttgtcacc tccaagacag tgctttggcc caatgggcta 2460
agcctggata tcccagctgg gcgcctctac tgggtggatg ccttctatga ccgaattgag 2520
accatactgc tcaatggcac agaccggaag attgtatacg agggtcctga actgaatcac 2580
gccttcggcc tgtgtcacca cggcaactac ctcttttgga ctgagtatcg gagcggcagt 2640
gtctaccgct tggagcgggg tgtggcaggc gcacagccca ctgtgaccct tctgcgcagc 2700
gagcgacctc ctatctttga gatccgaatg tacgacgcgc agcagcagca agtgggtacc 2760
aacaaatgcc gggtaaataa cggaggctgc agcagtctgt gcctagccac cccggggagt 2820
cgccagtgcg cctgcgctga ggaccaggtg ttggatgcgg atggcgtcac ctgcctggcg 2880
aacccatcct acgtgccccc accccagtgc cagccgggcg agtttgcctg tgccaacaac 2940
cgctgcatcc aggagcgctg gaagtgtgat ggagataacg actgtctgga caacagtgat 3000
gaggccccgg cactgtgcca tcaacacacc tgtccctcgg accgattcaa atgtgagaac 3060
aaccgatgta tccccaaccg ctggctctgt gatgggggata acgactgtgg caacagcgag 3120
gacgagtcca atgccacgtg ctcagcgcgc acctgcccac ccaaccagtt ctcctgtgcc 3180
agtggccgat gcatccctat ctcttggacc tgtgatcttg atgatgactg tggggaccgc 3240
tccgatgagt cagcctcatg cgcctacccc acctgtttcc ccctgactca gtttacctgc 3300
aacaatggca gatgcattaa catcaactgg cggtgtgaca acgacaatga ctgtggagac 3360
aatagtgacg aagccggctg cagtcactcc tgctccagta cccagttcaa gtgcaacagt 3420
ggcagatgca tccccgagca ctggacttgt gacggggaca acgactgtgg agactacagt 3480
gatgagaccc atgcaaactg taccaaccag gccacaagac ctcctggtgg ctgccactca 3540
gatgagttcc agtgccggct agatggcctg tgcatccccc tgcggtggcg ctgtgatggg 3600
gacactgact gcatggactc tagtgatgag aagggctgtg agggggtgac ccacgtctgt 3660
gatccgaatg tcaagtttgg ctgcaaggac tcagctcggt gcatcagcaa agcatgggtg 3720
tgtgatggtg acagtgactg tgaagataac tcagacgagg agaactgtga ggccctggcc 3780
tgcaggccac cgtcacatcc ctgtgccaac aacacctccg tctgcctgtc ccctgataag 3840
ctgtgtgatg gcaaggatga ctgtggagat ggctccgacg agggcgagct ctgtgaccag 3900
tgttctctga ataatggtgg ctgtagtcac aactgctcgg tggcccctgg tgaaggcatt 3960
gtgtgctctt gccctctggg catggagctg ggacctgaca accacacctg ccagatccag 4020
agctactgtg ccaagcacct caaatgcagc cagaagtgcg accagaacaa gttcagtgtg 4080
aagtgctcct gctatgaggg ctgggtcttg gaaccagacg gggagagctg ccgcagcctg 4140
gatcccttca aaccgttcat catcttctcc aaccgccatg agatcagacg cattgacctt 4200
cacaaggggg actacagcgt cctagtgccc ggcctgcgca acaccattgc cctggacttt 4260
cacctcagcc agagtgccct ctactggacc gatgtggtag aggacaagat ctaccgtggg 4320
aagctgctgg acaacggagc actgaccagc tttgaggtgg tgattcagta tggcttggcc 4380

```
accccagagg gcctggctgt agactggata gcaggcaaca tctactgggt ggaaagcaac   4440
ctggaccaga tcgaggtggc caagctggat ggaaccctcc gaaccactct gctggcgggc   4500
gacattgagc acccaagggc aattgctctg gaccctcggg atgggattct gttttggaca   4560
gattgggatg ccagtctgcc ccgaattgaa gcagcatcca tgagtggggc cgggcgccga   4620
accatccacc gagagacagg ctctgggggt tggcccaacg ggctcaccgt ggactacctg   4680
gagaagcgca tcctctggat cgatgccagg tcagatgcta tctactcagc ccgttatgac   4740
ggctccggcc acatggaggt gctccggggg catgagttcc tgtctcaccc gtttgccgtg   4800
acactgtatg gtggggaggt gtactggact gactggcgaa caaacacact ggctaaggcc   4860
aacaagtgga ccggccacaa tgtcactgtg gtacagagga ccaacaccca gcccttcgac   4920
ctgcaggtgt atcacccttc tcggcagccc atggctccaa acccatgtga ggccaatggg   4980
ggccggggtc cctgttccca cctgtgcctc atcaactaca accggacggt ctcctgtgct   5040
tgtccccatc tcatgaaact ccacaatgac aacaccacct gctacgagtt taagaagttc   5100
ctgctgtacg cacgtcagat ggagatccgg ggtgtggacc tggacgcccc gtactacaat   5160
tacatcatct ccttcacggt gcccgacatt gacaatgtca cagtgctgga ctatgatgcc   5220
cgagagcagc gagtttactg gtctgacgtg cgaacccaag ccatcaaacg ggcattcatc   5280
aacggcacag gcgtggagac cgttgtctct gcagacttgc caaatgccca tgggctggct   5340
gtggactggg tgtcccgaaa tctgttctgg accagttatg acaccaacaa gaagcagatt   5400
aacgtggccc ggctagatgg ctccttcaag aatgcggtgg tgcagggcct ggagcagccc   5460
cacggcctgg ttgtccaccc gcttcgtggc aagctctact ggacggacgg ggacaatatc   5520
agcatggtca acatggatgg gagcaaccgg actctgctct tcagtggcca gaagggccct   5580
gtgggcttag ccattgactt ccctgagagc aaactctact ggatcagctc tgggaaccac   5640
acgatcaacc gttgcaatct ggatgggagt gagctggagg tcatcgacac catgcgtagc   5700
cagctgggca aggccactgc cctggccatc atgggggaca agctgtggtg ggcagatcag   5760
gtgtcagaga agatgggcac atgcaacaag gccgacggct ccgggtcggt ggtgctgcgg   5820
aacagcacca cgttggttat gcacatgaag gtgtatgatg agagcatcca gctagagcat   5880
gagggcacca acccctgcag tgtcaacaat ggagactgct cccagctctg cctgccaaca   5940
tcagagacaa ctcgctcctg tatgtgtaca gctggttaca gcctccggag cggacagcag   6000
gcctgtgagg gtgtgggttc ttttctcctg tattctgtcc atgagggaat tcgggggatc   6060
ccactggatc ccaatgacaa gtcggatgcc ctggtcccag tgtcgggaac gtcactggct   6120
gttggaatcg acttccatgc tgaaaatgac actatttatt gggtggacat gggtctaagc   6180
accatcagca gggccaagcg tgaccagaca tggcgagagg atgtggtgac caatggcatt   6240
ggccgtgtgg agggcatcgc ggtggactgg atcgcaggca acatctactg gacagaccag   6300
ggctttgatg tcatcgaggt tgcccgactc aatggatctt tccgttatgt ggtcatttcc   6360
cagggtctag acaagcctcg ggccatcact gtccacccag agaaggggta cttgttctgg   6420
actgagtggg gtcactaccc acggattgag cggtctcgcc ttgacggcac agagagagtg   6480
gtgctggtta atgtcagcat cagctggccc aatggcatct cagtagacta tcagggcggc   6540
aagctctact ggtgtgatgc ccggatggac aagatcgaac gtatcgatct ggagacgggt   6600
gagaaccgtg aggtggtcct gtccagtaac aacatggaca tgttctctgt gtctgtgttt   6660
gaggatttca tctactggag tgacagaact cacgccaacg gctccatcaa gcgtggatgc   6720
```

-continued

```
aaagacaatg ccacagactc cgtgcctctg agaacgggca ttggcgtgca gcttaaagac   6780

atcaaggtct tcaacaggga caggcagaag ggtaccaacg tgtgcgcagt agccaacggt   6840

gggtgccagc aactatgctt atatcggggt ggtggacagc gagcctgtgc ctgtgcccat   6900

ggaatgctgg cagaagatgg ggcttcgtgc cgagagtatg ctggctacct gctctattca   6960

gagcgtacca tcctcaagag catccacctg tcagatgagc gtaacctcaa cgcaccggtg   7020

cagcctttcg aagaccctga gcacatgaaa aatgtcatcg ccctagcttt tgactaccgg   7080

gcaggcacct ccccagggac ccctaaccgc atcttcttca gtgacatcca ctttgggaat   7140

atccagcaga tcaatgacga tggctcgggg aggaccacca tcgtggaaaa tgtgggctct   7200

gtggaaggcc tggcctatca cagaggctgg gacacactgt actggacaag ctacacgaca   7260

tccaccatca cccgccatac cgtggaccag actcgcccag ggcctttga gagggagacg    7320

gtcatcacca tgtctggaga tgatcaccca agggcatttg tgctggacga gtgccagaac   7380

ctgatgttct ggaccaattg gaatgagctt cacccaagca tcatgcgggc agccctatct   7440

ggagccaacg tcctgaccct catcgagaag gacatccgca cacccaatgg gttggccatc   7500

gaccaccggg ccgagaagct ttacttctcg gacgccacat tggacaagat cgagcgctgt   7560

gaatatgatg gctcccatcg ctatgtgatc ctgaagtcag agcccgtcca cccctttggg   7620

ttggcagtgt acggagagca cattttctgg actgactggg tgcggcgggc tgtgcagcgg   7680

gccaacaagt atgtgggcag tgacatgaag ctgctgcgag tagacatccc ccagcagccc   7740

atgggcatca tcgctgtggc caatgacacc aacagctgtg aactttcccc ctgccgtatc   7800

aacaatggcg gctgtcagga tctgtgtctg ctcacccacc aaggccatgt caactgttcc   7860

tgtcgagggg gccggatcct ccaggaggat ttcacctgcc gggctatgaa ctcctcttgt   7920

cgggcacaag atgagttcga gtgcgccaat ggagagtgta tcagcttcag cctcacctgt   7980

gatggtgtct cccactgcaa ggacaagtct gatgagaagc cctcctactg caactcacgc   8040

cgctgcaaga agactttccg ccagtgcaac aacggccgct gtgtatctaa catgctgtgg   8100

tgcaatgggg tggacgactg tggcgatggc tccgatgaga ttccttgcaa caagaccgcc   8160

tgcggcgtgg gtgaattccg ctgccgggat gggtcctgca tcgggaactc cagtcgctgc   8220

aaccagtttg tggattgtga ggatgcctcg gatgagatga attgcagcgc caccgactgc   8280

agcagttatt tccgcctggg cgtgaaaggt gtcctcttcc agccttgcga gcggacatcc   8340

ctctgctatg cacccagctg ggtgtgcgat ggtgccaacg actgtggaga ctacagtgac   8400

gagcgtgact gcccaggtgt gaagcgccca cggtgcccac tcaattactt tgcctgcccc   8460

agcgggcgct gcatccccat gagctggacg tgtgacaaag aggacgattg tgagaacggc   8520

gaggatgaga cccactgcaa caagttctgc tcggaggccc agtttgagtg ccagaaccac   8580

cggtgtatct ccaagcagtg gctgtgtgac ggcagcgatg actgcgggga cggctccgat   8640

gaggcagctc actgtgaagg caagacttgc ggcccctcct ccttctcctg tcctggcacc   8700

cacgtgtgtg tccccgagcg ctggctctgt gacggtgaca aggactgtgc tgatggcgcg   8760

gatgagagca tctcagctgg ctgcctgtac aacagcacct gtgacgaccg tgagttcatg   8820

tgccagaacc gcctgtgtat tcccaagcat tttgtgtgtg accatgaccg cgactgtgcc   8880

gatggctctg atgaatcccc tgagtgtgaa tacccaacct gcggccccaa cgaattccgc   8940

tgcgccaatg ggcgttgtct gagctcccgc cagtgggagt gtgatgggga gaatgactgt   9000

catgaccaca gtgatgaggc tcccaagaac ccacactgca caagcccaga gcacaaatgc   9060

aatgcctcat cacagttcct gtgcagcagc gggcgctgcg tggctgaggc gttgctctgc   9120
```

```
aatggccagg acgactgcgg ggatggttca gacgaacgcg ggtgccacgt caacgagtgt   9180
ctcagccgca agctcagtgg ctgcagtcag gactgcgagg acctcaagat aggctttaag   9240
tgccgctgtc gccctggctt ccggctaaag gatgatggca gaacctgtgc tgatgtggac   9300
gagtgcagca ccaccttccc ctgcagccag ctctgcatca acacccatgg cagttacaag   9360
tgtctgtgtg tggagggcta tgcacccccgc ggtggtgacc cccacagctg caaagctgtg   9420
accgatgagg agccgtttct catctttgcg aaccggtact acctgcgcaa gctcaacttg   9480
gacggctcca actacacact gcttaagcag ggcctgaaca atgcagttgc cttggacttt   9540
gactaccggg ggcagatgat ctactggaca gacgtgacga cccagggcag catgatccga   9600
aggatgcacc tcaatggtag caacgtgcag gttctgcacc ggacaggcct tagtaacccc   9660
gatgggctgg ctgtggactg ggtgggtggc aacctgtact ggtgtgacaa gggcagagac   9720
actattgagg tgtccaagct caacggggcc tatcggacag tgctggtcag ctctggcctc   9780
cgtgagccca gagctcttgt ggtggatgta cagaacgggt acctctactg gacagactgg   9840
ggtgaccact cactgatcgg tcggattggc atggatgggt ctggccgcag tatcattgtg   9900
gacactaaga tcacatggcc caatggcctg actgtggact acgtcacgga gcgcatctac   9960
tgggctgatg cccgtgagga ctacatcgag tttgccagcc tggatggatc caaccgccat  10020
gttgtgctga gccaagacat cccacacatc tttgcactga ccctatttga ggattacgtc  10080
tactggaccg actgggaaac aaagtccatc aaccgggccc ataagaccac gggtgccaac  10140
aaaaccctcc tcatcagcac cctgcaccgg cccatggacc tacatgtctt ccacgccctg  10200
cgccagccag atgtgcccaa tcacccctgc aaagtcaaca acggtggctg cagcaacctg  10260
tgcctgctgt ctcctggggg tggtcacaaa tgcgcctgcc ccaccaactt ctatctgggt  10320
ggtgacggcc gtacctgtgt gtctaactgc acagcaagcc agtttgtatg caagaatgac  10380
aagtgcatcc ccttctggtg gaagtgtgac actgaggacg attgtgggga ccactcagac  10440
gagcctccag actgtcccga gttcaagtgc cgcccaggcc agttccagtg ctccaccggc  10500
atctgcacca accctgcctt catctgtgat ggggacaatg actgccaaga caatagtgac  10560
gaggccaact gtgacatcca cgtctgcttg cccagtcaat tcaagtgcac caacaccaac  10620
cgctgtatcc ctggcatctt ccgttgcaac gggcaggaca actgtgggga cggcgaggat  10680
gaacgggatt gccctgaggt gacctgtgcc cccaaccagt tccagtgctc tatcaccaag  10740
cgctgcatcc cccgagtctg ggtctgcgac agggacaatg actgtgtgga cggaagtgat  10800
gaacctgcca actgcaccca gatgacctgc ggggtggatg agttccgctg caaggactcg  10860
ggccgctgca tccctgcacg ctggaagtgt gacggagaag acgactgtgg ggacggctca  10920
gatgagccca aggaagagtg tgatgagcgc acctgtgagc cataccagtt ccgctgcaaa  10980
aacaaccgct gtgtgccagg ccgctggcag tgtgactatg acaatgactg tggagataac  11040
tcagacgagg agagctgcac acctcggccc tgctctgaga gtgaattttc ctgtgccaac  11100
ggccgctgca ttgctgggcg ctggaagtgt gacggcgatc atgactgtgc cgacggctcc  11160
gatgagaaag actgcacccc ccgctgtgat atggaccagt tccagtgcaa gagtggtcac  11220
tgcatccccc tgcgctggcg ctgtgatgcg gatgctgact gtatggacgg cagtgatgag  11280
gaagcctgcg gcactggggt gaggacctgc cccttggatg aatttcaatg taacaacacc  11340
ctgtgcaagc cactggcctg gaagtgtgac ggagaggacg actgtggaga caactcagat  11400
gagaaccctg aggaatgcac ccggttccag tgccctccta accgaccctt ccgctgcaag  11460
```

aatgaccgtg tctgcctgtg gattgggcgc cagtgtgacg gcaccgacaa ctgtggggat 11520
gggactgacg aggaggactg tgagcccccc acagcccaga acccccactg caaagacaag 11580
aaggagttcc tgtgccggaa ccagcgctgt ctgtcatcct cgctgcgctg taacatgttt 11640
gatgactgtg gcgatggctc tgatgaagaa gactgcagca tagaccccaa gctgaccagc 11700
tgtgccacca atgccagcat gtgtggggac gaagcacgtt gtgtgcgcac cgagaaggct 11760
gcctactgtg cctgccgccc gggcttccat actgtgccgg gccagcccgg atgccaggac 11820
atcaacgagt gcctgcgctt cggcacctgc tctcagctct gcaacaatac caagggaggc 11880
cacctctgca gctgtgcacg caacttcatg aagacacaca atacctgcaa agctgaaggc 11940
tccgagtacc aggtgctata catcgctgat gacaacgaga tccgaagctt gttcccgggg 12000
cacccccact cagcctatga gcaggccttc cagggtgacg agagtgtccg catagatgcc 12060
atggacgtcc atgtcaaggc cggccgtgtc tactggacta actggcacac gggcactatc 12120
tcctatagga gcctaccccc tgctgcccct cctaccactt ccaaccgtca ccggaggcag 12180
atcgaccgtg gagtcaccca cctcaatatt tcagggctga agatgccgag ggcattgcc 12240 atcgactggg tggctgggaa tgtgtactgg accgactccg gccgagacgt gattgaggtg 12300
gcgcaaatga agggagagaa ccgcaagacg ctcatctcgg gcatgattga tgagccccac 12360
gccatcgtgg tggacccact gaggggcacc atgtactggt cagactgggg gaaccacccc 12420
aagattgaaa cagccgcgat ggatgggacc ctacgggaga ccctcgtgca agacaacatt 12480
cagtggccca caggtctggc cgtcgactat cacaatgaac ggctgtactg ggcggatgcc 12540
aaactatcgg tcatcggcag catccggctc aacggcaccg accccattgt ggctgttgac 12600
agtaaacgag gcctgagtca ccccttcagc atcgacgtgt tcgaggacta catctatggc 12660
gtcacttaca tcaacaaccg tgtcttcaag atccacaagt ttggacacag cccccttgatc 12720 aacctgacag gggggcctgag ccacgcctct gatgtggtcc tgtaccatca acacaagcag 12780
cctgaagtga ctaacccctg tgaccgcaag aaatgtgaat ggctgtgtct gctgagcccc 12840
agtgggcctg tctgcacctg tcccaatgga aagaggctgg acaatggcac ctgtgtgcct 12900
gtgccctctc cgacaccccc tccagatgcc cctaggcctg gaacctgtac cctgcagtgc 12960
ttcaatggtg gtagctgttt cctcaatgct cggaggcagc ccaagtgccg ctgccagccc 13020
cgttacacag gcgataagtg tgagctggac cagtgctggg aatactgtca caacggaggc 13080
acctgtgcag cctccccatc tggcatgccc acgtgccgct gtcccacagg cttcacaggc 13140
cccagatgca cccagcaggt gtgtgcaggc tactgtgcta acaacagcac ctgcaccgtc 13200
aaccagggta accagcccca gtgccgatgt ctacctggct tcctgggtga ccgttgccag 13260
taccggcagt gctcaggctt ctgtgagaac tttggcacct gtcagatggc cgccgatggc 13320
tcccgacaat gtcgatgcac tgtctacttt gagggaacga ggtgtgaggt gaacaagtgt 13380
agtcgctgtc tccagggagc ctgtgtggtc aataagcaga cgggagatgt cacctgcaac 13440
tgcactgatg gccgggtagc tcccagttgt ctgacctgca tcgaccactg tagcaatggt 13500
ggctcctgca ccatgaacag caagatgatg ccagagtgcc agtgcccacc ccatatgaca 13560
ggaccccggt gcgaggagca ggttgtcagt cagcaacagc ctgggcatat gacctccatc 13620
ctgatccctc tgctgctgct gctcctgctg ctgctggtgg caggcgtggt gttctggtat 13680
aagcggcgag tccgaggggc taagggcttc cagcaccagc ggatgaccaa tggggccatg 13740
aatgtggaaa tcggaaaccc tacctacaag atgtatgaag gtggagagcc cgacgatgtg 13800
gggggcctcc tggatgctga ttttgccctt gaccctgaca agcctaccaa cttcaccaac 13860

```
ccagtgtatg ccacgctcta catggggggt catggcagcc gccactccct ggccagcacg  13920

gacgagaagc gagaactgct gggccgggga cctgaagatg agatagggga tcccttagca  13980

tagggccctg ccccaacgga cgtccccaga aagcccctgc cacacgagtc tttcaatgag  14040

ccctctcccc agccagccct tctccggccc tgccggatgt acaaatgtaa aaatgaagga  14100

attacttttt atatgtgagt gagcaagcac agtattatct ctttgcattt cctttctgcc  14160

tgctcctcgg catcccctcc ccccatgctg ccttgagggg gcagggaggg ctctgtggct  14220

caaaggtatg aaggagtcca catacgttcc cttaccccgg gaagctggcg gcacagcctc  14280

tcgcctgtac aagacactca acagggctcc agtgtcccag ctttcctttc ctggggttag  14340

ttctggggag gtggagttct ctgctgaacc tgtctggaat atctggctct agctgaggta  14400

ggagtatttt ttagttgagg gaagtcaccc caagccccag ctcccacttt taggggcacg  14460

tctgggatgg ccatgctcag tatcccttcc agacaggtct ttgcctctcc agtgccccct  14520

ctgtggctcc tagggctgaa cacattcttt ggtaactgtc ccccagtctc ccctcccctg  14580

aggaccagga agaattgggg cacaccaagg aagggcaagt gggcagcccc attttgggga  14640

cgtgaacgtt ttaataattt ttgctgaatt cctttacaac taaataacac agatattgtt  14700

ataaataaaa ttgt                                                     14714
```

<210> SEQ ID NO 9
<211> LENGTH: 5
<212> TYPE: PRT
<213> ORGANISM: Artificial Sequence
<220> FEATURE:
<223> OTHER INFORMATION: VHCDR1

<400> SEQUENCE: 9

```
Ser Tyr Ala Met Ser
1               5
```

<210> SEQ ID NO 10
<211> LENGTH: 17
<212> TYPE: PRT
<213> ORGANISM: Artificial Sequence
<220> FEATURE:
<223> OTHER INFORMATION: VHCDR2

<400> SEQUENCE: 10

```
Ala Ile Ser Gly Ser Gly Gly Ser Thr Tyr Tyr Ala Asp Ser Val Lys
1               5                   10                  15

Gly
```

<210> SEQ ID NO 11
<211> LENGTH: 8
<212> TYPE: PRT
<213> ORGANISM: Artificial Sequence
<220> FEATURE:
<223> OTHER INFORMATION: VHCDR3

<400> SEQUENCE: 11

```
Arg Thr Gly Thr Leu Phe Asp Tyr
1               5
```

<210> SEQ ID NO 12
<211> LENGTH: 11
<212> TYPE: PRT
<213> ORGANISM: Artificial Sequence
<220> FEATURE:
<223> OTHER INFORMATION: VLCDR1

<400> SEQUENCE: 12

Gln Gly Asp Ser Leu Arg Ser Tyr Tyr Ala Ser
1 5 10

<210> SEQ ID NO 13
<211> LENGTH: 7
<212> TYPE: PRT
<213> ORGANISM: Artificial Sequence
<220> FEATURE:
<223> OTHER INFORMATION: VLCDR2

<400> SEQUENCE: 13

Gly Lys Asn Asn Arg Pro Ser
1 5

<210> SEQ ID NO 14
<211> LENGTH: 11
<212> TYPE: PRT
<213> ORGANISM: Artificial Sequence
<220> FEATURE:
<223> OTHER INFORMATION: VLCDR3

<400> SEQUENCE: 14

Asn Ser Ser Gln Ala Gln Arg Asn Ala Val Val
1 5 10

<210> SEQ ID NO 15
<211> LENGTH: 117
<212> TYPE: PRT
<213> ORGANISM: Artificial Sequence
<220> FEATURE:
<223> OTHER INFORMATION: VH

<400> SEQUENCE: 15

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Arg Thr Gly Thr Leu Phe Asp Tyr Trp Gly Gln Gly Thr Leu
100 105 110

Val Thr Val Ser Ser
115

<210> SEQ ID NO 16
<211> LENGTH: 109
<212> TYPE: PRT
<213> ORGANISM: Artificial Sequence
<220> FEATURE:
<223> OTHER INFORMATION: VL

<400> SEQUENCE: 16

Ser Ser Glu Leu Thr Gln Asp Pro Ala Val Ser Val Ala Leu Gly Gln
1 5 10 15

```
Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Ser Gln Ala Gln Arg Asn Ala
                85                  90                  95

Val Val Phe Gly Gly Gly Thr Lys Leu Thr Val Leu Gly
            100                 105


<210> SEQ ID NO 17
<211> LENGTH: 351
<212> TYPE: DNA
<213> ORGANISM: Artificial Sequence
<220> FEATURE:
<223> OTHER INFORMATION: VH

<400> SEQUENCE: 17

gaagtccaac tgctggaatc gggtggtggt ctggtgcaac cgggcggctc gctgcgtctg      60

tcatgtgctg cgtcgggctt tacctttagc tcttatgcaa tgtcctgggt gcgtcaggca     120

ccgggtaaag gtctggaatg ggttagcgca attagtggct ccggcggtag cacctattac     180

gccgattctg ttaaaggtcg ttttaccatc tcacgcgaca actcgaaaaa tacgctgtat     240

ctgcagatga acagtctgcg cgcagaagat accgctgtct attactgcgc aaaacggact     300

gggactttgt tcgactactg gggccaaggt acgctggtta cggttagcag c             351


<210> SEQ ID NO 18
<211> LENGTH: 327
<212> TYPE: DNA
<213> ORGANISM: Artificial Sequence
<220> FEATURE:
<223> OTHER INFORMATION: VL

<400> SEQUENCE: 18

tcgtctgaac tgacgcaaga tccggctgtt tctgtggcac tgggtcaaac ggttcgtatc      60

acgtgtcaag gcgattcact gcgctcctat tacgcaagtt ggtatcagca aaaaccgggc     120

caggctccgg tgctggttat ttacggcaaa aacaatcgtc cgtccggtat cccggatcgc     180

ttttcaggca gctctagtgg taacaccgcg tcgctgacca ttacgggtgc gcaagccgaa     240

gatgaagcag actattactg caatagctcc caggcgcagc ggaatgcggt tgtctttggt     300

ggtggtacga aactgaccgt cctgggc                                         327


<210> SEQ ID NO 19
<211> LENGTH: 240
<212> TYPE: PRT
<213> ORGANISM: Artificial Sequence
<220> FEATURE:
<223> OTHER INFORMATION: scFv

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
```

```
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Thr Gly Thr Leu Phe Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Ser Glu Leu Thr Gln Asp Pro Ala Val Ser Val Ala
    130                 135                 140

Leu Gly Gln Thr Val Arg Ile Thr Cys Gln Gly Asp Ser Leu Arg Ser
145                 150                 155                 160

Tyr Tyr Ala Ser Trp Tyr Gln Gln Lys Pro Gly Gln Ala Pro Val Leu
                165                 170                 175

Val Ile Tyr Gly Lys Asn Asn Arg Pro Ser Gly Ile Pro Asp Arg Phe
            180                 185                 190

Ser Gly Ser Ser Ser Gly Asn Thr Ala Ser Leu Thr Ile Thr Gly Ala
        195                 200                 205

Gln Ala Glu Asp Glu Ala Asp Tyr Tyr Cys Asn Ser Ser Gln Ala Gln
    210                 215                 220

Arg Asn Ala Val Val Phe Gly Gly Gly Thr Lys Leu Thr Val Leu Gly
225                 230                 235                 240
```

<210> SEQ ID NO 20
<211> LENGTH: 720
<212> TYPE: DNA
<213> ORGANISM: Artificial Sequence
<220> FEATURE:
<223> OTHER INFORMATION: scFv

<400> SEQUENCE: 20

```
gaagtccaac tgctggaatc gggtggtggt ctggtgcaac cgggcggctc gctgcgtctg     60

tcatgtgctg cgtcgggctt tacctttagc tcttatgcaa tgtcctgggt gcgtcaggca    120

ccgggtaaag gtctggaatg ggttagcgca attagtggct ccggcggtag cacctattac    180

gccgattctg ttaaaggtcg ttttaccatc tcacgcgaca actcgaaaaa tacgctgtat    240

ctgcagatga acagtctgcg cgcagaagat accgctgtct attactgcgc aaaacggact    300

gggactttgt tcgactactg gggccaaggt acgctggtta cggttagcag cggcggtggt    360

ggcagcggtg gtggcggctc gggtggtggc ggctcgtctg aactgacgca agatccggct    420

gtttctgtgg cactgggtca aacggttcgt atcacgtgtc aaggcgattc actgcgctcc    480

tattacgcaa gttggtatca gcaaaaaccg ggccaggctc cggtgctggt tatttacggc    540

aaaaacaatc gtccgtccgg tatcccggat cgcttttcag gcagctctag tggtaacacc    600

gcgtcgctga ccattacggg tgcgcaagcc gaagatgaag cagactatta ctgcaatagc    660

tcccaggcgc agcggaatgc ggttgtcttt ggtggtggta cgaaactgac cgtcctgggc    720
```

<210> SEQ ID NO 21
<211> LENGTH: 29
<212> TYPE: DNA
<213> ORGANISM: Artificial Sequence
<220> FEATURE:
<223> OTHER INFORMATION: primer/ LRP1_C2_01

<400> SEQUENCE: 21
gcgatggatc ctccggaggt tccactagt 29

<210> SEQ ID NO 22
<211> LENGTH: 52
<212> TYPE: DNA
<213> ORGANISM: Artificial Sequence
<220> FEATURE:
<223> OTHER INFORMATION: primer/ LRP1_C2_06

<400> SEQUENCE: 22
gcatcaattg tcaggaacca gtagaagctc cctcacagct cttctcatcg ct 52

<210> SEQ ID NO 23
<211> LENGTH: 52
<212> TYPE: DNA
<213> ORGANISM: Artificial Sequence
<220> FEATURE:
<223> OTHER INFORMATION: primer/ LRP1_C2_08

<400> SEQUENCE: 23
gcatcaattg tcaggaacca gtagaagcgg actcgcagtt ctcctcgtcc ga 52

<210> SEQ ID NO 24
<211> LENGTH: 52
<212> TYPE: DNA
<213> ORGANISM: Artificial Sequence
<220> FEATURE:
<223> OTHER INFORMATION: primer/ LRP1_C2_02

<400> SEQUENCE: 24
gcatcaattg tcaggaacca gtagaagcgg ctgaacaagt ggcattggac tc 52

<210> SEQ ID NO 25
<211> LENGTH: 52
<212> TYPE: DNA
<213> ORGANISM: Artificial Sequence
<220> FEATURE:
<223> OTHER INFORMATION: primer/ LRP1_C2_04

<400> SEQUENCE: 25
gcatcaattg tcaggaacca gtagaagcgt tggtgcagtt ggcgtgtgtc tc 52

<210> SEQ ID NO 26
<211> LENGTH: 8
<212> TYPE: PRT
<213> ORGANISM: Artificial Sequence
<220> FEATURE:
<223> OTHER INFORMATION: C2_F8 VH CDR3

<400> SEQUENCE: 26

Thr Thr Gly His Leu Phe Asp Tyr
1               5

<210> SEQ ID NO 27
<211> LENGTH: 11
<212> TYPE: PRT
<213> ORGANISM: Artificial Sequence
<220> FEATURE:
<223> OTHER INFORMATION: C2_F8 VL CDR3

<400> SEQUENCE: 27

Asn Ser Ser Asn Pro Arg Arg Gln Arg Val Val
1               5                   10

<210> SEQ ID NO 28
<211> LENGTH: 8
<212> TYPE: PRT
<213> ORGANISM: Artificial Sequence
<220> FEATURE:
<223> OTHER INFORMATION: C2_G3 VH CDR3

<400> SEQUENCE: 28

```
Thr Thr Gly Glu Leu Phe Asp Tyr
1               5
```

<210> SEQ ID NO 29
<211> LENGTH: 11
<212> TYPE: PRT
<213> ORGANISM: Artificial Sequence
<220> FEATURE:
<223> OTHER INFORMATION: C2_G3 VL CDR3

<400> SEQUENCE: 29

```
Asn Ser Ser Arg Arg Arg Lys His His Val Val
1               5                   10
```

<210> SEQ ID NO 30
<211> LENGTH: 8
<212> TYPE: PRT
<213> ORGANISM: Artificial Sequence
<220> FEATURE:
<223> OTHER INFORMATION: C2_G9 VH CDR3

<400> SEQUENCE: 30

```
Asn Thr Gly Ala Ser Phe Asp Tyr
1               5
```

<210> SEQ ID NO 31
<211> LENGTH: 8
<212> TYPE: PRT
<213> ORGANISM: Artificial Sequence
<220> FEATURE:
<223> OTHER INFORMATION: C2_G9 VL CDR3

<400> SEQUENCE: 31

```
Asn Thr Gly Ala Ser Phe Asp Tyr
1               5
```

<210> SEQ ID NO 32
<211> LENGTH: 11
<212> TYPE: PRT
<213> ORGANISM: Artificial Sequence
<220> FEATURE:
<223> OTHER INFORMATION: Anti-OVA (Control) VH CDR3

<400> SEQUENCE: 32

```
Gly Phe Thr Phe Ser Ser Tyr Ala Phe Asp Tyr
1               5                   10
```

<210> SEQ ID NO 33
<211> LENGTH: 11
<212> TYPE: PRT
<213> ORGANISM: Artificial Sequence
<220> FEATURE:
<223> OTHER INFORMATION: Anti-OVA (Control) VL CDR3

<400> SEQUENCE: 33

```
Asn Ser Ser Ser Leu Arg Ser Tyr Tyr Val Val
1               5                   10
```

<210> SEQ ID NO 34
<211> LENGTH: 243
<212> TYPE: PRT
<213> ORGANISM: Artificial Sequence
<220> FEATURE:
<223> OTHER INFORMATION: scFv with randomized moieties
<220> FEATURE:
<221> NAME/KEY: misc_feature
<222> LOCATION: (101)..(104)
<223> OTHER INFORMATION: Xaa can be any naturally occurring amino acid
<220> FEATURE:
<221> NAME/KEY: misc_feature
<222> LOCATION: (223)..(228)
<223> OTHER INFORMATION: Xaa can be any naturally occurring amino acid

<400> SEQUENCE: 34

```
Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Ala Ile Ser Gly Ser Gly Gly Ser Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Xaa Xaa Xaa Xaa Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Ser Glu Leu Thr Gln Asp Pro Ala Val Ser Val
    130                 135                 140

Ala Leu Gly Gln Thr Val Arg Ile Thr Cys Gln Gly Asp Ser Leu Arg
145                 150                 155                 160

Ser Tyr Tyr Ala Ser Trp Tyr Gln Gln Lys Pro Gly Gln Ala Pro Val
                165                 170                 175

Leu Val Ile Tyr Gly Lys Asn Asn Arg Pro Ser Gly Ile Pro Asp Arg
            180                 185                 190

Phe Ser Gly Ser Ser Ser Gly Asn Thr Ala Ser Leu Thr Ile Thr Gly
        195                 200                 205

Ala Gln Ala Glu Asp Glu Ala Asp Tyr Tyr Cys Asn Ser Ser Xaa Xaa
    210                 215                 220

Xaa Xaa Xaa Xaa Val Val Phe Gly Gly Gly Thr Lys Leu Thr Val Leu
225                 230                 235                 240

Gly Ala Ala
```

<210> SEQ ID NO 35
<211> LENGTH: 244
<212> TYPE: PRT
<213> ORGANISM: Artificial Sequence
<220> FEATURE:
<223> OTHER INFORMATION: scFv with randomized moieties
<220> FEATURE:
<221> NAME/KEY: misc_feature
<222> LOCATION: (101)..(105)
<223> OTHER INFORMATION: Xaa can be any naturally occurring amino acid
<220> FEATURE:
<221> NAME/KEY: misc_feature
<222> LOCATION: (224)..(229)
<223> OTHER INFORMATION: Xaa can be any naturally occurring amino acid

<400> SEQUENCE: 35

Met Ala Glu Val Gln Leu Leu Glu Ser Gly Gly Gly Leu Val Gln Pro
1 5 10 15

Gly Gly Ser Leu Arg Leu Ser Cys Ala Ala Ser Gly Phe Thr Phe Ser
20 25 30

Ser Tyr Ala Met Ser Trp Val Arg Gln Ala Pro Gly Lys Gly Leu Glu
35 40 45

Trp Val Ser Ala Ile Ser Gly Ser Gly Gly Ser Thr Tyr Tyr Ala Asp
50 55 60

Ser Val Lys Gly Arg Phe Thr Ile Ser Arg Asp Asn Ser Lys Asn Thr
65 70 75 80

Leu Tyr Leu Gln Met Asn Ser Leu Arg Ala Glu Asp Thr Ala Val Tyr
85 90 95

Tyr Cys Ala Lys Xaa Xaa Xaa Xaa Xaa Phe Asp Tyr Trp Gly Gln Gly
100 105 110

Thr Leu Val Thr Val Ser Ser Gly Gly Gly Gly Ser Gly Gly Gly Gly
115 120 125

Ser Gly Gly Gly Gly Ser Ser Glu Leu Thr Gln Asp Pro Ala Val Ser
130 135 140

Val Ala Leu Gly Gln Thr Val Arg Ile Thr Cys Gln Gly Asp Ser Leu
145 150 155 160

Arg Ser Tyr Tyr Ala Ser Trp Tyr Gln Gln Lys Pro Gly Gln Ala Pro
165 170 175

Val Leu Val Ile Tyr Gly Lys Asn Asn Arg Pro Ser Gly Ile Pro Asp
180 185 190

Arg Phe Ser Gly Ser Ser Ser Gly Asn Thr Ala Ser Leu Thr Ile Thr
195 200 205

Gly Ala Gln Ala Glu Asp Glu Ala Asp Tyr Tyr Cys Asn Ser Ser Xaa
210 215 220

Xaa Xaa Xaa Xaa Xaa Val Val Phe Gly Gly Gly Thr Lys Leu Thr Val
225 230 235 240

Leu Gly Ala Ala

<210> SEQ ID NO 36
<211> LENGTH: 245
<212> TYPE: PRT
<213> ORGANISM: Artificial Sequence
<220> FEATURE:
<223> OTHER INFORMATION: scFv with randomized moieties
<220> FEATURE:
<221> NAME/KEY: misc_feature
<222> LOCATION: (101)..(106)
<223> OTHER INFORMATION: Xaa can be any naturally occurring amino acid
<220> FEATURE:
<221> NAME/KEY: misc_feature
<222> LOCATION: (225)..(230)
<223> OTHER INFORMATION: Xaa can be any naturally occurring amino acid

<400> SEQUENCE: 36

Met Ala Glu Val Gln Leu Leu Glu Ser Gly Gly Gly Leu Val Gln Pro
1 5 10 15

Gly Gly Ser Leu Arg Leu Ser Cys Ala Ala Ser Gly Phe Thr Phe Ser
20 25 30

Ser Tyr Ala Met Ser Trp Val Arg Gln Ala Pro Gly Lys Gly Leu Glu
35 40 45

Trp Val Ser Ala Ile Ser Gly Ser Gly Gly Ser Thr Tyr Tyr Ala Asp
50 55 60

```
Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Xaa Xaa Xaa Xaa Xaa Xaa Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Ser Glu Leu Thr Gln Asp Pro Ala Val
    130                 135                 140

Ser Val Ala Leu Gly Gln Thr Val Arg Ile Thr Cys Gln Gly Asp Ser
145                 150                 155                 160

Leu Arg Ser Tyr Tyr Ala Ser Trp Tyr Gln Gln Lys Pro Gly Gln Ala
                165                 170                 175

Pro Val Leu Val Ile Tyr Gly Lys Asn Asn Arg Pro Ser Gly Ile Pro
            180                 185                 190

Asp Arg Phe Ser Gly Ser Ser Ser Gly Asn Thr Ala Ser Leu Thr Ile
        195                 200                 205

Thr Gly Ala Gln Ala Glu Asp Glu Ala Asp Tyr Tyr Cys Asn Ser Ser
    210                 215                 220

Xaa Xaa Xaa Xaa Xaa Xaa Val Val Phe Gly Gly Gly Thr Lys Leu Thr
225                 230                 235                 240

Val Leu Gly Ala Ala
                245


<210> SEQ ID NO 37
<211> LENGTH: 246
<212> TYPE: PRT
<213> ORGANISM: Artificial Sequence
<220> FEATURE:
<223> OTHER INFORMATION: scFv with randomized moieties
<220> FEATURE:
<221> NAME/KEY: misc_feature
<222> LOCATION: (101)..(107)
<223> OTHER INFORMATION: Xaa can be any naturally occurring amino acid
<220> FEATURE:
<221> NAME/KEY: misc_feature
<222> LOCATION: (226)..(231)
<223> OTHER INFORMATION: Xaa can be any naturally occurring amino acid

<400> SEQUENCE: 37

Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Ala Ile Ser Gly Ser Gly Gly Ser Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Xaa Xaa Xaa Xaa Xaa Xaa Xaa Phe Asp Tyr Trp Gly
            100                 105                 110

Gln Gly Thr Leu Val Thr Val Ser Ser Gly Gly Gly Gly Ser Gly Gly
        115                 120                 125
```

-continued

```
Gly Gly Ser Gly Gly Gly Gly Ser Ser Glu Leu Thr Gln Asp Pro Ala
    130                 135                 140

Val Ser Val Ala Leu Gly Gln Thr Val Arg Ile Thr Cys Gln Gly Asp
145                 150                 155                 160

Ser Leu Arg Ser Tyr Tyr Ala Ser Trp Tyr Gln Gln Lys Pro Gly Gln
                165                 170                 175

Ala Pro Val Leu Val Ile Tyr Gly Lys Asn Asn Arg Pro Ser Gly Ile
            180                 185                 190

Pro Asp Arg Phe Ser Gly Ser Ser Ser Gly Asn Thr Ala Ser Leu Thr
        195                 200                 205

Ile Thr Gly Ala Gln Ala Glu Asp Glu Ala Asp Tyr Tyr Cys Asn Ser
    210                 215                 220

Ser Xaa Xaa Xaa Xaa Xaa Xaa Val Val Phe Gly Gly Gly Thr Lys Leu
225                 230                 235                 240

Thr Val Leu Gly Ala Ala
                245
```

OPTIC NERVE PROTECTING AGENT CONTAINING ANTI-LRP1 ANTIBODY

A computer readable text file, entitled "SequenceListing.txt," created on or about Jun. 22, 2026 with a file size of 258,805 bytes contains the sequence listing for this application and is hereby incorporated by reference in its entirety.

TECHNICAL FIELD

The present invention relates to an optic nerve protecting agent containing an anti-LRP1 antibody.

BACKGROUND ART

Glaucoma is a progressive neurodegenerative disease in which retinal ganglion cells constituting an optic nerve degenerate for a certain reason and visual field defects occur, and is the first leading cause of blindness in Japan and the second leading cause of blindness in the world.

Currently, the only approach for progression prevention and treatment of glaucoma is lowering intraocular pressure. In Japan, patients with normal intraocular pressure account for 70% of those with glaucoma, and there are lots of cases where symptoms of glaucoma still progress even if the intraocular pressure is controlled by an intraocular pressure lowering agent. Therefore, development of a glaucoma treatment method based on a new mechanism of action has been desired.

In glaucoma, retinal ganglion cells constituting the optic nerve are damaged. For the purpose of elucidating the mechanism of optic nerve degeneration in optic nerve diseases, the inventors of the present invention have focused on a lipoprotein derived from glial cells, being a factor that protect these retinal ganglion cells, and studied suppression of retinal nerve cell death in optic nerve degeneration such as glaucoma. As a result, it was confirmed in an in vitro system that an apolipoprotein E-containing lipoprotein (E-LP) derived from glial cells has a neuroprotective effect against apoptosis (Non Patent Literature 1, Non Patent Literature 2, and Non Patent Literature 3). Here, the apolipoprotein E-containing lipoprotein (E-LP) is an apolipoprotein-binding lipoprotein in which apolipoprotein E, being a kind of apolipoprotein, and a lipid are chemically associated with each other.

Furthermore, the inventors of the present invention have found that when E-LP is injected into the vitreous body of a mouse in which a large amount of lipoproteins are present, E-LP has a neuroprotective effect against apoptosis even in an in vivo system, and further, a complex of E-LP and a neuroprotective molecule such as low density lipoprotein receptor-related protein-1 (LRP1) that is a receptor of E-LP similarly has a neuroprotective effect against apoptosis in the in vivo system (Patent Literature 1).

In other words, the inventors of the present invention have so far clarified that E-LP provides protection of rat primary cultured retinal ganglion cells from apoptosis via LRP1 that is a receptor of E-LP, and have found that E-LP can be used as an inhibitor of a neuroprotective inhibitory effect (Patent Literature 1).

PRIOR-ARTS

Non Patent Literature Documents

Non Patent Literature Document 1: Hayashi, H., et al., J. Neurosci., Feb. 21, 2007, 27 (8): 1933-1941

Non Patent Literature Document 2: Hayashi, Hideki, et al.: Neurochemistry Vol. 49 No. 2/3 Page 483 (2010)

Non Patent Literature Document 3: Hayashi, H., et al., J Biol Chem: Vol. 284 No. 43 pp. 29605-29613 (2009)

Patent Literature Document

Patent Literature Document 1: JP 6031718

SUMMARY OF THE INVENTION

Problem to be Solved by the Invention

An object of the present invention is to provide an optic nerve protecting agent containing an anti-LRP1 antibody.

Means to Solve the Problem

The inventors of the present invention have further conducted intensive studies, and elucidated that an antibody against LRP1, being a receptor of E-LP, suppresses nerve disorders induced in primary cultured retinal ganglion cells and a rat glaucoma model. This result suggests a possibility of glaucoma treatment with an antibody based on the protective effect on the retinal ganglion cells via LRP1.

Namely, the present invention relates to:

[1] an optic nerve protecting agent for protecting optic nerve in a subject, comprising an anti-low density lipoprotein receptor-related protein 1 (LRP1) antibody or an anti-LRP1 antibody fragment;

[2] the optic nerve protecting agent according to [1], wherein the anti-LRP1 antibody or the antibody fragment specifically binds to C2 domain of the LRP1;

[3] the optic nerve protecting agent according to [1] or [2], wherein the anti-LRP1 antibody or the antibody fragment recognizes an epitope:

(a) in a region of amino acids at positions 786 to 1165 in an amino acid sequence of LRP1 having an amino acid sequence represented by SEQ ID NO: 1, (b) in a region of amino acids at positions 787 to 1166 in an amino acid sequence of LRP1 having an amino acid sequence represented by SEQ ID NO: 2, (c) in a region of amino acids at positions 786 to 1165 in an amino acid sequence of LRP1 having an amino acid sequence represented by SEQ ID NO: 3, or (d) in a region of amino acids at positions 787 to 1166 in an amino acid sequence of LRP1 having an amino acid sequence represented by SEQ ID NO: 4;

[4] the optic nerve protecting agent according to any one of [1] to [3], wherein (i) the anti-LRP1 antibody or the antibody fragment comprises:

a heavy chain complementarity determining region 1 (VH CDR1) that comprises an amino acid sequence having a sequence identity of 80% or more to an amino acid sequence represented by SEQ ID NO: 9;

a heavy chain complementarity determining region 2 (VH CDR2) that comprises an amino acid sequence having a sequence identity of 80% or more to an amino acid sequence represented by SEQ ID NO: 10;

a heavy chain complementarity determining region 3 (VH CDR3) that comprises an amino acid sequence having a sequence identity of 80% or more to an amino acid sequence represented by SEQ ID NO: 11;

a light chain complementarity determining region 1 (VL CDR1) that comprises an amino acid sequence having a sequence identity of 80% or more to an amino acid sequence represented by SEQ ID NO: 12;

a light chain complementarity determining region 2 (VL CDR2) that comprises an amino acid sequence having a sequence identity of 80% or more to an amino acid sequence represented by SEQ ID NO: 13; and a light chain complementarity determining region 3 (VL CDR3) that comprises an amino acid sequence having a sequence identity of 80% or more to an amino acid sequence represented by SEQ ID NO: 14, or (ii) the anti-LRP1 antibody or the antibody fragment comprises:

a heavy chain variable region that comprises an amino acid sequence having a sequence identity of 80% or more to an amino acid sequence represented by SEQ ID NO: 15, and a light chain variable region that comprises an amino acid sequence having a sequence identity of 80% or more to an amino acid sequence represented by SEQ ID NO: 16, or (iii) the anti-LRP1 antibody or the antibody fragment comprises an amino acid sequence having a sequence identity of 80% or more to an amino acid sequence represented by SEQ ID NO: 19;

[5] the optic nerve protecting agent according to any one of [1] to [4], wherein the anti-LRP1 antibody or the antibody fragment is a humanized antibody or a human antibody;

[6] the optic nerve protecting agent according to any one of [1] to [5], wherein the anti-LRP1 antibody or the antibody fragment binds to LRP1 with a dissociation constant (Kd) of $1\times10^{-7}$ M to $1\times10^{-11}$ M;

[7] a composition comprising the optic nerve protecting agent according to any one of [1] to [6];

[8] the composition according to [7], wherein the composition is topically administered to the subject;

[9] the composition according to [8], wherein the topical administration is intravitreal administration;

[10] the composition according to [8] or [9], wherein the composition is in a form of eye drops;

[11] the composition according to any one of [8] to [10], for treating glaucoma;

[12] the composition according to any one of [8] to [11], wherein the subject has an intraocular pressure of 10 to 21 mmHg;

[13] an anti-LRP1 antibody or an anti-LRP1 antibody fragment, comprising:

(i) a heavy chain complementarity determining region 1 (VH CDR1) that comprises an amino acid sequence having a sequence identity of 80% or more to an amino acid sequence represented by SEQ ID NO: 9;

a heavy chain complementarity determining region 2 (VH CDR2) that comprises an amino acid sequence having a sequence identity of 80% or more to an amino acid sequence represented by SEQ ID NO: 10;

a heavy chain complementarity determining region 3 (VH CDR3) that comprises an amino acid sequence having a sequence identity of 80% or more to an amino acid sequence represented by SEQ ID NO: 11;

a light chain complementarity determining region 1 (VL CDR1) that comprises an amino acid sequence having a sequence identity of 80% or more to an amino acid sequence represented by SEQ ID NO: 12;

a light chain complementarity determining region 2 (VL CDR2) that comprises an amino acid sequence having a sequence identity of 80% or more to an amino acid sequence represented by SEQ ID NO: 13; and a light chain complementarity determining region 3 (VL CDR3) that comprises an amino acid sequence having a sequence identity of 80% or more to an amino acid sequence represented by SEQ ID NO: 14, or (ii) a heavy chain variable region that comprises an amino acid sequence having a sequence identity of 80% or more to an amino acid sequence represented by SEQ ID NO: 15, and a light chain variable region that comprises an amino acid sequence having a sequence identity of 80% or more to an amino acid sequence represented by SEQ ID NO: 16, or (iii) an amino acid sequence having a sequence identity of 80% or more to an amino acid sequence represented by SEQ ID NO: 19; and

[14] a composition comprising the anti-LRP1 antibody or the anti-LRP1 antibody fragment according to.

Effects of Invention

According to the present invention, an optic nerve protecting agent containing an anti-LRP1 antibody can be provided.

BRIEF DESCRIPTION OF THE DRAWINGS

FIG. 1 shows an outline of a neuroprotective mechanism via an antibody.

FIG. 2A shows a schematic diagram of LRP1 and each ligand-binding domain protein.

FIG. 2B shows a diagram plotting reactivity of each clone (in a horizontal axis).

FIG. 2C shows amino acid sequences of a heavy chain and a light chain of scFv (SEQ ID NOs: 34 to 37).

FIG. 2D shows SDS-PAGE of each purified scFv.

FIG. 2E shows results of ELISA for each purified scFv.

FIG. 3A shows a protective effect on retinal ganglion cells of scFv (Group #1) against glutamate neurotoxicity.

FIG. 3B shows a protective effect on retinal ganglion cells of scFv (Group #2) against glutamate neurotoxicity.

FIG. 3C shows a protective effect on retinal ganglion cells of scFv (Group #3) against glutamate neurotoxicity.

FIG. 4 shows a protective effect on retinal ganglion cells of scFv (C2-D11) on rats with NMDA-induced optic nerve degeneration (analysis results of immunoblotting of a retina).

FIG. 5 shows a protective effect on retinal ganglion cells of scFv (C2-D11) on rats with NMDA-induced optic nerve degeneration (summary of the analysis results of immunoblotting of the retina).

FIG. 6 shows a protective effect on retinal ganglion cells of scFv (C2-D11) on rats with NMDA-induced optic nerve degeneration (HE staining of retinal tissue sections).

FIG. 7 shows a protective effect on retinal ganglion cells of scFv (C2-D11) on rats with NMDA-induced optic nerve degeneration (analysis of HE stained images of the retinal tissue sections and the number of retinal ganglion cells).

FIG. 8A shows a protective effect on retinal ganglion cells of scFv (C2-D11) on rats with NMDA-induced optic nerve degeneration (analysis of the HE stained images of the retinal tissue sections and thickness of an inner plexiform layer).

FIG. 8B shows a protective effect on retinal ganglion cells of scFv (C2-D11) on rats with NMDA-induced optic nerve degeneration (analysis of the HE stained images of the retinal tissue sections and thickness of the inner plexiform layer) obtained from a test commissioned to a third party organization.

FIG. 9 shows thickness of the retinal inside from the inner plexiform layer measured by an optical coherence tomography.

FIG. 10 shows a schematic diagram illustrating a method for producing an anti-LRP1 human IgG1 antibody from scFv.

FIG. 11A shows results of ELISA for an anti-LRP1 human IgG1 antibody.

FIG. 11B shows results of ELISA for an anti-OVA antibody (as a control).

FIG. 12 shows binding of the anti-LRP1 human IgG1 antibody to immobilized LRP1-Fc.

FIG. 13 shows a protective effect on retinal ganglion cells using intracellular calcium influx by glutamate stimulation as an index.

FIG. 14 shows localization of the anti-LRP1 human IgG1 antibody after intravitreal administration.

FIG. 15 shows neuroprotective effects by the anti-LRP1 human IgG1 antibody at various concentrations.

FIG. 16A shows analysis results of electrophoresis gel staining of LRP1 recombinant protein-deficient variants.

FIG. 16B shows analysis results of immunoblotting of the LRP1 recombinant protein-deficient variants.

DETAILED DESCRIPTION OF EMBODIMENTS

Hereinafter, the present invention will be described in more detail.

Specifically, a first aspect of the present invention relates to an optic nerve protecting agent containing an anti-LRP1 antibody or an anti-LRP1 antibody fragment.

As described above, the inventors of the present invention have so far found that E-LP protects rat primary cultured retinal ganglion cells from apoptosis via LRP1, being one of receptors of E-LP, and E-LP can be used as an inhibitor of a neuroprotective inhibitory effect. In the present invention, the anti-LRP1 antibody is used in place of E-LP to protect ganglion cells from apoptosis. Specifically, as shown in FIG. 1, the anti-LRP1 antibody specifically binds to LRP1 present in a membrane, thereby activating a neuroprotective molecule, and inactivating or suppressing a neurodegeneration inducing molecule, and thus avoids apoptosis of ganglion cells and protects nerves. Here, examples of the neuroprotective molecule include phospholipase C ("PLCγ1" in FIG. 1) and protein kinase Cδ ("PKCδ" in FIG. 1), and examples of the neurodegeneration inducing molecule include NMDA-type glutamate receptor ("NMDAR" in FIG. 1), calcium ("$Ca^{2+}$" in FIG. 1), and GSK3β.

The inventors of the present invention have further developed the above studies and succeeded in inducing the protection of optic nerve cells via LRP1 with the anti-LRP1 antibody or the anti-LRP1 antibody fragment. When E-LP is used, there is a concern that the antibody may bind to a target other than LRP1, but the antibody is specific to the target, and has excellent uniformity and high stability. From this point of view, the antibody according to the present invention can also be useful in pharmaceutical applications.

LRP1 also includes a protein containing an amino acid sequence in which one or more amino acids are deleted, substituted, inserted and/or added in the amino acid sequence of the protein, and being functionally equivalent to the protein. Here, the "functionally equivalent protein" is a protein having an activity equivalent to the activity of the protein, and the "functionally equivalent protein" includes a protein having, for example, a sequence identity of 80% or more, 83% or more, 85% or more, 86% or more, 87% or more, 88% or more, 89% or more, 90% or more, 91% or more, 92% or more, 93% or more, 94% or more, 95% or more, 96% or more, 97% or more, 98% or more, 98.5% or more, 99% or more, 99.1% or more, 99.2% or more, 99.3% or more, 99.4% or more, 99.5% or more, 99.6% or more, 99.7% or more, 99.8% or more, or 99.9% or more to the amino acid sequence of the protein.

Therefore, the term "LRP1" includes a protein having an amino acid sequence having a sequence identity of 80% or more, 83% or more, 85% or more, 86% or more, 87% or more, 88% or more, 89% or more, 90% or more, 91% or more, 92% or more, 93% or more, 94% or more, 95% or more, 96% or more, 97% or more, 98% or more, 98.5% or more, 99% or more, 99.1% or more, 99.2% or more, 99.3% or more, 99.4% or more, 99.5% or more, 99.6% or more, 99.7% or more, 99.8% or more, or 99.9% or more to the amino acid sequence represented by a sequence number specified below, and having equivalent activity.

LRP1 includes an amino acid sequence represented by any of SEQ ID NO: 1 to SEQ ID NO: 4. Here, the amino acid sequence of LRP1 can be obtained from a database known in the art. Examples of the amino acid sequence of LRP1 are shown below:

SEQ ID NO: 1 (Low-density lipoprotein receptor-related protein 1 preproprotein [*Homo sapiens*], NCBI Reference Sequence: NP_002323.2 (4544 amino acids)), SEQ ID NO: 2 (Low-density lipoprotein receptor-related protein 1 [*Mus musculus*], NCBI Reference Sequence: NP_032538.2 (4545 amino acids)), SEQ ID NO: 3 (Low-density lipoprotein receptor-related protein 1 [*Macaca mulatta*], NCBI Reference Sequence: XP_015007567.1 (4544 amino acids)).

SEQ ID NO: 4 (Low-density lipoprotein receptor-related protein 1 [*Rattus norvegicus*], NCBI Reference Sequence: NP_001123962.1 (4545 amino acids))

The LRP1 in the present invention includes a protein having an amino acid sequence having, for example, a sequence identity of 80% or more, 83% or more, 85% or more, 86% or more, 87% or more, 88% or more, 89% or more, 90% or more, 91% or more, 92% or more, 93% or more, 94% or more, 95% or more, 96% or more, 97% or more, 98% or more, 98.5% or more, 99% or more, 99.1% or more, 99.2% or more, 99.3% or more, 99.4% or more, 99.5% or more, 99.6% or more, 99.7% or more, 99.8% or more, or 99.9% to the amino acid sequence specified by SEQ ID NO: 1, 2, 3, or 4.

Further, examples of a base sequence of a gene encoding LRP1 are shown below:

SEQ ID NO: 5 (*Homo sapiens* LDL receptor related protein 1 (LRP1), mRNA, NCBI Reference Sequence: NM 002332.3 (14923 base pairs)), SEQ ID NO: 6 (*Mus musculus* low density lipoprotein receptor-related protein 1 (Lrp1), mRNA, NCBI Reference Sequence: NM 008512.2 (14907 base pairs)).

SEQ ID NO: 7 (PREDICTED: *Macaca mulatta* LDL receptor related protein 1 (LRP1), mRNA, NCBI Reference Sequence: XM 015152081.2 (14900 base pairs)).

SEQ ID NO: 8 (*Rattus norvegicus* LDL receptor related protein 1 (Lrp1), mRNA, NCBI Reference Sequence: NM 001130490.1 (14714 base pairs)).

As used herein, the term "antibody" is intended to include not only an antibody itself, but also a fragment of the antibody, particularly an antigen-binding fragment. Therefore, as used herein, in a case where the term "antibody" is described, the term "antibody" is intended to include an antibody and an antibody fragment thereof. Specifically, the term "anti-LRP1 antibody" is intended to include both an anti-LRP1 antibody and an anti-LRP1 antibody fragment.

The term "antibody fragment" includes, for example, a single-chain antibody (scFv), a scFv dimer, a disulfide-stabilized V-region fragment (dsFv), Fv, Fab, Fab', F(ab')2, a domain antibody, and the like.

In one embodiment, the anti-LRP1 antibody may be a single-chain antibody (scFv). In another embodiment, the anti-LRP1 antibody may be an IgG antibody, an IgA antibody, an IgE antibody, or an IgM antibody.

In a case where the anti-LRP1 antibody is a single-chain antibody (scFv), it can be produced by a method known in the art, and for example, it may be produced by chemical synthesis in addition to being produced by a microorganism using a phagemid, a plasmid, and the like. For example, the anti-LRP1 antibody, being a single-chain antibody, is formed by linking a heavy chain variable domain and a light chain variable domain by a flexible linker.

In a case where the anti-LRP1 antibody is an IgG antibody, the antibody may be a mouse antibody, a chimeric antibody, a humanized antibody or a human antibody, preferably a humanized antibody or a human antibody. In a case where the antibody is an IgG antibody, it can be produced by a method known in the art. One example of the method for producing an IgG antibody will be described later, but the method is not limited thereto.

The optic nerve protecting agent containing an anti-LRP1 antibody or an anti-LRP1 antibody fragment according to the present invention protects the optic nerve in vitro or in vivo. Here, the term "optic nerve protecting agent" includes not only a case of containing other components in addition to the anti-LRP1 antibody and/or the antigen fragment thereof, but also a case of containing only the anti-LRP1 antibody and/or the antigen fragment thereof.

"Protection of optic nerve" refers to preventing degeneration of optic nerve cells, and specifically refers to inhibiting degeneration of retinal ganglion cells and reducing disorders in retinal ganglion cells, and protecting axon of retinal ganglion cells constituting the optic nerve. Here, the term "degeneration" with respect to nerves includes apoptosis, necrosis and necroptosis. The "protection of the optic nerve" can be confirmed by means known in the art, and can be confirmed, for example, by a method of hematoxylin-eosin staining (hereinafter, it is also referred to as "HE staining") of retinal sections, immunoblotting of a marker protein of retinal ganglion cells, or electroretinogram (hereinafter, it is also referred to as "ERG"). Further, since degeneration of nerves can be detected by an immunohistological method, the "protection of optic nerve" may be confirmed using this method.

In one embodiment, the optic nerve protecting agent protects the optic nerve in a subject. As used herein, the term "subject" broadly includes animals. The animal is, for example, a vertebrate, preferably a mammal. As used herein, the term "mammal" is used to refer to any animal classified as a mammal, including, but not limited to, a human, mouse, rat, monkey, cow, horse, sheep, dog, and cat. As used herein, a preferred mammal is a human.

The anti-LRP1 antibody or the antibody fragment thereof is an antibody that specifically binds to the C2 domain of LRP1.

In one embodiment, the anti-LRP1 antibody or the antibody fragment thereof recognizes an epitope:

(a) in a region of amino acids at positions 786 to 1165 in the amino acid sequence of LRP1 having an amino acid sequence represented by SEQ ID NO: 1, (b) in a region of amino acids at positions 787 to 1166 in the amino acid sequence of LRP1 having an amino acid sequence represented by SEQ ID NO: 2, or (c) in a region of amino acids at positions 786 to 1165 in the amino acid sequence of LRP1 having an amino acid sequence represented by SEQ ID NO: 3, (d) in a region of amino acids at positions 787 to 1166 in the amino acid sequence of LRP1 having an amino acid sequence represented by SEQ ID NO: 4.

In the present invention, an "epitope" means a partial peptide of an LRP1 polypeptide having antigenicity and/or immunogen in the body of an animal, preferably a mammal, more preferably a human, mouse, rat or monkey. An epitope that is the partial peptide of LRP1 having antigenicity can be determined by a method known to those skilled in the art, such as immunoassay. The epitope can be determined, for example, by the following method. To start with, various partial structures of the LRP1 polypeptide are produced using known oligopeptide synthesis techniques. Specifically, it can be determined by examining a series of polypeptides sequentially shortened by an arbitrary length from the C-terminus or N-terminus of the LRP1 polypeptide, determining a rough recognition site, then synthesizing shorter peptides, and examining the reactivity with them. As another specific method, it can be determined by expressing each domain structure as a recombinant protein using each domain structure of LRP1 as a basic unit, and examining a difference in binding to these recombinant proteins.

In a case where the anti-LRP1 antibody or the antibody fragment thereof is an anti-LRP1 human IgG antibody, the anti-LRP1 antibody or the antibody fragment thereof binds to LRP1 with a dissociation constant (Kd) of, for example, $1\times10^{-5}$ M to $1\times10^{-12}$ M, preferably $1\times10^{-7}$ M to $1\times10^{-11}$ M, more preferably $1\times10^{-8}$ M to $1\times10^{-10}$ M, and still more preferably $1\times10^{-8}$ M to $1\times10^{-9}$ M.

The anti-LRP1 antibody or the antibody fragment thereof according to the present invention includes, for example, the following complementarity determining regions (CDRs):

a heavy chain complementarity determining region 1 (VH CDR1) that includes an amino acid sequence having a sequence identity of 80% or more, 83% or more, 85% or more, 90% or more, 93% or more, 95% or more, 97% or more, 98% or more, or 99% or more to an amino acid sequence represented by SEQ ID NO: 9;

a heavy chain complementarity determining region 2 (VH CDR2) that includes an amino acid sequence having a sequence identity of 80% or more, 83% or more, 85% or more, 90% or more, 93% or more, 95% or more, 97% or more, 98% or more, or 99% or more to an amino acid sequence represented by SEQ ID NO: 10;

a heavy chain complementarity determining region 3 (VH CDR3) that includes an amino acid sequence having a sequence identity of 80% or more, 83% or more, 85% or more, 90% or more, 93% or more, 95% or more, 97% or more, 98% or more, or 99% or more to an amino acid sequence represented by SEQ ID NO: 11;

a light chain complementarity determining region 1 (VL CDR1) that includes an amino acid sequence having a sequence identity of 80% or more, 83% or more, 85% or more, 90% or more, 93% or more, 95% or more, 97% or more, 98% or more, or 99% or more to an amino acid sequence represented by SEQ ID NO: 12;

a light chain complementarity determining region 2 (VL CDR2) that includes an amino acid sequence having a sequence identity of 80% or more, 83% or more, 85% or more, 90% or more, 93% or more, 95% or more, 97% or more, 98% or more, or 99% or more to an amino acid sequence represented by SEQ ID NO: 13; and a light chain complementarity determining region 3 (VL CDR3) that includes an amino acid sequence having a sequence identity of 80% or more, 83% or more, 85% or more, 90% or more, 93% or more, 95% or more, 97% or more, 98% or more, or 99% or more to an amino acid sequence represented by SEQ ID NO: 14.

In a preferred embodiment, the anti-LRP1 antibody or the antibody fragment thereof includes:

a heavy chain complementarity determining region 1 (VH CDR1) that includes the amino acid sequence represented by SEQ ID NO: 9;

a heavy chain complementarity determining region 2 (VH CDR2) that includes the amino acid sequence represented by SEQ ID NO: 10;

a heavy chain complementarity determining region 3 (VH CDR3) that includes the amino acid sequence represented by SEQ ID NO: 11;

a light chain complementarity determining region 1 (VL CDR1) that includes the amino acid sequence represented by SEQ ID NO: 12;

a light chain complementarity determining region 2 (VL CDR2) that includes the amino acid sequence represented by SEQ ID NO: 13; and a light chain complementarity determining region 3 (VL CDR3) that includes the amino acid sequence represented by SEQ ID NO: 14.

TABLE 1

| | |
|---|---|
| Heavy chain complementarity determining region 1 (VH CDR1) | Light chain complementarity determining region 1 (VL CDR1) |
| SYAMS (SEQ ID NO: 9) | QGDSLRSYYAS (SEQ ID NO: 12) |
| Heavy chain complementarity determining region 2 (VH CDR2) | Light chain complementarity determining region 2 (VL CDR2) |
| AISGSGGSTYYADSVKG (SEQ ID NO: 10) | GKNNRPS (SEQ ID NO: 13) |
| Heavy chain complementarity determining region 3 (VH CDR3) | Light chain complementarity determining region 3 (VL CDR3) |
| RTGTLFDY (SEQ ID NO: 11) | NSSQAQRNAVV (SEQ ID NO: 14) |

In another embodiment, the anti-LRP1 antibody or the antibody fragment thereof includes:

a heavy chain variable region that includes an amino acid sequence having a sequence identity of 80% or more, 83% or more, 85% or more, 90% or more, 93% or more, 95% or more, 97% or more, 98% or more, or 99% or more to an amino acid sequence represented by SEQ ID NO: 15, and a light chain variable region that includes an amino acid sequence having a sequence identity of 80% or more, 83% or more, 85% or more, 90% or more, 93% or more, 95% or more, 97% or more, 98% or more, or 99% or more to an amino acid sequence represented by SEQ ID NO: 16.

In another preferred embodiment, the anti-LRP1 antibody or the antibody fragment thereof includes:

a heavy chain variable region that includes the amino acid sequence represented by SEQ ID NO: 15, and a light chain variable region that includes the amino acid sequence represented by SEQ ID NO: 16. The heavy chain variable region and the light chain variable region are preferably linked by a linker.

TABLE 2

| |
|---|
| Amino acid sequence of heavy chain variable region |
| EVQLLESGGGLVQPGGSLRLSCAASGFTFSSYAMSWVRQAPGKGLEWVSA |
| ISGSGGSTYYADSVKGRFTISRDNSKNTLYLQMNSLRAEDTAVYYCAKRT |
| GTLFDYWGQGTLVTVSS |
| (SEQ ID NO: 15) |
| Amino acid sequence of light chain variable region |
| SSELTQDPAVSVALGQTVRITCQGDSLRSYYASWYQQKPGQAPVLVIYGK |
| NNRPSGIPDRFSGSSSGNTASLTITGAQAEDEADYYCNSSQAQRNAVVFG |
| GGTKLTVLG |
| (SEQ ID NO: 16) |
| Base sequence of heavy chain variable region |
| gaagtccaactgctggaatcgggtggtggtctggtgcaaacgggcggctc |
| gctgcgtctgtcatgtgctgcgtcgggctttacctttagctcttatgcaa |
| tgtcctgggtgcgtcaggcaccgggtaaaggtctggaatgggttagcgca |
| attagtggctccggcggtagcacctattacgccgattctgttaaaggtcg |
| ttttaccatctcacgcgacaactcgaaaatacgctgtatctgcagatgaa |
| cagtctgcgcgcagaagataccgctgtctattctgcgcaaaacggactgg |
| gactttgttcgactactggggccaaggtacgctggttacggttagcagc |
| (SEQ ID NO: 17) |
| Base sequence of light chain variable region |
| tcgtctgaactgacgcaagatccggctgtttctgtggcactgggtcaaac |
| ggttcgtatcacgtgtcaaggcgattcactgcgctcctattacgcaagtt |
| ggtatcagcaaaaaacgggccaggctccggtgctggttatttacggcaaa |
| aacaatcgtccgtccggtatcccggatcgcttttcaggcagctctagtgg |
| taacaccgcgtcgctgaccattacgggtgcgcaagccgaagatgaagcag |
| actattactgcaatagctcccaggcgcagcggaatgcggttgtctttggt |
| ggtggtacgaaactgaccgtcctgggc |
| (SEQ ID NO: 18) |

In still another embodiment, the anti-LRP1 antibody or the antibody fragment thereof includes an amino acid sequence having a sequence identity of 80% or more, 83% or more, 85% or more, 90% or more, 93% or more, 95% or more, 97% or more, 98% or more, or 99% or more to the amino acid sequence represented by SEQ ID NO: 19.

In still another preferred embodiment, the anti-LRP1 antibody or the antibody fragment thereof includes the amino acid sequence represented by SEQ ID NO: 19.

TABLE 3

| |
|---|
| Amino acid sequence of scFv antibody |
| EVQLLESGGGLVQPGGSLRLSCAASGFTFSSYAMSWVRQAPGKGLEWVSA |
| ISQSGGSTYYADSVKGRETISRDNSKNTLYLQMNSLRAEDTAVYYCAKRT |
| GTLFDYWGQGTLVTVSSGGGSGGGGSGGGGSSELTQDPAYSVALGQTVRI |
| TCQGDSLRSYYASWYQQKPGQAPVLVIYGKNNRPSGIPDRFSGSSSGNTA |
| SLTITGAQAEDEADYYCNSSQAQRNAVVFGGGTKLTVLG |
| (SEQ ID NO: 19) |
| Base sequence of scFv antibody |
| gaagtccaactgctggaatcgggtggtggtctggtgcaaccgggcggctc |
| gctgcgtctgtcatgtgctgcgtcgggctttacctttagctcttatgcaa |
| tgtcctgggtgcgtcaggcaccgggtaaaggtctggaatgggttagcgca |
| attagtggctccggcggtagcacctattacgccgattctgttaaaggtcg |
| ttttaccatctcacgcgacaactcgaaaatacgctgtatctgcagatgaa |
| cagtctgcgcgcagaagataccgctgtctattactgcgcaaaacggactg |
| ggactttgttcgactactggggccaaggtacgctggttacggttagcagc |
| ggcggtggtggcagcggtggtggcggctcgggtggtggcggctcgtctga |
| actgacgcaagatccggctgtttctgtggcactgggtcaaacggttcgta |
| tcacgtgtcaaggcgattcactgcgctcctattacgcaagttggtatcag |
| cacgctgaccattacgggtgcgcaagccgaagatgcaagcagactattac |
| tgcaatagctcccaggcgcagcggaatgcggttgtctttggtggtggtac |
| gaaactgaccgtcctgggc |
| (SEQ ID NO: 20) |

Another embodiment of the present invention relates to an expression vector for producing an anti-LRP1 antibody or an anti-LRP1 antibody fragment. The expression vector includes one or more nucleic acids encoding the anti-LRP1 antibody of the present invention or a part thereof. Here, the nucleic acid is operably linked to a control sequence recognized by a host cell in a case where the host cell is transfected with a vector.

The expression vector according to the present invention includes, for example, at least one nucleic acid selected from the followings:

a DNA encoding a protein having the amino acid sequence represented by SEQ ID NO: 15 and a DNA encoding a protein having the amino acid sequence represented by SEQ ID NO: 16, a DNA having a polynucleotide sequence represented by SEQ ID NO: 17 and a DNA having a polynucleotide sequence represented by SEQ ID NO: 18, a DNA hybridizing with a DNA having a polynucleotide sequence complementary to the polynucleotide sequence represented by SEQ ID NO: 17 and the polynucleotide sequence represented by SEQ ID NO: 18 under a stringent condition, and encoding a protein that specifically binds to LRP1, a DNA including a polynucleotide sequence having a sequence identity of 80% or more to the polynucleotide sequence represented by SEQ ID NO: 17 and a polynucleotide sequence having a sequence identity of 80% or more to the polynucleotide sequence represented by SEQ ID NO: 18, and encoding a protein that specifically binds to LRP1, a DNA including a degenerate isomer of the polynucleotide sequence represented by SEQ ID NO: 17 and a degenerate isomer of the polynucleotide sequence represented by SEQ ID NO: 18, a DNA encoding a protein having the amino acid sequence represented by SEQ ID NO: 19, a DNA having a polynucleotide sequence represented by SEQ ID NO: 20, a DNA hybridizing with a DNA having a polynucleotide sequence complementary to the polynucleotide sequence represented by SEQ ID NO: 20 under a stringent condition, and encoding a protein that specifically binds to LRP1, a DNA including a polynucleotide sequence having a sequence identity of 80% or more to the polynucleotide sequence represented by SEQ ID NO: 20, and encoding a protein that specifically binds to LRP1, a DNA encoding a protein including an amino acid sequence having 1 to 10 amino acids deleted, substituted, inserted and/or added to the amino acid sequence of the protein encoded by the polynucleotide sequence represented by SEQ ID NO: 20, and encoding a protein that specifically binds to LRP1, a DNA including a degenerate isomer of the polynucleotide sequence represented by SEQ ID NO: 20.

The present invention also provides a host cell including one or more expression vectors, and a method for producing an anti-LRP1 antibody or an antigen fragment thereof using such a host cell. Here, the production method includes at least one of culturing a host cell containing an expression vector that produces an anti-LRP1 antibody or an antigen fragment thereof in a medium, and isolating the anti-LRP1 antibody or the antigen fragment thereof from the host cell or the medium. The present invention also provides a host cell genetically modified to express an anti-LRP1 antibody or an antigen fragment thereof in the absence of a vector as described above.

Yet another aspect of the invention is a composition containing the anti-LRP1 antibody or the anti-LRP1 antibody fragment or an optic nerve protecting agent previously described. Here, the term "composition" is intended to include not only a case of containing an anti-LRP1 antibody, an antigen fragment thereof, and other components other than an optic nerve protecting agent, but also a case of containing only an anti-LRP1 antibody, an antigen fragment thereof, and/or an optic nerve protecting agent (in other words, the case where other components are not contained). In one embodiment, the composition according to the present invention is a composition containing an anti-LRP1 antibody or an anti-LRP1 antibody fragment and a solvent. The composition according to the present invention is preferably a pharmaceutical composition containing an anti-LRP1 antibody or an anti-LRP1 antibody fragment at a therapeutically effective amount.

In one embodiment, the composition according to the present invention is a composition for topical administration, which is administered topically to a subject. Topical administration is, for example, instillation administration, subconjunctival injection, intravitreal administration and intraocular implant.

The composition according to the present invention can be administered orally or parenterally, preferably parenterally. Examples of a dosage form of the composition include a tablet, a capsule, a fine granule, a pill, a troche, a transfusion, an injection, eye drops, a suppository, an ointment, a patch and the like.

In one embodiment, the composition according to the present invention is a pharmaceutical composition for prevention or treatment of glaucoma. As described above, a certain percentage of glaucoma patients are patients with normal intraocular pressure, and there are many cases which still progresses even when the intraocular pressure is controlled by an intraocular pressure lowering agent. Therefore, the pharmaceutical composition of the present invention is preferably used for glaucoma patients having normal intraocular pressure. Specifically, glaucoma patients have an intraocular pressure, for example, in the range of 10 to 23 mmHg, preferably 10 to 21 mmHg, more preferably in the range of 10 to 20 mmHg.

Examples of glaucoma include primary open-angle glaucoma, normal-tension glaucoma, aqueous excessive glaucoma, ocular hypertension, acute angle-closure glaucoma, chronic angle-closure glaucoma, plateau iris syndrome, combined mechanism glaucoma, steroid-induced glaucoma, capsular glaucoma of crystalline lens, pigmentary glaucoma, amyloid glaucoma, neovascular glaucoma, malignant glaucoma, and the like.

As used herein, with respect to glaucoma, the term "treatment" is intended to include inhibiting or reducing glaucoma in addition to treating glaucoma. The term "treatment" specifically includes inhibiting a progression of optic nerve degeneration, and preventing apoptosis, necrosis and/or necroptosis of the optic nerve.

The subject includes a subject suffering from glaucoma who has received treatment by administration of an intraocular pressure lowering agent in the past, in particular, a subject suffering from glaucoma who has received treatment by administration of an intraocular pressure lowering agent in the past, and whose glaucoma symptoms are still progressing. Here, the intraocular pressure lowering agent is an intraocular pressure lowering agent known in the art, and examples thereof include an adrenaline α2 receptor agonist (Aiphagan (registered trademark) ophthalmic solution), a prostaglandin F2α derivative (Tapros (registered trademark) ophthalmic solution), a Rho kinase inhibitor (Granatec (registered trademark) ophthalmic solution), and the like, but are not limited thereto. The subject may further include a subject that has undergone a surgical procedure for the treatment of glaucoma.

In a case where the composition according to the present invention is applied to a subject for the prophylaxis or treatment of glaucoma, the composition is administered parenterally, preferably topically, more preferably intravitreally. Thus, in a case where the composition according to the present invention is a pharmaceutical composition, it is for example for parenteral administration, preferably for topical administration, more preferably for vitreous administration.

The dosage form of the composition according to the present invention is not particularly limited, but when applied to a subject for treatment of glaucoma, it is preferably eye drops or an ophthalmic injection.

The composition according to the present invention may typically contain a pharmaceutically acceptable additive, for example, a pharmaceutically acceptable excipient, binder, auxiliary agent, lubricant, solvent, diluent, stabilizer, emulsifier, preservative, carrier, solubilizing agent, tonicity agent and the like known in the art.

A dosage of the composition according to the present invention may be appropriately adjusted depending on the age, weight, disease state, and the like of the subject.

The optic nerve protecting agent and the pharmaceutical composition according to the present invention may be used as a combination agent in combination with an additional agent or pharmaceutical composition. With regard to the combination agent, active ingredients in the respective pharmaceutical compositions (that is, the first active ingredient and the second active ingredient) may be administered together, sequentially or individually, in one combined unit dosage form or in two separate unit dosage forms. A therapeutically effective amount of each active ingredient of the combination according to the present invention may be administered simultaneously, individually or in any order, sequentially or successively. In the combination agent, the first active ingredient and the second active ingredient may be individually present in each of plural units. The combination agent also includes, for example, a kit containing respective active ingredients and instructions for use.

According to the present invention, an optic nerve protecting agent and a composition containing an anti-LRP1 antibody or an anti-LRP1 antibody fragment that specifically binds to LRP1 can be provided. Since an anti-LRP1 antibody or an anti-LRP1 antibody fragment having high specificity is used, it is possible to specifically act on a factor involved in degeneration of optic nerve cells, and therefore degeneration of the optic nerve can be suppressed while reducing undesired side effects.

Furthermore, according to the present invention, an anti-LRP1 antibody or an anti-LRP1 antibody fragment can protect the optic nerve with a mechanism of action other than intraocular pressure reduction, and thus is expected to be a new therapeutic approach to glaucoma. Furthermore, due to the mechanism of avoiding degeneration of the optic nerve cells, it is expected to be able to provide another option of treatment in patients with glaucoma who have received treatment with the intraocular pressure lowering agent in the past and patients with optic nerve degeneration with normal intraocular pressure.

EXAMPLES

Hereinafter, the present invention will be described more specifically with reference to examples, but the present invention is not limited by these examples at all.

<Primary Culture of Retinal Ganglion Cells>

The primary culture of retinal ganglion cells was performed using a two-day old Sprague Dawley (SD) rat according to a method slightly modified from the method of Barres et al. (Barres et al., 1988) (Hayashi et al., J. Biol. Chem. 2009). Isolated retinal ganglion cells (RGCs) were suspended in a basic medium of RGC medium (containing 1 mM glutamine, 5 μg/ml insulin, 60 μg/ml N-acetylcysteine, 62 ng/ml progesterone, 16 μg/ml putrescine, 40 ng/ml sodium selenite, 0.1 mg/ml bovine serum albumin, 40 ng/ml triiodothyronine, 0.1 mg/ml transferrin, 1 mM sodium pyruvate, 2% B27 supplement (Invitrogen, Carlsbad, CA), 10 μM forskolin (Sigma, St. Louis, MO), 50 ng/ml brain-derived neurotrophic factor (BDNF; PeproTech, Rocky Hill, NJ), 50 ng/ml ciliary neurotrophic factor (CNTF; PeproTech), and 50 ng/ml basic fibroblast growth factor (bFGF; PeproTech). A 96 well plate was coated with poly-d-lysine (Sigma) and laminin (Sigma), and mounted with RGCs to 5,000 cells per well for a 96 well plate and 5,000 cells per culture insert for a microdish. The cells were subsequently cultured for at least 10 days before experiments.

<Preparation of Reconstituted Apolipoprotein E-Containing Lipoprotein>

The reconstituted apolipoprotein E-containing lipoprotein was prepared as described in the prior literature (Hayashi et al., J. Neurosci. 2007). This reconstituted apolipoprotein E-containing lipoprotein was composed of 1-palmitoyl-2-oleyl-glycerophosphocholine (POPC; P3017, Sigma), cholesterol (C3045, Sigma) and recombinant human apolipoprotein E, and a molar ratio of the components was 100:10:1 or 100:0:1. A solution containing a preparation medium, plasma or reconstituted apolipoprotein E-containing lipoprotein was subjected to a non-continuous sucrose gradient. A composition of the solution used was 3 ml for a density of 1.30 g/ml, 3 ml for a density of 1.2 g/ml, 3 ml for a density of 1.1 g/ml and 6 ml for a density of 1.006 g/ml.

The sucrose gradient was subjected to centrifugation using an SRP28SA1 rotor (Hitachi, Tokyo, Japan) at 100,000 g for 72 hours at 4° C. Ten fractions (1.5 ml) were collected from the top of the gradient, and subjected to immunoblotting for apolipoprotein E as follows. Fractions containing apolipoprotein E (typically fractions 5 to 7) were combined, and concentrated using an Amicon Ultra filter (50 kDa molecular weight cut-off; Millipore, Bedford, MA). The mass of lipoprotein was adjusted by a cholesterol concentration (2 μg/ml) for HDL, and by a protein concentration (100 ng/ml) for reconstituted lipoprotein. The concentrations of the cholesterol and protein were measured by a LabAssay cholesterol kit (Wako) and a BCA protein assay kit (Thermo Fisher Scientific Inc., Rockford, IL), respectively.

<Screening of Anti-LRP1 Antibody>

Using commercially available proteins derived from LRP1 partial domain and Human Fc (three species: C2, C3, C4) as an antigen, scFv for each cluster of LRP1 (that is, C2, C3 and C4) was obtained from a human scFv phage library. FIG. 2A shows a schematic diagram of the antigen used, i.e. LRP1.

scFvs that specifically bind to clusters 2, 3, and 4 of LRP1 (that is, C2, C3 and C4) were subjected to screening (panning) from the human scFv phagelibrary. As a result, a large number of scFvs specific to each of the LRP1 clusters 2, 3, and 4 were obtained. The results of plotting the reactivity of each clone (in the horizontal axis) are shown in FIG. 2B. Multiple phage clones (52, 45 and 47 clones, respectively) that specifically react to each domain of LRP1 (ligand binding clusters C2, C3 and C4) were obtained from the clones after three times of pannings (93 clones each). Each scFv was subjected to sequencing, and most of them were confirmed to have different CDR3 sequences. The scFv library used for the screening was derived from DP47-DPL16 (PDB: 3GHE), which is a library in which random sequences were introduced into CDR3 regions of each of the heavy chain and the light chain. FIG. 2C shows the amino acid sequences of the heavy chain (in the drawing, "H chain") and the light chain (in the drawing, "L chain") of scFv, with randomized moieties shown as "X" in each chain.

<Evaluation of Binding Site in LRP1 of Anti-LRP1 Antibody>

Four scFv clones for the LRP1 clusters were purified. These clones were selected for the stability of *E. coli* retention of phagemid and stability in purification as an index. The sequence of the VH and VL CDR3 of the four scFv clones, and a feed rate are shown in the following table.

TABLE 4

| Clone name | VH CDR3 | VL CDR3 | Feed rate (in PBS) |
|---|---|---|---|
| C2_D11 | RTGTLFDY (SEQ ID NO: 11) | NSSQAQRNAVV (SEQ ID NO: 14) | 0.758 mg/ml × 100 ul |
| C2_F8 | TTGHLFDY (SEQ ID NO:26) | NSSNPRRQRVV (SEQ ID NO:27) | 0.508 mg/ml × 100 ul |
| C2_G3 | TTGELFDY (SEQ ID NO:28) | NSSRRRKHHVV (SEQ ID NO:29) | 0.739 mg/ml × 100 ul |
| C2_G9 | NTGASFDY (SEQ ID NO:30) | NSSRYRKHPVV (SEQ ID NO:31) | 0.675 mg/ml × 100 ul |
| Anti-OVA (Control) | GFTFSSYAFDY (SEQ ID NO:32) | NSSSLRSYYVV (SEQ ID NO:33) | 1.0 mg/ml × 100 ul |

SDS-PAGE of each purified scFv is shown in FIG. 2D. Each purified scFv had a purity of 90% or more. FIG. 2E shows the results of ELISA for C2-D11, C2-F8, C2-G3, and C2-G9 among the purified scFvs.

Materials and conditions used in ELISA are shown in the following table.

[Table 5]

TABLE 5

| Details of ELISA for binding test of antibody to antigen | |
|---|---|
| ELISA to test mAbs for reactivity with antigen<br><Material><br>-Nune-Immuno ™ Plate MaxSorp ™ (Nune 439454)<br>-Plate seal<br>-PBS<br>-Wash buffer: PBS containing 0.05% Tween20 and 0.05% azide<br>-BSA blocking buffer (BBB): PBS containing 0.5% BSA and 0.1% azide<br>-BBBT: BBB containing 0.05% Tween20<br>-p-Nitrophenylphosphoric Acid Disodium Salt | <Samples or standards><br>Prepare Antibody sample.<br>Wash the plate 1× with Wash buffer<br>Add 50 ul/well of the antibody solution<br>Incubate at RT for > 60 min or 4 degree overnight<br>2nd Antibody<br>Dilute ALP-labeled 2nd Ab (For example, goat anti-mouse Fc at 1:1000 with BBBT)<br>Wash the plates 2× with Wash buffer<br>Add 50 ul/well of the |

TABLE 5-continued

| Details of ELISA for binding test of antibody to antigen | |
|---|---|
| -1× ALP buffer: 0.2M diethanolamine, 0.5 mM Magnesium chloride, 0.04% azide, pH 9.8<br><Coating><br>Dilute antigen protein to 2 ug/ml in PBS.<br>Add 50 ul/well (50-100 ng/well) to Nune-Immuno ™ Plate MaxSorp ™ (Nune 439454)<br>Seal the plate, mix to make the solution surface even<br>Incubate at RT for 4-6 hrs or at 4 degree for overnight<br><Blocking (optional, usually not necessary)><br>Add 100 ul/well blocking buffer (for example, 1% BSA in PBS, 0.1% sodium azide)<br>Incubate at R.T. for > 30 min | diluted 2nd antibody<br><Development><br>Prepare 1 mg/ml papp solution with 1× ALP buffer<br>Wash the plate 4× with Wash buffer<br>Add 50 ul/well of the papp solution<br>Incubate at RT for 10-30 min<br>(optional) Add 50 ul/well of 0.5M EDTA to stop the reaction<br>Measure OD at 405 nm |

The results shown in FIG. 2E revealed that at a low concentration of 100 ng/ml, these scFvs show specific reactivity to C2-Fc (C2 domain).

<Protective Effect of scFv on Glutamate-Induced Neurotoxicityin Primary Cultured Retinal Ganglion Cells>

Apoptosis was induced with 300 μM glutamic acid and 10 μM glycine for two hours. scFv was used at a concentration of 1 μg/ml, and E-LP was used at a concentration of 100 ng/ml as a positive control. Anti-OVA (ovalbumin) scFv was used as a negative control. Nuclear aggregation 24 hours after glutamate-induced neurotoxicity was analyzed by Hoechst staining. The results regarding the protective effect on retinal ganglion cells of scFv in Group #1 (n=4 to 5), Group #2 (n=5) and Group #3 (n=5) are shown in FIGS. 3A, 3B and 3C, respectively. From these results, among the scFv clones binding to the Ligand-Binding Cluster C2 (D11, F8, G3, G9, G5, and A7), D11 was confirmed to have a protective effect on retinal ganglion cells, while no neuroprotective effect was observed in the scFv clone binding to C3 and the scFv clone binding to C4.

<Immunoblotting>

The proteins were dissolved in 62.5 mM Tris-HCl (pH 6.8), 10% glycerol, 2% sodium dodecyl sulfate (SDS) and 5% β-mercaptoethanol (sample buffer) and boiled for five minutes. The proteins were separated by electrophoresis on polyacrylamide gels containing 0.1% SDS, and then transferred to a polyvinylidene difluoride membrane. The membranes were incubated for one hour at room temperature with 5% skim milk in TBS-T (10 mM Tris-HCl (pH 7.4), 150 mM NaCl and 0.1% Tween 20), and then probed overnight at 4° C. with a primary antibody in TBS-T containing 5% bovine serum albumin. The membranes were subsequently probed for one hour at room temperature with peroxidase-conjugated goat anti-mouse IgG (Thermo), goat anti-human IgG (Thermo), or mouse anti-goat IgG (Thermo). Immunoreactive proteins were visualized with enhanced chemiluminescence (GE Healthcare, Buckinghamshire, UK) or Super Signal West Dura (Thermo). The primary antibodies used were as follows: human C2-D11 IgG (0.5 μg/ml), mouse antibody β-actin (a5441, diluention 1:10,000, Sigma), goat anti-human Brn-3a (sc-31984, diluention 1:1000, Santa Cruz). Brn-3a is a marker protein of retinal ganglion cells, and β-actin was used as a loading control. scFv (C2-D11) was administered intravitreally simultaneously with N-methyl-D-aspartic acid (NMDA). The results are shown in FIGS. 4 and 5.

FIG. 4 shows analysis results of immunoblotting of the retina, demonstrating the protective effect on retinal ganglion cells of scFv (C2-D11) on rats with NMDA-induced optic nerve degeneration. FIG. 5 shows the protective effect on retinal ganglion cells of scFv (C2-D11) on the rats with NMDA-induced optic nerve degeneration by summarizing the results of immunoblot analysis (3 to 6 cases) of FIG. 4 (summary of the analysis results of the immunoblotting of the retina). From FIGS. 4 and 5, the protective effect on retinal ganglion cells of scFv (C2-D11) was confirmed.

<Induction and Detection of Apoptosis in Retinal Ganglion Cells (RGCs)>

RGCs were washed twice with Hanks' Balanced Salt Solution (HBSS; 14170, Invitrogen) containing 2.4 mM $CaCl_2$), 20 mM HEPES and no magnesium, and then incubated at 37° C. for two hours with 300 μM glutamic acid and 10 μM glycine with or without E-LP, C2-D11 scFv or C2-D11 IgG in HBSS containing 2.4 mM $CaCl_2$), 20 mM HEPES and no magnesium. After glutamic acid treatment, RGCs were cultured at 37° C. for 22 hours with a culture medium for RGC without forskolin, BDNF, CNTF or bFGF. For the detection of apoptosis, RGCs were stained with 1 μg/ml of Hoechst 33342 (346-07951, Kumamoto, DOJINDO). Fluorescence images were observed using an Olympus IX 71 microscope. Fragmented or shrunken nuclei stained with Hoechst dye were counted as apoptotic neurons, and round and smooth nuclei were counted as healthy neurons.

<Protective Effect of C2-D11 Antibody on NMDA-Induced Retinal Degeneration in Rats>

Intravitreal injection of NMDA (Sigma) was performed with minor modifications, similar to the method described in the prior literature (Tsutsumi T. et al., Invest Ophthalmol Vis Sci. 2016, 57 (14): 6461-6473). Specifically, 7-week-old rats were anesthetized with 5% isoflurane, and then maintained with 2.5% isoflurane. The pupil was dilated by instillation of phenylephrine hydrochloride and tropicamide. Subsequently, PBS as a vehicle control or 20 nmol/eye NMDA with or without 5 ng/eye E-LP, 0.15 μg/eye C2-D11 scFv or 0.75 μg/eye C2-D11 IgG in a total volume of 4 μl was injected into the vitreous cavity. Injections were performed under a microscope using a 34-gauge needle (Nanopass, Terumo, Tokyo, Japan) connected to a microsyringe (80008, Hamilton, Reno, NV) equipped with an injection pump (Fusion 200, Chemyx Inc., Stafford, TX), and the needle was inserted approximately 1.0 mm behind the corneal limbus. The eyeballs were enucleated three days after NMDA injection and retinae were removed from the sclerae, added into lysis buffer [1% Triton X-100; MP Biomedicals (Santa Ana, CA, CA, USA), 0.1% sodium deoxycholate; Wako (Osaka, Japan), 1% EDTA; DOJINDO (Kumamoto, Japan), Complete protease inhibitor cocktail; Roche (Basel, Switzerland), PhosStop phosphatase inhibitor cocktail; Roche, 50 mM Tris-buffered saline), and then sonicated with Ultrasonic Liquid Processor Q125 (QSONICA) at 4° C. for 20 seconds (2 seconds sonication×10 times). Protein concentration of retinal sample was measured by a BCA protein assay kit (Thermo Fisher Scientific Inc.) and subjected to immunoblotting.

<Frozen Specimen Preparation and HE Staining of Rat Eyeballs>

The frozen specimen preparation and HE staining of eyeballs were performed according to the following procedure.

(1) Eyeballs were removed on the third day after NMDA+/C2-D11 scFv administration.

(2) The eyeballs were gently grasped with ring tweezers, the conjunctiva was cut with scissors, and then the optic nerve was cut long and immersed in Super Fix at 4° C. for two hours.

(3) After fixation for two hours, an eye cup was prepared.

(4) The procedure was returned to Super Fix again, and the eye cup was fixed for 22 hours (overnight, at 4° C.).

(5) After 22 hours, the eye cup was transferred to 20% sucrose and soaked at room temperature until it submerged. Then the eye cup was transferred to 30% sucrose and repeated until 40% sucrose.

(6) The eye cup submerged in 40% sucrose was removed.

(7) The OCT compound was placed in Cryomold into which the eye cup was submerged.

(8) The eye cup was embedded in isopentane cooled with liquid nitrogen.

(9) The temperature of a cryostat sample stand was set to −20° C.

(10) The eye cup was thinly sliced at a thickness of 10 μm.

(11) Thinly sliced sections were HE stained.

(12) After HE staining, the number of retinal ganglion cells (RGCs) and the thickness of the inner plexiform layer (IPL) at positions 1 mm to 1.5 mm from the optic disc were measured. The results are shown in FIGS. 6, 7, and 8. In FIG. 6, GCL represents a ganglion cell layer, and IPL represents an inner plexiform layer.

As a result of counting the number of cells in the ganglion cell layer (GCL) of HE stained images in FIG. 6 (4 to 6 cases), it was shown that scFv (C2-D11) has a protective effect on the decrease in the number of GCL cells by NMDA (FIG. 7). Further, as a result of measuring the thickness of the inner plexiform layer (IPL) in the HE stained images of FIG. 6 (4 to 6 cases), it was shown that scFv (C2-D11) has an inhibitory effect (protective effect) on the decrease in the thickness of IPL by NMDA (FIG. 8A). Further, FIG. 8B shows results obtained by requesting a third party organization to perform the same experiment. The results of FIG. 8B showed that good reproducibility was obtained.

<Measurement of Thickness of Inner Plexiform Layer by Optical Coherence Tomography>

The thickness of the inner plexiform layer of the retina at the sixth day after treatment with each sample was measured by an optical coherence tomography (OCT). The thickness of the retinal inside from the inner plexiform layer is shown in FIG. 9. The thickness of the inner plexiform layer was significantly decreased in a NMDA administration group and a NMDA+OVA administration group compared to a PBS administration group, and no decrease was observed in a NMDA+LP administration group and a NMDA+C2-D11 scFv administration group. From these results, the retinal protective effect of C2-D11 scFv was confirmed.

<Production of Anti-LRP1 Human IgG1 Antibody from scFv Antibody C2_D11>

As schematically shown in FIG. 10, the anti-LRP1 human IgG1 antibody was produced from C2_D11. From the scFv sequence of C2 D11, amino acid sequences corresponding to VL and VH, respectively, were analyzed from a gene sequence of a phagemid vector, and each of VL and VH was incorporated into a gene expression vector having a Fc region of human IgG1. Each plasmid was double-transfected into a eukaryotic cell expression system (HEK-293) to establish cells that transiently express the antibody. From the culture supernatant after culture for about one week, the expressed antibody was isolated and purified by affinity purification with protein A. pY03'-FLAG-C2-D11, a phagemid capable of expressing a fusion protein of the M13 phage with g3 protein, has been deposited under the accession number NITE BP-03322 in the National Institute of Technology and Evaluation, Biotechnology Center, Patent Microorganisms Depositary (NPMD) (Address: Room 122, Kazusa kamatari 2-5-8, Kisarazu-shi, Chiba) on Nov. 20, 2020.

<Binding Specificity of Anti-LRP1 Human IgG1 Antibody>

The binding specificity of an anti-LRP1 human IgG1 antibody to LRP1 was evaluated by ELISA and a biosensor. The results of ELISA for the anti-LRP1 human IgG1 antibody are shown in FIG. 11A, and the results of ELISA for an anti-OVA antibody as a control are shown in FIG. 11B. After immobilizing the C2 domain of LRP-1 to an ELISA plate, a purified antibody was added to the plate and the amount of bound antibody was quantified by colorimetric determination. Furthermore, the binding of the anti-LRP1 human IgG1 antibody to an immobilized LRP1-Fc was shown in FIG. 12. The affinity of the antibody for LRP-1 was determined by immobilizing the C2 domain protein of LRP-1 on a biosensor chip, continuously adding antibodies with C2 D11 in the VL and VH at the concentrations shown in FIG. 12, and calculating the on-rate (Kon) and off-rate (Koff) values at each binding. From these results, a value of the dissociation constant (Kd) of the anti-LRP human IgG1 antibody prepared from C2 D11 was 0.9 nM, indicating that it has strong affinity and binding specificity for LRP1.

<Intracellular Calcium Analysis in Retinal Ganglion Cells (RGCs)>

RGCs were maintained through an experiment with a heating element (Tokai Hit, Shizuoka, Japan). Cells were cultured in the microdish for at least 14 days and incubated for 30 minutes at 37° C. with 3 μM Fluo-8 acetoxy metal ester (AAT Bioquest, Sunnyvale, CA). After washing the cells twice with 500 μl HBSS containing 2.4 mM $CaCl_2$), 20 mM HEPES, and no magnesium, 300 μM glutamic acid and 10 μM glycine with or without 100 ng/ml E-LP or 100 μg/ml C2-D11 IgG were administered. Fluorescence images were acquired every 500 msec using an ORCA-R2 digital CCD camera (Hamamatsu Photonics, Hamamatsu, Japan) and analyzed by MetaFluor fluorescence ratio imaging software (Molecular Devices, Sunnyvale, CA). In this test, 100 μg/ml C2-D11 IgG was evaluated using 100 ng/ml apolipoprotein E-containing lipoprotein (E-LP) as a positive control and the anti-OVA antibody as a negative control. The results are shown in FIG. 13.

FIG. 13 shows an evaluation of the protective effect on retinal ganglion cells using intracellular calcium influx by glutamate stimulation as an index. intracellular calcium influx was observed by 300 μM glutamic acid, and as a result, 100 μg/ml C2-D11 IgG exhibited a stronger inhibitory effect on intracellular calcium influx than E-LP. Since excessive calcium influx by 300 μM glutamic acid induces apoptosis, this result is considered to indicate one of neuroprotective mechanisms of C2-D11 IgG.

<Frozen Specimen Preparation and Immunofluorescence Staining of Rat Eyeballs>

Frozen specimen preparation and immunofluorescence staining of rat eyeballs were performed in the following procedures.

(1) Thinly sliced sections were prepared in the same manner as in the HE staining method.
(2) 15% blocking buffer (in PBS, goat 15% serum, 0.05% Tween 20) was added and reacted at room temperature for one hour.
(3) Washing was performed with PBS for 15 minutes.
(4) A Primary antibody (human anti-LRP1 IgG in 1% blocking buffer) was added and incubated overnight at 4° C.
(5) Washing was performed with PBS for 15 minutes.
(6) A secondary antibody (Alexa Fluor 488-bound goat anti-rabbit IgG (dilution 1:500, Invitrogen)) and Alexa Fluor 594-bound goat anti-human IgG (dilution 1:500, Invitrogen)) were added and reacted at room temperature for one hour.
(7) Washing was performed with PBS containing Heochst33342 (1:2000 dilution) for 10 minutes.
(8) After encapsulation, observation was performed with a fluorescence microscope. The results are shown in FIG. 14.

In the above experiment, it was observed by fluorescent immunostaining whether C2-D11 IgG binds to LRP1 of retinal ganglion cells after being administered into the vitreous body of rats. From the results shown in FIG. 14, it was revealed that C2-D11 IgG and LRP1 colocalize in the ganglion cell layer (arrows in the drawing). On the other hand, it was shown that the anti-OVA antibody was not colocalized. This result indicates that C2-D11 IgG binds to LRP1 on retinal ganglion cells and exerts a neuroprotective effect.

<Neuroprotective Effect of Anti-LRP1 Human IgG1 Antibody on Glutamate-Induced Retinal Ganglion Cell Death>

Glutamic acid was administered in combination with various concentrations of the anti-LRP1 human IgG1 antibody, and the rate of cell death was examined. Specifically, 300 μM glutamic acid and 10 μM glycine were used to induce apoptosis for two hours. The anti-LRP1 human IgG1 antibody was used at a concentration of 0.01 μg/ml to 10 μg/ml. Nuclear aggregation 24 hours after glutamate-induced neurotoxicity was analyzed by Hoechst staining. The results are shown in FIG. 15. From FIG. 15, the neuroprotective effect was observed by an IgG antibody at 10 μg/mL (n=5).

<Production of Recombinant Protein of LRP1>

Various deficient variants of Cluster II of human low-density lipoprotein receptor-associated protein 1 (LRP1) were prepared for epitope mapping. A GST-tag was fused to each of the prepared deficient variants of Cluster II of human LRP1. A CDNA fragment of Cluster II of human low-density lipoprotein receptor-associated protein 1 (LRP1) was synthesized to encode forward linker SGGSTS, Cluster II (position, 786-1165) and backward linker ASTGS (Thermo Fisher Scientific, Waltham, MA). A CDNA fragment encoding each deficient variant of Cluster II was prepared by PCR using primer sets shown in the following table and the cDNA fragment of Cluster II as a template. An expression vector was obtained by digesting the cDNA fragment with BamHI and EcoRI and inserting it into the corresponding restriction site on pGEX-6P-1 expression vector (Cytiva, Marlborough, MA). BL21 cells having the expression vector were then cultured in MagicMedia (Thermo Fisher Scientific), and each recombinant protein (each deficient variant) was produced according to the manufacturer's protocol (Cytiva, Marlborough, MA). After lysis of *E. coli* by sonication, a GST fusion protein was pulled down with glutathione-sepharose (Cytiva) and used for immunoblotting.

[Table 6]

Table 6: Primer Set

TABLE 6 TABLE 6

Primer set

| rProtein | Structure | Primer | Sequence (5'-3') |
|---|---|---|---|
| GST_ LRP1- C2_del1 | GST_EGF- like4_LDL receptor class A3_A4_A5_A6_A7 | LRP1_C2_01 | GCGATGGATCCTCCGGAGGTTCCACTAGT (SEQ ID NO: 21) |
| | | LRP1_C2_06 | GCATCAATTGTCAGGAACCAGTAGAAGCT CCCTCACAGCTCTTCTCATCGCT (SEQ ID NO: 22) |
| GST_ LRP1- C2_del2 | GST_EGF- like4_LDL receptor class A3_A4_A5 | LRP1_C2_01 | GCGATGGATCCTCCGGAGGTTCCACTAGT (SEQ ID NO: 21) |
| | | LRP1_C2_08 | GCATCAATTGTCAGGAACCAGTAGAAGCG GACTCGCAGTTCTCCTCGTCCGA (SEQ ID NO: 23) |
| GST_ LRP1- C2_del3 | GST_EGF- like4_LDL receptor class A3_A4_A5_A6_A7_ A8_A9 | LRP1_C2_01 | GCGATGGATCCTCCGGAGGTTCCACTAGT (SEQ ID NO: 21) |
| | | LRP1_C2_02 | GCATCAATTGTCAGGAACCAGTAGAAGCG GCTGAACAAGTGCCATTOGACIC (SEQ ID NO: 24) |
| GST_ LRP1- C2_del4 | GST_EGF- like4_LDL receptor class A3_A4_A5_A6_A7_ A8 | LRP1_C2_02 | GCGATGGATCCTCCGGAGGTTCCACTAGT (SEQ ID NO: 21) |
| | | LRP1_C2_04 | GCATCAATTGTCAGGAACCAGTAGAAGCG TTGGTGCAGTTGGCGTGTGTCTC (SEQ ID NO: 25) |

<Identification of Epitope>

The prepared deficient variants were subjected to electrophoresis, and gel staining was performed using Coomassie Brilliant Blue R250. The results are shown in FIG. 16A. Further, immunoblotting of the prepared deficient variants was performed using C2-D11 IgG in 5% BSA/TBS-T in the same manner as shown in the section of <Immunoblotting> above. As a secondary antibody, a goat anti-human IgG bound to HRP was used. The results are shown in FIG. 16B. From FIG. 16B, an epitope of C2-D11 was identified.

What is claimed is:

1. An optic nerve protecting agent comprising an anti-low density lipoprotein receptor-related protein 1 (LRP1) antibody or an anti-LRP1 antibody fragment, wherein:

(i) the anti-LRP1 antibody or the antibody fragment comprises:

a heavy chain complementarity determining region 1 (VH CDR1) that comprises the amino acid sequence represented by SEQ ID NO: 9;

a heavy chain complementarity determining region 2 (VH CDR2) that comprises the amino acid sequence represented by SEQ ID NO: 10;

a heavy chain complementarity determining region 3 (VH CDR3) that comprises the amino acid sequence represented by SEQ ID NO: 11;

a light chain complementarity determining region 1 (VL CDR1) that comprises the amino acid sequence represented by SEQ ID NO: 12;

a light chain complementarity determining region 2 (VL CDR2) that comprises the amino acid sequence represented by SEQ ID NO: 13; and a light chain complementarity determining region 3 (VL CDR3) that comprises the amino acid sequence represented by SEQ ID NO: 14, or (ii) the anti-LRP1 antibody or the antibody fragment comprises a heavy chain variable region that comprises the amino acid sequence represented by SEQ ID NO: 15, and a light chain variable region that comprises the amino acid sequence represented by SEQ ID NO: 16, or (iii) the anti-LRP1 antibody or the antibody fragment comprises the amino acid sequence represented by SEQ ID NO: 19.

2. The optic nerve protecting agent according to claim 1, wherein the anti-LRP1 antibody or the antibody fragment specifically binds to C2 domain of the LRP1.

3. The optic nerve protecting agent according to claim 1, wherein the anti-LRP1 antibody or the antibody fragment recognizes an epitope:

(a) in a region of amino acids at positions 786 to 1165 in an amino acid sequence of LRP1 consisting of an amino acid sequence represented by SEQ ID NO: 1, (b) in a region of amino acids at positions 787 to 1166 in an amino acid sequence of LRP1 consisting of an amino acid sequence represented by SEQ ID NO: 2, (c) in a region of amino acids at positions 786 to 1165 in an amino acid sequence of LRP1 consisting of an amino acid sequence represented by SEQ ID NO: 3, or (d) in a region of amino acids at positions 787 to 1166 in an amino acid sequence of LRP1 consisting of an amino acid sequence represented by SEQ ID NO: 4.

4. The optic nerve protecting agent according to claim 1, wherein the anti-LRP1 antibody or the antibody fragment is a humanized antibody or a human antibody.

5. The optic nerve protecting agent according to claim 1, wherein the anti-LRP1 antibody or the antibody fragment binds to LRP1 with a dissociation constant (Kd) of $1\times10^{-7}$ M to $1\times10^{-11}$ M.

6. A composition comprising the optic nerve protecting agent according to claim 1.

7. The composition according to claim 6, wherein the composition is topically administered to a subject.

8. The composition according to claim 7, wherein the topical administration is intravitreal administration.

9. The composition according to claim 7, wherein the composition is in a form of eye drops.

10. The composition according to claim 7, for treating glaucoma.

11. The composition according to claim 6, wherein the composition is topically administered to a subject having an intraocular pressure of 10 to 21 mm Hg.

12. An anti-LRP1 antibody or an anti-LRP1 antibody fragment, comprising:

(i) a heavy chain complementarity determining region 1 (VH CDR1) that comprises the amino acid sequence represented by SEQ ID NO: 9;

a heavy chain complementarity determining region 2 (VH CDR2) that comprises the amino acid sequence represented by SEQ ID NO: 10;

a heavy chain complementarity determining region 3 (VH CDR3) that comprises the amino acid sequence represented by SEQ ID NO: 11;

a light chain complementarity determining region 1 (VL CDR1) that comprises the amino acid sequence represented by SEQ ID NO: 12;

a light chain complementarity determining region 2 (VL CDR2) that comprises the amino acid sequence represented by SEQ ID NO: 13; and a light chain complementarity determining region 3 (VL CDR3) that comprises the amino acid sequence represented by SEQ ID NO: 14 or (ii) a heavy chain variable region that comprises the amino acid sequence represented by SEQ ID NO: 15, and a light chain variable region that comprises the amino acid sequence represented by SEQ ID NO: 16, or (iii) the amino acid sequence represented by SEQ ID NO: 19.

13. A composition comprising the anti-LRP1 antibody or the anti-LRP1 antibody fragment according to claim 12.

* * * * *